United States Patent [19]
Sandbrink et al.

[11] Patent Number: 5,985,793
[45] Date of Patent: Nov. 16, 1999

[54] SEQUENTIAL APPLICATION METHOD FOR TREATING PLANTS WITH EXOGENOUS CHEMICALS

[75] Inventors: Joseph J. Sandbrink, Des Peres; James M. Warner, University City; Daniel R. Wright, St. Louis; Paul C. C. Feng, Ellisville, all of Mo.

[73] Assignee: Monsanto Company, St. Louis, Mo.

[21] Appl. No.: 08/911,290

[22] Filed: Aug. 14, 1997

Related U.S. Application Data

[60] Provisional application No. 60/024,081, Aug. 16, 1996, provisional application No. 60/033,489, Dec. 20, 1996, and provisional application No. 60/049,096, Jun. 9, 1997.

[51] Int. Cl.⁶ .............................. A01N 25/30; C05G 3/00
[52] U.S. Cl. ..................... 504/116; 504/206; 504/208; 504/212; 504/250; 504/253; 504/258; 504/274; 504/291; 504/323; 504/324; 504/339; 504/342; 504/347; 504/352; 71/DIG. 1; 424/405; 512/772; 512/975
[58] Field of Search .................... 504/206, 116, 504/208, 212, 250, 253, 258, 274, 291, 323, 324, 339, 342, 347, 352; 71/DIG. 1; 424/405; 512/975, 772

[56] References Cited

U.S. PATENT DOCUMENTS

| | | | |
|---|---|---|---|
| 2,732,398 | 1/1956 | Brice et al. | 260/503 |
| 2,764,602 | 9/1956 | Ahlbrecht | 260/404.5 |
| 2,764,603 | 9/1956 | Ahlbrecht | 260/404.5 |
| 2,803,656 | 8/1957 | Ahlbrecht et al. | 260/556 |
| 2,809,990 | 10/1957 | Brown | 260/534 |
| 3,147,064 | 9/1964 | Brown et al. | 8/116.2 |
| 3,255,131 | 6/1966 | Ahlbrecht et al. | 260/22 |
| 3,450,755 | 6/1969 | Ahlbrecht | 260/556 |
| 3,505,377 | 4/1970 | Morehouse | 260/448.2 |
| 3,723,512 | 3/1973 | Niederprum et al. | 260/501.15 |
| 3,799,758 | 3/1974 | Franz | 71/86 |
| 3,980,688 | 9/1976 | Litteral et al. | 260/448.8 R |
| 4,000,168 | 12/1976 | Bertocchio et al. | 260/404.5 |
| 4,042,522 | 8/1977 | Falk | 252/8.05 |
| 4,069,158 | 1/1978 | Bertocchio et al. | 252/3 |
| 4,069,244 | 1/1978 | Mueller | 260/501.12 |
| 4,090,967 | 5/1978 | Falk | 252/3 |
| 4,160,776 | 7/1979 | Scardera et al. | 260/448.8 |
| 4,161,590 | 7/1979 | Mueller | 544/159 |
| 4,161,602 | 7/1979 | Mueller | 546/335 |
| 4,226,794 | 10/1980 | Scardera et al. | 556/443 |
| 4,313,847 | 2/1982 | Chasin et al. | 252/356 |
| 4,337,168 | 6/1982 | Scardera et al. | 252/312 |
| 4,405,531 | 9/1983 | Franz | 260/501.12 |
| 4,431,789 | 2/1984 | Okazaki et al. | 528/18 |
| 4,481,365 | 11/1984 | Forster et al. | 556/422 |
| 4,488,896 | 12/1984 | Lamb et al. | 71/92 |
| 4,506,831 | 3/1985 | Ghyczy et al. | 239/10 |
| 4,629,499 | 12/1986 | Felix et al. | 71/100 |
| 4,695,313 | 9/1987 | Bordas et al. | 71/100 |
| 4,840,659 | 6/1989 | Franz | 71/86 |
| 4,902,333 | 2/1990 | Quimby, Jr. | 71/79 |
| 5,043,464 | 8/1991 | Yamamoto | 556/437 |
| 5,104,647 | 4/1992 | Policello | 514/772 |
| 5,147,444 | 9/1992 | Decor et al. | 71/86 |
| 5,187,184 | 2/1993 | Lovell | 514/406 |
| 5,246,936 | 9/1993 | Treacy et al. | 514/256 |
| 5,332,714 | 7/1994 | Albrecht et al. | 504/116 |
| 5,463,180 | 10/1995 | Gednalske et al. | 504/323 |
| 5,489,569 | 2/1996 | Bryant et al. | 504/166 |
| 5,504,054 | 4/1996 | Murphy | 504/116 |
| 5,510,316 | 4/1996 | Charudattan et al. | 504/117 |

(List continued on next page.)

FOREIGN PATENT DOCUMENTS

| | | | |
|---|---|---|---|
| 38389/89 | 5/1991 | Australia | A01N 25/30 |
| 0 394 211 | 10/1990 | European Pat. Off. | A01N 25/14 |
| 0 427 991 | 5/1991 | European Pat. Off. | A01N 25/28 |
| 0 514 769 A1 | 11/1992 | European Pat. Off. | A01N 43/76 |
| 0 517 669 A1 | 12/1992 | European Pat. Off. | A01N 25/28 |
| 0 432 062 A1 | 6/1991 | France | A01N 25/04 |
| 6345604 | 12/1994 | Japan | A01N 25/02 |
| 1122580 | 8/1968 | United Kingdom | C07C 123/00 |
| WO 96/05721 | 2/1996 | WIPO | A01G 7/06 |

OTHER PUBLICATIONS

Ahrens, John F., "Postemergence Herbicides for Apples and Grapes," *Proc. Northeastern Weed Science Society 40th Annual Meeting*, p. 160, 1986.

Baker, Edward A., Hunt, Grace M. and Stevens, Peter J. G., "Studies of Plant Cuticle and Spray Droplet Interactions: a Fresh Approach," *Pesticide Science*, vol. 14, pp. 645–658, 1983.

Balneaves, J. M., Gaskin, R. E. and Zabkiewicz, J. A., "The Effect of Varying Rates of Glyphosate and an Organosilicone Surfactant on the Control of Gorse," *Aspects of Applied Biology*, vol. 122, pp. 531–536, 1993.

Baylis, A. D. and Hart, C. A., "Varying Responses Among Weed Species to Glyphosate–Trimesium in the Presence of an Organosilicone Surfactant," *Proc. Brighton Crop Protection Conference—Weeds*, pp. 1331–1336, 1993.

Bishop, N. G. and Field, R. J., "Improved Performance of Glyphosate in the Full Season Control of Perennial Ryegrass," *Aspects of Applied Biology*, vol. 4, pp. 363–370, 1983.

(List continued on next page.)

*Primary Examiner*—S. Mark Clardy
*Attorney, Agent, or Firm*—James C. Forbes; Arnold, White & Durkee

[57] ABSTRACT

A novel method is provided wherein plants are first treated with an exogenous chemical (e.g., glyphosate herbicide) and then sequentially treated with a liquid accession agent which provides improved biological (e.g., herbicidal) effectiveness such that plants are controlled with lower rates of the applied exogenous chemical (e.g., glyphosate herbicide). Sequential application has been demonstrated to reduce the antagonism to herbicidal effectiveness that can be exhibited when the accession agent is added to a herbicide in a tank mix or simple coformulation. Typical accession agents employed in the disclosed method include a class of surfactants known as superwetting agents, such as certain organosilicone-based and fluorocarbon-based surfactants.

92 Claims, 2 Drawing Sheets

U.S. PATENT DOCUMENTS

| | | |
|---|---|---|
| 5,518,991 | 5/1996 | Fisch . |
| 5,527,760 | 6/1996 | Rensing et al. .......................... 504/100 |
| 5,543,383 | 8/1996 | Parker et al. ............................ 504/116 |
| 5,558,806 | 9/1996 | Policello et al. ........................ 252/355 |
| 5,561,100 | 10/1996 | Hagen et al. ............................ 504/130 |
| 5,571,772 | 11/1996 | Willms et al. ........................... 504/106 |
| 5,580,841 | 12/1996 | Chan et al. .............................. 504/206 |
| 5,821,195 | 10/1998 | Sandbrink et al. ...................... 504/206 |

OTHER PUBLICATIONS

Blumhorst, Michael R. and Kapusta, George, "Mefluidide as an Enhancing Agent for Postmergence Broadleaf Herbicides in Soybeans," *Weed Technology,* vol. 1, No. 2, pp. 149–153, Apr. 1987.

Boerboom, Chris M. and Wyse, Donald L., "Influence of Glyphosate Concentration on Glyphosate Absorption and Translocation in Canada Thistle (*Cirsium arvense*), " *Weed Science,* vol. 36, No. 3, pp. 291–295, May 1988.

Buick, R. D. and Field, R. J., "The Mechanism of Organosilicone Surfactant–Induced Uptake of Amine and Ester Formulations of Triclopyr," Proceedings 1st International Weed Control Congress, Melbourne, vol 2, pp. 103–105, 1992.

Buick, R. D., Field, R. J. and Robson, A. B., "The Effects of Silwet L77 on Triclopyr Absorption," *Proc. 43rd New Zealand Weed and Pest Control Conference,* pp. 174–177, 1990.

Buick, Rosalind D., Buchan, Graeme D. and Field, Roger J., "The Role of Surface Tension of Spreading Droplets in Absorption of a herbicide Formulation via Leaf Stomata," *Pesticide Science,* vol. 38, pp. 227–235, 1993.

Caseley, J. C. and Coupland, D., "Environmental and Plant Factors Affecting Glyphosate Uptake, Movement, and Activity," In *The Herbicide Glyphosate,* ed. E. Grossbard and D. Atkinson, Chapter 7, pp. 92–123, Butterworths, London, 1985.

Coggins, Jr., Charles W., Henning, Gilbert L. and Anthony, Michael F., "Possible Methods to Increase Efficacy of Gibberellic Acid Applied to Navel Orange Trees," In *Adjuvants for Agrochemicals,* ed. C. L. Foy, Chapter 55, pp. 567–572, CRC Press, Boca Raton, Florida, 1992.

Combellack, Joseph H., McShane, A. and Richardson, Robert G., "The Influence of Adjuvants on the Performance of A Glyphosate/2,4–D Mixture," In *Adjuvants for Agrochemicals,* ed. C. L. Foy, Chapter 29, pp. 303–310, CRC Press, Boca Raton, Florida, 1992.

Dastgheib, F., Field, R. J. and Searle, H., "Surfactant Effects on the Uptake of Different Herbicides by Gorse," *Proc. 47th New Zealand Weed and Pest Control Conference,* pp. 392–396, 1994.

de Ruiter, H., Verbeek, M. A. M. and Uffing, A. J. M., "Mode of Action of a Nonionic and a Cationic Surfactant in Relation to Glyphosate," In *Pesticide Fomulations: Innovations and Developments,* ed. B. Cross and H. B. Scher, Chapter 5, pp. 44–55, American Chemical Society, Washington, DC, 1988.

deRuiter, Hans, Meinen, Esther and Verbeek, Monique A. M., "Influence of the Type and Concentration of Surfactant on Glyphosate Absorption; Relevance of Drop Spreading and Drying Time," In *Adjuvants for Agrochemicals,* ed. C. L. Foy, Chapter 8, pp. 109–116, CRC Press, Boca Raton, Florida, 1992.

Field, R. J. and Bishop, N. G., "The Mechanism of Action of Silwet L77$^R$ in Improving the Performance of Glyphosate Applied to Perennial Ryegrass," *Proc. 8th Australian Weeds Conference,* pp. 411–415, 1987.

Field, R. J. and Tisdall, L. J., "The Mechanism of Organosilicone Surfactant–Induced Antagonism of Glyphosate Uptake," *Proc. 9th Australian Weeds Conference,* pp. 332–335, Aug. 6–10, 1990.

Field, Roger J. and Bishop, Nicholas G., "Promotion of Stomatal Infiltration of Glyphosate by an Organosilicone Surfactant Reduces the Critical Rainfall Period," *Pesticide Science,* vol. 24, pp. 55–62, 1988.

Field, Roger J., Dobson, Nicole N. and Tisdall, Lynnore J., "Species–Specific Sensitivity to Organosilicone Surfactant–Enhancementof Glyphosate Uptake," In *Adjuvants for Agrochemicals,* ed. C. L. Foy, Chapter 40, pp. 423–431, CRC Press, Boca Raton, Florida, 1992.

Foloni, L. L., "Adjuvant Effects on Sulphosate and Glyphosate for Control of Red–Rice in Rice," *Proc. Brighton Crop Protection Conference—Weeds,* pp. 743–746, 1995.

Forster, W. A. and Zabkiewicz, J. A., "Effect of an Organosilicone Surfactant on Spray Drop Adhesion and Retention by Pea (*Pisum sativum*) Leaf Surfaces," *Proc. 47th New Zealand Weed and Pest Control Conference,* pp. 387–391, 1994.

Gaskin, R. E. and Kirkwood, R. C., "The Effect of Certain Nonionic Surfactants on the Uptake and Translocation of Herbicides in Bracken (*Pteridium aquilinum*[L.]Kuhn)," In *Adjuvants and Agrochemicals, vol. 1: Mode of Action and Physiological Activity,* ed. P. N. P. Chow, C. A. Grant, A. M. Hinshalwood and E. Simmundsson, Chapter 13, pp. 129–139, CRC Press, Boca Raton, Florida, 1989.

Gaskin, R. E. and Zabkiewicz, J. A., "A Comparison Between Two Commercial Organosilicone Surfactants; Their Effect on the Uptake and Translocation of Glyphosate in Gorse (*Ulex europaeus*)," *Proc. 44th New Zealand Weed and Pest Control Conference,* pp. 109–111, 1991.

Gaskin, R. E. and Zabkiewicz, J. A., "The Effect of Surfactants on the Uptake and Translocation of Glyphosate in Yorkshire Fog," *Proc. 42nd New Zealand Weed and Pest Control Conference,* pp. 128–131, 1989.

Gaskin, Robyn E. and Holloway, Peter J., "Some Physiochemical Factors Influencing Foliar Uptake Enhancement of Glyphosate–mono(isopropylammonium)by Polyoxyethylene Surfactants," *Pesticide Science,* vol. 34, pp. 195–206, 1992.

Gaskin, Robyn E. and Stevens, Peter J. G., "Antagonism of the Foliar Uptake of Glyphosate into Grasses by Organosilicone Surfactants. Part 1: Effects of Plant Species, Formulation, Concentrations and Timing of Application," *Pesticide Science,* vol. 38, pp. 185–192, 1993.

Gaskin, Robyn E. and Stevens, Peter J. G., "Antagonism of the Foliar Uptake of Glyphosate into Grasses by Organosilicone. Part 2: Effects of Surfactant Structure and Glycerol Addition," *Pesticide Science,* vol. 38, pp. 193–200, 1993.

Gaskin, Robyn E. and Zabkiewicz, Jerzy A., "Effect of Plant Age and Adjuvant on the Foliar Penetration and Translocation of Glyphosate in Pampas Grass (*Cortaderia selloana*)," In *Adjuvants for Agrochemicals,* ed. C. L. Foy, Chapter 38, pp. 405–409, CRC Press, Boca Raton, Florida, 1992.

Goddard, E. D. and Padmanabhan, K. P. A., "A Mechanistic Study of the Wetting, Spreading, and Solution Properties of Organosilicone Surfactants," In *Adjuvants for Agrochemicals,* ed. C. L. Foy, Chapter 35, pp. 373–383, CRC Press, Boca Raton, Florida, 1992.

Goudey, J. S., Dale, M. and Hoddinott, J., "The Effects of Oil Spill Chemicals on Transpiration, CO2 Exchange, and Cuticular Structure in *Salix interior,*" *Can. J. Bot.,* vol. 63, pp. 2340–2344, 1985.

Klein, K. D., Wilkowski, S. and Selby, J., "Silane Surfactants—Novel Adjuvants for Agricultural Applications," *Proceedings 4th International Symposium of Adjuvants for Agrochemicals,* pp. 27–31, Oct. 1995.

Kudsk, P. and Mathiassen, S. K., "Effects of Broadleaf Herbicides on Imazamethabenz–methyl Performance on Wild Oat (*Avena fatua* L.)," *Weed Research,* vol. 34, pp. 251–263, 1994.

Leung, John W., "A Fluorometric Method to Determine Rainfastness, Volatilization and Photostability of Glyphosate from Glass Slides, After Application of Vision® with Two Adjuvants," *J. Environ. Sci. Health,* vol. B29, No. 2, pp. 341–363, 1994.

Osi Specialties, Inc., "Bibliography of Silwet® Organosilicone Surfactants as Agricultural Adjuvants," Mar. 1996.

Osi Specialties, Inc., "Silwet® Surfactants," pp. 1–20, Jun. 1994.

Photographs of Truck–Mounted Double Boom Spray Apparatus, observed in Trenton, Missouri May 1997.

Policello, George A., Stevens, Peter J. G., Forster, W. Alison and Murphy, Gerald J., "The Influence of pH on the Performance of Organosilicone Surfactants," In *Pesticide Formulation and Application Systems:* 14th vol., pp. 313–317, ASTM Spec. Tech. Publ., 1995.

Qureshi, F. A. and Vanden Born, W. H., "Spray Droplet Distribution and Herbicide Uptake in Sequential Applications of Diclofop–methyl and MCPA for Weed Control in Barley," *Can. J. Plant Sci.,* vol. 89, pp. 93–98, Jan. 1979.

Roggenbuck, Frank C., Burow, Richard F. and Penner, Donald, "Relationship of Leaf Position to Herbicide Absorption and Organosilicone Adjuvant Efficacy," *Weed Technology,* vol. 8, No. 3, pp. 582–585, Jul.–Sep. 1994.

Roggenbuck, Frank C., Penner, Donald, Burow, Richard F. and Thomas, Bryan, "Study of the Enhancement of Herbicide Activity and Rainfastness by an Organosilicone Adjuvant Utilizing Radiolabeled Herbicide and Adjuvant," *Pesticide Science,* vol. 37, pp. 121–125, 1993.

Rohitha, B. H., Gaskin, Hartley, R. E., T. and Karl, A. K., "Evaluation of Silwet L–77 for Postharvest Disinfestation of Thrip in Asparagus," *Proc. 45th New Zealand Weed and Pest Control Conference,* pp. 17–20, 1992.

Schönherr, Jörg and Bauer, Hubert, "Analysis of Effects of Surfactants on Permeability of Plant Cuticles," In *Adjuvants and Agrochemicals, vol. 1: Mode of Action and Physiological Activity,* ed. P. N. P. Chow, C. A. Grant, A. M. Hinshalwood and E. Simmundsson, Chapter 2, pp. 17–35, CRC Press, Boca Raton, Florida, 1989.

Sherrick, Stewart L., Holt, Harvey A. and Hess, F. Dan, "Absorption and Translocation of MON 0818 Adjuvant in Field Bindweed (*Convolvulus arvensis*)," *Weed Science,* vol. 34, No. 6, pp. 817–823, Nov. 1986.

Steurbaut, Walter, Megahed, Van Roey, H. S., G., Melkebeke, T. and Dejonckheere, W., "Influence of Surfactant–Oil Combinations on the Activity of Foliar–Applied Fungicides," In *Adjuvants for Agrochemicals,* ed. C. L. Foy, Chapter 61, pp. 623–635, CRC Press, Boca Raton, Florida, 1992.

Stevens, P. J. G. and Zabkiewicz, J. A., "New Formulation Technology—Silwet® Organosilicone Surfactants Have Physical and Physiological Properties which Enhance the Performance of Sprays," *Proc. 9th Australian Weeds Conference,* pp. 327–331, Ayg. 6–10, 1990.

Stevens, P. J. G., Caseley, J. C. and Bond, C., "Organosilicones as Adjuvants for Graminicides," *Proc. Brighton Crop Protection Conference—Weeds,* pp. 757–762, 1995.

Stevens, P. J. G., Walker, J. T. S., Shaw, P. W. and Suckling, D. M., "Organosilicone Surfactants: Tools for Horticultural Crop Protection," *Proc. Brighton Crop Protection Conference—Pests and Diseases,* pp. 755–760, 1994.

Stevens, Peter J. G., "Organosilicone Surfactants as Adjuvants for Agrochemicals," *Pesticide Science,* vol. 38, pp. 103–122, 1993.

Stevens, Peter J. G., Baker, Edward A. and Anderson, Nicholas H., "Factors Affecting the Foliar Absorption and Redistribution of Pesticides. 2. Physiochemical Properties of the Active Ingredient and the Role of Surfactant," *Pesticide Science,* vol. 24, pp. 31–53, 1988.

Stevens, Peter J. G., Gaskin, Robyn E., Hong, Sung–Ok and Zabkiewicz, Jerzy A., "Pathways and Mechanisms of Foliar Uptake as Influenced by Surfactants," In *Adjuvants for Agrochemicals,* ed. C. L. Foy, Chapter 36, pp. 385–398, CRC Press, Boca Raton, Florida, 1992.

Stevens, Peter J. G., Gaskin, Robyn E., Hong, Sung–Ok and Zabkiewicz, Jerzy A., "Contributions of Stomatal Infiltration and Cuticular Penetration to Enhancements of Foliar Uptake by Surfactants," *Pesticide Science,* vol. 33, pp. 371–382, 1991.

Stevens, Peter J. G., Zabkiewicz, Jerzy A., Barran, Jonathan H., Klitscher, K. R. and Ede, Fiona "Spray Formulation with Silwet® Organosilicone Surfactants," In *Adjuvants for Agrochemicals,* ed. C. L. Foy, Chapter 37, pp. 399–403, CRC Press, Boca Raton, Florida, 1992.

Sundaram, A. et al. "Effect of Glycerol on Spreading and Drying of Vision(R) Droplets containing Silwet(R) L–77: Relevance to Rainfastness and Herbicidal Activity of Glyphosate on Trembling Aspen (*Populus tremuloides* Michx.)" *Journal of Environmental Science and Health,* vol. B31(4), pp. 901–912 (1996).

Sundaram, Alam, "Influence of Two Polymeric Adjuvants on Bioavailability of Glyphosate in Vision® Formulation: Relevance to Rainwashing of Deposits from Foliar Surfaces," In *Adjuvants and Agrochemicals, vol. 1: Mode of Action and Physiological Activity,* ed. P. N. P. Chow, C. A. Grant, A. M. Hinshalwood and E. Simmundsson, Chapter 5, pp. 77–85, CRC Press, Boca Raton, Florida, 1989.

Tan, Siyuan and Crabtree, Garvin D., "Effects of Nonionic Surfactants on Cuticular Sorption and Penetration of 2,4–Dichlorophenoxy Acetic Acid," *Pesticide Science,* vol. 35, pp. 299–303, 1992.

Turner, D. J., "Effects on Glyphosate Performance of Formulation, Additives and Mixing with Other Herbicides," In *The Herbicide Glyphosate,* ed. E. Grossbard and D. Atkinson, Chapter 15, pp. 221–240, Butterworths, London, 1985.

Wyrill III, J. B. and Burnside, O. C., "Glyphosate Toxicity to Common Milkweed and Hemp Dogbane as Influenced by Surfactants," *Weed Science,* vol. 25, No. 3, pp. 275–287, May 1977.

Yokomi, R. K., Jimenez, D. R., Osborne, L. S. and Shapiro, J. P., "Comparison of Silverleaf Whitefly Induced and Chlormequat Chloride Induced Leaf Silvering in *Cucurbita pepo*," *Plant Disease*, vol. 79, No. 9, pp. 950–955, Sep. 1995.

Zabkiewicz, J. A. and Gaskin, R. E., "Effect of Adjuvants on Uptake and Translocation of Glyphosate in Gorse (*Ulex europaeus* L.)," In *Adjuvants and Agrochemicals, vol 1: Mode of Action and Physiological Activity*, ed. P. N. P. Chow, C. A. Grant, A. M. Hinshalwood and E. Simmundsson, Chapter 14, pp. 141–149, CRC Press, Boca Raton, Florida, 1989.

Zabkiewicz, J. A., Coupland, D. and Ede, F., "Effects of Surfactants on Droplet Spreading and Drying Rates in Relation to Foliar Uptake," In *Pesticide Formulations: Innovations and Developments*, ed. B. Cross and H. B. Scher, Chapter 7, pp. 77–89, American Chemical Society, Washington DC, 1988.

Zabkiewicz, Jerzy A., Stevens, Peter J. G., Forster, W. Allison and Steele, Kevin D., "Foliar Uptake of Organosilicone Surfactant Oligomers into Bean Leaf in the Presence and Absence of Glyphosate," *Pesticide Science*, vol. 38, pp. 135–143, 1993.

SEQUENTIAL APPLICATION METHOD FOR TREATING PLANTS WITH EXOGENOUS CHEMICALS

This application claims the benefit of provisional application Ser. No. 60/024,081 filed Aug. 16, 1996, provisional application Ser. No. 60/033,489 filed Dec. 20, 1996, and provisional application Ser. No. 60/049,096 filed Jun. 9, 1997.

This invention relates to a method of enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like. Specifically, the present invention relates to a method that uses an agent of a class referred to herein as "accession agents" to enhance the biological effectiveness of an exogenous chemical in or on a plant through sequential application of an accession agent after application of a composition comprising an exogenous chemical. This method is an improvement over methods known in the art. It has been found that sequential application of an accession agent (rather than application concurrent with an exogenous chemical, as for example, in a tank mix or simple coformulation of the exogenous chemical and the accession agent) provides unique redistribution of pre-applied exogenous chemical compositions on and in the foliar parts of plants. Such sequential treatment has been found to enhance the biological effectiveness of exogenous chemicals on many species, with minimal antagonism on other species.

This invention especially relates to a method of enhancing the herbicidal effectiveness of herbicidal compositions, in particular compositions comprising N-phosphonomethylglycine or a herbicidal derivative thereof, most particularly a salt of N-phosphonomethylglycine. Unless otherwise indicated, the word "glyphosate" as used herein encompasses N-phosphonomethylglycine and its agriculturally acceptable salts. Specifically, the present invention relates to the use of an accession agent to enhance the herbicidal effectiveness of glyphosate on a variety of plant species, but without the antagonistic effect such agents otherwise frequently exhibit when used with glyphosate on certain plant species by methods previously described in the art. It has been found that sequential application of an accession agent (rather than application concurrent with glyphosate as for example in a tank mix) provides unique enhancement of the herbicidal effectiveness of pre-applied glyphosate compositions on and in the foliar parts of plants. Such sequential treatment has been found to enhance the herbicidal effectiveness of glyphosate and its herbicidal derivatives on many species, with minimal antagonism on other species.

BACKGROUND OF THE INVENTION

The agricultural industry is under pressure to reduce pesticide, particularly herbicide, usage. This is evidenced by symposia on the subject, such as that held in 1993 by the Weed Science Society of America and documented in *Weed Technology* 1994, Vol. 8, pp. 331–86. Reduced use rates are desirable both environmentally and economically, in that the treatment cost per unit area decreases. In the case of exogenous chemicals applied to foliage of a plant, herein referred to as "foliar-applied" exogenous chemicals, enhanced delivery efficiency can also improve the ability or tendency of an exogenous chemical such as a pesticide to retain its biological effectiveness when the treated plant is exposed to natural or artificial rain or overhead irrigation within a short period (such as a few minutes to a few hours) after application. This property is generally referred to as "rainfastness." In many cases, enhanced delivery efficiency leads to earlier manifestation of outward signs or symptoms that the applied exogenous chemical is exerting its desired effect in or on a treated plant, on parasites or pathogens of the plant, or on organisms, particularly invertebrate animals such as insects, feeding on non-woody or woody parts of the plant.

Exogenous chemicals, especially foliar-applied exogenous chemicals including foliar-applied herbicides, are commonly formulated with surfactants or wetting agents, so that when water is added, the resulting sprayable composition is more easily and effectively retained on the foliage (e.g., the leaves or other photosynthesizing organs) of plants. Surfactants can also bring other benefits, including improved contact of spray droplets with a waxy leaf surface and, in some cases, improved penetration of the accompanying exogenous chemical into the interior of leaves. Through these and perhaps other effects, surfactants have long been known to increase the biological effectiveness of herbicide compositions, or other compositions of exogenous chemicals, when added to or included in such compositions. Thus, for example, the herbicide glyphosate is typically formulated with surfactants such as polyoxyalkylene or polyglycoside surfactants. More particularly, certain commercial formulations of glyphosate herbicide marketed under the trademark ROUNDUP® have been formulated with a polyoxyalkylene alkylamine, in particular polyoxyethylene (15) tallowamine.

European Patent No. 0 394 21 1 discloses solid granular formulations of glyphosate containing organosilicone wetting agents or fluoro-organic wetting agents. Some commercial formulations of glyphosate herbicide have been formulated with such surfactants, including a particular group of polyoxyalkylene polysiloxane surfactants exemplified by the commercial organosilicone surfactant Silwet L-77, which has been reported to affect the foliar absorption of glyphosate by plants. A number of studies relating to the use of Silwet L-77 with glyphosate and other herbicides have been published. It should be noted that surfactants have been combined with glyphosate or other exogenous chemicals either in a concentrate liquid or dry composition (herein referred to as a "simple coformulation") containing an intimate admixture (i.e. not partitioned in separate phases of the concentrate composition) of both exogenous chemical and surfactant, or in a diluted mixture that is prepared from separate exogenous chemical (e.g. glyphosate) and surfactant compositions immediately prior to use in the field (herein referred to as a "tank mix"). Simple coformulations and tank mixes, and methods for applying them, are herein distinguished from the "sequential application" methods that are the subject of this invention.

A foliar uptake study of glyphosate herbicide, wherein an organosilicone surfactant (Silwet L-77) was applied together with glyphosate to simulate a tank mix, is reported by Field & Bishop, *Pestic. Sci.*, 1988, Vol. 24, pp. 55–62. When these tank mix compositions were applied to the adaxial leaf surfaces of perennial ryegrass plants, complete surface wetting was observed at Silwet L-77 concentrations of 0.1–0.5% by volume. Through timed experiments wherein radio-labeled glyphosate was applied to the leaves followed by washing of the leaves, it was concluded that use of Silwet L-77 provides a reduced critical rain-free period after application because of an enhanced rate of glyphosate uptake. Rapid uptake was observed into stomata of the plants treated with the tank mix. Visual confirmation of stomatal uptake was confirmed by dye studies. However, these workers found Silwet L-77 antagonistic to glyphosate uptake over a 48 hour period. Herbicidal effects were reported in terms of tiller regrowth (expressed as percentage of tiller number at time of glyphosate application). Stevens et al, *Pestic. Sci.,* 1991, Vol. 33, pp. 371–82, note an enhancement of herbicide uptake over a 0–6 hour period for tank mixes of glyphosate and Silwet L-77.

Another study of the effects of Silwet L-77 upon the foliar uptake of glyphosate herbicide is reported in an article by Gaskin & Stevens, *Pestic. Sci.,* 1993, Vol. 38, pp. 185–92. In this study, radio-labeled glyphosate (specifically the isopropylammonium salt of glyphosate) was utilized to determine the uptake of herbicide in wheat plants. The authors measured the foliar uptake when Silwet L-77 was applied before (pretreatment), during (i.e., in a tank mix), and after (posttreatment) application of the glyphosate herbicide to the plants. Pretreatment of the plants with Silwet L-77 reduced the uptake of glyphosate by the foliage over the course of the study and generally failed to increase even the initial rate of uptake of glyphosate into the plant. Both simultaneous (i.e., tank mix) and post-treatment of the plants with Silwet L-77 at 4 and 8 hours after herbicide application were found to increase the initial rate of uptake of glyphosate; but these workers concluded that "the initial enhancements provided by both simultaneous and sequential application of Silwet L-77 slowed down rapidly thereafter in all treatments." The article reports no measurements of herbicidal effectiveness for any species. The article states that Silwet L-77 may be beneficial as a spray (i.e., a tank mix) adjuvant if rain falls after its application but not in the absence of rain. Further study of the antagonism of glyphosate uptake by Silwet L-77 is reported by Gaskin & Stevens, *Pestic. Sci.,* 1993, Vol. 38, pp. 193–200.

An extensive review of 160 citations relating to the use of organosilicone surfactants as adjuvants for agrochemicals was provided by Stevens, *Pestic. Sci.,* 1993, Vol. 38, pp. 103–22. Stevens reviews work reporting the use of organosilicone surfactants in formulations of herbicides, foliar nutrients, growth regulators, insecticides, and fungicides. Although Stevens discusses extensively work relating to coformulations or tank mixes of organosilicones with, e.g., herbicides, there is no discussion of work relating to sequential application of these materials.

The effects of Silwet L-77 on the foliar uptake of other herbicides has been investigated. Buick et al., *Pestic. Sci.,* 1993, Vol. 38, pp. 227–35, report increases in uptake of triclopyr triethylamine in field bean over time periods of one hour and six hours by inclusion of Silwet L-77 in a simulated tank mix. These workers posit infiltration of foliar stomata to explain this effect. Other workers have questioned the significance of stomatal infiltration to the operation of organosilicone surfactants. Roggenbuck et al., *Weed Tech.,* 1994, Vol. 8, pp. 582–85, conclude there is no relationship between the number of stomata covered and the degree to which herbicide uptake is influenced by addition of Sylgard 309, an organosilicone surfactant.

Antagonistic effects with respect to the herbicidal effectiveness or uptake of glyphosate have been reported in the following species for tank mixes containing Silwet L-77:

colonial bentgrass (*Agrostis tenuis*)
downy brome (*Bromus tectorum*)
orchardgrass (*Dactylis glomerata*)
crabgrass (Digitaria sp.)
barnyardgrass (*Echinochloa crus-galli*)
goosegrass (*Eleusine indica*)
quackgrass (*Elymus repens*)
wild poinsettia (*Euphorbia heterophylla*)
common velvetgrass (*Holcus lanatus*)
dallisgrass (*Paspalum dilatatum*)
prostrate knotweed (*Polygonum aviculare*)
green foxtail (*Setaria viridis*)
johnsongrass (*Sorghum halepense*)
wheat (*Triticum aestivum*)
cocklebur (*Xanthium pennsylvanicum*)

See Gaskin & Stevens, *Pestic. Sci.,* 1993, Vol. 38, pp. 185–92; Baylis & Hart, *Brighton Crop Protection Conference,* 1993, pp. 1331–36; Field & Tisdall, *Ninth Australian Weed Conference,* 1990, pp. 332–35; Australian Patent Publication No. 38389/89.

Blumrhorst & Kapusta, *Weed Technolog,* 1987, Vol.1, pp. 149–53, have investigated sequential and tank mix applications of plant growth regulators (specifically, mefluidide) with herbicides. A study of the sequential application of herbicide materials is reported by Qureshi & VandenBorn, *Canadian Journal of Plant Science,* 1979, Vol. 59, pp. 93–98.

Because surfactants can enhance herbicidal effects when coformulated with or added in a tank mix to herbicidal compositions, numerous workers have studied the effects of various surfactants. One extensive study was conducted by Wyrill & Burnside, *Weed Science,* 1977, Vol. 25, pp. 285–87. These investigators concluded that "the effectiveness of surfactant combinations was quite variable and difficult to predict. Therefore, the indiscriminate addition of surfactants into glyphosate spray mixtures which already contain a surfactant should be avoided." However, this study did not include any organosilicone or fluoro-organic surfactant treatment. Another study of surfactant effects on glyphosate is set forth in Gaskin & Kirkwood, *Adjuvants and Agrochemicals,* 1989, Vol. 1, Chapter 13, pp. 129–39. In this study, surfactants (including Silwet L-77) are compared and rated for selected herbicides, based upon plant uptake and translocation measurements. Silwet L-77 was shown to be superior to two non-organosilicone surfactants for enhancing glyphosate uptake and translocation in bracken when added to the glyphosate spray solution as a tank mix.

So many studies are reported in this area that OSi Specialties (a unit of Witco Corporation) has published a *Bibliography of Silwet Organosilicone Surfactants As Agricultural Adjuvants* (1996), which is indexed for computer searching. This bibliography lists hundreds of published studies of commercial organosilicone surfactants in agricultural applications. This bibliography is available to the public through the publisher's office in Tarrytown, N.Y.

Bishop & Field, *Aspects of Applied Biology,* 1983, Vol. 4, pp. 363–70, report that Silwet L-77 in tank mix enhanced the performance of glyphosate in field trials on perennial ryegrass. "Spectacular" leaf wetting was observed for tank mixes including 0.5% by volume Silwet L-77, indicating pronounced spreading of the herbicide over the foliar portions of the plant. Stevens et al., *Pestic. Sci.,* 1991, Vol. 33, pp. 371–82, report that in vicia bean leaves, stomatal infiltration of Silwet L-77 is antagonized by the surfactant coformulant in ROUNDUP® herbicide. Baylis & Hart, *Brighton Crop Protection Conference,* 1993, pp. 1331–36, have concluded that the effect of Silwet L-77 in tank mix on the herbicidal efficacy of glyphosate-trimesium (the trimethylsulfonium salt of glyphosate) varies with plant species, and could not be explained simply by stomatal infiltration.

Many have investigated the possible mechanisms of herbicide antagonism by Silwet L-77 and, therefore, the means to avoid it. As used herein, "antagonism" refers to a decrease in biological (such as herbicidal) effectiveness of an exogenous chemical (such as a herbicide) when a material (such as Silwet L-77) is used in combination with the exogenous chemical; although it has been used in some of the literature cited herein to refer to a decrease in uptake or translocation. Reduction of antagonism is believed to be one of the means by which the sequential application method of this invention improves the result obtained through tank mixes or coformulations of surfactants with exogenous chemicals.

Australian Patent Application No. 38389/89 reports the use of tank mixed formulations of glyphosate and Silwet L-77, in combination with a humectant such as glycerin. An uptake investigation of similar formulations is reported by Field & Tisdall, *Ninth Australian Weed Conference,* 1990, pp. 332–35. Glycerin was claimed to promote the uptake of glyphosate from formulations containing Silwet L-77. In this study, paspalum leaves were treated with formulations containing Silwet L-77, with and without glycerin. Pretreatment of the paspalum leaf surfaces with Silwet L-77 two hours prior to application of glyphosate stimulated uptake. Silwet L-77 tank mixed with glyphosate did not. These investigators stated that "glycerin does not appear to have a pronounced humectant effect and it is concluded that antagonism and its alleviation by glycerin involves specific leaf surface - solution interactions that are clearly species specific." They concluded that no stomatal infiltration occurred even at Silwet L-77 concentrations as high as 0.5% by volume.

From the numerous publications on the subject of formulating exogenous chemicals such as glyphosate herbicide with various surfactants, particularly organosilicone surfactants and others that can induce stomatal infiltration, it must be concluded that the effects observed vary with the plant species, exogenous chemical, and surfactant. Tank mixed formulations containing Silwet L-77 (or other surfactants) can yield improved results on some species, but frequently antagonize the biological effectiveness for others. In the case of herbicides, this provides a disincentive to use surfactants like Silwet L-77, because multiple weed species are typically treated in the same field and the surfactant is likely to prove antagonistic for at least some of the weed species present. Similar disincentives hold for other classes of exogenous chemicals.

The problem addressed by the present invention can be stated in its broadest sense as follows. Significant benefit in the efficiency of delivery to the interior of a plant, and therefore in the ultimate biological effectiveness in the plant, of an exogenous chemical can often be obtained, as shown in the art, by adding a stomatal infiltrant such as an organosilicone surfactant in tank mix or simple coformulation to the exogenous chemical. However, this benefit is offset by a risk that the stomatal infiltrant will antagonize, rather than enhance, the biological effectiveness of the exogenous chemical. The occurrence of such antagonism is largely unpredictable. A method that consistently reduced such antagonism whenever it occurred, or that substantially removed the risk of antagonism, while still offering the benefit of enhanced delivery sought from the stomatal infiltrant, would be a great advance in the art.

SUMMARY OF THE INVENTION

A process that enhances the biological effectiveness of exogenous chemicals, such as herbicides, in plants has been discovered. This process comprises sequentially (1) applying a biologically effective amount of an exogenous chemical composition to foliage of a plant, followed by (2) applying to at least a part of the same foliage an accession agent in an amount effective to provide stomatal infiltration of the accession agent from the surface of the foliage. It has been discovered that for a spectrum of plant species, sequential application of these materials is superior to application as a tank mix or simple coformulation in the biological effectiveness exhibited. This improved effectiveness in many cases results from a reduction or elimination of antagonism by the accession agent to the biological effectiveness of the exogenous chemical by comparison with the level of antagonism exhibited when the accession agent is applied in a tank mix or simple coformulation with the exogenous chemical.

The term "accession agent" as used herein means a liquid agent which has the property that it infiltrates microscopic pores in a hydrophobic surface, and which, when applied to foliage of a plant after application of an exogenous chemical to at least a part of the same foliage, provides reduced antagonism to biological effectiveness of the exogenous chemical than is obtained by application of the same liquid agent in mixture with the exogenous chemical.

The process that has been discovered dramatically reduces antagonism by accession agents to the herbicidal effectiveness of glyphosate compositions. Thus, this process more particularly comprises sequentially (1) applying a herbicidally effective amount of a glyphosate composition to foliage of a plant, followed by (2) applying to at least a part of the same foliage an accession agent in an amount effective to provide stomatal infiltration of the accession agent from the surface of the foliage. Preferably the accession agent is applied over the whole area of foliage previously treated with the exogenous chemical. This sequential application yields a dramatic and unexpected result, in that it reduces or eliminates antagonism to herbicidal effectiveness exhibited when the to glyphosate and accession agent are premixed and applied in admixture (i.e., in the standard "tank mix" processes). It has been discovered that for a spectrum of plant species, sequential application of these materials provides superior overall herbicidal effectiveness to application of the same materials in a tank mix. For those plant species in the spectrum on which tank-mixed glyphosate and accession agent are antagonistic, the antagonism is generally reduced and often eliminated. For those plant species in the spectrum on which the tank-mixed glyphosate and accession agent are not antagonistic, sequential application of these materials produces a herbicidal effectiveness that is generally not significantly inferior to that obtained with the corresponding tank mix and is sometimes superior to that obtained with the tank mix.

Accordingly, one aspect of the invention concerns a process comprising the sequential steps of (a) contacting foliage of a plant with a biologically effective amount of an exogenous chemical, and (b) thereafter contacting at least a part of the same foliage with an accession agent, whereby antagonism to biological effectiveness of the exogenous chemical that would result from contacting the plant with a tank mix or diluted simple coformulation of the exogenous chemical and the accession agent is substantially reduced, for example to an extent that the biological effectiveness is visibly better than that of the corresponding tank mix or simple coformulation.

Another aspect of the invention concerns a herbicidal process comprising the sequential steps of (a) contacting foliage of a plant with a herbicidally effective amount of a herbicide, for example N-phosphonomethylglycine or a herbicidal derivative thereof, and (b) thereafter contacting the same foliage with an accession agent, whereby antagonism to herbicidal effectiveness that would result from contacting the plant with a tank mix or diluted simple coformulation of the herbicide and the accession agent is substantially reduced, for example to an extent that the herbicidal effectiveness is visibly better than that of the corresponding tank mix or simple coformulation. Preferably, the sequential application method reduces antagonism by at least 30% (e.g., if the herbicide sprayed alone provides herbicidal effectiveness to the degree of 90% plant inhibition, and a tank mix of the herbicide with the accession agent provides herbicidal effectiveness to the degree of 30% plant inhibition, the sequential application method preferably produces herbicidal effectiveness to the degree of about 48% or greater plant inhibition). Put another way, if plant inhibition with the herbicide alone is x % and that with a tank mix of herbicide and accession agent is y %, and if y<x, then sequential application of herbicide followed by accession agent preferably produces a plant inhibition greater than or equal to about (y+0.3(x−y))%. Most preferably antagonism is completely eliminated. In some instances, the herbicidal control from sequential application is greater than that produced by the herbicide alone.

The invention, as it pertains to glyphosate or any other foliar-applied herbicide, can also be generally described as a method for enhancing the herbicidal effectiveness of a herbicide for a plurality of plant species in a field. Such a method comprises the steps of (a) applying to foliage of the plurality of plant species in the field a herbicidally effective amount of a herbicide, for example N-phosphonomethylglycine or a herbicidal derivative thereof, and (b) thereafter applying to the same foliage an accession agent, whereby the herbicidal effectiveness of the herbicide for at least one of the plurality of plant species is enhanced by at least about 5 percentage points of herbicidal inhibition (e.g., from 80% to 85% herbicidal inhibition), preferably by at least about 10 percentage points.

In addition, the invention as it pertains particularly to glyphosate herbicide, can be generally described as a method for reducing the antagonism of an accession agent to the herbicidal effectiveness of a composition comprising N-phosphonomethylglycine or a herbicidal derivative thereof. Such a method comprises the steps of (a) applying a herbicidally effective amount of the composition to foliage of a plant of a species on which the accession agent is sometimes antagonistic to the herbicidal effectiveness of the composition when tank mixed or coformulated therewith and (b) thereafter applying the accession agent to the same foliage, whereby the herbicidal effectiveness of the composition is substantially preserved (e.g., reduction in herbicidal inhibition is no greater than about 10 percentage points by comparison with the composition in the absence of the accession agent) or enhanced.

Further, the invention, as it pertains to glyphosate herbicide, can also be generally described as a method for enhancing the yield of a field crop. Such a method comprises the steps of (a) planting a crop in a field, (b) substantially freeing an area of the field of a weed species (e.g., achieving herbicidal inhibition of at least about 85% for that weed species across the entire area) that would otherwise diminish the yield of the crop, step (b) being accomplished by (i) applying to foliage of the weed species a herbicidally effective amount of a herbicidal composition comprising N-phosphonomethylglycine or a herbicidal derivative thereof and (ii) thereafter applying to the same foliage an accession agent, whereby antagonism to herbicidal effectiveness that would be exhibited by application of a tank mix or diluted simple coformulation of the herbicidal composition and the accession agent is substantially reduced (as described above), (c) allowing the crop to mature, and (d) harvesting the crop. In this method of enhancing the yield of a field crop, the order of the above steps (a) and (b) can be altered, in which case a field for planting a crop is selected and, before the crop is planted in the field, an area of the field is substantially freed of a weed species that would otherwise diminish the yield of the crop.

Another embodiment of the invention is a method of applying an exogenous chemical to a plant, comprising sequentially the steps of (a) contacting foliage of the plant with a biologically effective amount of an exogenous chemical composition, and (b) thereafter contacting at least a part of the same foliage of the plant with an aqueous solution or dispersion of a sulfonylamino compound having the formula

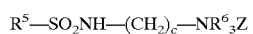

where $R^5$ is alkyl having from about 6 to about 20 carbon atoms and optionally being fluorinated, c is 1–4, $R^6$ groups are independently $C_{1-4}$ alkyl and Z is an agriculturally acceptable counterion, with hydroxide, halide, sulfate, phosphate and acetate being suitable examples. $R^5$ unless perfluorinated preferably has from about 12 to about 18 carbon atoms. $R^5$ is preferably perfluorinated, in which case it preferably has from about 6 to about 12 carbon atoms. Preferably c is 3. $R^6$ groups are preferably methyl.

Sequential application of the exogenous chemical composition followed by the composition containing the sulfonylamino compound provides enhanced performance of the exogenous chemical, as compared to applying the exogenous chemical composition to the foliage of the plant without step (b).

Another embodiment of the invention is a method of applying an exogenous chemical to a plant, comprising contacting foliage of the plant with an aqueous composition comprising a biologically effective amount of an exogenous chemical composition and a sulfonylamino compound having the formula

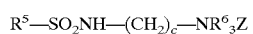

where $R^5$, $R^6$, c and Z are as specified above. The aqueous composition may be prepared on site as a tank mix, or by dilution, dispersion or dissolution in water of a coformulation of the exogenous chemical substance and the sulfonylamino compound.

Another embodiment of the invention is an exogenous chemical composition that comprises (a) an exogenous chemical, and (b) a sulfonylamino compound having the formula

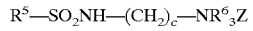

where $R^5$, $R^6$, c, and Z are as specified above. The composition can optionally further comprise a diluent such as water. This composition can take the form of, for example, a dry composition, a liquid concentrate, or a dilute spray solution. This composition can be applied to the foliage of a plant and will provide enhanced performance of the exogenous chemical, as compared to applying the exogenous chemical to the foliage of the plant without the sulfonylamino compound.

Especially preferred sulfonylamino compounds for use in the above-described methods and composition are 3-(heptadecafluorooctyl)sulfonyl)amino)-N,N,N-trimethyl-1-propaminium iodide, available for example as Fluorad FC-135, and the corresponding chloride, available for example as Fluorad FC-754, both from 3M Co.

DESCRIPTION OF ILLUSTRATIVE EMBODIMENTS

Figure 1:
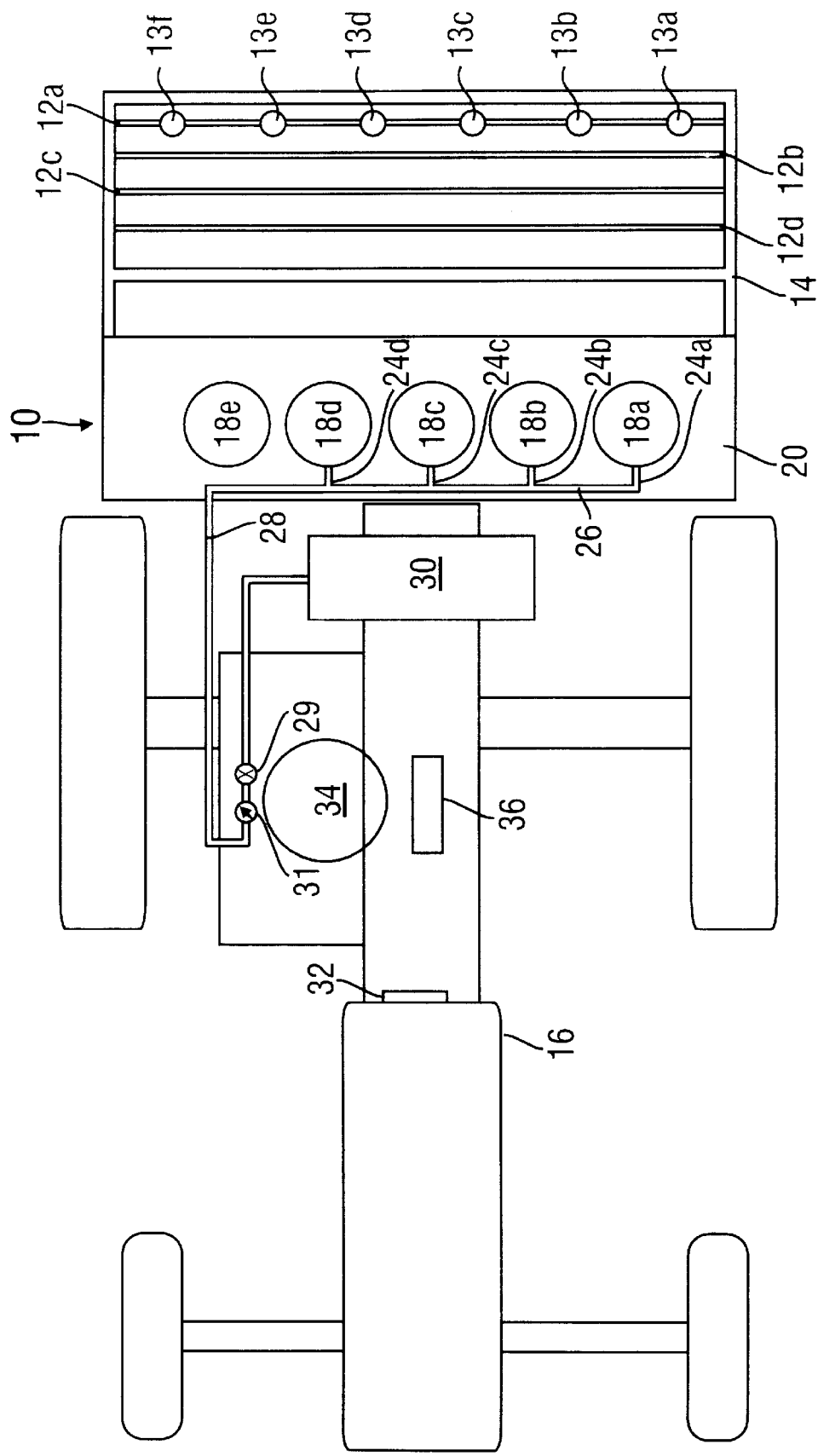
FIG. 1 is a plan view of a tractor having mounted on it spraying apparatus that can be used in the method of the present invention.

The following sets forth in detail the novel process of the present invention, wherein the sequential application of a suitable accession agent, following the application of an exogenous chemical, results in better biological effectiveness of the exogenous chemical than is obtained with conventional tank mix applications, principally through reduction of antagonism. In the case of glyphosate herbicides, the following sets forth in detail the novel method of the present invention, wherein the sequential application of a suitable accession agent, following application of glyphosate, reduces or eliminates the antagonism to herbicidal effectiveness of the glyphosate obtained with conventional tank mix applications.

Exogenous Chemicals

Examples of exogenous chemical substances include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. A preferred group of exogenous chemicals are those that are normally applied post-emergence to the foliage of plants, i.e. foliar-applied exogenous chemicals.

Some exogenous chemicals useful in the present invention are water soluble, for example salts that comprise biologically active ions, and also comprise counterions, which may be biologically inert or relatively inactive. A particularly preferred group of these water soluble exogenous chemicals or their biologically active ions or moieties are systemic in plants. Especially preferred among these are herbicides, plant growth regulators and nematicides, particularly those that have a molecular weight, excluding counterions, of less than about 300. More especially preferred among these are exogenous chemical compounds having one or more functional groups selected from amine, carboxylate, phosphonate and phosphinate groups.

Among such compounds, an even more preferred group are herbicidal or plant growth regulating exogenous chemical compounds having at least one of each of amine, carboxylate, and either phosphonate or phosphinate functional groups. Salts of N-phosphonomethylglycine are examples of this group of exogenous chemicals. A further example is glufosinate-ammonium (ammonium DL-homoalanin-4-yl (methyl) phosphinate).

Another preferred group of exogenous chemicals which can be applied by the method of the invention are nematicides such as those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

An example of a suitable insecticide is malathion.

Exogenous chemicals which can usefully be applied by the method of the present invention are normally, but not exclusively, those which have a beneficial effect on the overall growth or yield of desired plants such as crops, or a deleterious or lethal effect on the growth of undesirable plants such as weeds. Exogenous chemicals for which the method of the present invention can preferably be used are pesticides, plant growth regulators, and gametocides. The method of the present invention is particularly useful for herbicides, especially those that are normally applied post-emergence to the foliage of unwanted vegetation.

Herbicides which can be applied by the method of the present invention include but are not limited to any listed in standard reference works such as the "Herbicide Handbook," *Weed Science Society of America,* 1994, 7th ed. Illustratively these herbicides include acetanilides such as acetochlor, alachlor and metolachlor, aminotriazole, asulam, bentazon, bialaphos, bipyridyls such as paraquat, bromacil, cyclohexenones such as clethodim and sethoxydim, dicamba, diflufenican, dinitroanilines such as pendimethalin, diphenylethers such as acifluorfen, fomesafen and oxyfluorfen, fosamine, flupoxam, glufosinate, glyphosate, hydroxybenzonitriles such as bromoxynil, imidazolinones such as imazaquin and imazethapyr, isoxaben, norflurazon, phenoxies such as 2,4-D, phenoxypropionates such as diclofop, fluazifop and quizalofop, picloram, propanil, substituted ureas such as fluometuron and isoproturon, sulfonylureas such as chlorimuron, chlorsulfuron, halosulfuron, metsulfuron, primisulfuron, sulfometuron and sulfosulfuron, thiocarbamates such as triallate, triazines such as atrazine and metribuzin, and triclopyr. Not all of these herbicides exhibit antagonism with all accession agents, but where antagonism is exhibited, the method of the present invention reduces or eliminates that antagonism. Herbicidally active derivatives of any known herbicide are also within the scope of the present invention if applied by the method herein described. A herbicidally active derivative is any compound which is a minor structural modification, most commonly but not restrictively a salt or ester, of a known herbicide. These compounds retain the essential activity of the parent herbicide, but do not necessarily have a potency equal to that of the parent herbicide. These compounds convert to the parent herbicide before or after they enter the treated plant. Mixtures or coformulations of a herbicide with other ingredients, or of more than one herbicide, can likewise be employed. Preferred herbicides for use according to the method of the present invention are those which are normally foliar-applied rather than soil-applied. Especially preferred foliar-applied herbicides are those which show a degree of systemicity in the plant, in other words are to some extent translocated from the point of entry to a point of action in the plant at some distance from the point of entry.

An especially preferred herbicide for which the method of the present invention is particularly useful is N-phosphonomethylglycine, a salt or ester thereof, or a compound which is converted to glyphosate in plant tissues or which otherwise provides glyphosate ion. Glyphosate salts that can be used according to this invention include but are not restricted to alkali metal, for example sodium and potassium, salts; ammonium salt; alkylamine, for example dimethylamine and isopropylamine, salts; alkanolamine, for example ethanolamine, salts; alkylsulfonium, for example trimethylsulfonium, salts; sulfoxonium salts; and mixtures thereof. The herbicidal compositions sold by Monsanto Company as ROUNDUP® and ACCORD® contain the monoisopropylamine (IPA) salt of N-phosphonomethylglycine. The herbicidal compositions sold by Monsanto Company as ROUNDUP® Dry and RIVAL® contain the monoammonium salt of N-phosphonomethylglycine. The herbicidal composition sold by Monsanto Company as ROUNDUP® Geoforce contains the monosodium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and trisodium salts, and the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate is applied to foliage of plants, followed by treatment of at least a part of the same foliage with a suitable amount of an accession agent, selected in accordance with this invention. Such an aqueous solution can be obtained by dilution of a concentrated glyphosate salt solution with water, or dissolution or dispersion in water of a dry (e.g. granular, powder, tablet or briquette) glyphosate formulation.

Exogenous chemicals should be applied to plants at a rate sufficient to give the desired effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through the sequential application method of this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plant species worldwide. Particularly important species for which glyphosate compositions are used are exemplified without limitation by the following:

Annual broadleaves:
velvetleaf (*Abutilon theophrasti*)
pigweed (Amaranthus spp.)
buttonweed (Borreria spp.)
oilseed rape, canola, indian mustard, etc. (Brassica spp.)
commelina (Commelina spp.)
filaree (Erodium spp.)
sunflower (Helianthus spp.)
morningglory (Ipomoea spp.)
kochia (*Kochia scoparia*)
mallow (Malva spp.)
wild buckwheat, smartweed, etc. (Polygonum spp.)
purslane (Portulaca spp.)
russian thistle (Salsola spp.)
sida (Sida spp.)
wild mustard (*Sinapis arvensis*)
cocklebur (Xanthium spp.)
Annual narrowleaves:
wild oat (*Avena fatua*)
carpetgrass (Axonopus spp.)
downy brome (*Bromus tectorum*)
crabgrass (Digitaria spp.)
barnyardgrass (*Echinochloa crus-galli*)
goosegrass (*Eleusine indica*)
annual ryegrass (*Lolium multiflorum*)
rice (*Oryza sativa*)
ottochloa (*Ottochloa nodosa*)
bahiagrass (*Paspalum notatum*)
canarygrass (Phalaris spp.)
foxtail (Setaria spp.)
wheat (*Triticum aestivum*)
corn (*Zea mays*)

Perennial broadleaves:
mugwort (Artemisia spp.)
milkweed (Asclepias spp.)
canada thistle (*Cirsium arvense*)
field bindweed (*Convolvulus arvensis*)
kudzu (Pueraria spp.)
Perennial narrowleaves:
brachiaria (Brachiaria spp.)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)
perennial ryegrass (*Lolium perenne*)
guineagrass (*Panicum maximum*)
dallisgrass (*Paspalum dilatatum*)
reed (Phragmites spp.)
johnsongrass (*Sorghum halepense*)
cattail (Typha spp.)
Other perennials:
horsetail (Equisetum spp.)
bracken (*Pteridium aquilinum*)
blackberry (Rubus spp.)
gorse (*Ulex europaeus*)

Thus, the method of the present invention, as it pertains to glyphosate herbicide, can be useful on any of the above species.

In a preferred embodiment of the present invention, the exogenous chemical is applied in an aqueous spray composition further comprising a surfactant. Typically this surfactant is not one that in aqueous solution or dispersion behaves as an accession agent as herein defined. Preferably it is a surfactant selected to provide good biological effectiveness of the exogenous chemical regardless of whether an accession agent is also used. For example, when the exogenous chemical is glyphosate, an appropriate surfactant for use in the glyphosate spray composition is one comprising or based on polyoxyethylene alkylamine, such as MON-0818. It has been found that the greatest and most consistent benefits of practicing the sequential method of the invention are generally obtained when the exogenous chemical composition comprises a surfactant.

Accession Agents

Although many of the accession agents of this invention are aqueous solutions or dispersions of compounds known in the art as "surfactants," not all aqueous surfactant solutions and dispersions perform as accession agents according to the invention. A property common to all accession agents as defined herein, whether or not they comprise a surfactant, is that they infiltrate microscopic pores in a hydrophobic surface. For example, accession agents infiltrate stomata or other openings such as cracks or wounds, and ultimately internal voids connected thereto, of a leaf of the plant species to be treated by the method of the invention. This property is referred to herein as "stomatal infiltration." Although this property is important to determining whether a particular material will perform as an accession agent in the method of the present invention, it is not known whether the property of stomatal infiltration plays any part in the mechanism by which the sequential application method of the invention provides its surprising benefits in enhancing herbicidal or other biological effectiveness while reducing antagonism.

A further category of liquid agents providing superior biological effectiveness of an exogenous chemical, for example superior herbicidal effectiveness of glyphosate, when applied sequentially after rather than concurrently with the exogenous chemical, comprises aqueous solutions or dispersions of anionic surfactants, whether or not these are accession agents as defined herein.

The accession agents of this invention should be introduced as a flowable bulk material, such as a liquid (e.g., an oil or an aqueous surfactant solution or dispersion). Useful accession agents should wet the leaf. Preferred accession agents typically exhibit rapid, almost instantaneous spreading when applied to leaf surfaces. Stomatal infiltration of preferred accession agents involves mass flow in addition to any purely capillary flow or diffusion through stomatal apertures. The accession agents useful in the practice of this invention can be identified through any one of several tests for stomatal infiltration.

The following test is one of several that can be useful in determining whether a liquid is a potential stomatal infiltrant, and therefore can function as an accession agent in the method of the present invention. Plants of a suitable test species are grown, for example in a greenhouse or growth chamber, to such a size that they have fully expanded leaves. Velvetleaf (Abutilon theophrasti) has been found to be a convenient species for this test, but other species having stomata on the upper surface of the leaves are similarly useful. Growing conditions immediately prior to the test should be such as to favor the fully expanded leaves having their stomata open; normally this means that the plants should have been exposed for at least one hour to a light intensity of about 475 microeinsteins or more, and that the plants should not be subject to physiological stress from excess or deficiency of water, from excessively high or low temperature, or from other adverse environmental conditions.

The procedure described herein relates to velvetleaf. Modifications may be found necessary or desirable if another species is chosen. Potted velvetleaf plants are brought from the greenhouse and immediately sprayed with ROUNDUP® herbicide at a rate of 350 g glyphosate acid equivalent (a.e.)/ha in a spray volume of 93 l/ha, using a track sprayer. The spray solution is made by diluting 1 ml of ROUNDUP® herbicide to 95 ml is with tap water. After spraying, the plants are returned to a well illuminated greenhouse, where they are maintained for at least 10 minutes and preferably not more than one hour, during which time the spray deposit on the leaves substantially dries (i.e., the leaf surface is visibly dry).

A liquid to be tested as a candidate stomatal infiltrant is prepared, for example by dilution of a surfactant in water at a desired concentration, and fluorescein is dissolved in the liquid at 0.1% by volume. An automatic syringe is used to dispense 0.8 microliters of the liquid containing fluorescein to each of three loci on the surface of one or more fully expanded leaves. The treated leaves remain attached to the plants throughout the procedure.

Exactly 10 minutes after dispensing the liquid, each treated leaf is washed with copious amounts of water (for example, at least 10 ml) to remove substantially all, i.e. all visually perceptible amount, of the fluorescein from the leaf surface. The plants are then removed to a darkened place where the treated leaves are observed with the naked eye under long-wave ultraviolet illumination. If fluorescence is observed at or close to the loci of deposition of the candidate liquid, it can be concluded that the liquid has infiltrated stomata. Any such liquid has the potential to be an accession agent in the method of the present invention. If desired, the degree of fluorescence can be quantified by appropriate instrumentation, but this is unnecessary if the objective is simply to know whether or not a liquid is a stomatal infiltrant. Lack of observed fluorescence indicates no significant stomatal infiltration.

To verify that plants are in suitable condition for the test, a known accession agent can be tested by the above procedure. An aqueous solution of Silwet L-77 at 0.05% by volume typically gives a weak fluorescence signal indicating that modest infiltration has occurred. An aqueous solution of Silwet L-77 at 0.5% by volume typically gives a very strong fluorescence signal, indicating that a substantial amount of the solution has infiltrated stomata.

An alternative test has now been developed which does not employ plants or other living material, and therefore has the major advantage that it is unaffected by the normal biological variability characteristic of in vivo assays such as the one described immediately above. This test, described herein as an in vitro test or assay to reflect its non-use of living material, is a further embodiment of the present invention and can be used to determine whether a liquid agent is capable of penetrating or infiltrating microscopic pores in a hydrophobic surface, such as stomata of a leaf. While the test is useful for any application where it is desired to know if a liquid agent is a potential stomatal infiltrant, its use is exemplified herein as a means of predicting whether or not a liquid can function as an accession agent, and in particular whether or not it will show reduced antagonism of biological effectiveness of an exogenous chemical applied to a plant when applied sequentially after, as opposed to concurrently with, the exogenous chemical in the present method.

The in vitro test of the present invention can be used for any liquid agent. If the agent is a solution or dispersion of a liquid or solid material, such as for example a surfactant, in a liquid medium, such a solution or dispersion is first prepared. For most applications, the desired liquid medium is likely to be water, in which case it is preferred that the solution or dispersion of the candidate material be prepared in deionized water. The candidate material can be dissolved or dispersed in the liquid medium at any desired concentration, depending on the concentration to be used in the desired application. For example, if the desired application is as an accession agent according to the present invention, suitable concentrations in water range, depending on the candidate material, from about 0.1% to about 10% by weight, for example from about 0.25% to about 3% by weight.

A smooth solid substrate and an opaque membrane filter are selected having contrasting colors. Preferably the substrate is dark colored, for example black, and the membrane filter light colored or white. The membrane filter is composed of a hydrophobic material, preferably polytetrafluoroethylene (PTFE), and has a multiplicity of pores. Pore size of the membrane filter is selected to reflect the typical dimensions of pores which it is desired to infiltrate with the liquid agent; for example in the case of an agent being tested as a potential stomatal infiltrant, a membrane filter should be selected having pores of diameter about 0.5 to about 2.5 $\mu$m, for example about 1 $\mu$m.

The selected membrane filter is placed on the substrate; in the case of a membrane filter having a smooth face and an opposing rough face, the membrane filter is placed with the smooth face adjacent to the substrate. One or more drops of the liquid agent are then placed on the membrane filter. Any convenient drop size and number can be used; in the case of a PTFE membrane filter having 1 $\mu$m diameter pores, it has been found useful to apply 1–10, for example 3, drops each of 1–5 $\mu$l, for example 2 $\mu$l, volume. The drops are allowed to remain in contact on the surface of the membrane filter for a convenient length of time. The time for which the drops are allowed to remain on the filter depends on the application for which the test is being used and an optimum length of time can easily be determined without undue experimentation. For example, in testing a liquid agent as a potential stomatal infiltrant or accession agent, it has been found useful to leave the drops on the filter for a minimum of 1–30 minutes, for example a minimum of about 15 minutes.

At the end of this time, it can readily be seen if the liquid agent has permeated the pores of the membrane filter, because such permeation renders the membrane filter to some extent transparent, and the contrasting color of the substrate shows through the membrane filter. Permeation of the pores of the membrane filter in this test is a good predictive indication of penetration or infiltration of microscopic pores in the hydrophobic surface characteristic of the application of interest. For example, permeation of pores in a PTFE membrane filter having 1 $\mu$m porosity after a period of at least about 15 minutes is a good predictive indication of stomatal infiltration in plant leaves.

Particular test conditions which can be used to predict whether a 0.5% solution or dispersion of a candidate material is a useful accession agent in the present method are as follows. A solution or dispersion of the candidate material is prepared at a concentration of 0.5% by weight in deionized water to form a candidate accession agent. A black bottle cap (ca. 40 mm diameter) is placed on a solid surface such that the closed side of the bottle cap is down and the open, threaded side is up. A suitable PTFE membrane filter (47 mm diameter, 1.0 $\mu$m porosity, MSI brand, catalog no. F10LP04700) has two faces: a smooth, shiny face and a rough, dull face. The filter is placed atop the cap so that the rough, dull face points upward. Three 2 $\mu$l drops of the aqueous candidate accession agent are applied to the rough, dull face of the PTFE membrane filter. The drops are allowed to stand on the filter for at least 15 minutes. During this time, it is noted whether the aqueous candidate accession agent has permeated the PTFE membrane filter. This can be determined visually because permeation causes the white filter to become transparent and the black bottle cap can be seen through the filter. If after 15 minutes no permeation has occurred, this is deemed a negative result and the test is terminated. A negative result indicates that the candidate agent is predicted not to be useful as an accession agent for application to plants in the method of the invention. If permeation has occurred within 15 minutes, this is deemed a positive result and the candidate agent is predicted to be a useful accession agent for application to plants in the method of the invention.

This in vitro test is not applicable for aqueous solutions or dispersions of anionic surfactants. Relatively few anionic surfactants, in aqueous solution or dispersion, are able to permeate a PTFE membrane filter having pores of 1 $\mu$m diameter. Without being bound by theory, it is believed that this is due to the negative electric charge carried by the anionic surfactant being repelled by negative charges on the PTFE membrane filter surface. Most anionic surfactants have been found to be useful in the sequential application method of the present invention, whether or not they are accession agents as defined herein.

Preferred accession agents useful in the process of this invention are aqueous solutions of a particular category of surfactants in a concentration sufficient to induce stomatal infiltration of the leaves or other foliage to be treated, as detected by any suitable test procedure, such as those described above. This category of surfactants is of a type known as "superwetting" or "superspreading" surfactants, and they are well known in the art.

Two classes of superwetting surfactants have been found to contain numerous agents that are particularly useful as accession agents in the method of the present invention. Thus, the accession agent of the present invention is preferably an aqueous solution of a superwetting surfactant selected from the group consisting of silicone based surfactants (referred to herein as "organosilicone wetting agents" or simply "organosilicones") and fluorocarbon based surfactants (referred to herein as "fluoro-organic wetting agents" or simply "fluoro-organics").

There are many classes of organosilicone wetting agents. One preferred class has the following general formula:

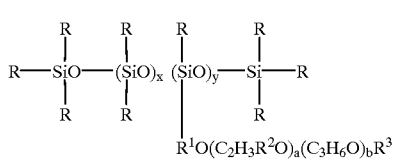

(I)

where each R is independently a monovalent saturated or unsaturated alkyl radical having 1–20 carbon atoms, more preferably having 1–6 carbon atoms, $R^1$ is a divalent alkylidene radical having 1–20 carbon atoms, more preferably having 1–6 carbon atoms, $R^2$ is independently hydrogen or a $C_1$–$C_4$ alkyl radical, $R^3$ is hydrogen or a monovalent saturated or unsaturated alkyl radical having 1–20 carbon atoms, more preferably having 1–10 carbon atoms, x is an integer or average of integers greater than or equal to zero and preferably less than 100, y and a are integers or averages of integers independently greater than or equal to one and preferably less than 30, and b is an integer or average of integers greater than or equal to zero and preferably less than 30.

In a preferred subclass of the compounds of Formula I, R and $R^3$ are —$CH_3$, $R^1$ is —$C_3H_6$—, $R^2$ is hydrogen, x is zero or one, y is one to five, a is five to 20, and b is zero. A second preferred subclass of the compounds of Formula I can be represented by the following formula:

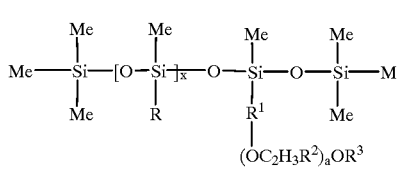

(II)

where a is one to 20, x is zero or one, R is $C_1$–$C_6$ alkyl, $R^1$ is divalent $C_1$–$C_6$ alkylidene, $R^2$ is independently H or —$CH_3$, and $R^3$ is H, $C_1$–$C_4$ alkyl, or $C_2$–$C_4$ acyl. A particularly preferred organosilicone wetting agent within the two preferred subclasses of Formula I is the compound having the following formula:

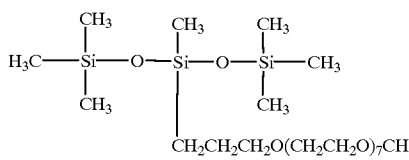

(III)

Another preferred class of organosilicone wetting agents has the general formula:

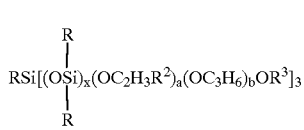

(IV)

where R, $R^2$, $R^3$, x, a and b are as defined above for Formula I, except that x must be greater than one. Preferably in compounds of Formula IV, R and $R^3$ are —$CH_3$, $R^2$ is hydrogen, a is five to 20 and b is zero.

Organosilicones of the above formulas are generally described in product literature of Union Carbide Corp. and OSi Specialties, Inc. (e.g., "Silwet® Surfactants," OSi Specialties, Inc., Danbury, Conn., 1994), and in U.S. Pat. No. 3,505,377, the disclosure of which is incorporated herein by reference. Several of such ethoxylated organosilicone wetting agents are available from OSi Specialties as Silwet silicone glycol copolymers. Preferred Silwet surface active copolymers include Silwet L-77, Silwet 408, and Silwet 800. Silwet L-77 is an especially preferred ethoxylated organosilicone wetting agent which has an average formula corresponding to Formula III above. Another preferred organosilicone is Sylgard 309 of Dow Corning.

An additional class of organosilicone wetting agents has the average formula:

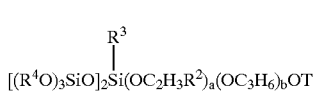

(V)

where $R^2$, $R^3$, a, and b are as defined above for Formula IV, each $R^4$ group is independently a monovalent saturated or unsaturated alkyl radical preferably having 1–20 carbon atoms, and T is hydrogen, a monovalent saturated or unsaturated alkyl radical preferably having 1–20 carbon atoms, or a group of the formula —$Si(R^3)[OSi(OR^4)_3]_2$. Representative ethoxylated organosilicone wetting agents of Formula V are described in product literature of Olin Corporation and in U.S. Pat. Nos. 4,160,776, 4,226,794, and 4,337,168, the disclosures of which are incorporated herein by reference.

An additional class of organosilicone wetting agents has the average formula:

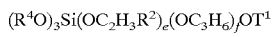

(VI)

where $R^2$ and $R^4$ are as defined immediately above, e is at least four and preferably less than 30, f is greater than or equal to zero and preferably less than 30, and $T^1$ is hydrogen, a monovalent saturated or unsaturated alkyl radical preferably having 1–20 carbon atoms, or a group of the formula —$Si(OR^4)_3$.

Fluoro-organic wetting agents useful in this invention are organic molecules represented by the formula:

$$R_f\text{—}G$$

wherein $R_f$ is a fluoroaliphatic radical and G is a group which contains at least one hydrophilic group such as cationic, anionic, nonionic, or amphoteric groups. $R_f$ is a fluorinated, monovalent, aliphatic organic radical containing at least four carbon atoms. Preferably, it is a saturated perfluoroaliphatic monovalent organic radical. However, hydrogen or chlorine atoms can be present as substituents on the skeletal chain. Although radicals containing a large number of carbon atoms can function adequately, compounds containing not more than about 20 carbon atoms are preferred because large radicals usually represent a less efficient utilization of fluorine than is possible with shorter skeletal chains. Preferably, $R_f$ contains about 5 to 14 carbon atoms.

The cationic groups which are usable in the fluoro-organic wetting agents employed in this invention can include an amine or a quaternary ammonium cationic group. Such amine and quaternary ammonium cationic hydrophilic groups can have formulas such as —$NH_2$, —$NHR^2$, —$N(R^2)_2$, —$(NH_3)X$, —$(NH_2R^2)X$, —$(NH(R^2)_2)X$, or —$(N(R^2)_3)X$, where X is an anionic counterion such as halide, hydroxide, sulfate, bisulfate, acetate or carboxylate, $R^2$ is H or a $C_{1-18}$ alkyl group, and each $R^2$ can be the same as or different from other $R^2$ groups. Preferably, X is halide, hydroxide, or bisulfate. Preferably, the cationic fluoro-organic wetting agents used in this invention contain hydrophilic groups which are quaternary ammonium cationic groups. The anionic groups which are usable in the fluoro-organic wetting agents employed in this invention include groups which by ionization can become radicals of anions. The anionic groups can have formulas such as —COOM, —$SO_3M$, —$OSO_3M$, —$PO_3M_2$, —$PO_3HM$, —$OPO_3M_2$, or —$OPO_3HM$, where M is H, an alkali metal ion, $(NR^1_4)^+$, or $(SR^1_3)^+$, where each $R^1$ is independently H or substituted or unsubstituted $C_1$–$C_6$ alkyl. Preferably M is $Na^+$ or $K^+$. The preferred anionic groups of the fluoro-organic wetting agents used in this invention have the formula —COOM or —$SO_3M$.

The amphoteric groups which are usable in the fluoro-organic wetting agents employed in this invention include groups which contain at least one cationic group as defined above and at least one anionic group as defined above. Other useful amphoteric groups are amine oxides.

The nonionic groups which are usable in the fluoro-organic wetting agents employed in this invention include groups which are hydrophilic but which under pH conditions of normal agronomic use are not ionized. The nonionic groups can have formulas such as —$O(CH_2CH_2)_xH$ where x is greater than zero, preferably 1–30, —$SO_2NH_2$, —$SO_2NHCH_2CH_2OH$, —$SO_2N(CH_2CH_2OH)_2$, —$CONH_2$, —$CONHCH_2CH_2OH$, or —$CON(CH_2CH_2OH)_2$.

Cationic fluoro-organic wetting agents useful herein include those cationic fluorochemicals described, for example, in U.S. Pat. Nos. 2,764,602, 2,764,603, 3,147,064, and 4,069,158. Amphoteric fluoro-organic wetting agents useful herein include those amphoteric fluorochemicals described, for example, in U.S. Pat. Nos. 2,764,602, 4,042,522, 4,069,158, 4,069,244, 4,090,967, 4,161,590, and 4,161,602. Anionic fluoro-organic wetting agents useful herein include those anionic fluorochemicals described, for example, in U.S. Pat. Nos. 2,803,656, 3,255,131, 3,450,755, and 4,090,967. The pertinent disclosure of the above patents is incorporated here by reference.

Several fluoro-organic wetting agents suitable for use as accession agents in the method of the invention are available from 3M under the Fluorad trademark. They include anionic agents Fluorad FC-120, Fluorad FC-129 and Fluorad FC-99, cationic agent Fluorad FC-750, and nonionic agents Fluorad FC-170C, Fluorad FC-171 and Fluorad FC-430.

Especially preferred surfactants for use as components of accession agents include those organosilicone and fluoro-organic surfactants that are capable of reducing the surface tension of water to very low levels (typically below about 25 dyne/cm).

Classes of anionic surfactant (excluding fluoro-organics) which can be dissolved or dispersed in water to form liquid agents useful for sequential application following application of an exogenous chemical according to the invention include:

alkyl and alkylaryl carboxylates (e.g. heptanoate, Na salt; hexanoate, Na salt), alkyl and alkylaryl polyoxyalkylene carboxylates (e.g. Emcol CNP-110), alkyl and alkylaryl sulfates and sulfonates (e.g. Alpha-Step MC-48; Bio-Soft MG-50; hexanesulfonate, Na salt; Ninate 401-HF; PolyStep B-25; PolyStep B-29; Stepanol AEM; Stepanol ME Dry; Stepanol WAC), alkyl and alkylaryl polyoxyalkylene sulfates and sulfonates (e.g. Soprophor 4D384; Steol CS-370), naphthalene sulfonates and formaldehyde condensates thereof (e.g. Aerosol OS; Daxad 15; Emery 5366), lignosulfonates (e.g. Polyfon H; Reax 100M; Reax 85A; Reax 88B), sulfosuccinates and semisulfosuccinates (e.g. Aerosol A-102; Aerosol A-103; Aerosol OT), alkyl and alkylaryl polyoxyalkylene phosphates (e.g. Emphos CS-121; Emphos CS-136; Emphos CS-141; Emphos PS-131; Emphos PS-21A; Emphos PS-400; Stepfac 8170; Stepfac 8171; Stepfac 8172; Stepfac 8173; Tryfac 5552; Tryfac 5556).

Classes of cationic surfactant (excluding fluoro-organics) which can be dissolved or dispersed in water to form accession agents of the invention (subject to a test showing they infiltrate microscopic pores in a hydrophobic surface) include:

polyoxyalkylene alkylamines and alkyletheramines (e.g. Ethomeen C/12).

Classes of nonionic surfactant (excluding fluoro-organics and organosilicones) which can be dissolved or dispersed in water to form accession agents of the invention (subject to a test showing they infiltrate microscopic pores in a hydrophobic surface) include:

polyoxyalkylene alkyl and alkylaryl ethers (e.g. Ethylan CPG-945; Makon 4; Neodol 1–5; nonanols 2EO and 4EO; Tergitol 15-S-7; Tergitol TMN-6; Toximul 8304), polyoxyalkylene alkyl and alkylaryl thioethers (e.g. Alcodet 260; Alcodet SK), and glyceryl alkylesters (e.g. Witconol 18L).

Surfactants mentioned here by trade name, and other surfactants that can be useful in the method of the invention, are indexed in standard reference works such as McCutcheon's Emulsifiers and Detergents, 1997 edition, and Handbook of Industrial Surfactants, 1993, published by Gower.

Any number of accession agents can be employed in the method of this invention, and can be identified as useful through the procedures described above. Surfactant solutions that provide the appropriate indicia of stomatal infiltration at the concentrations tested are likely to prove useful in the method of this invention. A concentration of surfactant shown to be useful by these tests is termed herein an "effective concentration" of, for example, an aqueous solution used as an accession agent.

The accession agents employed in this invention are liquids which provide rapid and enhanced access of the exogenous chemical (e.g., glyphosate herbicide) to the plant system wherein the exogenous chemical (e.g., glyphosate herbicide) is biologically effective. While not being held to any theory of operation of the accession agents employed in the method of this invention, we have found that infiltration, which likely proceeds through foliar stomata, allows flow of liquid from the foliar surface into substomatal and other voids in the interior of the foliage (such as intercellular voids). By infiltrating stomata, it appears that the accession agents employed in this invention carry with them previously applied chemicals. The manner by which they do this is not yet understood, but the results at least on some species are certainly at variance with the effect observed when such agents are mixed (either in tank mix or in simple coformulation) with, for example, a herbicide prior to application to the plants. As demonstrated below, these accession agents can be antagonistic to the biological effectiveness of the exogenous chemical (on certain species and under certain application conditions) when employed in a tank mix, and can give greater biological effect when used in the sequential method of this invention. In the case of herbicides, superior herbicidal effect can be obtained using the sequential method of this invention, with the result being that plants can be controlled with lower rates of the applied herbicide.

Because leaf morphologies and consequent leaf/liquid interactions vary, different liquids show varying degrees of success on individual plant species when used in the method of this invention. However, sequential application of all operative accession agents useful in this invention reduces to some degree the antagonism observed in the corresponding tank mix methods for a variety of plant species.

Application of Accession Agents

For accession agents which are surfactant solutions or dispersions, the concentration of surfactant therein is important to achieving enhanced biological efficacy of pre-applied exogenous chemical compositions. Regarding such solutions or dispersions, the solution or dispersion itself is referred to herein as the "accession agent." The "concentration" of the "accession agent" refers to the concentration of the component ingredients (normally surfactants) of the "accession agent" in the aqueous solution or dispersion as applied.

Even if a specific surfactant at a specific concentration in water is observed (by one of the procedures outlined above) to infiltrate leaf stomata and penetrate the subsurface foliar voids, this concentration sometimes nonetheless proves insufficient to enhance the biological effect of the exogenous chemical. In such cases, it can prove desirable to employ as an accession agent a solution containing a higher concentration of the surfactant. Typically, the minimum concentration of the accession agent needed to obtain a desired enhancement of biological effectiveness with minimal antagonism is highly variable from one accession agent to another, and could be determined by a person of ordinary skill in the art. For a polyoxyethylene trisiloxane surfactant such as Silwet L-77, a preferred concentration is in excess of 0.25% by volume, in the method of the present invention with glyphosate herbicide as the exogenous chemical. (Concentrations are expressed herein in percent by weight or percent by volume, but in dilute solutions (below about 5% concentration) it makes no practical difference for most purposes and the terms "by weight" and "by volume" can be used interchangeably in those situations.) Other accession agents have higher or lower minimum effective concentrations. It is highly preferred for glyphosate herbicide to use polyoxyethylene trisiloxane accession agents in concentrations of about 0.35% to about 0.6% by volume. Higher concentrations can certainly be employed but the cost of employing such higher concentrations has to be balanced against the extent of improvement in results obtainable. However, significant enhancement of herbicidal effectiveness for glyphosate has been obtained applying polyoxyethylene trisiloxane accession agents at a concentration of at least about 0.5% by volume or greater. It has been found that for certain surfactants, much higher concentrations (i.e., greater than 1% and up to 5% by volume) must be used to obtain the enhanced effect (at least in herbicides) that is a feature of this invention.

Certain accession agents are neat liquids, in which case this invention can be practiced without a solvent or diluent. When a solvent or diluent is used as the major component of an accession agent, its specifics are not important to this invention, provided such solvent or diluent is capable of carrying the previously applied exogenous chemical along with it into the plant structure. Thus, when the exogenous chemical is water-soluble, as in the case of a glyphosate salt, water suffices as a solvent in the accession agent.

Additional agriculturally acceptable chemicals can also be admixed with the accession agent or the exogenous chemical, or both. For example, when the exogenous chemical is a herbicide, liquid nitrogen fertilizer or ammonium sulfate can be applied with the accession agent, with the exogenous chemical, or with both.

Application rates for accession agents vary depending upon a number of factors, including the type and concentration of accession agent and the plant species involved. Application rates for accession agents generally should not be so high as to wash significant amounts of the exogenous chemical off the foliage. Useful rates for applying an aqueous solution or dispersion of liquid accession agent to a field of foliage are from about 25 to about 1,000 liters per hectare (l/ha) by spray application. The preferred application rates for aqueous solutions or dispersions are in the range from about 50 to about 300 l/ha.

Many exogenous chemicals (including glyphosate herbicides) must be taken up by living tissues of the plant and translocated within the plant in order to produce the desired biological (e.g., herbicidal) effect. Thus, it is normally important that the accession agent not be applied in such a manner, concentration, or amount as to excessively injure and interrupt the normal functioning of the plant. However, some limited degree of local injury can be insignificant, or even beneficial, in its impact on the biological effectiveness of certain exogenous chemicals, such as glyphosate herbicide. We have observed that application at night or in cold weather can prove relatively ineffective. It is possible that this is because leaf stomata contract and restrict infiltration under these conditions, but these observations might be explainable on the basis of some other theory as well.

The accession agent can be applied almost immediately, for example within seconds, after the exogenous chemical. It can be applied with productive effect up to 96 hours or more later, provided there has been no intervening overhead irrigation or rainfall of such a volume or intensity as to remove a significant amount of the exogenous chemical from the leaf surface. Typically, when the concentration of the accession agent is relatively low (i.e., about 0.25% by volume in the case of a polyoxyethylene trisiloxane), a preferred time period for application of the accession agent is from about one hour to about 24 hours, most preferably from about one hour to about three hours, after application of the exogenous chemical. However, significant enhancement has been observed when the liquid accession agent is applied within about 3 minutes, and in field trials within a few seconds, after application of the exogenous chemical. The accession agent can be deployed in a single, sequential application following a spray of an exogenous chemical composition. It can also be employed in multiple sequential applications.

The method of this invention can also be practiced using a system whereby separate spray solutions are applied sequentially to plants from a single moving vehicle. This can be accomplished in a number of different ways, e.g., by using a double boom system or its equivalent. In this particular use of the present invention, a single vehicle carries two booms, one spraying a liquid exogenous chemical composition (such as a glyphosate herbicide composition) and the other spraying a liquid accession agent. Each of the booms employed in this exemplary use of the present invention can employ any conventional means for spraying liquids, such as spray nozzles, atomizers, or the like. The boom delivering the accession agent is preferably disposed approximately parallel to the boom delivering the exogenous chemical, and posterior to it in the direction of travel of the vehicle. Instead of two booms, each with a plurality of spray nozzles, the method of the present invention can also be carried out with a single boom having two sets of nozzles or the like, one set spraying a liquid exogenous chemical composition and the other set spraying a liquid accession agent. The two sets of nozzles should be oriented differently on the single boom so that, as the vehicle carrying the boom moves forward, the exogenous chemical composition contacts the plants being treated prior to the time when the accession agent contacts the same plants.

In any of these approaches, the period of time between the application of the exogenous chemical composition and the application of the accession agent depends upon the distance between the two spray booms (or the distance between spray paths created by the two differently oriented sets of spray nozzles where a single boom is employed) and the speed of the vehicle carrying the boom or booms. A preferred period of time between the two applications is from about 0.005 to about 10 seconds. A period of about 0.01–1.0 seconds is especially preferred. The great convenience and cost savings of such a single moving vehicle system can in many cases compensate for the somewhat weaker overall enhancement by comparison with a more delayed sequential application.

The method of the present invention can also employ aerial application techniques. For example, an exogenous chemical such as a herbicide can be applied by spraying from an airplane onto plants in a field, using conventional aerial spraying equipment known to persons skilled in the art, and then the accession agent can be applied in a second pass of aerial spraying, either from the same plane or a different plane. Alternatively, the exogenous chemical can be applied to the plants by means of ground-based spraying, and after an entire field or plurality of fields have been so sprayed, an accession agent can be applied to the plants in that field or plurality of fields by spraying from an airplane. The latter approach minimizes the danger of the exogenous chemical spray drifting and contacting plants outside the target zone, and thus eliminates the need for a buffer zone, as off-target deposition of an accession agent alone is unlikely to be of concern.

The method of this invention can also be practiced by a single application to plants of particular coformulations of an exogenous chemical and an accession agent that are themselves designed to provide the advantages of sequential application. Such coformulations are an embodiment of the invention and provide a time delay between the initial contacting of the plant foliage by the exogenous chemical (e.g., herbicide) and the initial contacting of the plant foliage by the accession agent (e.g., superwetting surfactant in aqueous solution or dispersion). This time delay is accomplished by having the exogenous chemical and the surfactant component of the accession agent partitioned to a greater or lesser extent in selected physical environments within the bulk state of the coformulation. In this respect such coformulations differ from the simple coformulations and tank mixes previously known. The presence of surfactant in the form of simple micelles or in solution in a liquid coformulation, or adsorbed or absorbed on a solid carrier (which may or may not be the exogenous chemical) in a dry coformulation, does not of itself accomplish the required partitioning. Coformulations having different physical environments permitting partitioning of exogenous chemical and accession agent as required by this embodiment of the invention include, without limitation, colloidal systems such as emulsions (water/oil, oil/water, or multiple, e.g., water/oil/water emulsions having an inner aqueous phase and an outer aqueous phase), foams or microemulsions, or systems containing microparticulates, microcapsules, liposomes, vesicles, or the like. Especially preferred methods involving partitioned coformulations are those wherein the accession agent comprises a surfactant at least 50% of which is encapsulated within microcapsules, liposomes, vesicles or the inner aqueous phase of a multiple emulsion.

Analogous partitioned coformulations providing a time delay between initial contact of an exogenous chemical and initial contact of an anionic surfactant (whether or not the anionic surfactant forms an accession agent as defined herein) are likewise an embodiment of the present invention.

In all partitioned coformulations of the invention and methods of using such partitioned coformulations, a preferred exogenous chemical is a herbicide comprising N-phosphonomethylglycine or a herbicidal derivative thereof.

Glyphosate is known generally to be effective at lower rates as a herbicide for grasses than for broadleaf plants, although it is widely used on all species. We have found, however, that for both classes of plant species for which glyphosate and an accession agent are antagonistic in a simple coformulation or tank mix, superior results are achieved through the sequential application method of this invention.

Tank Mixes v. Sequential Application

The sequential application method of the present invention provides a novel method for delivery of exogenous chemicals, which generally produces a greater biological effect than when accession agent and exogenous chemical are employed together in a tank mix. This enhancement, which can involve a reduction or elimination of antagonism, offers a number of practical and commercial advantages over the prior tank mix methods.

In the case of herbicides, this invention facilitates use of accession agents in fields infested with a variety of plant species. When used in a tank mix, the accession agent may enhance herbicidal activity with respect to some species, but reduce activity with respect to others (antagonism). A single application of the herbicide tank mix will, in such cases, prove ineffective to control the desired plurality of plant species, unless the herbicide is introduced at significantly higher levels, thereby defeating the purpose of the accession agent. In contrast, as demonstrated below, the sequential application process of this invention preserves or in some cases further magnifies the enhancements of herbicidal efficacy provided by the tank mix, but substantially reduces or eliminates antagonism for individual plant species that might be found in the subject field. This invention therefore permits use of accession agents over a broad spectrum of plant species, unlike tank mix methods which can enhance or decrease herbicidal activity depending on the plant species. Similar benefits occur for other classes of exogenous chemicals.

We have observed antagonistic effects of Silwet L-77 in tank mix with glyphosate on the following species:

velvetleaf (*Abutilon theophrasti*)
redroot pigweed (*Amaranthus retroflexus*)
wild oat (*Avena fatua*)
broadleaf signalgrass (*Brachiaria platyphylla*)
canola (*Brassica napus*)
downy brome (*Bromus tectorum*)
sicklepod (*Cassia obtusifolia*)
common lambsquarter (*Chenopodium album*)
barnyardgrass (*Echinochloa crus-galli*)
redstem filaree (*Erodium cicutarium*)
cutleaf geranium (*Geranium dissectum*)
soybean (*Glycine max*)
little barley (*Hordeum pusillum*)
pitted morningglory (*Ipomoea lacunosa*)
annual ryegrass (*Lolium multiflorum*)
annual bluegrass (*Poa annua*)
wild buckwheat (*Polygonum convolvulus*)
cutleaf evening primrose (*Primula trientalis*)
curly dock (*Rumex crispus*)
hemp sesbania (*Sesbania exaltata*)
prickly sida (*Sida spinosa*)
wild mustard (*Sinapis arvensis*)
johnsongrass (*Sorghum halepense*)
wheat (*Triticum aestivum*)

The present invention can also reduce the work required to screen accession agents for varying effectiveness as enhancing agents for (and/or possible antagonism of) exogenous chemicals across multiple plant species. In those instances where tank mixes of an exogenous chemical and an accession agent are antagonistic, use of the sequential method of this invention substantially reduces or eliminates such antagonism. In those instances where the accession agent improves the biological effectiveness of the exogenous chemical in a tank mix, the sequential application method of this invention generally yields at least comparable results. Thus, as a result of the sequential method of this invention, increased use of accession agents is made possible, because when used in the method of the present invention, such accession agents provide enhanced biological activity in some plant species without antagonistic effect in others.

EXAMPLES

The following examples are provided for illustrative purposes only and are not intended to limit the scope of the present invention. In these examples, percentage amounts refer to percent by volume unless otherwise noted.

In the following examples, experiments were performed using the following (and other) formulations:

Formulation A: which consists of 41% by weight of the monoisopropylamine salt of glyphosate in aqueous solution with a coformulant (7.5% by weight) of a surfactant (MON-0818 of Monsanto Company) based upon polyoxyethylene (15) tallowamine.

Formulation B: which consists of 41% by weight of the monoisopropylamine salt of glyphosate in aqueous solution.

Formulation C: which consists of 41% by weight of the monoisopropylamine salt of glyphosate in aqueous solution with a coformulant (15% by weight) of MON-0818 surfactant.

Formulation J: which consists of 41% by weight of the monoisopropylamine salt of glyphosate in aqueous solution, together with surfactant. This formulation is sold in the USA by Monsanto Company under the ROUNDUP® Ultra trademark.

All of these formulations contain about 360 (nominally 356) grams of glyphosate acid equivalent per liter (g a.e./l). Other formulations used are described in the particular Examples where they occur.

Example 1

Seeds of velvetleaf (*Abutilon theophrasti*, ABUTH) were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated. Initial treatments with Formulation A, alone or in tank mix with a candidate accession agent, were applied 20 days after planting. Initial treatments were applied by spraying with a track sprayer fitted with a 9501E nozzle calibrated to deliver a spray volume of 93 liters per hectare (l/ha) at a pressure of 166 kilopascals (kPa). Plants treated according to methods of prior art, for comparative purposes, received an initial treatment only. Plants treated by a method illustrative of the present invention received an initial application of Formulation A followed sequentially by a subsequent application of a candidate accession agent. Various intervals between initial and subsequent applications were tested in this Example. Some treatments involved a single subsequent application of a candidate accession agent; others involved multiple subsequent treatments. All subsequent applications in this Example were applied by spraying a candidate accession agent with a track sprayer fitted exactly as for the initial application and calibrated to deliver a spray volume of 93 l/ha at a pressure of 166 kPa.

Formulation A was applied without candidate accession agent at a range of rates from 300 to 1000 g a.e./ha. When a candidate accession agent was included in the treatment, either in tank mix with Formulation A or as a subsequent application, only the two lowest rates of Formulation A, 300 and 400 g a.e./ha, were tested. This Example uses only one candidate accession agent, an aqueous solution containing 5% glycerin and 0.25% Silwet L-77 (abbreviated in data tables herein as L-77). SilwetL-77 is a commercial polyethoxylated trisiloxane surfactant having the chemical structure shown above and is a product of Witco Corporation, OSi Specialties Group. As this surfactant is known to be hydrolytically unstable in aqueous solution, spray solutions were prepared immediately before application. The time interval between initial and subsequent applications was varied from about 0.05 hour (the shortest interval that could practically be tested using the procedure of this Example) to 24 hours.

In this and subsequent examples, when applied as a tank mix, the indicated concentrations of Silwet L-77 reflect percentages by volume of the herbicide spray solution.

subsequent application, all pots remained in the greenhouse until ready for evaluation.

Twenty-three days after the initial application, all plants in the test were examined by a single practiced technician to evaluate percent inhibition, which is a visual measurement of the herbicidal effectiveness of the treatment by comparison with untreated plants. A percent inhibition of 0% indicates no effect, and a percent inhibition of 100% indicates that all of the specimens are completely dead. A percent inhibition of 85% or more is in most cases considered acceptable for normal herbicidal uses.

Treatments and corresponding percent inhibitions are given in Table 1. The percent inhibition data given in this and the other Examples herein are averages of all (in most cases three) replicates of each treatment.

TABLE 1

| Initial application 93 l/ha | | Glyphosate rate | Subsequent application 93 l/ha | % Inhibition |
|---|---|---|---|---|
| herbicide | accession agent | g a.e./ha | accession agent | ABUTH |
| Formulation A | none | 300 | none | 43 |
| Formulation A | none | 400 | none | 63 |
| Formulation A | none | 500 | none | 82 |
| Formulation A | none | 600 | none | 75 |
| Formulation A | none | 800 | none | 98 |
| Formulation A | none | 1000 | none | 99 |
| Formulation A | 5% glycerin + 0.25% L-77 | 300 | none | 14 |
| Formulation A | 5% glycerin + 0.25% L-77 | 400 | none | 10 |
| Formulation A | none | 300 | 5% glycerin + 0.25% L-77 at ~0.05 hr | 31 |
| Formulation A | none | 400 | 5% glycerin + 0.25% L-77 at ~0.05 hr | 44 |
| Formulation A | none | 300 | 5% glycerin + 0.25% L-77 at 1 hr | 30 |
| Formulation A | none | 400 | 5% glycerin + 0.25% L-77 at 1 hr | 53 |
| Formulation A | none | 300 | 5% glycerin + 0.25% L-77 at 3 hrs | 56 |
| Formulation A | none | 400 | 5% glycerin + 0.25% L-77 at 3 hrs | 69 |
| Formulation A | none | 300 | 5% glycerin + 0.25% L-77 at 6 hrs | 60 |
| Formulation A | none | 400 | 5% glycerin + 0.25% L-77 at 6 hrs | 54 |
| Formulation A | none | 300 | 5% glycerin + 0.25% L-77 at 24 hrs | 38 |
| Formulation A | none | 400 | 5% glycerin + 0.25% L-77 at 24 hrs | 61 |
| Formulation A | none | 300 | 5% glycerin + 0.25% L-77 at 1 and 3 hrs | 57 |
| Formulation A | none | 400 | 5% glycerin + 0.25% L-77 at 1 and 3 hrs | 71 |
| Formulation A | none | 300 | 5% glycerin + 0.25% L-77 at 1, 3 and 6 hrs | 56 |
| Formulation A | none | 400 | 5% glycerin + 0.25% L-77 at 1, 3 and 6 hrs | 82 |
| Formulation A | none | 300 | 5% glycerin + 0.25% L77 at 1, 3, 6 and 24 hrs | 69 |
| Formulation A | none | 400 | 5% glycerin + 0.25% L77 at 1, 3, 6 and 24 hrs | 74 |

When applied subsequently, the indicated concentrations of Silwet L-77 reflect percentages by volume of the candidate accession agent spray solution.

Except for pots subjected to the ~0.05 hour interval between initial and subsequent applications, pots were returned to the greenhouse between applications. After the The comparative tank mix treatments of this Example, employing an accession agent which is a combination of glycerin and Silwet L-77 in aqueous solution, were noticeably antagonistic to herbicidal effectiveness of glyphosate. This antagonism was reduced significantly when the same accession agent was applied sequentially following the glyphosate, instead of being included with the glyphosate in tank mix. Significant improvement in herbicidal effectiveness of glyphosate was found in treatments involving multiple sequential applications of the same accession agent. Glycerin has been used and proposed as a humectant material to improve tank mix performance of Silwet L-77.

Example 2

Velvetleaf (*Abutilon theophrasti*, ABUTH) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied in a spray volume of 93 l/ha at a pressure of 166 kPa, 22 days after planting. All subsequent applications in this Example were applied by spraying a candidate accession agent at a spray volume of 280 l/ha at a pressure of 166 kPa.

Formulation A was applied without candidate accession agent at a range of rates from 200 to 800 g a.e./ha. When a candidate accession agent was included in the treatment, either in tank mix with Formulation A or as a subsequent application, only the three lowest rates of Formulation A, 200, 300 and 400 g a.e./ha, were tested. This Example includes only one candidate accession agent, an aqueous solution containing 0.5% Silwet L-77. The time interval between initial and subsequent applications was about 0.05 hour or 4 hours.

Twenty-one days after the initial application, all plants in the test were examined by a single practiced technician to evaluate percent inhibition. Treatments and corresponding percent inhibitions are given in Table 2.

TABLE 2

| Initial application 93 l/ha | | Glyphosate rate | Subsequent application 280 l/ha | % Inhibition |
|---|---|---|---|---|
| herbicide | accession agent | g a.e./ha | agent | ABUTH |
| Formulation A | none | 200 | none | 0 |
| Formulation A | none | 300 | none | 13 |
| Formulation A | none | 400 | none | 40 |
| Formulation A | none | 500 | none | 50 |
| Formulation A | none | 600 | none | 55 |
| Formulation A | none | 800 | none | 75 |
| Formulation A | 0.5% L-77 | 200 | none | 49 |
| Formulation A | 0.5% L-77 | 300 | none | 48 |
| Formulation A | 0.5% L-77 | 400 | none | 61 |
| Formulation A | none | 200 | 0.5% L-77 at ~0.05 hr | 60 |
| Formulation A | none | 300 | 0.5% L-77 at ~0.05 hr | 73 |
| Formulation A | none | 400 | 0.5% L-77 at ~0.05 hr | 77 |
| Formulation A | none | 200 | 0.5% L-77 at 4 hrs | 66 |
| Formulation A | none | 300 | 0.5% L-77 at 4 hrs | 77 |
| Formulation A | none | 400 | 0.5% L-77 at 4 hrs | 78 |

Here, Silwet L-77 in tank mix formulation gave some enhancement of herbicidal effectiveness. Somewhat greater enhancement was obtained through sequential application of Silwet L-77.

Example 3

Prickly sida (*Sida spinosa*, SIDSP) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied 29 days after planting. Formulation A was applied without candidate accession agent at a range of rates from 300 to 1000 g a.e./ha. When a candidate accession agent was included in the treatment, either in tank mix with Formulation A or as a subsequent application, only the three lowest rates of Formulation A, 300, 400 and 500 g a.e./ha, were tested. This Example includes as candidate accession agent an aqueous solution containing 0.5% or 0.25% Silwet L-77. The time interval between initial and subsequent applications was varied from about 0.05 hour to 3 hours.

Twenty-three days after the initial application, all plants in the test were examined by a single practiced technician to evaluate percent inhibition. Treatments and corresponding percent inhibitions are given in Table 3.

TABLE 3

| Initial application 93 l/ha | | Glyphosate rate | Subsequent application 93 l/ha | % Inhibition |
|---|---|---|---|---|
| herbicide | accession agent | g a.e./ha | agent | SIDSP |
| Formulation A | none | 300 | none | 58 |
| Formulation A | none | 400 | none | 84 |
| Formulation A | none | 500 | none | 93 |
| Formulation A | none | 600 | none | 96 |
| Formulation A | none | 800 | none | 99 |
| Formulation A | none | 1000 | none | 100 |
| Formulation A | 0.5% L-77 | 300 | none | 44 |
| Formulation A | 0.5% L-77 | 400 | none | 74 |
| Formulation A | 0.5% L-77 | 500 | none | 84 |
| Formulation A | none | 300 | 0.5% L-77 at ~0.05 hr | 67 |
| Formulation A | none | 400 | 0.5% L-77 at ~0.05 hr | 66 |
| Formulation A | none | 500 | 0.5% L-77 at ~0.05 hr | 80 |
| Formulation A | none | 300 | 0.5% L-77 at 1 hr | 89 |
| Formulation A | none | 400 | 0.5% L-77 at 1 hr | 94 |
| Formulation A | none | 500 | 0.5% L-77 at 1 hr | 94 |
| Formulation A | none | 300 | 0.5% L-77 at 3 hrs | 76 |
| Formulation A | none | 400 | 0.5% L-77 at 3 hrs | 89 |
| Formulation A | none | 500 | 0.5% L-77 at 3 hrs | 90 |
| Formulation A | none | 300 | 0.25% L-77 at 1 hr | 74 |
| Formulation A | none | 400 | 0.25% L-77 at 1 hr | 77 |
| Formulation A | none | 500 | 0.25% L-77 at 1 hr | 82 |

Silwet L-77 in tank mix formulation was mildly antagonistic to the effectiveness of the herbicidal composition in prickly sida. This antagonism was overcome through sequential application after one and three hours, which gave significant improvement of effectiveness over the herbicidal composition applied without Silwet L-77, and applied with Silwet L-77 in tank mix.

Example 4

Morningglory (Ipomoea sp., IPOSS) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 29 days after planting. Formulations were each applied without candidate accession agent at a range of rates from 400 to 800 g a.e./ha. When a candidate accession agent was included in the treatment, either in tank mix or as a subsequent application, only the two lowest rates of each glyphosate formulation, 400 and 600 g a.e./ha, were tested. This Example includes as candidate accession agent an aqueous solution containing 0.5% Silwet L-77.

All subsequent applications in this Example were made by spraying the candidate accession agent with a track sprayer fitted as in Example 1 but calibrated to deliver a spray volume of 280 l/ha at a pressure of 166 kPa. The time interval between initial and subsequent applications was 1 hour.

Twenty-two days after the initial application, all plants in the test were examined by a single practiced technician to evaluate percent inhibition. Treatments and corresponding percent inhibitions are given in Table 4.

TABLE 4

| Initial application 93 l/ha | | Glyphosate | Subsequent application | % |
|---|---|---|---|---|
| herbicide | accession agent | rate g a.e./ha | 280 l/ha accession agent | Inhibition IPOSS |
| Formulation A | none | 400 | none | 47 |
| Formulation A | none | 600 | none | 85 |
| Formulation A | none | 800 | none | 85 |
| Formulation A | 0.5% L-77 | 400 | none | 63 |
| Formulation A | 0.5% L-77 | 600 | none | 70 |
| Formulation A | none | 400 | 0.5% L-77 at 1 hr | 91 |
| Formulation A | none | 600 | 0.5% L-77 at 1 hr | 95 |
| Formulation B | none | 400 | none | 13 |
| Formulation B | none | 600 | none | 69 |
| Formulation B | none | 800 | none | 70 |
| Formulation B | 0.5% L-77 | 400 | none | 72 |
| Formulation B | 0.5% L-77 | 600 | none | 87 |
| Formulation B | none | 400 | 0.5% L-77 at 1 hr | 91 |
| Formulation B | none | 600 | 0.5% L-77 at 1 hr | 94 |
| Formulation C | none | 400 | none | 62 |
| Formulation C | none | 600 | none | 87 |
| Formulation C | none | 800 | none | 96 |
| Formulation C | 0.5% L-77 | 400 | none | 81 |
| Formulation C | 0.5% L-77 | 600 | none | 83 |
| Formulation C | none | 400 | 0.5% L-77 at 1 hr | 89 |
| Formulation C | none | 600 | 0.5% L-77 at 1 hr | 100 |

Remarkable improvement (over the comparative tank mix treatment) in herbicidal effectiveness was achieved in this Example by applying the accession agent subsequent to the initial herbicide application for each of Formulation A, Formulation B and Formulation C.

Example 5

Russian thistle (*Salsola iberica*, SASKR) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

The experimental design included only two replicate pots per treatment. Initial applications of Formulation A, alone or in tank mix with a candidate accession agent, were applied 27 days after planting. Formulation A was applied without candidate accession agent at a range of rates from 200 to 800 g a.e./ha. When a candidate accession agent was included in the treatment, either in tank mix or as a subsequent application, the rates of Formulation A tested were 200, 300 and 400 g a.e./ha. This Example includes as candidate accession agent an aqueous solution containing 0.5% Silwet L-77. The time interval between initial and subsequent applications was varied from about 0.05 hour to 3 hours.

Twenty days after the initial application, all plants in the test were examined by a single practiced technician to evaluate percent inhibition. Treatments and corresponding percent inhibitions are given in Table 5.

TABLE 5

| Initial application 93 l/ha | | Glyphosate | Subsequent application | % Inihib- |
|---|---|---|---|---|
| herbicide | accession agent | rate g a.e./ha | 93 l/ha accession agent | ition SASKR |
| Formulation A | none | 200 | none | 15 |
| Formulation A | none | 300 | none | 69 |
| Formulation A | none | 400 | none | 86 |
| Formulation A | none | 500 | none | 93 |
| Formulation A | none | 600 | none | 100 |
| Formulation A | none | 800 | none | 100 |
| Formulation A | 0.5% L-77 | 200 | none | 50 |
| Formulation A | 0.5% L-77 | 300 | none | 37 |
| Formulation A | 0.5% L-77 | 400 | none | 78 |
| Formulation A | none | 200 | 0.5% L-77 at ~0.05 hr | 20 |
| Formulation A | none | 300 | 0.5% L-77 at ~0.05 hr | 55 |
| Formulation A | none | 400 | 0.5% L-77 at ~0.05 hr | 87 |
| Formulation A | none | 200 | 0.5% L-77 at 1 hr | 43 |
| Formulation A | none | 300 | 0.5% L-77 at 1 hr | 66 |
| Formulation A | none | 400 | 0.5% L-77 at 1 hr | 81 |
| Formulation A | none | 200 | 0.5% L-77 at 3 hrs | 31 |
| Formulation A | none | 300 | 0.5% L-77 at 3 hrs | 63 |
| Formulation A | none | 400 | 0.5% L-77 at 3 hrs | 74 |

Silwet L-77 enhanced the effectiveness of the herbicidal composition for russian thistle when added in tank mix. The enhancement was comparable to that achieved when Silwet L-77 was applied sequentially.

Example 6

Wild buckwheat (*Polygonum convolvulus*, POLCO) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied 24 days after planting. Formulation A was applied without candidate accession agent at a range of rates from 250 to 600 g a.e./ha. When a candidate accession agent was included in the treatment, either in tank mix or as a subsequent application, Formulation A was tested only at the lowest rate. This Example includes as candidate accession agents aqueous solutions containing Silwet L-77 at a range of concentrations from 0.25% to 1.5%. The time interval between initial and subsequent applications was varied from about 0.05 hour to 24 hours.

Fourteen days after the initial application, all plants in the test were examined by a single practiced technician to evaluate percent inhibition. Treatments and corresponding percent inhibitions are given in Table 6.

TABLE 6

| Initial application 93 l/ha | | Glyphosate rate | Subsequent application 93 l/ha | % Inhibition |
|---|---|---|---|---|
| herbicide | accession agent | g a.e./ha | accession agent | POLCO |
| Formulation A | none | 250 | none | 63 |
| Formulation A | none | 450 | none | 87 |
| Formulation A | none | 600 | none | 97 |
| Formulation A | 0.25% L-77 | 250 | none | 37 |
| Formulation A | 0.5% L-77 | 250 | none | 53 |
| Formulation A | 1.0% L-77 | 250 | none | 83 |
| Formulation A | 1.5% L-77 | 250 | none | 97 |
| Formulation A | none | 250 | 0.25% L-77 at ~0.05 hr | 35 |
| Formulation A | none | 250 | 0.5% L-77 at ~0.05 hr | 73 |
| Formulation A | none | 250 | 1.0% L-77 at ~0.05 hr | 86 |
| Formulation A | none | 250 | 1.5% L-77 at ~0.05 hr | 95 |
| Formulation A | none | 250 | 0.25% L-77 at 4 hrs | 33 |
| Formulation A | none | 250 | 0.5% L-77 at 4 hrs | 65 |
| Formulation A | none | 250 | 1.0% L-77 at 4 hrs | 71 |
| Formulation A | none | 250 | 1.5% L-77 at 4 hrs | 81 |
| Formulation A | none | 250 | 0.25% L-77 at 8 hrs | 48 |
| Formulation A | none | 250 | 0.5% L-77 at 8 hrs | 62 |
| Formulation A | none | 250 | 1.0% L-77 at 8 hrs | 53 |
| Formulation A | none | 250 | 1.5% L-77 at 8 hrs | 49 |
| Formulation A | none | 250 | 0.25% L-77 at 24 hrs | 38 |
| Formulation A | none | 250 | 0.5% L-77 at 24 hrs | 58 |
| Formulation A | none | 250 | 1.0% L-77 at 24 hrs | 48 |
| Formulation A | none | 250 | 1.5% L-77 at 24 hrs | 38 |

Silwet L-77 in tank mix enhanced the effectiveness of the herbicidal composition on wild buckwheat at higher concentrations of the accession agent, but was antagonistic for lower concentrations. The effect of sequential application was comparable, except for a loss of enhancement at higher Silwet L-77 concentrations (~1%) applied at later times (8 hours or more later).

Example 7

Yellow nutsedge (*Cyperus esculentus*, CYPES) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied 22 days after planting. Formulation A was applied without candidate accession agent at a range of rates from 1200 to 2000 g a.e./ha. When a candidate accession agent was included in the treatment, either in tank mix or as a subsequent application, Formulation A was tested only at the lowest rate. This Example includes as candidate accession agents aqueous solutions containing Silwet L-77 at a range of concentrations from 0.125% to 1.5%. The time interval between initial and subsequent applications was varied from about 0.05 hour to 24 hours.

Nineteen days after the initial application, all plants in the test were examined by a single practiced technician to evaluate percent inhibition. Treatments and corresponding percent inhibitions are given in Table 7.

TABLE 7

| Initial application 93 l/ha | | Glyphosate rate | Subsequent application 93 l/ha | % Inhibition |
|---|---|---|---|---|
| herbicide | accession agent | g a.e./ha | accession agent | CYPES |
| Formulation A | none | 1200 | none | 41 |
| Formulation A | none | 1600 | none | 96 |
| Formulation A | none | 2000 | none | 97 |
| Formulation A | 0.125% L-77 | 1200 | none | 70 |
| Formulation A | 0.25% L-77 | 1200 | none | 81 |
| Formulation A | 0.5% L-77 | 1200 | none | 92 |
| Formulation A | 1.0% L-77 | 1200 | none | 81 |
| Formulation A | 1.5% L-77 | 1200 | none | 74 |
| Formulation A | none | 1200 | 0.125% L-77 at ~0.05 hr | 73 |
| Formulation A | none | 1200 | 0.25% L-77 at ~0.05 hr | 87 |
| Formulation A | none | 1200 | 0.5% L-77 at ~0.05 hr | 86 |
| Formulation A | none | 1200 | 1.0% L-77 at ~0.05 hr | 89 |
| Formulation A | none | 1200 | 1.5% L-77 at ~0.05 hr | 86 |
| Formulation A | none | 1200 | 0.125% L-77 at 4 hrs | 59 |
| Formulation A | none | 1200 | 0.25% L-77 at 4 hrs | 79 |
| Formulation A | none | 1200 | 0.5% L-77 at 4 hrs | 89 |
| Formulation A | none | 1200 | 1.0% L-77 at 4 hrs | 88 |
| Formulation A | none | 1200 | 1.5% L-77 at 4 hrs | 69 |

TABLE 7-continued

| Initial application 93 l/ha | | Glyphosate rate | Subsequent application 93 l/ha | % Inhibition |
|---|---|---|---|---|
| herbicide | accession agent | g a.e./ha | accession agent | CYPES |
| Formulation A | none | 1200 | 0.125% L-77 at 8 hrs | 70 |
| Formulation A | none | 1200 | 0.25% L-77 at 8 hrs | 67 |
| Formulation A | none | 1200 | 0.5% L-77 at 8 hrs | 95 |
| Formulation A | none | 1200 | 1.0% L-77 at 8 hrs | 83 |
| Formulation A | none | 1200 | 1.5% L-77 at 8 hrs | 83 |
| Formulation A | none | 1200 | 0.125% L-77 at 24 hrs | 86 |
| Formulation A | none | 1200 | 0.25% L-77 at 24 hrs | 94 |
| Formulation A | none | 1200 | 0.5% L-77 at 24 hrs | 59 |
| Formulation A | none | 1200 | 1.0% L-77 at 24 hrs | 81 |
| Formulation A | none | 1200 | 1.5% L-77 at 24 hrs | 68 |

Silwet L-77 in tank mix significantly enhanced the effectiveness of the herbicidal composition on yellow nutsedge at all the tested accession agent concentrations. The effect of sequential application of the accession agent was generally comparable.

Example 8

Winter wheat (*Triticum aestivum*, TRZAW) plants were grown in pots, maintained in a greenhouse and treated with initial and subsequent applications by procedures exactly as described for Example 1, except where otherwise noted below.

Initial applications of Formulations B and C, alone or in tank mix with a candidate accession agent, were applied 14 days after planting. Formulations were each applied without candidate accession agent at a range of rates from 75 to 450 g a.e./ha. When a candidate accession agent was included in the treatment, either in tank mix or as a subsequent application, formulations were tested across the same range of rates. This Example includes as candidate accession agents aqueous solutions containing Silwet L-77 at a range of concentrations from 0.2% to 1.0%. The time interval between initial and subsequent applications was 4 or 8 hours.

Fourteen days after the initial application, all plants in the test were examined by a single practiced technician to evaluate percent inhibition. Treatments and corresponding percent inhibitions are given in Table 8.

TABLE 8

| Initial application 93 l/ha | | Glyphosate rate | Subsequent application 93 l/ha | % Inhibition |
|---|---|---|---|---|
| herbicide | accession agent | g a.e./ha | accession agent | TRZAW |
| Formulation B | none | 75 | none | 8 |
| Formulation B | none | 150 | none | 22 |
| Formulation B | none | 450 | none | 55 |
| Formulation B | 0.2% L-77 | 75 | none | 11 |
| Formulation B | 0.2% L-77 | 150 | none | 20 |
| Formulation B | 0.2% L-77 | 450 | none | 93 |
| Formulation B | none | 75 | 0.2% L-77 at 4 hrs | 13 |
| Formulation B | none | 150 | 0.2% L-77 at 4 hrs | 15 |
| Formulation B | none | 450 | 0.2% L-77 at 4 hrs | 45 |
| Formulation B | none | 75 | 0.2% L-77 at 8 hrs | 30 |
| Formulation B | none | 150 | 0.2% L-77 at 8 hrs | 18 |
| Formulation B | none | 450 | 0.2% L-77 at 8 hrs | 56 |
| Formulation B | 0.5% L-77 | 75 | none | 62 |
| Formulation B | 0.5% L-77 | 150 | none | 44 |
| Formulation B | 0.5% L-77 | 450 | none | 68 |
| Formulation B | none | 75 | 0.5% L-77 at 4 hrs | 37 |
| Formulation B | none | 150 | 0.5% L-77 at 4 hrs | 21 |
| Formulation B | none | 450 | 0.5% L-77 at 4 hrs | 67 |
| Formulation B | none | 75 | 0.5% L-77 at 8 hrs | 30 |
| Formulation B | none | 150 | 0.5% L-77 at 8 hrs | 33 |
| Formulation B | none | 450 | 0.5% L-77 at 8 hrs | 67 |
| Formulation B | 1.0% L-77 | 75 | none | 56 |
| Formulation B | 1.0% L-77 | 150 | none | 83 |
| Formulation B | 1.0% L-77 | 450 | none | 100 |
| Formulation B | none | 75 | 1.0% L-77 at 4 hrs | 15 |
| Formulation B | none | 150 | 1.0% L-77 at 4 hrs | 38 |
| Formulation B | none | 450 | 1.0% L-77 at 4 hrs | 69 |
| Formulation B | none | 75 | 1.0% L-77 at 8 hrs | 34 |
| Formulation B | none | 150 | 1.0% L-77 at 8 hrs | 34 |
| Formulation B | none | 450 | 1.0% L-77 at 8 hrs | 59 |
| Formulation C | none | 75 | none | 76 |
| Formulation C | none | 150 | none | 93 |
| Formulation C | none | 450 | none | 100 |
| Formulation C | 0.2% L-77 | 75 | none | 44 |
| Formulation C | 0.2% L-77 | 150 | none | 53 |
| Formulation C | 0.2% L-77 | 450 | none | 98 |
| Formulation C | none | 75 | 0.2% L-77 at 4 hrs | 58 |
| Formulation C | none | 150 | 0.2% L-77 at 4 hrs | 78 |
| Formulation C | none | 450 | 0.2% L-77 at 4 hrs | 99 |
| Formulation C | none | 75 | 0.2% L-77 at 8 hrs | 58 |
| Formulation C | none | 150 | 0.2% L-77 at 8 hrs | 77 |
| Formulation C | none | 450 | 0.2% L-77 at 8 hrs | 97 |
| Formulation C | 0.5% L-77 | 75 | none | 27 |
| Formulation C | 0.5% L-77 | 150 | none | 48 |
| Formulation C | 0.5% L-77 | 450 | none | 98 |
| Formulation C | none | 75 | 0.5% L-77 at 4 hrs | 66 |
| Formulation C | none | 150 | 0.5% L-77 at 4 hrs | 94 |
| Formulation C | none | 450 | 0.5% L-77 at 4 hrs | 99 |
| Formulation C | none | 75 | 0.5% L-77 at 8 hrs | 66 |
| Formulation C | none | 150 | 0.5% L-77 at 8 hrs | 85 |
| Formulation C | none | 450 | 0.5% L-77 at 8 hrs | 99 |
| Formulation C | 1.0% L-77 | 75 | none | 49 |
| Formulation C | 1.0% L-77 | 150 | none | 64 |
| Formulation C | 1.0% L-77 | 450 | none | 99 |
| Formulation C | none | 75 | 1.0% L-77 at 4 hrs | 71 |
| Formulation C | none | 150 | 1.0% L-77 at 4 hrs | 88 |
| Formulation C | none | 450 | 1.0% L-77 at 4 hrs | 97 |
| Formulation C | none | 75 | 1.0% L-77 at 8 hrs | 66 |
| Formulation C | none | 150 | 1.0% L-77 at 8 hrs | 81 |
| Formulation C | none | 450 | 1.0% L-77 at 8 hrs | 100 |

The greatest improvement of herbicidal effectiveness through sequential application of an accession agent in this Example was in the case of Formulation C, which includes a polyethoxylated tallowamine based surfactant, unlike Formulation B, which contains no surfactant.

Example 9

Soybean (*Glycine max*, GLXMA) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied 18 days after planting. Formulation A was applied without candidate accession agent at a range of rates from 250 to 800 g a.c./ha. When a candidate accession agent was included in the treatment, either in tank mix or as a subsequent application, Formulation A was tested only at the lowest rate. This Example includes as candidate accession agents aqueous solutions containing Silwet L-77 at a range of concentrations from 0.125% to 1.0%. The time interval between initial and subsequent applications was varied from about 0.05 to 24 hours.

Sixteen days after the initial application, all plants in the test were examined by a single practiced technician to evaluate percent inhibition. Treatments and corresponding percent inhibitions are given in Table 9.

described for Example 1, except where otherwise noted below. Greenhouse temperature was maintained at approximately 21° C. during the day and 16° C. during the night.

The experimental design included only two replicate pots per treatment. Initial applications of Formulation A, alone or in tank mix with a candidate accession agent, were applied 26 days after planting. Formulation A was applied without candidate accession agent at a range of rates from 100 to 800 g a.e./ha. When a candidate accession agent was included in the treatment, either in tank mix or as a subsequent application, Formulation A was tested only at 100, 200 and 300 g a.e./ha. This Example includes as candidate accession agent an aqueous solution containing 0.5% Silwet L-77. The time interval between initial and subsequent applications was varied from about 0.05 to 3 hours.

Twenty days after the initial application, all plants in the test were examined by a single practiced technician to evaluate percent inhibition. Treatments and corresponding percent inhibitions are given in Table 10.

TABLE 9

| Initial application 93 l/ha | | Glyphosate rate | Subsequent application 93 l/ha | % Inhibition |
|---|---|---|---|---|
| herbicide | accession agent | g a.e./ha | accession agent | GLXMA |
| Formulation A | none | 250 | none | 72 |
| Formulation A | none | 500 | none | 93 |
| Formulation A | none | 800 | none | 94 |
| Formulation A | 0.125% L-77 | 250 | none | 45 |
| Formulation A | 0.25% L-77 | 250 | none | 44 |
| Formulation A | 0.5% L-77 | 250 | none | 45 |
| Formulation A | 1.0% L-77 | 250 | none | 61 |
| Formulation A | none | 250 | 0.125% L-77 at ~0.05 hr | 74 |
| Formulation A | none | 250 | 0.25% L-77 at ~0.05 hr | 59 |
| Formulation A | none | 250 | 0.5% L-77 at ~0.05 hr | 60 |
| Formulation A | none | 250 | 1.0% L-77 at ~0.05 hr | 46 |
| Formulation A | none | 250 | 0.125% L-77 at 4 hrs | 76 |
| Formulation A | none | 250 | 0.25% L-77 at 4 hrs | 74 |
| Formulation A | none | 250 | 0.5% L-77 at 4 hrs | 67 |
| Formulation A | none | 250 | 1.0% L-77 at 4 hrs | 70 |
| Formulation A | none | 250 | 0.125% L-77 at 8 hrs | 71 |
| Formulation A | none | 250 | 0.25% L-77 at 8 hrs | 62 |
| Formulation A | none | 250 | 0.5% L-77 at 8 hrs | 67 |
| Formulation A | none | 250 | 1.0% L-77 at 8 hrs | 67 |
| Formulation A | none | 250 | 0.125% L-77 at 24 hrs | 75 |
| Formulation A | none | 250 | 0.25% L-77 at 24 hrs | 75 |
| Formulation A | none | 250 | 0.5% L-77 at 24 hrs | 69 |
| Formulation A | none | 250 | 1.0% L-77 at 24 hrs | 66 |

Silwet L-77 in tank mix was strongly antagonistic to the effectiveness of the herbicidal composition in soybean. This antagonism was overcome through sequential application after four hours.

Example 10

Downy brome (*Bromus tectorum*, BROTE) and annual ryegrass (*Lolium multiflorum*, LOLMG) plants were grown in pots, maintained in a greenhouse and treated with initial and subsequent applications by procedures exactly as

TABLE 10

| Initial application 93 l/ha | | Glyphosate rate | Subsequent application 93 l/ha | % Inhibition | |
|---|---|---|---|---|---|
| herbicide | accession agent | g a.e./ ha | accession agent 0.5% L-77 | BROTE | LOLMG |
| Formulation A | none | 100 | none | 35 | 17 |
| Formulation A | none | 200 | none | 64 | 60 |
| Formulation A | none | 300 | none | 83 | 85 |

TABLE 10-continued

| Initial application 93 l/ha | | Glyphosate rate | Subsequent application 93 l/ha accession | % Inhibition | |
|---|---|---|---|---|---|
| herbicide | accession agent | g a.e./ ha | agent 0.5% L-77 | BROTE | LOLMG |
| Formulation A | none | 400 | none | 71 | 83 |
| Formulation A | none | 500 | none | 94 | 100 |
| Formulation A | none | 600 | none | 94 | 100 |
| Formulation A | none | 800 | none | 100 | 100 |
| Formulation A | 0.5% L-77 | 100 | none | 3 | 0 |
| Formulation A | 0.5% L-77 | 200 | none | 18 | 38 |
| Formulation A | 0.5% L-77 | 300 | none | 45 | 55 |
| Formulation A | none | 100 | at ~0.05 hr | 30 | 18 |
| Formulation A | none | 200 | at ~0.05 hr | 68 | 70 |
| Formulation A | none | 300 | at ~0.05 hr | 78 | 92 |
| Formulation A | none | 100 | at 1 hr | 38 | 42 |
| Formulation A | none | 200 | at 1 hr | 65 | 82 |
| Formulation A | none | 300 | at 1 hr | 79 | 85 |
| Formulation A | none | 100 | at 3 hrs | 53 | 85 |
| Formulation A | none | 200 | at 3 hrs | 81 | 80 |
| Formulation A | none | 300 | at 3 hrs | 97 | 90 |

The data in Table 10 show better herbicidal results in the sequential process of this invention than in the comparative tank mix treatment as applied to both downy brome and annual ryegrass. Substantial tank mix antagonism was eliminated or reversed, with the best results for application of the Silwet L-77 accession agent obtained three hours after application of the herbicide.

Example 11

Velvetleaf (*Abutilon theophrasti*, ABUTH) and Japanese millet, a form of barnyardgrass (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, alone or in tank mix with a candidate accession agent, were applied on the same day, 19 days after planting velvetleaf and 14 days after planting Japanese millet. Formulations were applied without candidate accession agent at a range of rates from 200 to 600 g a.e./ha. When a candidate accession agent was included in the treatment, either in tank mix or as a subsequent application, formulations were tested only at the lowest rate. This Example includes as candidate accession agent an aqueous solution containing 0.5% Silwet L-77. The time interval between initial and subsequent applications was 4 hours.

Nineteen days after the initial application, all plants in the test were examined by a single practiced technician to evaluate percent inhibition. Treatments and corresponding percent inhibitions are given in Table 11.

TABLE 11

| Initial application 93 l/ha | | Glyphosate rate | Subsequent application 93 l/ha accession | % Inhibition | |
|---|---|---|---|---|---|
| herbicide | accession agent | g a.e./ ha | agent 0.5% L-77 | ABUTH | ECHCF |
| Formulation A | none | 200 | none | 40 | 79 |
| Formulation A | none | 300 | none | 71 | 100 |
| Formulation A | none | 400 | none | 89 | 100 |
| Formulation A | none | 600 | none | 97 | 100 |
| Formulation A | 0.5% L-77 | 200 | none | 84 | 16 |
| Formulation A | none | 200 | at 4 hrs | 83 | 77 |
| Formulation B | none | 200 | none | 12 | 57 |
| Formulation B | none | 300 | none | 22 | 52 |
| Formulation B | none | 400 | none | 60 | 55 |
| Formulation B | none | 600 | none | 67 | 89 |
| Formulation B | 0.5% L-77 | 200 | none | 87 | 12 |
| Formulation B | none | 200 | at 4 hrs | 86 | 16 |

The data in Table 11 show, in the case of Formulation A, strong enhancement of velvetleaf control by glyphosate when Silwet L-77 is added in tank mix. At the same time, the data show serious antagonism of Japanese millet control with the same tank mix treatment. This is a dramatic illustration of the major problem of using the prior art method wherein an accession agent is tank mixed or coformulated with a glyphosate herbicide. Attempts to gain enhancement on one species, in this Example velvetleaf, were confounded by the resulting antagonism on another species, in this Example Japanese millet. It will be noted that the method of the present invention, where the accession agent was applied sequentially 4 hours after application of the glyphosate herbicide, gave enhancement of velvetleaf control equal to that provided by the tank mix, yet eliminated the antagonism of Japanese millet control seen with the tank mix treatment.

In this Example, antagonism was not overcome by sequential application of accession agent after Formulation B. As noted above, Formulation B contains no surfactant.

Example 12

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, and of glyphosate acid, alone or in tank mix with a candidate accession agent, were applied on the same day, 17 days after planting velvetleaf and 20 days after planting Japanese millet. Glyphosate acid was not prepared as a concentrate formulation but was simply dissolved in water to make the dilute spray solutions of this Example. Formulations and glyphosate acid were applied without candidate accession agent at a range of rates from 250 to 800 g a.e./ha. When a candidate accession agent was included in the treatment, either in tank mix or as a subsequent application, formulations were tested only at 250 and 500 g a.e./ha. This Example includes as candidate accession agent an aqueous solution containing 0.5% Silwet L-77. Initial applications were made in a spray volume of 93 l/ha, and subsequent applications in a spray volume of 280 l/ha. The time interval between initial and subsequent applications was 4 hours.

Twenty days after the initial application, all plants in the test were examined by a single practiced technician to evaluate percent inhibition. Treatments and corresponding percent inhibitions are given in Table 12.

TABLE 12

| Initial application 93 l/ha | | Glyphosate rate | Subsequent application 93 l/ha accession | % Inhibition | |
|---|---|---|---|---|---|
| herbicide | accession agent | g a.e./ ha | agent 0.5% L-77 | ABUTH | ECHCF |
| Formulation A | none | 250 | none | 39 | 85 |
| Formulation A | none | 500 | none | 67 | 85 |
| Formulation A | none | 800 | none | 88 | 100 |
| Formulation A | 0.5% L-77 | 250 | none | 65 | 40 |
| Formulation A | 0.5% L-77 | 500 | none | 89 | 21 |
| Formulation A | none | 250 | at 4 hrs | 89 | 46 |
| Formulation A | none | 500 | at 4 hrs | 92 | 57 |
| Formulation B | none | 250 | none | 13 | 24 |
| Formulation B | none | 500 | none | 39 | 77 |
| Formulation B | none | 800 | none | 53 | 93 |
| Formulation B | 0.5% L-77 | 250 | none | 76 | 25 |
| Formulation B | 0.5% L-77 | 500 | none | 92 | 49 |
| Formulation B | none | 250 | at 4 hrs | 77 | 28 |
| Formulation B | none | 500 | at 4 hrs | 89 | 21 |
| glyphosate acid | none | 250 | none | 17 | 7 |
| glyphosate acid | none | 500 | none | 7 | 10 |
| glyphosate acid | none | 800 | none | 18 | 17 |
| glyphosate acid | 0.5% L-77 | 250 | none | 64 | 12 |
| glyphosate acid | 0.5% L-77 | 500 | none | 42 | 23 |
| glyphosate acid | none | 250 | at 4 hrs | 78 | 7 |
| glyphosate acid | none | 500 | at 4 hrs | 84 | 21 |

The data for glyphosate acid in this Example show an unusually low level of inhibition, especially on barnyardgrass. It is possible that the glyphosate acid was not fully dissolved in the spray solution at the time of spraying.

Example 13

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A, alone or in tank mix with a candidate accession agent, were applied on the same day, 13 days after planting velvetleaf and 16 days after planting Japanese millet. Formulation A was applied without candidate accession agent at a range of rates from 200 to 500 g a.e./ha. When a candidate accession agent was included in the treatment, either in tank mix or as a subsequent application, Formulation A was tested only at the lowest rate.

Three different spray volumes were used for initial and subsequent applications. In one set of treatments, the initial spray volume was 93 l/ha; in a second set of treatments 47 l/ha; and in a third set of treatments 28 l/ha. For each initial spray volume, three subsequent application spray volumes were tested, again 93, 47 and 28 l/ha. Candidate accession agents in this Example were aqueous solutions containing Silwet L-77. For each spray volume tested, three Silwet L-77 concentrations were used. These were set in such a way as to provide approximately equal dosage rates (200, 300 and 600 g/ha) of Silwet L-77 across different spray volumes. The time interval between initial and subsequent applications was 4 hours.

Twenty days after the initial application, all plants in the test were examined by a single practiced technician to evaluate percent inhibition. Treatments and corresponding percent inhibitions are given in Tables 13a, 13b and 13c. Each table relates to one initial application spray volume.

TABLE 13a

| Initial application 93 l/ha | | Glyphosate rate | Subsequent application at 4 hrs accession agent, | % Inhibition | |
|---|---|---|---|---|---|
| herbicide | accession agent | g a.e./ ha | spray volume | ABUTH | ECHCF |
| Formulation A | none | 200 | none | 98 | 96 |
| Formulation A | none | 300 | none | 96 | 100 |
| Formulation A | none | 500 | none | 100 | 100 |
| Formulation A | 0.21% L-77 | 200 | none | 79 | 33 |
| Formulation A | 0.31% L-77 | 200 | none | 96 | 22 |
| Formulation A | 0.63% L-77 | 200 | none | 98 | 25 |
| Formulation A | none | 200 | 0.21% L-77, 93 l/ha | 93 | 94 |
| Formulation A | none | 200 | 0.31% L-77, 93 l/ha | 93 | 99 |
| Formulation A | none | 200 | 0.63% L-77, 93 l/ha | 97 | 99 |
| Formulation A | none | 200 | 0.42% L-77, 47 l/ha | 86 | 98 |
| Formulation A | none | 200 | 0.63% L-77, 47 l/ha | 95 | 96 |
| Formulation A | none | 200 | 1.25% L-77, 47 l/ha | 86 | 91 |
| Formulation A | none | 200 | 0.64% L-77, 28 l/ha | 87 | 99 |
| Formulation A | none | 200 | 0.98% L-77, 28 l/ha | 86 | 100 |
| Formulation A | none | 200 | 1.95% L-77, 28 l/ha | 75 | 96 |

TABLE 13b

| Initial application 47 l/ha | | Glyphosate rate | Subsequent application at 4 hrs accession agent, | % Inhibition | |
|---|---|---|---|---|---|
| herbicide | accession agent | g a.e./ ha | spray volume | ABUTH | ECHCF |
| Formulation A | none | 200 | none | 95 | 100 |
| Formulation A | none | 300 | none | 100 | 96 |
| Formulation A | none | 200 | none | 95 | 100 |
| Formulation A | none | 300 | none | 100 | 96 |
| Formulation A | none | 500 | none | 100 | 100 |
| Formulation A | 0.21% L-77 | 200 | none | 80 | 76 |
| Formulation A | 0.31% L-77 | 200 | none | 93 | 55 |
| Formulation A | 0.63% L-77 | 200 | none | 95 | 49 |
| Formulation A | none | 200 | 0.21% L-77, 93 l/ha | 93 | 96 |
| Formulation A | none | 200 | 0.31% L-77, 93 l/ha | 95 | 97 |
| Formulation A | none | 200 | 0.63% L-77, 93 l/ha | 91 | 99 |
| Formulation A | none | 200 | 0.42% L-77, 47 l/ha | 98 | 100 |

TABLE 13b-continued

| Initial application 47 l/ha | | Glyphosate rate | Subsequent application at 4 hrs accession agent, | % Inhibition | |
|---|---|---|---|---|---|
| herbicide | accession agent | g a.e./ ha | spray volume | ABUTH | ECHCF |
| Formulation A | none | 200 | 0.63% L-77, 47 l/ha | 97 | 98 |
| Formulation A | none | 200 | 1.25% L-77, 47 l/ha | 95 | 95 |
| Formulation A | none | 200 | 0.64% L-77, 28 l/ha | 92 | 95 |
| Formulation A | none | 200 | 0.98% L-77, 28 l/ha | 94 | 98 |
| Formulation A | none | 200 | 1.95% L-77, l/ha | 93 | 100 |

TABLE 13c

| Initial application 28 l/ha | | Glyphosate rate | Subsequent application at 4 hrs accession agent, | % Inhibition | |
|---|---|---|---|---|---|
| herbicide | accession agent | g a.e./ ha | spray volume | ABUTH | ECHCF |
| Formulation A | none | 200 | none | 99 | 100 |
| Formulation A | none | 300 | none | 100 | 100 |
| Formulation A | none | 500 | none | 100 | 100 |
| Formulation A | 0.21% L-77 | 200 | none | 100 | 85 |
| Formulation A | 0.31% L-77 | 200 | none | 99 | 62 |
| Formulation A | 0.63% L-77 | 200 | none | 96 | 85 |
| Formulation A | none | 200 | 0.21%L-77, 93 l/ha | 95 | 99 |
| Formulation A | none | 200 | 0.31% L-77, 93 l/ha | 96 | 98 |
| Formulation A | none | 200 | 0.63% L-77, 93 l/ha | 98 | 100 |
| Formulation A | none | 200 | 0.42% L-77, 47 l/ha | 91 | 95 |
| Formulation A | none | 200 | 0.63% L-77, 47 l/ha | 99 | 100 |
| Formulation A | none | 200 | 1.25% L-77, 47 l/ha | 95 | 98 |
| Formulation A | none | 200 | 0.64% L-77, 28 l/ha | 92 | 90 |
| Formulation A | none | 200 | 0.98% L-77, 28 l/ha | 80 | 93 |
| Formulation A | none | 200 | 1.95% L-77, 28 l/ha | 71 | 92 |

Silwet L-77 in tank mix was most antagonistic to glyphosate on Japanese millet when spray volume was high; however at all spray volumes and Silwet L-77 concentrations tested the antagonism was reduced or eliminated by sequential application of Silwet L-77 after glyphosate.

Example 14

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation A, alone or in tank mix with a candidate accession agent, were applied on the same day, 15 days after planting velvetleaf and 17 days after planting Japanese millet. Formulation A was applied without candidate accession agent at a range of rates from 150 to 750 g a.e./ha. When a candidate accession agent was included in the treatment, either in tank mix or as a subsequent application, Formulation A was tested at a range of rates from 150 to 550 g a.e./ha. This Example includes as candidate accession agent an aqueous solution containing 0.5% Silwet L-77. The time interval between initial and subsequent applications was varied from about 0.05 to 24 hours.

Nineteen days after the initial application, all plants in the test were examined by a single practiced technician to evaluate percent inhibition. Treatments and corresponding percent inhibitions are given in Table 14.

TABLE 14

| Initial application 93 l/ha | | Glyphosate rate | Subsequent application 93 l/ha accession | % Inhibition | |
|---|---|---|---|---|---|
| herbicide | accession agent | g a.e./ ha | 0.5% L-77 | ABUTH | ECHCF |
| Formulation A | none | 150 | none | 6 | 78 |
| Formulation A | none | 250 | none | 49 | 100 |
| Formulation A | none | 350 | none | 67 | 100 |
| Formulation A | none | 550 | none | 90 | 100 |
| Formulation A | none | 750 | none | 100 | 100 |
| Formulation A | 0.5% L-77 | 150 | none | 51 | 7 |
| Formulation A | 0.5% L-77 | 250 | none | 68 | 9 |
| Formulation A | 0.5% L-77 | 350 | none | 80 | 10 |
| Formulation A | 0.5% L-77 | 550 | none | 94 | 35 |
| Formulation A | none | 150 | at ~0.05 hr | 51 | 13 |
| Formulation A | none | 250 | at ~0.05 hr | 63 | 75 |
| Formulation A | none | 350 | at ~0.05 hr | 84 | 72 |
| Formulation A | none | 550 | at ~0.05 hr | 92 | 97 |
| Formulation A | none | 150 | at 4 hrs | 58 | 59 |
| Formulation A | none | 250 | at 4 hrs | 79 | 91 |
| Formulation A | none | 350 | at 4 hrs | 82 | 90 |
| Formulation A | none | 550 | at 4 hrs | 92 | 95 |
| Formulation A | none | 150 | at 8 hrs | 56 | 52 |
| Formulation A | none | 250 | at 8 hrs | 79 | 59 |
| Formulation A | none | 350 | at 8 hrs | 84 | 79 |
| Formulation A | none | 550 | at 8 hrs | 96 | 98 |
| Formulation A | none | 150 | at 24 hrs | 69 | 42 |
| Formulation A | none | 250 | at 24 hrs | 84 | 79 |
| Formulation A | none | 350 | at 24 hrs | 96 | 79 |
| Formulation A | none | 550 | at 24 hrs | 100 | 97 |

Very severe antagonism was noted when Silwet L-77 was applied in tank mix with glyphosate on Japanese millet. Applying the Silwet L-77 as a sequential application after the glyphosate greatly reduced the antagonism, even when the delay between glyphosate and Silwet L-77 applications was as short as about 0.05 hour (3 minutes). However, greater reduction in antagonism was seen when the delay was longer. The most effective interval in this test was 4 hours.

Example 15

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, alone or in tank mix with a candidate accession agent, were applied on the same day, 17 days after planting velvetleaf and 19 days after planting Japanese millet. Formulations were applied without candidate accession agent at a range of rates from 350 to 850 g a.e./ha. When a candidate accession agent was included in the treatment, either in tank mix or as a subsequent application, formulations were tested only at the lowest rate. This Example includes as candidate accession agents aqueous solutions containing Fluorad FC-98 or Fluorad FC-99 at a range of concentrations from 0.03% to 0.48%. Fluorad FC-98 and Fluorad FC-99 are perfluoroalkyl sulfonate surfactants, with potassium and amine counterions respectively, of 3M Company and are abbreviated in tables herein by omission of the 'Fluorad' trademark. The time interval between initial and subsequent applications was 4 hours.

Fifteen days after the initial application, all plants in the test were examined by a single practiced technician to evaluate percent inhibition. Treatments and corresponding percent inhibitions are given in Table 15.

TABLE 15

| Initial application 93 l/ha | | Glyphosate rate | Subsequent application 93 l/ha accession | % Inhibition | |
|---|---|---|---|---|---|
| herbicide | accession agent | g a.e./ ha | agent 0.5% L-77 | ABUTH | ECHCF |
| Formulation A | none | 350 | none | 48 | 58 |
| Formulation A | none | 450 | none | 57 | 83 |
| Formulation A | none | 550 | none | 68 | 97 |
| Formulation A | none | 650 | none | 77 | 99 |
| Formulation A | none | 850 | none | 87 | 99 |
| Formulation A | 0.03% FC-98 | 350 | none | 42 | 33 |
| Formulation A | 0.06% FC-98 | 350 | none | 28 | 22 |
| Formulation A | 0.12% FC-98 | 350 | none | 25 | 22 |
| Formulation A | 0.24% FC-98 | 350 | none | 33 | 28 |
| Formulation A | 0.48% FC-98 | 350 | none | 22 | 27 |
| Formulation A | none | 350 | 0.03% FC-98 | 57 | 43 |
| Formulation A | none | 350 | 0.06% FC-98 | 53 | 63 |
| Formulation A | none | 350 | 0.12% FC-98 | 42 | 65 |
| Formulation A | none | 350 | 0.24% FC-98 | 40 | 57 |
| Formulation A | none | 350 | 0.48% FC-98 | 37 | 77 |
| Formulation A | 0.03% FC-99 | 350 | none | 27 | 30 |
| Formulation A | 0.06% FC-99 | 350 | none | 22 | 22 |
| Formulation A | 0.12% FC-99 | 350 | none | 22 | 10 |
| Formulation A | 0.24% FC-99 | 350 | none | 28 | 10 |
| Formulation A | 0.48% FC-99 | 350 | none | 42 | 10 |
| Formulation A | none | 350 | 0.03% FC-99 | 47 | 80 |
| Formulation A | none | 350 | 0.06% FC-99 | 48 | 88 |
| Formulation A | none | 350 | 0.12% FC-99 | 45 | 67 |
| Formulation A | none | 350 | 0.24% FC-99 | 40 | 67 |
| Formulation A | none | 350 | 0.48% FC-99 | 48 | 68 |
| Formulation B | none | 350 | none | 27 | 28 |
| Formulation B | none | 450 | none | 30 | 32 |
| Formulation B | none | 550 | none | 42 | 33 |
| Formulation B | none | 650 | none | 60 | 37 |
| Formulation B | none | 850 | none | 68 | 40 |
| Formulation B | 0.03% FC-98 | 350 | none | 22 | 22 |
| Formulation B | 0.06% FC-98 | 350 | none | 20 | 20 |
| Formulation B | 0.12% FC-98 | 350 | none | 22 | 30 |
| Formulation B | 0.24% FC-98 | 350 | none | 27 | 30 |
| Formulation B | 0.48% FC-98 | 350 | none | 37 | 25 |
| Formulation B | none | 350 | 0.03% FC-98 | 27 | 38 |
| Formulation B | none | 350 | 0.06% FC-98 | 30 | 38 |
| Formulation B | none | 350 | 0.12% FC-98 | 28 | 35 |
| Formulation B | none | 350 | 0.24% FC-98 | 32 | 30 |
| Formulation B | none | 350 | 0.48% FC-98 | 33 | 68 |
| Formulation B | 0.03% FC-99 | 350 | none | 25 | 22 |
| Formulation B | 0.06% FC-99 | 350 | none | 27 | 22 |
| Formulation B | 0.12% FC-99 | 350 | none | 30 | 25 |
| Formulation B | 0.24% FC-99 | 350 | none | 42 | 15 |
| Formulation B | 0.48% FC-99 | 350 | none | 58 | 12 |
| Formulation B | none | 350 | 0.03% FC-99 | 27 | 48 |
| Formulation B | none | 350 | 0.06% FC-99 | 32 | 57 |
| Formulation B | none | 350 | 0.12% FC-99 | 27 | 45 |
| Formulation B | none | 350 | 0.24% FC-99 | 25 | 37 |
| Formulation B | none | 350 | 0.48% FC-99 | 35 | 32 |

For the herbicidal compositions containing a surfactant coformulant, the Fluorad FC-98 and Fluorad FC-99 surfactants in tank mix were significantly antagonistic to the effectiveness of the herbicidal composition in Japanese millet, and somewhat less antagonistic in velvetleaf. This antagonism was overcome through sequential application, which (in some cases, especially in Japanese millet) gave significant improvement of effectiveness over the herbicidal composition applied without Fluorad FC-98 or Fluorad FC-99. For the herbicidal composition (Formulation B) which does not contain a surfactant coformulant, antagonism was less pronounced, but sequential application of accession agent generally gave some improvement of effectiveness over comparable tank mix application.

Example 16

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, alone or in tank mix with a candidate accession agent, were applied on the same day, 18 days after planting velvetleaf and 20 days after planting Japanese millet. Formulation B was applied without candidate accession agent at a range of rates from 350 to 650 g a.e./ha. When a candidate accession agent was included in the treatment, either in tank mix or as a subsequent application, Formulation B was tested only at the lowest rate. This Example includes several candidate accession agents, all aqueous solutions of surfactants or of surfactant blends at a total surfactant concentration of 0.125% or 0.5%. The time interval between initial and subsequent applications was 4 hours.

Surfactants in the candidate accession agents of this Example included Silwet L-77, Fluorad FC-98 and Fluorad FC-135, a product of 3M Company disclosed in McCutcheon's Emulsifiers and Detergents, North American Edition, 1994 (hereinafter, McCutcheon's), as fluorinated alkyl quaternary ammonium iodides. Other surfactants used in this Example included the following:

Surfynol 465 of Air Products and Chemicals, Inc.: disclosed in McCutcheon's (loc. cit.) as ethoxylated tetramethyl decynediol, abbreviated in tables herein as 'Surf 465'.

Agrimul PG 2069 of Henkel Corporation: disclosed in Henkel Technical Bulletin 105B, 1993, as a composition containing 50% alkyl polyglucoside, abbreviated in tables herein as 'PG 2069'. A newsletter from Henkel dated July 1996 and titled "Solutions in the field: Agrimul PG surfactants" discloses that Agrimul PG 2069 has a C9–11 alkyl chain and that its degree of polymerization (moles glucose per mole surfactant) is 1.6.

Silamine C-100 of Siltech Inc.: abbreviated in tables herein as 'Silamine'.

Seventeen days after the initial application, all plants in the test were examined by a single practiced technician to evaluate percent inhibition. Treatments and corresponding percent inhibitions are given in Table 16.

TABLE 16

| Initial application 93 l/ha | | Glyphosate rate g a.e./ ha | Subsequent application 93 l/ha, at 4 hrs | % Inhibition | |
|---|---|---|---|---|---|
| herbicide | accession agent | | accession agent | ABUTH | ECHCF |
| Formulation B | none | 350 | none | 51 | 24 |
| Formulation B | none | 450 | none | 68 | 25 |
| Formulation B | none | 650 | none | 77 | 66 |
| Formulation B | 0.125% L-77 | 350 | none | 29 | 5 |
| Formulation B | 0.5% L-77 | 350 | none | 87 | 0 |
| Formulation B | none | 350 | 0.125% L-77 | 36 | 29 |
| Formulation B | none | 350 | 0.5% L-77 | nodata | 29 |
| Formulation B | 0.125% FC-98 | 350 | none | 43 | 11 |
| Formulation B | 0.5% FC-98 | 350 | none | 55 | 12 |
| Formulation B | none | 350 | 0.125% FC-98 | 44 | 25 |
| Formulation B | none | 350 | 0.5% FC-98 | 67 | 20 |
| Formulation B | 0.125% FC-135 | 350 | none | 68 | 35 |
| Formulation B | 0.5% FC-135 | 350 | none | 80 | 75 |
| Formulation B | none | 350 | 0.125% FC-135 | 77 | 24 |
| Formulation B | none | 350 | 0.5% FC-135 | 64 | 29 |
| Formulation B | 0.125% Surf 465 | 350 | none | 67 | 33 |
| Formulation B | 0.5% Surf 465 | 350 | none | 61 | 30 |
| Formulation B | none | 350 | 0.125% Surf 465 | 58 | 27 |
| Formulation B | none | 350 | 0.5% Surf 465 | 53 | 29 |
| Formulation B | 0.125% Surf 465 +L-77, 1:1 | 350 | none | 25 | 12 |
| Formulation B | 0.5% Surf 465 + L-77, 1:1 | 350 | none | 79 | 26 |
| Formulation B | none | 350 | 0.125% Surf 465 + L-77,1:1 | 43 | |
| Formulation B | none | 350 | 0.5% Surf 465 + L-77, 1:1 | 55 | 17 |
| Formulation B | 0.125% PG 2069 | 350 | none | 53 | 43 |
| Formulation B | 0.5% PG 2069 | 350 | none | 68 | 55 |
| Formulation B | none | 350 | 0.125% PG 2069 | 66 | 43 |
| Formulation B | none | 350 | 0.5% PG 2069 | 61 | 27 |
| Formulation B | 0.125% PG 2069 + L-77, 1:1 | 350 | none | 41 | 36 |
| Formulation B | 0.5% PG 2069 + L-77, 1:1 | 350 | none | 71 | 12 |
| Formulation B | none | 350 | 0.125% PG 2069 + +L-77, 1:1 | 49 | 18 |
| Formulation B | none | 350 | 0.5% PG 2069 + L-77, 1:1 | 58 | 47 |
| Formulation B | 0.125% Silamine | 350 | none | 58 | 46 |
| Formulation B | 0.5% Silamine | 350 | none | 69 | 39 |
| Formulation B | none | 350 | 0.125% Silamine | 55 | 25 |
| Formulation B | none | 350 | 0.5% Silamine | 57 | 45 |

In this Example not all surfactant solutions tested caused antagonism of glyphosate activity in tank mix. Note that glyphosate Formulation B does not contain any surfactant itself. All surfactant solutions which antagonized glyphosate activity in tank mix gave less or no antagonism when applied as sequential applications according to the present invention.

Example 17

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation B, the disodium salt of glyphosate (Formulation D) and the trisodium salt of glyphosate (Formulation E), alone or in tank mix with a candidate accession agent, were applied on the same day, 17 days after planting velvetleaf and 19 days after planting Japanese millet. Formulations D and E were not prepared as concentrate formulations but were made by simply dissolving the respective salts in water to make the dilute spray solutions of this Example. Formulations were applied without candidate accession agent at a range of rates from 200 to 800 g a.e./ha. When a candidate accession agent was included in the treatment, either in tank mix or as a subsequent application, comparative testing was conducted only at 200 and 400 g a.e./ha. This Example includes as candidate accession agent an aqueous solution containing 0.5% Silwet L-77. The time interval between initial and subsequent applications was about 0.05 or 3 hours.

Seventeen days after the initial application, all plants in the test were examined by a single practiced technician to evaluate percent inhibition. Treatments and corresponding percent inhibitions are given in Table 17.

TABLE 17

| Initial application 93 l/ha | | Glyphosate rate | Subsequent application 93 l/ha accession | % Inhibition | |
|---|---|---|---|---|---|
| herbicide | accession agent | g a.e./ ha | 0.5% L-77 agent | ABUTH | ECHCF |
| Formulation B | none | 200 | none | 22 | 30 |
| Formulation B | none | 400 | none | 42 | 61 |
| Formulation B | none | 600 | none | 77 | 83 |
| Formulation B | none | 800 | none | 69 | 90 |
| Formulation B | 0.5% L-77 | 200 | none | 83 | 3 |
| Formulation B | 0.5% L-77 | 400 | none | 89 | 43 |
| Formulation B | none | 200 | at ~0.05 hr | 78 | 7 |
| Formulation B | none | 400 | at ~0.05 hr | 79 | 27 |
| Formulation B | none | 200 | at 3 hrs | 81 | 35 |
| Formulation B | none | 400 | at 3 hrs | 86 | 37 |
| Formulation D | none | 200 | none | 2 | 21 |
| Formulation D | none | 400 | none | 5 | 50 |
| Formulation D | none | 600 | none | 43 | 47 |
| Formulation D | none | 800 | none | 71 | 60 |
| Formulation D | 0.5% L-77 | 200 | none | 77 | 0 |
| Formulation D | 0.5% L-77 | 400 | none | 82 | 10 |
| Formulation D | none | 200 | at ~0.05 hr | 74 | 10 |
| Formulation D | none | 400 | at ~0.05 hr | 93 | 31 |
| Formulation D | none | 200 | at 3 hrs | 77 | 16 |
| Formulation D | none | 400 | at 3 hrs | 83 | 19 |
| Formulation E | none | 200 | none | 0 | 2 |
| Formulation E | none | 400 | none | 31 | 8 |
| Formulation B | none | 600 | none | 56 | 32 |
| Formulation E | none | 800 | none | 64 | 35 |
| Formulation B | 0.5% L-77 | 200 | none | 69 | 0 |
| Formulation E | 0.5% L-77 | 400 | none | 75 | 3 |
| Formulation E | none | 200 | 0.05 hrs | 75 | 0 |
| Formulation E | none | 400 | 0.05 hrs | 86 | 17 |
| Formulation E | none | 200 | 3 hrs | 82 | 2 |
| Formulation E | none | 400 | 3 hrs | 83 | 33 |
| Formulation B | 0.5% L-77 | 400 | none | 89 | 43 |
| Formulation B | none | 200 | at ~0.05 hr | 78 | 7 |
| Formulation B | none | 400 | at ~0.05 hr | 79 | 27 |
| Formulation B | none | 200 | at 3 hrs | 81 | 35 |
| Formulation B | none | 400 | at 3 hrs | 86 | 37 |
| Formulation D | none | 200 | none | 2 | 21 |
| Formulation D | none | 400 | none | 5 | 50 |
| Formulation D | none | 600 | none | 43 | 47 |
| Formulation D | none | 800 | none | 71 | 60 |
| Formulation D | 0.5% L-77 | 200 | none | 77 | 0 |
| Formulation D | 0.5% L-77 | 400 | none | 82 | 10 |
| Formulation D | none | 200 | at ~0.05 hr | 74 | 10 |
| Formulation D | none | 400 | at ~0.05 hr | 93 | 31 |
| Formulation D | none | 200 | at 3 hrs | 77 | 16 |
| Formulation D | none | 400 | at 3 hrs | 83 | 19 |
| Formulation E | none | 200 | none | 0 | 2 |
| Formulation E | none | 400 | none | 31 | 8 |
| Formulation B | none | 600 | none | 56 | 32 |
| Formulation E | none | 800 | none | 64 | 35 |
| Formulation B | 0.5% L-77 | 200 | none | 69 | 0 |
| Formulation E | 0.5% L-77 | 400 | none | 75 | 3 |
| Formulation E | none | 200 | 0.05 hrs | 75 | 0 |
| Formulation E | none | 400 | 0.05 hrs | 86 | 17 |
| Formulation E | none | 200 | 3 hrs | 82 | 2 |
| Formulation E | none | 400 | 3 hrs | 83 | 33 |

Silwet L-77 antagonized glyphosate activity on Japanese millet when tank mixed with any of the three glyphosate salts used in this Example, though the antagonism was more difficult to detect in the case of the trisodium salt (Formulation E) which itself showed very poor efficacy. In all cases antagonism was reduced or eliminated by applying the Silwet L-77 after the glyphosate salt according to the present invention.

Example 18

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation B, and of Formulations F-I as defined below, alone or in tank mix with a candidate accession agent, were applied on the same day, 15–17 days after planting velvetleaf and 17–19 days after planting Japanese millet. Formulations F, G, H and I are aqueous solutions of the monosodium, monopotassium, monoammoniumn and mono(trimethylsulfonium) salts respectively of glyphosate. Formulations F and G were not prepared as concentrate formulations but were made by simply dissolving the respective salts in water to make the dilute spray solutions of this Example. Formulation H was prepared from a water soluble granular concentrate of monoammonium glyphosate, containing no surfactant, as sold by Monsanto Company. Formulation I was prepared from an aqueous concentrate product sold in the USA by Zeneca under the trademark Touchdown which is believed to have no coformulated surfactant. All applications of glyphosate salt formulations were made with the addition to the spray solution of 0.09% MON-0818 surfactant of Monsanto Company. Formulations were applied without candidate accession agent at 200 and 400 g a.e./ha. When a candidate accession agent was included in the treatment, either in tank mix or as a subsequent application, formulations were tested at the same two rates. This Example includes as candidate accession agent an aqueous solution containing 0.5% Silwet L-77. The time interval between initial and subsequent applications was about 0.05 or 3 hours.

Seventeen days after the initial application, all plants in the test were examined by a single practiced technician to evaluate percent inhibition. Treatments and corresponding percent inhibitions are given in Table 18.

TABLE 18

| Initial application 93 l/ha | | Glyphosate rate | Subsequent application 93 l/ha accession | % Inhibition | |
|---|---|---|---|---|---|
| herbicide | accession agent | g a.e./ ha | 0.5% L-77 agent | ABUTH | ECHCF |
| Formulation B | none | 200 | none | 56 | 91 |
| Formulation B | none | 400 | none | 85 | 100 |
| Formulation B | 0.5% L-77 | 200 | none | 65 | 33 |
| Formulation B | 0.5% L-77 | 400 | none | 71 | 51 |
| Formulation B | none | 200 | at ~0.05 hr | 83 | 66 |
| Formulation B | none | 400 | at ~0.05 hr | 91 | 93 |
| Formulation B | none | 200 | at 3 hrs | 43 | 75 |
| Formulation B | none | 400 | at 3 hrs | 81 | 100 |
| Formulation F | none | 200 | none | 36 | 100 |
| Formulation F | none | 400 | none | 85 | 100 |
| Formulation F | 0.5% L-77 | 200 | none | 54 | 36 |
| Formulation F | 0.5% L-77 | 400 | none | 81 | 63 |
| Formulation F | none | 200 | at ~0.05 hr | 51 | 64 |
| Formulation F | none | 400 | at ~0.05 hr | 80 | 91 |
| Formulation F | none | 200 | at 3 hrs | 41 | 73 |
| Formulation F | none | 400 | at 3 hrs | 88 | 100 |
| Formulation G | none | 200 | none | 68 | 93 |
| Formulation G | none | 400 | none | 86 | 100 |
| Formulation G | 0.5% L-77 | 200 | none | 55 | 33 |
| Formulation G | 0.5% L-77 | 400 | none | 80 | 43 |
| Formulation G | none | 200 | ~0.05 hrs | 63 | 50 |
| Formulation G | none | 400 | ~0.05 hrs | 76 | 80 |
| Formulation G | none | 200 | 3 hrs | 46 | 81 |
| Formulation G | none | 400 | 3 hrs | 66 | 99 |
| Formulation H | none | 200 | none | 69 | 93 |
| Formulation H | none | 400 | none | 86 | 100 |
| Formulation H | 0.5% L-77 | 200 | none | 64 | 48 |
| Formulation H | 0.5% L-77 | 400 | none | 78 | 59 |
| Formulation H | none | 200 | ~0.05 hrs | 73 | 69 |
| Formulation H | none | 400 | ~0.05 hrs | 89 | 81 |
| Formulation H | none | 200 | 3 hrs | 40 | 81 |
| Formulation H | none | 400 | 3 hrs | 75 | 99 |
| Formulation I | none | 200 | none | no data | 96 |
| Formulation I | none | 400 | none | no data | 100 |
| Formulation I | 0.5% L-77 | 200 | none | no data | 30 |
| Formulation I | 0.5% L-77 | 400 | none | no data | 53 |
| Formulation I | none | 200 | ~0.05 hrs | no data | 75 |
| Formulation I | none | 400 | ~0.05 hrs | no data | 84 |
| Formulation I | none | 200 | 3 hrs | no data | 88 |
| Formulation I | none | 400 | 3 hrs | no data | 89 |

All salts of glyphosate tested in this Example were antagonized by Silwet L-77 in tank mix on Japanese millet. Antagonism was reduced in all cases by applying the Silwet L-77 as a sequential treatment according to the present invention.

Example 19

Canada thistle (*Cirsium arvense*, CIRAR) plants were grown in pots, maintained in a greenhouse and treated with initial and subsequent applications by procedures exactly as described for Example 1, except where otherwise noted below.

Greenhouse temperature was maintained at approximately 21° C. during the day and 13° C. during the night. Initial applications of Formulations A and B, alone or in tank mix with a candidate accession agent, were applied 40 days after planting. Formulations were each applied without candidate accession agent at 250 and 500 g a.e./ha. When a candidate accession agent was included in the treatment, either in tank mix or as a subsequent application, formulations were tested only at the lower rate. This Example includes as candidate accession agents aqueous solutions containing Silwet L-77 at a range of concentrations from 0.5% to 2.0%. The time interval between initial and subsequent applications was varied from about 0.05 hour to 24 hours.

Twenty-six days after the initial application, all plants in the test were examined by a single practiced technician to evaluate percent inhibition. Treatments and corresponding percent inhibitions are given in Table 19.

TABLE 19

| Initial application 93 l/ha | | Glyphosate rate | Subsequent application 93 l/ha | % Inhibition |
|---|---|---|---|---|
| herbicide | accession agent | g a.e./ ha | accession agent | CIRAR |
| Formulation A | none | 250 | none | 66 |
| Formulation A | none | 500 | none | 79 |
| Formulation A | 0.5% L-77 | 250 | none | 52 |
| Formulation A | 1.0% L-77 | 250 | none | 71 |
| Formulation A | 2.0% L-77 | 250 | none | 81 |
| Formulation A | none | 250 | 0.5% L-77 at ~0.05 hr | 80 |
| Formulation A | none | 250 | 1.0% L-77 at ~0.05 hr | 84 |
| Formulation A | none | 250 | 2.0% L-77 at ~0.05 hr | 83 |
| Formulation A | none | 250 | 0.5% L-77 at 4 hrs | 75 |
| Formulation A | none | 250 | 1.0% L-77 at 4 hrs | 93 |
| Formulation A | none | 250 | 2.0% L-77 at 4 hrs | 81 |
| Formulation A | none | 250 | 0.5% L-77 at 24 hrs | 78 |
| Formulation A | none | 250 | 1.0% L-77 at 24 hrs | 73 |
| Formulation A | none | 250 | 2.0% L-77 at 24 hrs | 78 |
| Formulation B | none | 250 | none | 70 |
| Formulation B | none | 500 | none | 77 |
| Formulation B | 0.5% L-77 | 250 | none | 79 |
| Formulation B | 1.0% L-77 | 250 | none | 75 |
| Formulation B | 2.0% L-77 | 250 | none | 71 |
| Formulation B | none | 250 | 0.5% L-77 at ~0.05 hr | 85 |
| Formulation B | none | 250 | 1.0% L-77 at ~0.05 hr | 85 |
| Formulation B | none | 250 | 2.0% L-77 at ~0.05 hr | 75 |
| Formulation B | none | 250 | 0.5% L-77 at 4 hrs | 71 |
| Formulation B | none | 250 | 1.0% L-77 at 4 hrs | 64 |
| Formulation B | none | 250 | 2.0% L-77 at 4 hrs | 80 |
| Formulation B | none | 250 | 0.5% L-77 at 24 hrs | 84 |
| Formulation B | none | 250 | 1.0% L-77 at 24 hrs | 71 |
| Formulation B | none | 250 | 2.0% L-77 at 24 hrs | 80 |

Although Silwet L-77 in tank mix was not significantly antagonistic to herbicidal effectiveness in canada thistle, sequential application of the accession agent gave generally enhanced effectiveness.

Example 20

Soybean (*Glycine max*, GLXMA) plants were grown in pots, maintained in a greenhouse and treated with initial and subsequent applications by procedures exactly as described for Example 1, except where otherwise noted below.

Initial applications of Formulations A and B and glyphosate acid, alone or in tank mix with a candidate accession agent, were applied 16 days after planting. Glyphosate acid was applied in the same way as in Example 12. Formulations were each applied without candidate accession agent at a range of rates from 250 to 800 g a.e./ha. When a candidate accession agent was included in the treatment, either in tank mix or as a subsequent application, formulations were tested only at 250 and 500 g a.e./ha. This Example includes as candidate accession agent an aqueous solution containing 0.5% Silwet L-77. The time interval between initial and subsequent applications was 3 hours.

Twenty days after the initial application, all plants in the test were examined by a single practiced technician to evaluate percent inhibition. Treatments and corresponding percent inhibitions are given in Table 20.

TABLE 20

| Initial application 93 l/ha | | Glyphosate rate g a.e./ha | Subsequent application 93 l/ha | |
|---|---|---|---|---|
| herbicide | accession agent | | accession agent | % Inhibition GLXMA |
| Formulation A | none | 250 | none | 70 |
| Formulation A | none | 500 | none | 83 |
| Formulation A | none | 800 | none | 92 |
| Formulation A | 0.5% L-77 | 250 | none | 38 |
| Formulation A | 0.5% L-77 | 500 | none | 53 |
| Formulation A | none | 250 | 0.5% L-77 at 3 hrs | 56 |
| Formulation A | none | 500 | 0.5% L-77 at 3 hrs | 66 |
| Formulation B | none | 250 | none | 17 |
| Formulation B | none | 500 | none | 25 |
| Formulation B | none | 800 | none | 41 |
| Formulation B | 0.5% L-77 | 250 | none | 42 |
| Formulation B | 0.5% L-77 | 500 | none | 54 |
| Formulation B | none | 250 | 0.5% L-77 at 3 hrs | 38 |
| Formulation B | none | 500 | 0.5% L-77 at 3 hrs | 43 |
| glyphosate acid | none | 250 | none | 7 |
| glyphosate acid | none | 500 | none | 3 |
| glyphosate acid | none | 800 | none | 8 |
| glyphosate acid | 0.5% L-77 | 250 | none | 33 |
| glyphosate acid | 0.5% L-77 | 500 | none | 48 |
| glyphosate acid | none | 250 | 0.5% L-77 at 3 hrs | 39 |
| glyphosate acid | none | 500 | 0.5% L-77 at 3 hrs | 28 |

Silwet L-77 in tank mix improved the herbicidal effectiveness of both glyphosate acid and the herbicidal composition (Formulation B) that lacked a surfactant coformulant for soybean. It was somewhat antagonistic for the herbicidal composition that includes a surfactant coformulant, and this antagonism was somewhat reduced through sequential application.

Example 21

Giant ragweed (*Ambrosia trifida*, AMBTR) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 21 days after planting. Formulations were each applied without candidate accession agent at a range of rates from 200 to 800 g a.e./ha. When a candidate accession agent was included in the treatment, either in tank mix or as a subsequent application, formulations were tested only at 200 and 500 g a.e./ha. This Example includes as candidate accession agent an aqueous solution containing 0.5% Silwet L-77. The time interval between initial and subsequent applications was 3 hours.

Twenty-one days after the initial application, all plants in the test were examined by a single practiced technician to evaluate percent inhibition. Treatments and corresponding percent inhibitions are given in Table 21.

TABLE 21

| Initial application 93 l/ha | | Glyphosate rate g a.e./ha | Subsequent application 93 l/ha | |
|---|---|---|---|---|
| herbicide | accession agent | | accession agent | % Inhibition AMBTR |
| Formulation A | none | 200 | none | 30 |
| Formulation A | none | 500 | none | 74 |
| Formulation A | none | 800 | none | 93 |
| Formulation A | 0.5% L-77 | 200 | none | 49 |
| Formulation A | 0.5% L-77 | 500 | none | 67 |
| Formulation A | none | 200 | 0.5% L-77 at 3 hrs | 47 |
| Formulation A | none | 500 | 0.5% L-77 at 3 hrs | 93 |
| Formulation B | none | 200 | none | 34 |
| Formulation B | none | 500 | none | 59 |
| Formulation B | none | 800 | none | 98 |
| Formulation B | 0.5% L-77 | 200 | none | 55 |
| Formulation B | 0.5% L-77 | 500 | none | 86 |
| Formulation B | none | 200 | 0.5% L-77 at 3 hrs | 47 |
| Formulation B | none | 500 | 0.5% L-77 at 3 hrs | 90 |
| Formulation C | none | 200 | none | 46 |
| Formulation C | none | 500 | none | 59 |
| Formulation C | none | 800 | none | 92 |
| Formulation C | 0.5% L-77 | 200 | none | 57 |
| Formulation C | 0.5% L-77 | 500 | none | 59 |
| Formulation C | none | 200 | 0.5% L-77 at 3 hrs | 49 |
| Formulation C | none | 500 | 0.5% L-77 at 3 hrs | 79 |

Silwet L-77 in tank mix slightly improved the effectiveness of the herbicidal composition against giant ragweed. Comparable improvement was achieved through sequential application of the accession agent.

Example 22

Hemp sesbania (*Sesbania exaltata*, SEBEX) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 24 days after planting. Formulations were each applied without candidate accession agent at a range of rates from 200 to 800 g a.e./ha. When a candidate accession agent was included in the treatment, either in tank mix or as a subsequent application, formulations were tested only at 200 and 500 g a.e./ha. This Example includes as candidate accession agent an aqueous solution containing 0.5% Silwet L-77. The time interval between initial and subsequent applications was 3 hours.

Twenty-one days after the initial application, all plants in the test were examined by a single practiced technician to evaluate percent inhibition. Treatments and corresponding percent inhibitions are given in Table 22.

TABLE 22

| Initial application 93 l/ha | | Glyphosate rate g a.e./ha | Subsequent application 93 l/ha | |
|---|---|---|---|---|
| herbicide | accession agent | | accession agent | % Inhibition SEBEX |
| Formulation A | none | 200 | none | 51 |
| Formulation A | none | 500 | none | 58 |

TABLE 22-continued

| herbicide | Initial application 93 l/ha accession agent | Glyphosate rate g a.e./ha | Subsequent application 93 l/ha accession agent | % Inhibition SEBEX |
|---|---|---|---|---|
| Formulation A | none | 800 | none | 73 |
| Formulation A | 0.5% L-77 | 200 | none | 16 |
| Formulation A | 0.5% L-77 | 500 | none | 55 |
| Formulation A | none | 200 | 0.5% L-77 at 3 hrs | 29 |
| Formulation A | none | 500 | 0.5% L-77 at 3 hrs | 62 |
| Formulation B | none | 200 | none | 7 |
| Formulation B | none | 500 | none | 25 |
| Formulation B | none | 800 | none | 27 |
| Formulation B | 0.5% L-77 | 200 | none | 13 |
| Formulation B | 0.5% L-77 | 500 | none | 33 |
| Formulation B | none | 200 | 0.5% L-77 at 3 hrs | 7 |
| Formulation B | none | 500 | 0.5% L-77 at 3 hrs | 28 |
| Formulation C | none | 200 | none | 50 |
| Formulation C | none | 500 | none | 62 |
| Formulation C | none | 800 | none | 77 |
| Formulation C | 0.5% L-77 | 200 | none | 19 |
| Formulation C | 0.5% L-77 | 500 | none | 94 |
| Formulation C | none | 200 | 0.5% L-77 at 3 hrs | 52 |
| Formulation C | none | 500 | 0.5% L-77 at 3 hrs | 48 |

Antagonism was in some cases observed in hemp sesbania for Silwet L-77 in tank mix with herbicidal compositions that employ a surfactant coformulant. In these cases, the antagonism was reduced through sequential application of the accession agent.

Example 23

Sicklepod (Cassia obtusifolia, CASOB) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 26 days after planting. Formulations were each applied without candidate accession agent at a range of rates from 400 to 1000 g a.e./ha. When a candidate accession agent was included in the treatment, either in tank mix or as a subsequent application, formulations were tested only at 400 and 600 g a.e./ha. This Example includes as candidate accession agent an aqueous solution containing 0.5% Silwet L-77. The time interval between initial and subsequent applications was 3 hours.

Eighteen days after the initial application, all plants in the test were examined by a single practiced technician to evaluate percent inhibition. Treatments and corresponding percent inhibitions are given in Table 23.

TABLE 23

| herbicide | Initial application 93 l/ha accession agent | Glyphosate rate g a.e./ha | Subsequent application 93 l/ha accession agent | % Inhibition CASOB |
|---|---|---|---|---|
| Formulation A | none | 400 | none | 62 |
| Formulation A | none | 600 | none | 81 |
| Formulation A | none | 1000 | none | 91 |

TABLE 23-continued

| herbicide | Initial application 93 l/ha accession agent | Glyphosate rate g a.e./ha | Subsequent application 93 l/ha accession agent | % Inhibition CASOB |
|---|---|---|---|---|
| Formulation A | 0.5% L-77 | 400 | none | 30 |
| Formulation A | 0.5% L-77 | 600 | none | 56 |
| Formulation A | none | 400 | 0.5% L-77 at 3 hrs | 66 |
| Formulation A | none | 600 | 0.5% L-77 at 3 hrs | 66 |
| Formulation B | none | 400 | none | 38 |
| Formulation B | none | 600 | none | 37 |
| Formulation B | none | 1000 | none | 44 |
| Formulation B | 0.5% L-77 | 400 | none | 33 |
| Formulation B | 0.5% L-77 | 600 | none | 46 |
| Formulation B | none | 400 | 0.5% L-77 at 3 hrs | 29 |
| Formulation B | none | 600 | 0.5% L-77 at 3 hrs | 23 |
| Formulation C | none | 400 | none | 72 |
| Formulation C | none | 600 | none | 81 |
| Formulation C | none | 1000 | none | 87 |
| Formulation C | 0.5% L-77 | 400 | none | 27 |
| Formulation C | 0.5% L-77 | 600 | none | 26 |
| Formulation C | none | 400 | 0.5% L-77 at 3 hrs | 60 |
| Formulation C | none | 600 | 0.5% L-77 at 3 hrs | 69 |

On sicklepod, Silwet L-77 in tank mix was significantly antagonistic for those herbicidal compositions that employ a surfactant coformulant. This antagonism was significantly reduced (and often eliminated) through sequential application of the accession agent.

Example 24

Yellow nutsedge (Cyperus esculentus, CYPES) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 21 days after planting. Formulations were each applied without candidate accession agent at a range of rates from 1600 to 3200 g a.e./ha. When a candidate accession agent was included in the treatment, either in tank mix or as a subsequent application, formulations were tested only at 1600 and 2200 g a.e./ha. This Example includes as candidate accession agent an aqueous solution containing 0.5% Silwet L-77. The time interval between initial and subsequent applications was 3 hours.

Twenty-five days after the initial application, all plants in the test were examined by a single practiced technician to evaluate percent inhibition. Treatments and corresponding percent inhibitions are given in Table 24.

TABLE 24

| herbicide | Initial application 93 l/ha accession agent | Glyphosate rate g a.e./ha | Subsequent application 93 l/ha accession agent | % Inhibition CYPES |
|---|---|---|---|---|
| Formulation A | none | 1600 | none | 100 |
| Formulation A | none | 2200 | none | 100 |
| Formulation A | none | 3200 | none | 100 |
| Formulation A | 0.5% L-77 | 1600 | none | 82 |

TABLE 24-continued

| Initial application 93 l/ha | | Glyphosate rate | Subsequent application 93 l/ha | |
|---|---|---|---|---|
| herbicide | accession agent | g a.e./ ha | accession agent | % Inhibition CYPES |
| Formulation A | 0.5% L-77 | 2200 | none | 96 |
| Formulation A | none | 1600 | 0.5% L-77 at 3 hrs | 78 |
| Formulation A | none | 2200 | 0.5% L-77 at 3 hrs | 97 |
| Formulation B | none | 1600 | none | 94 |
| Formulation B | none | 2200 | none | 100 |
| Formulation B | none | 3200 | none | 98 |
| Formulation B | 0.5% L-77 | 1600 | none | 91 |
| Formulation B | 0.5% L-77 | 2200 | none | 100 |
| Formulation B | none | 1600 | 0.5% L-77 at 3 hrs | 79 |
| Formulation B | none | 2200 | 0.5% L-77 at 3 hrs | 95 |
| Formulation C | none | 1600 | none | 99 |
| Formulation C | none | 2200 | none | 97 |
| Formulation C | none | 3200 | none | 98 |
| Formulation C | 0.5% L-77 | 1600 | none | 82 |
| Formulation C | 0.5% L-77 | 2200 | none | 96 |
| Formulation C | none | 1600 | 0.5% L-77 at 3 hrs | 94 |
| Formulation C | none | 2200 | 0.5% L-77 at 3 hrs | 100 |

On yellow nutsedge, Silwet L-77 in tank mix was mildly antagonistic for those herbicidal compositions that employ a surfactant coformulant. This antagonism was reduced through sequential application of the accession agent.

Example 25

Seedling johnsongrass (*Sorghum halepense*, SORHA) plants were grown in pots, maintained in a greenhouse and treated with initial and subsequent applications by procedures exactly as described for Example 1, except where otherwise noted below.

Initial applications of Formulations A, B and C, alone or in tank mix with a candidate accession agent, were applied 30 days after planting. Formulations were each applied without candidate accession agent at a range of rates from 150 to 400 g a.e./ha. When a candidate accession agent was included in the treatment, either in tank mix or as a subsequent application, formulations were tested only at 150 and 250 g a.e./ha. This Example includes as candidate accession agent an aqueous solution containing 0.5% Silwet L-77. The time interval between initial and subsequent applications was 6 hours.

Seventeen days after the initial application, all plants in the test were examined by a single practiced technician to evaluate percent inhibition. Treatments and corresponding percent inhibitions are given in Table 25.

TABLE 25

| Initial application 93 l/ha | | Glyphosate rate | Subsequent application 93 l/ha | |
|---|---|---|---|---|
| herbicide | accession agent | g a.e./ ha | accession agent | % Inhibition SORHA |
| Formulation A | none | 150 | none | 74 |
| Formulation A | none | 250 | none | 65 |
| Formulation A | none | 400 | none | 91 |
| Formulation A | 0.5% L-77 | 150 | none | 0 |
| Formulation A | 0.5% L-77 | 250 | none | 17 |
| Formulation A | none | 150 | 0.5% L-77 at 6 hrs | 46 |
| Formulation A | none | 250 | 0.5% L-77 at 6 hrs | 56 |
| Formulation B | none | 150 | none | 0 |
| Formulation B | none | 250 | none | 25 |
| Formulation B | none | 400 | none | 72 |
| Formulation B | 0.5% L-77 | 150 | none | 0 |
| Formulation B | 0.5% L-77 | 250 | none | 0 |
| Formulation B | none | 150 | 0.5% L-77 at 6 hrs | 19 |
| Formulation B | none | 250 | 0.5% L-77 at 6 hrs | 42 |
| Formulation C | none | 150 | none | 56 |
| Formulation C | none | 250 | none | 85 |
| Formulation C | none | 400 | none | 96 |
| Formulation C | 0.5% L-77 | 150 | none | 5 |
| Formulation C | 0.5% L-77 | 250 | none | 18 |
| Formulation C | none | 150 | 0.5% L-77 at 6 hrs | 33 |
| Formulation C | none | 250 | 0.5% L-77 at 6 hrs | 74 |

On seedling johnsongrass, Silwet L-77 in tank mix was significantly antagonistic (more so for those herbicidal compositions that employ a surfactant coformulant). This antagonism was significantly reduced (and often eliminated) through sequential application of the accession agent.

Example 26

Cutleaf geranium (*Geranium dissectum*, GERDI) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with a candidate accession agent, were applied 39 days after planting. Formulations were each applied without candidate accession agent at a range of rates from 300 to 900 g a.e./ha. When a candidate accession agent was included in the treatment, either in tank mix or as a subsequent application, formulations were tested only at 300 and 450 g a.e./ha. This Example includes as candidate accession agent an aqueous solution containing 0.5% Silwet L-77. The time interval between initial and subsequent applications was 4 hours.

Twenty-two days after the initial application, all plants in the test were examined by a single practiced technician to evaluate percent inhibition. Treatments and corresponding percent inhibitions are given in Table 26.

TABLE 26

| Initial application 93 l/ha | | Glyphosate rate | Subsequent application 93 l/ha | |
|---|---|---|---|---|
| herbicide | accession agent | g a.e./ ha | accession agent | % Inhibition GERDI |
| Formulation A | none | 300 | none | 49 |
| Formulation A | none | 450 | none | 94 |
| Formulation A | none | 900 | none | 93 |
| Formulation A | 0.5% L-77 | 300 | none | 13 |
| Formulation A | 0.5% L-77 | 450 | none | 52 |

TABLE 26-continued

| Initial application 93 l/ha | | Glyphosate rate | Subsequent application 93 l/ha | |
|---|---|---|---|---|
| herbicide | accession agent | g a.e./ ha | accession agent | % Inhibition GERDI |
| Formulation A | none | 300 | 0.5% L-77 at 4 hrs | 57 |
| Formulation A | none | 450 | 0.5% L-77 at 4 hrs | 67 |
| Formulation B | none | 300 | none | 22 |
| Formulation B | none | 450 | none | 43 |
| Formulation B | none | 900 | none | 70 |
| Formulation B | 0.5% L-77 | 300 | none | 16 |
| Formulation B | 0.5% L-77 | 450 | none | 48 |
| Formulation B | none | 300 | 0.5% L-77 at 4 hrs | 53 |
| Formulation B | none | 450 | 0.5% L-77 at 4 hrs | 59 |
| Formulation C | none | 300 | none | 85 |
| Formulation C | none | 450 | none | 90 |
| Formulation C | none | 900 | none | 95 |
| Formulation C | 0.5% L-77 | 300 | none | 43 |
| Formulation C | 0.5% L-77 | 450 | none | 53 |
| Formulation C | none | 300 | 0.5% L-77 at 4 hrs | 42 |
| Formulation C | none | 450 | 0.5% L-77 at 4 hrs | 60 |

On cutleaf geranium, Silwet L-77 in tank mix was strongly antagonistic for those herbicidal compositions that employ a surfactant coformulant. This antagonism was reduced through sequential application of the accession agent.

Example 27

Indian mustard (*Brassica juncea*, BRSJU) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with a candidate accession agent, were applied 26 days after planting. Formulations were each applied without candidate accession agent at a range of rates from 150 to 500 g a.e./ha. When a candidate accession agent was included in the treatment, either in tank mix or as a subsequent application, formulations were tested only at 150 and 250 g a.e./ha. This Example includes as candidate accession agent an aqueous solution containing 0.5% Silwet L-77. The time interval between initial and subsequent applications was 4 hours.

Eighteen days after the initial application, all plants in the test were examined by a single practiced technician to evaluate percent inhibition. Treatments and corresponding percent inhibitions are given in Table 27.

TABLE 27

| Initial application 93 l/ha | | Glyphosate rate | Subsequent application 93 l/ha | |
|---|---|---|---|---|
| herbicide | accession agent | g a.e./ ha | accession agent | % Inhibition BRSJU |
| Formulation A | none | 150 | none | 72 |
| Formulation A | none | 250 | none | 68 |
| Formulation A | none | 500 | none | 85 |
| Formulation A | 0.5% L-77 | 150 | none | 30 |
| Formulation A | 0.5% L-77 | 250 | none | 61 |

TABLE 27-continued

| Initial application 93 l/ha | | Glyphosate rate | Subsequent application 93 l/ha | |
|---|---|---|---|---|
| herbicide | accession agent | g a.e./ ha | accession agent | % Inhibition BRSJU |
| Formulation A | none | 150 | 0.5% L-77 at 3 hrs | 43 |
| Formulation A | none | 250 | 0.5% L-77 at 3 hrs | 70 |
| Formulation B | none | 150 | none | 5 |
| Formulation B | none | 250 | none | 35 |
| Formulation B | none | 500 | none | 79 |
| Formulation B | 0.5% L-77 | 150 | none | 22 |
| Formulation B | 0.5% L-77 | 250 | none | 53 |
| Formulation B | none | 150 | 0.5% L-77 at 3 hrs | 42 |
| Formulation B | none | 250 | 0.5% L-77 at 3 hrs | 69 |
| Formulation C | none | 150 | none | 54 |
| Formulation C | none | 250 | none | 78 |
| Formulation C | none | 500 | none | 87 |
| Formulation C | 0.5% L-77 | 150 | none | 26 |
| Formulation C | 0.5% L-77 | 250 | none | 42 |
| Formulation C | none | 150 | 0.5% L-77 at 3 hrs | 59 |
| Formulation C | none | 250 | 0.5% L-77 at 3 hrs | 63 |

On indian mustard, Silwet L-77 in tank mix was noticeably antagonistic for those herbicidal compositions that employ a surfactant coformulant. This antagonism was reduced through sequential application of the accession agent.

Example 28

Common lambsquarter (*Chenopodium album*, CHEAL) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with a candidate accession agent, were applied 33 days after planting. Formulations were each applied without candidate accession agent at a range of rates from 200 to 600 g a.e./ha. When a candidate accession agent was included in the treatment, either in tank mix or as a subsequent application, formulations were tested only at 200 and 400 g a.e./ha. This Example includes as candidate accession agent an aqueous solution containing 0.5% Silwet L-77. The time interval between initial and subsequent applications was 4 hours.

Sixteen days after the initial application, all plants in the test were examined by a single practiced technician to evaluate percent inhibition. Treatments and corresponding percent inhibitions are given in Table 28.

TABLE 28

| Initial application 93 l/ha | | Glyphosate rate | Subsequent application 93 l/ha | |
|---|---|---|---|---|
| herbicide | accession agent | g a.e./ ha | accession agent | % Inhibition CHEAL |
| Formulation A | none | 200 | none | 52 |
| Formulation A | none | 400 | none | 81 |
| Formulation A | none | 600 | none | 97 |
| Formulation A | 0.5% L-77 | 200 | none | 3 |

TABLE 28-continued

| Initial application 93 l/ha | | Glyphosate rate | Subsequent application 93 l/ha | % |
|---|---|---|---|---|
| herbicide | accession agent | g a.e./ ha | accession agent | Inhibition CHEAL |
| Formulation A | 0.5% L-77 | 400 | none | 7 |
| Formulation A | none | 200 | 0.5% L-77 at 3 hrs | 36 |
| Formulation A | none | 400 | 0.5% L-77 at 3 hrs | 73 |
| Formulation B | none | 200 | none | 2 |
| Formulation B | none | 400 | none | 3 |
| Formulation B | none | 600 | none | 5 |
| Formulation B | 0.5% L-77 | 200 | none | 0 |
| Formulation B | 0.5% L-77 | 400 | none | 39 |
| Formulation B | none | 200 | 0.5% L-77 at 3 hrs | 11 |
| Formulation B | none | 400 | 0.5% L-77 at 3 hrs | 4 |
| Formulation C | none | 200 | none | 65 |
| Formulation C | none | 400 | none | 95 |
| Formulation C | none | 600 | none | 98 |
| Formulation C | 0.5% L-77 | 200 | none | 2 |
| Formulation C | 0.5% L-77 | 400 | none | 21 |
| Formulation C | none | 200 | 0.5% L-77 at 3 hrs | 63 |
| Formulation C | none | 400 | 0.5% L-77 at 3 hrs | 87 |

On lambsquarter, Silwet L-77 tank mix was significantly antagonistic for those herbicidal compositions that employ a surfactant coformulant. This antagonism was reduced through sequential application of the accession agent.

Example 29

Annual bluegrass (*Poa annua*, POAAN) and redstem filaree (*Erodium cicutarium*, EROCI) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with a candidate accession agent, were applied 26 days after planting. Formulations were each applied without candidate accession agent at a range of rates from 300 to 1000 g a.e./ha. When a candidate accession agent was included in the treatment, either in tank mix or as a subsequent application, formulations were tested only at 300 and 600 g a.e./ha. This Example includes as candidate accession agent an aqueous solution containing 0.5% Silwet L-77. The time interval between initial and subsequent applications was 4 hours.

Twenty days after the initial application, all plants in the test were examined by a single practiced technician to evaluate percent inhibition. Treatments and corresponding percent inhibitions are given in Table 29.

TABLE 29

| Initial application 93 l/ha | | Glyphosate rate | Subsequent application 93 l/ha | % Inhibition | |
|---|---|---|---|---|---|
| herbicide | accession agent | g a.e./ ha | accession agent | POAAN | EROCI |
| Formulation A | none | 300 | none | 92 | 30 |
| Formulation A | none | 600 | none | 93 | 79 |
| Formulation A | none | 1000 | none | 98 | 93 |
| Formulation A | 0.5% L-77 | 300 | none | 35 | 49 |
| Formulation A | 0.5% L-77 | 600 | none | 77 | 77 |
| Formulation A | none | 300 | 0.5% L-77 at 4 hrs | 88 | 46 |
| Formulation A | none | 600 | 0.5% L-77 at 4 hrs | 93 | 79 |
| Formulation B | none | 300 | none | 57 | 17 |
| Formulation B | none | 600 | none | 78 | 58 |
| Formulation B | none | 1000 | none | 83 | 81 |
| Formulation B | 0.5% L-77 | 300 | none | 27 | 28 |
| Formulation B | 0.5% L-77 | 600 | none | 54 | 60 |
| Formulation B | none | 300 | 0.5% L-77 at 4 hrs | 50 | 15 |
| Formulation B | none | 600 | 0.5% L-77 at 4 hrs | 68 | 77 |
| Formulation C | none | 300 | none | 93 | 68 |
| Formulation C | none | 600 | none | 97 | 95 |
| Formulation C | none | 1000 | none | 98 | 97 |
| Formulation C | 0.5% L-77 | 300 | none | 51 | 29 |
| Formulation C | 0.5% L-77 | 600 | none | 81 | 59 |
| Formulation C | none | 300 | 0.5% L-77 at 4 hrs | 87 | 51 |
| Formulation C | none | 600 | 0.5% L-77 at 4 hrs | 94 | 82 |

On annual bluegrass, Silwet L-77 in tank mix was significantly antagonistic. This antagonism was significantly reduced (and often eliminated) through sequential application of the accession agent. In redstem filaree, Silwet L-77 in tank mix generally enhanced herbicidal effectiveness, and comparable enhancement was observed for sequential application.

Example 30

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, alone or in tank mix with MON-0818 surfactant and/or a candidate accession agent, were applied 14 days after planting velvetleaf and 17 days after planting Japanese millet. MON-0818 was used at a concentration of 0.09% in the spray solution. Formulation B (with and without MON-0818) was applied without candidate accession agent at a range of rates from 100 to 500 g a.e./ha. When a candidate accession agent was included in the treatment, either in tank mix or as a subsequent application, Formulation B was tested only at the lowest rate. This Example includes as candidate accession agents aqueous solutions containing Silwet L-77 at concentrations of 0.5% and 3.0%. Other candidate accession agents tested in this Example include aqueous solutions, at concentrations of 0.5% and 3.0%, of the following surfactants or other substances. In the case of surfactant or other products supplied as diluted products, spray solutions in this and other Examples were prepared to contain 0.5% or 3.0% of the primary ingredient, not on an "as is" basis.

Tergitol TMN-6 of Union Carbide Corporation: described in Union Carbide Product Information, 1989, as 90% ethoxylated 2,6,8-trimethyl-4-nonanol; with an average of 8 moles of ethylene oxide; abbreviated in Tables herein as TMN-6. Tergitol TMN-6 was also employed in mixture with Silwet L-77 at 1:49, 1:19, and 1:9 ratios.

Tween 20 of ICI Surfactants: described in McCutcheon's (loc. cit.) as polyoxyethylene (20) sorbitan monolaurate.

Dimethylsulfoxide: abbreviated herein as DMSO.

The time interval between initial and subsequent applications was 4 hours.

Eighteen days after the initial application, all plants in the test were examined by a single practiced technician to evaluate percent inhibition. Treatments and corresponding percent inhibitions are given in Table 30a (Formulation B applied without MON-0818) and 30b (Formulation B applied with 0.09% MON-0818).

TABLE 30a

| Initial application 93 l/ha, no MON-0818 herbicide | accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 40 | 50 |
| Formulation B | none | 300 | none | 74 | 73 |
| Formulation B | none | 400 | none | 85 | 80 |
| Formulation B | none | 500 | none | 94 | 89 |
| Formulation B | 0.5% L-77 | 100 | none | 80 | 10 |
| Formulation B | 3.0% L-77 | 100 | none | 78 | 10 |
| Formulation B | none | 100 | 0.5% L-77 | 78 | 28 |
| Formulation B | none | 100 | 3.0% L-77 | 70 | 20 |
| Formulation B | 0.5% TMN-6 | 100 | none | 35 | 23 |
| Formulation B | 3.0% TMN-6 | 100 | none | 55 | 15 |
| Formulation B | none | 100 | 0.5% TMN-6 | 30 | 23 |
| Formulation B | none | 100 | 3.0% TMN-6 | 55 | 20 |
| Formulation B | 0.5% Tween 20 | 100 | none | 53 | 53 |
| Formulation B | 3.0% Tween 20 | 100 | none | 75 | 73 |
| Formulation B | none | 100 | 0.5% Tween 20 | 28 | 55 |
| Formulation B | none | 100 | 3.0% Tween 20 | 40 | 40 |
| Formulation B | 0.5% DMSO | 100 | none | 50 | 28 |
| Formulation B | 3.0% DMSO | 100 | none | 48 | 45 |
| Formulation B | none | 100 | 0.5% DMSO | 45 | 33 |
| Formulation B | none | 100 | 3.0% DMSO | 33 | 40 |
| Formulation B | 0.5% TMN-6 + L-77, 1:49 | 100 | none | 88 | 15 |
| Formulation B | 3.0% TMN-6 + L-77, 1:49 | 100 | none | 75 | 15 |
| Formulation B | none | 100 | 0.5% TMN-6 + L-77, 1:49 | 70 | 28 |
| Formulation B | none | 100 | 3.0% TMN-6 + L-77, 1:49 | 50 | 15 |
| Formulation B | 0.5% TMN-6 + L-77, 1:19 | 100 | none | 65 | 10 |
| Formulation B | 3.0% TMN-6 + L-77, 1:19 | 100 | none | 65 | 15 |
| Formulation B | none | 100 | 0.5% TMN-6 + L-77, 1:19 | 73 | 25 |
| Formulation B | none | 100 | 3.0% TMN-6 + L-77, 1:19 | 70 | 35 |
| Formulation B | 0.5% TMN-6 + L-77, 1:9 | 100 | none | 84 | 20 |
| Formulation B | 3.0% TMN-6 + L-77, 1:9 | 100 | none | 78 | 23 |
| Formulation B | none | 100 | 0.5% TMN-6 + L-77, 1:9 | 75 | 20 |

TABLE 30a-continued

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | 3.0% TMN-6 + L-77, 1:9 | 65 | 35 |

TABLE 30b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 68 | 76 |
| Formulation B | none | 300 | none | 95 | 97 |
| Formulation B | none | 400 | none | 98 | 98 |
| Formulation B | none | 500 | none | 99 | 99 |
| Formulation B | 0.5% L-77 | 100 | none | 78 | 15 |
| Formulation B | 3.0% L-77 | 100 | none | 73 | 13 |
| Formulation B | none | 100 | 0.5% L-77 | 65 | 20 |
| Formulation B | none | 100 | 3.0% L-77 | 68 | 18 |
| Formulation B | 0.5% TMN-6 | 100 | none | 33 | 15 |
| Formulation B | 3.0% TMN-6 | 100 | none | 45 | 23 |
| Formulation B | none | 100 | 0.5% TMN-6 | 35 | 30 |
| Formulation B | none | 100 | 3.0% TMN-6 | 30 | 38 |
| Formulation B | 0.5% Tween 20 | 100 | none | 65 | 55 |
| Formulation B | 3.0% Tween 20 | 100 | none | 74 | 75 |
| Formulation B | none | 100 | 0.5% Tween 20 | 50 | 45 |
| Formulation B | none | 100 | 3.0% Tween 20 | 45 | 53 |
| Formulation B | 0.5% DMSO | 100 | none | 45 | 63 |
| Formulation B | 3.0% DMSO | 100 | none | 45 | 60 |
| Formulation B | none | 100 | 0.5% DMSO | 40 | 60 |
| Formulation B | none | 100 | 3.0% DMSO | 35 | 60 |
| Formulation B | 0.5% TMN-6 + L-77, 1:49 | 100 | none | 84 | 15 |
| Formulation B | 3.0% TMN-6 + L-77, 1:49 | 100 | none | 75 | 15 |
| Formulation B | none | 100 | 0.5% TMN-6 + L-77, 1:49 | 63 | 15 |
| Formulation B | none | 100 | 3.0% TMN-6 + L-77, 1:49 | 40 | 13 |
| Formulation B | 0.5% TMN-6 + L-77, 1:19 | 100 | none | 75 | 13 |
| Formulation B | 3.0% TMN-6 + L-77, 1:19 | 100 | none | 75 | 13 |
| Formulation B | none | 100 | 0.5% TMN-6 + L-77, 1:19 | 68 | 20 |
| Formulation B | none | 100 | 3.0% TMN-6 + L-77, 1:19 | 65 | 35 |
| Formulation B | 0.5% TMN-6 + L-77, 1:9 | 100 | none | 86 | 20 |
| Formulation B | 3.0% TMN-6 + L-77, 1:9 | 100 | none | 73 | 25 |
| Formulation F | none | 100 | 0.5% TMN-6 + L-77, 1:9 | 75 | 30 |
| Formulation F | none | 100 | 3.0% TMN-6 + L-77, 1:9 | 68 | 35 |

In this Example antagonism of glyphosate activity in tank mix was seen on Japanese millet, in the presence of MON-0818, with the following solutions: 0.5% and 3.0% Silwet L-77, 0.5% and 3.0% Tergitol TMN-6, 0.5% Tween 20, 0.5% and 3.0% DMSO, and all tested combinations of Tergitol TMN-6 and Silwet L-77. Sequential application reduced antagonism on Japanese millet caused by Silwet L-77 and Tergitol TMN-6 but not that caused by Tween 20 and DMSO.

Example 31

The procedures of Example 30 were repeated exactly except percent inhibition was determined nineteen days after initial application, and the candidate accession agents in addition to Silwet L-77 were:

Tergitol TMN-10 of Union Carbide Corporation: described in Union Carbide Product Information, 1989 as 90% ethoxylated 2,6,8-trimethyl-4-nonanol; with an average of 11 moles of ethylene oxide; abbreviated in Tables herein as TMN-10. Tergitol TMN-10 was also employed with Silwet L-77 at ratios of 1:49, 1:19, and 1:9.

Light mineral oil obtained from Fisher Scientific: abbreviated in Tables herein as "min oil."

R-Way Crop Oil Concentrate described on its label as containing 83% petroleum oil and 17% surfactant blend; abbreviated in Tables herein as COC.

The light mineral oil contains no surfactants for emulsification in the spray solution; a mixture was prepared by agitation and applied immediately before the oil separated significantly from the water.

Treatments and corresponding percent inhibitions are given in Table 31a (Formulation B applied without MON-0818) and 31b (Formulation B applied with 0.09% MON-0818).

TABLE 31a

| herbicide | Initial application 93 l/ha, no MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 43 | 60 |
| Formulation B | none | 300 | none | 90 | 94 |
| Formulation B | none | 400 | none | 91 | 95 |
| Formulation B | none | 500 | none | 98 | 98 |
| Formulation B | 0.5% L-77 | 100 | none | 90 | 25 |
| Formulation B | 3.0% L-77 | 100 | none | 73 | 23 |
| Formulation B | none | 100 | 0.5% L-77 | 81 | 53 |
| Formulation B | none | 100 | 3.0% L-77 | 70 | 38 |
| Formulation B | 0.5% TMN-10 | 100 | none | 70 | 50 |
| Formulation B | 3.0% TMN-10 | 100 | none | 48 | 40 |
| Formulation B | none | 100 | 0.5% TMN-10 | 71 | 35 |
| Formulation B | none | 100 | 3.0% TMN-10 | 45 | 40 |
| Formulation B | 0.5% min oil | 100 | none | 84 | 63 |
| Formulation B | 3.0% min oil | 100 | none | 81 | 76 |
| Formulation B | none | 100 | 0.5% min oil | 70 | 38 |
| Formulation B | none | 100 | 3.0% min oil | 53 | 50 |
| Formulation B | 0.5% COC | 100 | none | 63 | 25 |
| Formulation B | 3.0% COC | 100 | none | 60 | 23 |
| Formulation B | none | 100 | 0.5% COC | 68 | 38 |
| Formulation B | none | 100 | 3.0% COC | 58 | 40 |
| Formulation B | 0.5% TMN-10 +L-77, 1:49 | 100 | none | 89 | 13 |
| Formulation B | 3.0% TMN-10 +L-77, 1:49 | 100 | none | 76 | 23 |
| Formulation B | none | 100 | 0.5% TMN-10 + L-77, 1:49 | 78 | 25 |
| Formulation B | none | 100 | 3.0 %TMN-10 + L-77, 1:49 | 70 | 38 |
| Formulation B | 0.5% TMN-10 +L-77, 1:19 | 100 | none | 85 | 20 |
| Formulation B | 3.0% TMN-10 +L-77, 1:19 | 100 | none | 80 | 15 |
| Formulation B | none | 100 | 0.5% TMN-10 + L-77, 1:19 | 80 | 43 |
| Formulation B | none | 100 | 3.0% TMN-10 + L-77, 1:19 | 74 | 33 |
| Formulation B | 0.5% TMN-10 +L-77, 1:9 | 100 | none | 78 | 23 |
| Formulation B | 3.0% TMN-10 | 100 | none +L-77, 1:9 | 60 | 23 |
| Formulation B | none | 100 | 0.5% TMN-10 + L-77, 1:9 | 75 | 40 |
| Formulation B | none | 100 | 3.0% TMN-10 + L-77, 1:9 | 74 | 33 |

TABLE 31b

| Initial application 93 l/ha, 0.09% MON-0818 | | Glyphosate rate | Subsequent application 93 l/ha accession | | % Inhibition | |
|---|---|---|---|---|---|---|
| herbicide | accession agent | g a.e./ha | agent at 4 hrs | | ABUTH | ECHCF |
| Formulation B | none | 100 | none | | 81 | 81 |
| Formulation B | none | 300 | none | | 86 | 96 |
| Formulation B | none | 400 | none | | 99 | 98 |
| Formulation B | none | 500 | none | | 99 | 97 |
| Formulation B | 0.5% L-77 | 100 | none | | 90 | 25 |
| Formulation B | 3.0% L-77 | 100 | none | | 76 | 25 |
| Formulation B | none | 100 | 0.5% L-77 | | 79 | 50 |
| Formulation B | none | 100 | 3.0% L-77 | | 70 | 45 |
| Formulation B | 0.5% TMN-10 | 100 | none | | 70 | 75 |
| Formulation B | 3.0% TMN-10 | 100 | none | | 74 | 33 |
| Formulation B | none | 100 | 0.5% TMN-10 | | 73 | 60 |
| Formulation B | none | 100 | 3.0% TMN-10 | | 55 | 50 |
| Formulation B | 0.5% min oil | 100 | none | | 70 | 63 |
| Formulation B | 3.0% min oil | 100 | none | | 69 | 56 |
| Formulation B | none | 100 | 0.5% min oil | | 91 | 89 |
| Formulation B | none | 100 | 3.0% min oil | | 68 | 64 |
| Formulation B | 0.5% COC | 100 | none | | 69 | 48 |
| Formulation B | 3.0% COC | 100 | none | | 68 | 50 |
| Formulation B | none | 100 | 0.5% COC | | 71 | 55 |
| Formulation B | none | 100 | 3.0% COC | | 75 | 60 |
| Formulation B | 0.5% TMN-10 +L-77, 1:49 | 100 | none | | 89 | 23 |
| Formulation B | 3.0% TMN-10 +L-77, 1:49 | 100 | none | | 76 | 10 |
| Formulation B | none | 100 | 0.5% TMN-10 + L-77, 1:49 | | 78 | 30 |
| Formulation B | none | 100 | 3.0% TMN-10 + L-77, 1:49 | | 74 | 25 |
| Formulation B | 0.5% TMN-10 +L-77, 1:19 | 100 | none | | 79 | 20 |
| Formulation B | 3.0% TMN-10 +L-77, 1:19 | 100 | none | | 75 | 18 |
| Formulation B | none | 100 | 0.5% TMN-10 + L-77, 1:19 | | 81 | 40 |
| Formulation B | none | 100 | 3.0% TMN-10 + L-77, 1:19 | | 75 | 43 |
| Formulation B | 0.5% TMN-10 +L-77, 1:9 | 100 | none | | 68 | 30 |
| Formulation B | 3.0% TMN-10 +L-77, 1:9 | 100 | none | | 79 | 20 |
| Formulation B | none | 100 | 0.5% TMN-10 + L-77, 1:9 | | 78 | 40 |
| Formulation B | none | 100 | 3.0% TMN-10 + L-77, 1:9 | | 76 | 53 |

In this Example antagonism of glyphosate activity in tank mix was seen on Japanese millet, in the presence of MON-0818, with the following solutions or dispersions: 0.5% and 3.0% Silwet L-77, 0.5% and 3.0% Tergitol TMN-10, 0.5% and 3.0% light mineral oil, 0.5% and 3.0% Crop Oil Concentrate, and all tested combinations of Tergitol TMN-10 and Silwet L-77. Sequential application reduced antagonism on Japanese millet caused by Silwet L-77, Tergitol TMN-10 (3.0% only), light mineral oil and Crop Oil Concentrate but not that caused by Tergitol TMN-10 at 0.5%.

Example 32

The procedures of Example 30 were repeated exactly except that initial applications were made 17 days after planting velvetleaf and 20 days after planting Japanese millet, percent inhibition was determined sixteen days after initial application, and the candidate accession agents in addition to Silwet L-77 were:

Ethoduomeen T/13 and Ethoduomeen T/25 of Akzo Chemicals Inc.: described in Akzo's brochure titled "Ethoxylated and propoxylated surfactants" published 1991 as ethoxylated N-tallowalkyl-1,3-diaminopropanes having respectively 3 and 15 moles EO; the Ethoduomeen trademark is abbreviated in tables herein as "Edm".

Ethylan CPG945 of Akcros Chemicals: described in McCutcheon's (loc. cit.) as a modified alcohol ethoxylate; abbreviated in tables herein by omission of the Ethylan trademark.

Neodol 25-3 and Neodol 25-9 of Shell Chemical Company: described in McCutcheon's (loc. cit.) as $C_{12-15}$ primary alcohol ethoxylate having respectively 3 and 9 moles EO; the Neodol trademark is abbreviated herein as "Neo".

SAG-47: a widely used silicone antifoam of Witco Corporation, OSi Specialties Group.

Treatments and corresponding percent inhibitions are given in Table 32a (Formulation B applied without MON-0818) and 32b (Formulation B applied with 0.09% MON-0818).

TABLE 32a

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 20 | 88 |
| Formulation B | none | 300 | none | 50 | 98 |
| Formulation B | none | 400 | none | 78 | 97 |
| Formulation B | none | 500 | none | 88 | 99 |
| Formulation B | 0.5% L-77 | 100 | none | 40 | 5 |
| Formulation B | 3.0% L-77 | 100 | none | 45 | 38 |
| Formulation B | none | 100 | 0.5% L-77 | 45 | 30 |
| Formulation B | none | 100 | 3.0% L-77 | 43 | 13 |
| Formulation B | 0.5% Edm T/13 | 100 | none | 43 | 91 |
| Formulation B | 3.0% Edm T/13 | 100 | none | 73 | 85 |
| Formulation B | none | 100 | 0.5% Edm T/13 | 15 | 60 |
| Formulation B | none | 100 | 3.0% Edm T/13 | 43 | 55 |
| Formulation B | 0.5% Edm T/25 | 100 | none | 38 | 88 |
| Formulation B | 3.0% Edm T/25 | 100 | none | 74 | 91 |
| Formulation B | none | 100 | 0.5% Edm T/25 | 30 | 38 |
| Formulation B | none | 100 | 3.0% Edm T/25 | 35 | 20 |
| Formulation B | 0.5% CPG945 | 100 | none | 35 | 74 |
| Formulation B | 3.0% CPG945 | 100 | none | 40 | 71 |
| Formulation B | none | 100 | 0.5% CPG945 | 30 | 35 |
| Formulation B | none | 100 | 3.0% CPG945 | 33 | 35 |
| Formulation B | 0.5% Neo 25-3 | 100 | none | 33 | 20 |
| Formulation B | 3.0% Neo 25-3 | 100 | none | 35 | 20 |
| Formulation B | none | 1oo | 0.5% Neo 25-3 | 10 | 5 |
| Formulation B | none | 100 | 3.0% Neo 25-3 | 5 | 0 |
| Formulation B | 0.5% Neo 25-9 | 100 | none | 10 | 10 |
| Formulation B | 3.0% Neo 25-9 | 100 | none | 30 | 10 |
| Formulation B | none | 100 | 0.5% Neo 25-9 | 28 | 30 |
| Formulation B | none | 100 | 3.0% Neo 25-9 | 23 | 33 |
| Formulation B | 0.5% SAG 47 | 100 | none | 23 | 38 |
| Formulation B | 3.0% SAG 47 | 100 | none | 18 | 30 |
| Formulation B | none | 100 | 0.5% SAG 47 | 15 | 25 |
| Formulation B | none | 100 | 3.0% SAG 47 | 20 | 25 |

TABLE 32b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 18 | 86 |
| Formulation B | none | 300 | none | 84 | 99 |
| Formulation B | none | 400 | none | 95 | 99 |
| Formulation B | none | 500 | none | 95 | 99 |
| Formulation B | 0.5% L-77 | 100 | none | 45 | 28 |
| Formulation B | 3.0% L-77 | 100 | none | 50 | 18 |
| Formulation B | none | 100 | 0.5% L-77 | 43 | 74 |
| Formulation B | none | 100 | 3.0% L-77 | 40 | 48 |
| Formulation B | 0.5% Edm T/13 | 100 | none | 30 | 89 |
| Formulation B | 3.0% Edm T/13 | 100 | none | 75 | 96 |
| Formulation B | none | 100 | 0.5% Edm T/13 | 25 | 33 |
| Formulation B | none | 100 | 3.0% Edm T/13 | 43 | 98 |
| Formulation B | 0.5% Edm T/25 | 100 | none | 63 | 95 |
| Formulation B | 3.0% Edm T/25 | 100 | none | 75 | 95 |
| Formulation B | none | 100 | 0.5% Edm T/25 | 33 | 94 |
| Formulation B | none | 100 | 3.0% Edm T/25 | 70 | 83 |
| Formulation B | 0.5% CPG945 | 100 | none | 33 | 73 |
| Formulation B | 3.0% CPG945 | 100 | none | 53 | 75 |
| Formulation B | none | 100 | 0.5% CPG945 | 55 | 88 |
| Formulation B | none | 100 | 3.0% CPG945 | 45 | 86 |

TABLE 32b-continued

| | Initial application 93 l/ha, 0.09% MON-0818 | Glypho-sate rate | Subsequent application 93 l/ha accession | % Inhibition | |
|---|---|---|---|---|---|
| herbicide | accession agent | g a.e./ ha | agent at 4 hrs | ABUTH | ECHCF |
| Formulation B | 0.5% Neo 25-3 | 100 | none | 63 | 53 |
| Formulation B | 3.0% Neo 25-3 | 100 | none | 55 | 35 |
| Formulation B | none | 100 | 0.5% Neo 25-3 | 35 | 35 |
| Formulation B | none | 100 | 3.0% Neo 25-3 | 33 | 20 |
| Formulation B | 0.5% Neo 25-9 | 100 | none | 28 | 20 |
| Formulation B | 3.0% Neo 25-9 | 100 | none | 35 | 10 |
| Formulation B | none | 100 | 0.5% Neo 25-9 | 8 | 10 |
| Formulation B | none | 100 | 3.0% Neo 25-9 | 25 | 46 |
| Formulation B | 0.5% SAG 47 | 100 | none | 45 | 97 |
| Formulation B | 3.0% SAG 47 | 100 | none | 48 | 85 |
| Formulation B | none | 100 | 0.5% SAG 47 | 50 | 89 |
| Formulation B | none | 100 | 3.0% SAG 47 | 45 | 79 |

In this Example antagonism of glyphosate activity in tank mix was seen on Japanese millet, in the presence of MON-0818, with the following solutions: 0.5% and 3.0% Silwet L-77, 0.5% and 3.0% Ethylan CPG945, and 0.5% and 3.0% Neodol 25-3 and Neodol 25-9. Sequential application reduced antagonism on Japanese millet caused by Silwet L-77, Ethylan CPG945 and Neodol 25-9 (3.0% only) but not that caused by Neodol 25-3 and 0.5% Neodol 25-9.

Example 33

The procedures of Example 30 were repeated exactly except that initial applications were made 15 days after planting velvetleaf and 18 days after planting Japanese millet, percent inhibition was determined seventeen days after initial application, and the candidate accession agent in addition to Silwet L-77 was:

Nonanol (2EO) ethoxylate, supplied by Shell Chemical Company abbreviated in tables herein as "nonanol 2". Nonanol (2EO) ethoxylate was also employed in admixture with Silwet L-77 in ratios of 2:1, 1:2, 1:1, 1:9, and 9:1.

Treatments and corresponding percent inhibitions are given in Table 33a (Formulation B applied without MON-0818) and 33b (Formulation B applied with 0.09% MON-0818).

TABLE 33a

| | Initial application 93 l/ha, no MON-0818 | Glypho-sate rate | Subsequent application 93 l/ha accession | % Inhibition | |
|---|---|---|---|---|---|
| herbicide | accession agent | g a.e./ ha | agent at 4 hrs | ABUTH | ECHCF |
| Formulation B | none | 100 | none | 40 | 40 |
| Formulation B | none | 300 | none | 85 | 73 |
| Formulation B | none | 400 | none | 99 | 95 |
| Formulation B | none | 500 | none | 100 | 94 |
| Formulation B | 0.5% L-77 | 100 | none | 85 | 20 |
| Formulation B | 3.0% L-77 | 100 | none | 68 | 38 |
| Formulation B | none | 100 | 0.5% L-77 | 93 | 51 |
| Formulation B | none | 100 | 3.0% L-77 | 65 | 33 |
| Formulation B | 0.5% nonanol 2 | 100 | none | 24 | 20 |
| Formulation B | 3.0% nonanol 2 | 100 | none | 38 | 25 |
| Formulation B | none | 100 | 0.5% nonanol 2 | 53 | 64 |
| Formulation B | none | 100 | 3.0% nonanol 2 | 38 | 43 |
| Formulation B | 0.5% nonanol 2 +L-77, 2:1 | 100 | none | 68 | 20 |
| Formulation B | 3.0% nonanol 2 +L-77, 2:1 | 100 | none | 80 | 20 |
| Formulation B | none | 100 | 0.5% nonanol 2 + L-77, 2:1 | 53 | 64 |
| Formulation B | none | 100 | 3.0% nonanol 2 + L-77,2:1 | 50 | 65 |
| Fonnulation B | 0.5% nonanol 2 +L-77, 1:2 | 100 | none | 85 | 30 |
| Formulation B | 3.0% nonanol 2 +L-77, 1:2 | 100 | none | 78 | 48 |
| Formulation B | none | 100 | 0.5% nonanol 2 + L-77, 1:2 | 75 | 78 |

TABLE 33a-continued

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | 3.0% nonanol 2 + L-77, 1:2 | 63 | 48 |
| Formulation B | 0.5% nonanol 2 +L-77, 1:1 | 100 | none | 53 | 25 |
| Formulation B | 3.0% nonanol 2 +L-77, 1:1 | 100 | none | 70 | 23 |
| Formulation B | none | 100 | 0.5% nonanol 2 + L-77, 1:1 | 65 | 55 |
| Formulation B | none | 100 | 3.0% nonanol 2 + L-77, 1:1 | 45 | 33 |
| Formulation B | 0.5% nonanol 2 +L-77,1:9 | 100 | none | 91 | 20 |
| Formulation B | 3.0% nonanol 2 +L-77, 1:9 | 100 | none | 78 | 38 |
| Formulation B | none | 100 | 0.5% nonanol 2 + L-77, 1:9 | 68 | 48 |
| Formulation B | none | 100 | 3.0% nonanol 2 + L-77, 1:9 | 65 | 38 |
| Formulation B | 0.5% nonanol 2 +L-77, 9:1 | 100 | none | 40 | 33 |
| Formulation B | 3.0% nonanol 2 +L-77, 9:1 | 100 | none | 48 | 20 |
| Formulation B | none | 100 | 0.5% nonanol 2 + L-77, 9:1 | 40 | 40 |
| Formulation B | none | 100 | 3.0% nonanol 2 + L-77, 9:1 | 35 | 33 |

TABLE 33b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 73 | 97 |
| Formulation B | none | 300 | none | 99 | 98 |
| Formulation B | none | 400 | none | 97 | 100 |
| Formulation B | none | 500 | none | 100 | 100 |
| Formulation B | 0.5% L-77 | 100 | none | 89 | 30 |
| Formulation B | 3.0% L-77 | 100 | none | 68 | 40 |
| Formulation B | none | 100 | 0.5% L-77 | 73 | 81 |
| Formulation B | none | 100 | 3.0% L-77 | 60 | 75 |
| Formulation B | 0.5% nonanol 2 | 100 | none | 20 | 15 |
| Formulation B | 3.0% nonanol 2 | 100 | none | 45 | 15 |
| Formulation B | none | 100 | 0.5% nonanol 2 | 50 | 97 |
| Formulation B | none | 100 | 3.0% nonanol 2 | 45 | 81 |
| Formulation B | 0.5% nonanol 2 +L-77, 2:1 | 100 | none | 40 | 20 |
| Formulation B | 3.0% nonanol 2 +L-77, 2:1 | 100 | none | 75 | 25 |
| Formulation B | none | 100 | 0.5% nonanol 2 + L-77, 2:1 | 50 | 95 |
| Formulation B | none | 100 | 3.0% nonanol 2 + L-77, 2:1 | 70 | 86 |
| Formulation B | 0.5% nonanol 2 +L-77, 1:2 | 100 | none | 83 | 38 |
| Formulation B | 3.0% nonanol 2 +L-77, 1:2 | 100 | none | 80 | 58 |
| Formulation B | none | 100 | 0.5% nonanol 2 + L-77, 1:2 | 73 | 89 |
| Formulation B | none | 100 | 3.0% nonanol 2 + L-77, 1:2 | 68 | 85 |

TABLE 33b-continued

| herbicide | Initial application 93 l/ha, 0.09% MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | 0.5% nonanol 2 +L-77, 1:1 | 100 | none | 78 | 38 |
| Formulation B | 3.0% nonanol 2 +L-77, 1:1 | 100 | none | 75 | 53 |
| Formulation B | none | 100 | 0.5% nonanol 2 + L-77, 1:1 | 65 | 95 |
| Formulation B | none | 100 | 3.0% nonanol 2 + L-77, 1:1 | 65 | 85 |
| Formulation B | 0.5% nonanol 2 +L-77, 1:9 | 100 | none | 87 | 20 |
| Formulation B | 3.0% nonanol 2 +L-77, 1:9 | 100 | none | 75 | 45 |
| Formulation B | none | 100 | 0.5% nonanol 2 + L-77, 1:9 | 73 | 94 |
| Formulation B | none | 100 | 3.0% nonanol 2 + L-77, 1:9 | 68 | 76 |
| Formulation B | 0.5% nonanol 2 +L-77, 9:1 | 100 | none | 60 | 33 |
| Formulation B | 3.0% nonanol 2 +L-77, 9:1 | 100 | none | 48 | 23 |
| Formulation B | none | 100 | 0.5% nonanol2 + L-77, 9:1 | 55 | 88 |
| Formulation B | none | 100 | 3.0% nonanol 2 + L-77,9:1 | 38 | 80 |

In this Example antagonism of glyphosate activity in tank mix was seen on Japanese millet, in the presence of MON-0818, with all solutions tested. Sequential application reduced antagonism on Japanese millet in all cases.

Example 34

The procedures of Example 30 were repeated exactly except that initial applications were made 14 days after planting velvetleaf and 17 days after planting Japanese millet, percent inhibition was determined seventeen days after initial application, and the candidate accession agent in addition to Silwet L-77 was:

Nonanol (4EO) ethoxylate, supplied by Shell Chemical company abbreviated in tables herein as "nonanol 4". Nonanol (4EO) ethoxylate was also employed in admixture with Silwet L-77 in ratios of 2:1, 1:2, 1:1, 9:1, and 1:9.

Treatments and corresponding percent inhibitions are given in Table 34a (Formulation B applied without MON-0818) and 34b (Formulation B applied with 0.09% MON-0818).

TABLE 34a

| herbicide | Initial application 93 l/ha, no MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 65 | 45 |
| Formulation B | none | 300 | none | 85 | 90 |
| Formulation B | none | 400 | none | 93 | 91 |
| Formulation B | none | 500 | none | 96 | 99 |
| Formulation B | 0.5% L-77 | 100 | none | 80 | 23 |
| Formulation B | 3.0% L-77 | 100 | none | 75 | 23 |
| Formulation B | none | 100 | 0.5% L-77 | 73 | 55 |
| Formulation B | none | 100 | 3.0% L-77 | 74 | 45 |
| Formulation B | 0.5% nonanol 4 | 100 | none | 43 | 25 |
| Formulation B | 3.0% nonanol 4 | 100 | none | 68 | 43 |
| Formulation B | none | 100 | 0.5% nonanol 4 | 45 | 45 |
| Formulation B | none | 100 | 3.0% nonanol 4 | 45 | 48 |
| Formulation B | 0.5% nonanol 4 +L-77, 2:1 | 100 | none | 70 | 30 |
| Formulation B | 3.0% nonanol 4 +L-77, 2:1 | 100 | none | 84 | 38 |

TABLE 34a-continued

| herbicide | Initial application 93 l/ha, no MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | 0.5% nonanol 4 + L-77, 2:1 | 53 | 53 |
| Formulation B | none | 100 | 3.0% nonanol 4 + L-77, 2:1 | 74 | 53 |
| Formulation B | 0.5% nonanol 4 +L-77, 1:2 | 100 | none | 79 | 30 |
| Formulation B | 3.0% nonanol 4 +L-77, 1:2 | 100 | none | 80 | 48 |
| Formulation B | none | 100 | 0.5% nonanol 4 + L-77, 1:2 | 85 | 50 |
| Formulation B | none | 100 | 3.0% nonanol 4 + L-77, 1:2 | 79 | 53 |
| Formulation B | 0.5% nonanol 4 +L-77, 1:1 | 100 | none | 78 | 30 |
| Formulation B | 3.0% nonanol 4 +L-77, 1:1 | 100 | none | 84 | 50 |
| Formulation B | none | 100 | 0.5% nonanol 4 + L-77, 1:1 | 80 | 48 |
| Formulation B | none | 100 | 3.0% nonanol 4 + L-77, 1:1 | 71 | 48 |
| Formulation B | 0.5% nonanol 4 +L-77, 1:9 | 100 | none | 84 | 40 |
| Formulation B | 3.0% nonanol 4 +L-77, 1:9 | 100 | none | 76 | 45 |
| Formulation B | none | 100 | 0.5% nonanol 4 + L-77, 1:9 | 80 | 48 |
| Formulation B | none | 100 | 3.0% nonanol 4 + L-77, 1:9 | 71 | 43 |
| Formulation B | 0.5% nonanol 4 +L-77, 9:1 | 100 | none | 28 | 23 |
| Formulation B | 3.0% nonanol 4 +L-77, 9:1 | 100 | none | 65 | 10 |
| Formulation B | none | 100 | 0.5% nonanol 4 + L-77, 9:1 | 55 | 38 |
| Formulation B | none | 100 | 3.0% nonanol 4 + L-77, 9:1 | 35 | 30 |

TABLE 34b

| herbicide | Initial application 93 l/ha, 0.09% MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 78 | 88 |
| Formulation B | none | 300 | none | 93 | 100 |
| Formulation B | none | 400 | none | 96 | 100 |
| Formulation B | none | 500 | none | 97 | 100 |
| Formulation B | 0.5% L-77 | 100 | none | 70 | 30 |
| Formulation B | 3.0% L-77 | 100 | none | 76 | 35 |
| Formulation B | none | 100 | 0.5% L-77 | 89 | 55 |
| Formulation B | none | 100 | 3.0% L-77 | 70 | 65 |
| Formulation B | 0.5% nonanol 4 | 100 | none | 75 | 48 |
| Formulation B | 3.0% nonanol 4 | 100 | none | 65 | 18 |
| Formulation B | none | 100 | 0.5% nonanol 4 | 45 | 63 |
| Formulation B | none | 100 | 3.0% nonanol 4 | 45 | 83 |
| Formulation B | 0.5% nonanol 4 +L-77, 2:1 | 100 | none | 68 | 30 |
| Formulation B | 3.0% nonanol 4 +L-77, 2:1 | 100 | none | 91 | 40 |
| Formulation B | none | 100 | 0.5% nonanol 4 + L-77, 2:1 | 71 | 83 |

TABLE 34b-continued

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | 3.0% nonanol 4 + L-77, 2:1 | 73 | 85 |
| Formulation B | 0.5% nonanol 4 +L-77, 1:2 | 100 | none | 79 | 38 |
| Formulation B | 3.0% nonanol 4 +L-77, 1:2 | 100 | none | 80 | 55 |
| Formulation B | none | 100 | 0.5% nonanol 4 + L-77, 1:2 | 78 | 74 |
| Formulation B | none | 100 | 3.0% nonanol 4 + L-77, 1:2 | 78 | 78 |
| Formulation B | 0.5% nonanol 4 +L-77, 1:1 | 100 | none | 77 | 43 |
| Formulation B | 3.0% nonanol 4 +L-77,1:1 | 100 | none | 88 | 48 |
| Formulation B | none | 100 | 0.5% nonanol 4 + L-77,1:1 | 80 | 55 |
| Formulation B | none | 100 | 3.0% nonanol 4 + L-77, 1:1 | 70 | 70 |
| Formulation B | 0.5% nonanol 4 +L-77, 1:9 | 100 | none | 85 | 40 |
| Formulation B | 3.0% nonanol 4 +L-77,1:9 | 100 | none | 76 | 40 |
| Formulation B | none | 100 | 0.5% nonanol 4 + L-77, 1:9 | 80 | 60 |
| Formulation B | none | 100 | 3.0% nonanol 4 + L-77, 1:9 | 75 | 68 |
| Formulation B | 0.5% nonanol 4 +L-77, 9:1 | 100 | none | 25 | 38 |
| Formulation B | 3.0% nonanol 4 +L-77, 9:1 | 100 | none | 65 | 23 |
| Formulation B | none | 100 | 0.5% nonanol 4 + L-77, 9:1 | 43 | 58 |
| Formulation B | none | 100 | 3.0% nonanol 4 + L-77, 9:1 | 50 | 53 |

In this Example antagonism of glyphosate activity in tank mix was seen on Japanese millet, in the presence of MON-0818, with solutions tested. Sequential application reduced antagonism on Japanese millet in all cases.

Example 35

The procedures of Example 30 were repeated exactly except that initial applications were made 17 days after planting velvetleaf and 20 days after planting Japanese millet, percent inhibition was determined seventeen days after initial application, and the candidate accession agent in addition to Silwet L-77 was:

Neodol 1–5 of Shell Chemical Company: described in McCutcheon's (loc. cit.) as $C_{11}$ primary alcohol ethoxylate having 5 moles EO. Neodol 1–5 (labelled Neo 1–5) was also employed in admixture with Silwet L-77 in ratios of 2:1, 1:2, 1:1, 9:1, and 1:9.

Treatments and corresponding percent inhibitions are given in Table 35a (Formulation B applied without MON-0818) and 35b (Formulation B applied with MON-0818).

TABLE 35a

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 10 | 30 |
| Formulation B | none | 300 | none | 40 | 55 |
| Formulation B | none | 400 | none | 80 | 53 |
| Formulation B | none | 500 | none | 80 | 68 |
| Formulation B | 0.5% L-77 | 100 | none | 84 | 35 |
| Formulation B | 3.0% L-77 | 100 | none | 55 | 40 |

TABLE 35a-continued

| herbicide | Initial application 93 l/ha, no MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | 0.5% L-77 | 55 | 45 |
| Formulation B | none | 100 | 3.0% L-77 | 33 | 40 |
| Formulation B | 0.5% Neo 1-5 | 100 | none | 40 | 35 |
| Formulation B | 3.0% Neo 1-5 | 100 | none | 35 | 28 |
| Formulation B | none | 100 | 0.5% Neo 1-5 | 40 | 55 |
| Formulation B | none | 100 | 3.0% Neo 1-5 | 30 | 38 |
| Formulation B | 0.5% Neo 1-5 + L-77, 2:1 | 100 | none | 35 | 30 |
| Formulation B | none | 100 | 0.5% Neo 1-5 + L-77, 2:1 | 40 | 50 |
| Formulation B | none | 100 | 3.0% Neo 1-5 + L-77, 2:1 | 30 | 38 |
| Formulation B | 0.5% Neo 1-5 + L-77, 1:2 | 100 | none | 55 | 33 |
| Formulation B | 3.0% Neo 1-5 + L-77, 1:2 | 100 | none | 68 | 33 |
| Formulation B | none | 100 | 0.5% Neo 1-5 + L-77, 1:2 | 65 | 50 |
| Formulation B | none | 100 | 3.0% Neo 1-5 + L-77, 1:2 | 55 | 45 |
| Formulation B | 0.5% Neo 1-5 + L-77, 1:1 | 100 | none | 65 | 40 |
| Formulation B | 3.0% Neo 1-5 + L-77, 1:1 | 100 | none | 75 | 25 |
| Formulation B | none | 100 | 0.5% Neo 1-5 + L-77, 1:1 | 48 | 50 |
| Formulation B | none | 100 | 3.0% Neo 1-5 + L-77, 1:1 | 50 | 35 |
| Formulation B | 0.5% Neo 1-5 + L-77, 1:9 | 100 | none | 68 | 33 |
| Formulation B | 3.0% Neo 1-5 + L-77, 1:9 | 100 | none | 65 | 45 |
| Formulation B | none | 100 | 0.5% Neo 1-5 + L-77, 1:9 | 38 | 45 |
| Formulation B | none | 100 | 3.0% Neo 1-5 + L-77, 1:9 | 58 | 38 |
| Formulation B | 0.5% Neo 1-5 + L-77, 9:1 | 100 | none | 43 | 35 |
| Formulation B | 3.0% Neo 1-5 + L-77, 9:1 | 100 | none | 43 | 25 |
| Formulation B | none | 100 | 0.5% Neo 1-5 + L-77, 9:1 | 30 | 38 |
| Formulation B | none | 100 | 3.0% Neo 1-5 + L-77, 9:1 | 28 | 28 |

TABLE 35b

| herbicide | Initial application 93 l/ha, 0.09% MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 48 | 70 |
| Formulation B | none | 300 | none | 75 | 97 |
| Formulation B | none | 400 | none | 96 | 95 |
| Formulation B | none | 500 | none | 97 | 99 |
| Formulation B | 0.5% L-77 | 100 | none | 58 | 50 |
| Formulation B | 3.0% L-77 | 100 | none | 63 | 40 |
| Formulation B | none | 100 | 0.5% L-77 | 64 | 63 |
| Formulation B | none | 100 | 3.0% L-77 | 40 | 70 |
| Formulation B | 0.5% Neo 1-5 | 100 | none | 50 | 43 |
| Formulation B | 3.0% Neo 1-5 | 100 | none | 30 | 23 |
| Formulation B | none | 100 | 0.5% Neo 1-5 | 58 | 73 |

TABLE 35b-continued

| Initial application 93 l/ha, 0.09% MON-0818 | | Glyphosate rate | Subsequent application 93 l/ha accession | % Inhibition | |
|---|---|---|---|---|---|
| herbicide | accession agent | g a.e./ ha | agent at 4 hrs | ABUTH | ECHCF |
| Formulation B | none | 100 | 3.0% Neo 1-5 | 50 | 70 |
| Formulation B | 0.5% Neo 1-5 + L-77, 2:1 | 100 | none | 60 | 45 |
| Formulation B | 3.0% Neo 1-5 + L-77, 2:1 | 100 | none | 45 | 15 |
| Formulation B | none | 100 | 0.5% Neo 1-5 + L-77, 2:1 | 50 | 74 |
| Formulation B | none | 100 | 3.0% Neo 1-5 + L-77, 2:1 | 50 | 65 |
| Formulation B | 0.5% Neo 1-5 + L-77, 1:2 | 100 | none | 50 | 30 |
| Formulation B | 3.0% Neo 1-5 + L-77, 1:2 | 100 | none | 50 | 38 |
| Formulation B | none | 100 | 0.5% Neo 1-5 + L-77, 1:2 | 68 | 55 |
| Formulation B | none | 100 | 3.0% Neo 1-5 + L-77, 1:2 | 35 | 63 |
| Formulation B | 0.5% Neo 1-5 + L-77,1:1 | 100 | none | 50 | 28 |
| Formulation B | 3.0% Neo 1-5 + L-77,1:1 | 100 | none | 53 | 20 |
| Formulation B | none | 100 | 0.5% Neo 1-5 + L-77, 1:1 | 53 | 73 |
| Formulation B | none | 100 | 3.0% Neo 1-5 + L-77, 1:1 | 43 | 63 |
| Formulation B | 0.5% Neo 1-5 + L-77, 1:9 | 100 | none | 70 | 30 |
| Formulation B | 3.0% Neo 1-5 + L-77, 1:9 | 100 | none | 58 | 48 |
| Formulation B | none | 100 | 0.5% Neo 1-5 + L-77, 1:9 | 58 | 71 |
| Formulation B | none | 100 | 3.0% Neo 1-5 + L-77, 1:9 | 63 | 65 |
| Formulation B | 0.5% Neo 1-5 + L-77,9:1 | 100 | none | 45 | 45 |
| Formulation B | 3.0% Neo 1-5 + L-77, 9:1 | 100 | none | 48 | 35 |
| Formulation B | none | 100 | 0.5% Neo 1-5 + L-77, 9:1 | 50 | 70 |
| Formulation B | none | 100 | 3.0% Neo 1-5 + L-77, 9:1 | 50 | 58 |

In this Example antagonism of glyphosate activity in tank mix was seen on Japanese millet, in the presence of MON-0818, with all solutions tested. Sequntial application reduced antagonism on Japanese millet in all cases.

Example 36

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, in tank mix with MON-0818 surfactant and/or a candidate accession agent, were applied 22 days after planting velvetleaf and 20 days after planting Japanese millet. MON-0818 was used at a concentration of 0.09% in the initial application spray solution in all treatments, except where MON-0818 itself was being tested as a candidate accession agent (see below). Formulation B was applied without candidate accession agent at a range of rates from 200 to 1000 g a.e./ha. When a candidate accession agent was included in the treatment, either in tank mix or as a subsequent application, Formulation B was tested only at 200 and 400 g a.e./ha, with 0.09% MON-0818. This Example includes as a candidate accession agent an aqueous solution containing 0.5% Silwet L-77. Other candidate accession agents tested in this Example include aqueous solutions, at concentrations of 1.5% and 5.0%, of the following surfactants or other substances:

Neodol 91-8 of Shell Chemical Company: described in McCutcheon's (loc. cit.) as $C_{9-11}$ primary alcohol ethoxylate having 8 moles EO.

MON-0818: tallowamine (15EO) ethoxylate based surfactant of Monsanto Company. In the tank mix applications using MON-0818 as a candidate accession agent, a further 0.09% MON-0818 was not added to the tank mix.

Glycerin.

Tween 20 of ICI Surfactants: described in McCutcheon's (loc. cit.) as polyoxyethylene (20) sorbitan monolaurate.

Tergitol 15-S-9 of Union Carbide Corporation: described in McCutcheon's (loc.cit.) as $C_{11-15}$ secondary alcohol ethoxylate, believed to have 9 moles EO; abbreviated in tables herein as "15-S-9".

The time interval between initial and subsequent applications was 3 hours.

Nineteen days after the initial application, all plants in the test were examined by a single practiced technician to evaluate percent inhibition. Treatments and corresponding percent inhibitions are given in Table 36.

TABLE 36

| herbicide | Initial application 93 l/ha, 0.09% MON-0818 accession agent | Glyphosate rate g a.e./ ha | Subsequent application 93 l/ha accession agent at 3 hrs | % Inhibition ABUTH | ECHCF |
|---|---|---|---|---|---|
| Formulation B | none | 200 | none | 29 | 78 |
| Formulation B | none | 400 | none | 55 | 100 |
| Formulation B | none | 600 | none | 73 | 100 |
| Formulation B | none | 800 | none | 92 | 100 |
| Formulation B | none | 1000 | none | 95 | 100 |
| Formulation B | 0.5% L-77 | 200 | none | 54 | 20 |
| Formulation B | 0.5% L-77 | 400 | none | 81 | 31 |
| Formulation B | none | 200 | 0.5% L-77 | 54 | 58 |
| Formulation B | none | 400 | 0.5% L-77 | 75 | 85 |
| Formulation B | 1.5% Neo 91-8 | 200 | none | 44 | 70 |
| Formulation B | 1.5% Neo 91-8 | 400 | none | 50 | 91 |
| Formulation B | 5.0% Neo 91-8 | 200 | none | 18 | 35 |
| Formulation B | 5.0% Neo 91-8 | 400 | none | 49 | 76 |
| Formulation B | none | 200 | 1.5% Neo 91-8 | 40 | 72 |
| Formulation B | none | 400 | 1.5% Neo 91-8 | 50 | 93 |
| Formulation B | none | 200 | 5.0% Neo 91-8 | 27 | 65 |
| Formulation B | none | 400 | 5.0% Neo 91-8 | 49 | 83 |
| Formulation B | 1.5% MON-0818 | 200 | none | 66 | 84 |
| Formulation B | 1.5% MON-0818 | 400 | none | 76 | 100 |
| Formulation B | 5.0% MON-0818 | 200 | none | 35 | 91 |
| Formulation B | 5.0% MON-0818 | 400 | none | 63 | 93 |
| Formulation B | none | 200 | 1.5% MON-0818 | 31 | 88 |
| Formulation B | none | 400 | 1.5% MON-0818 | 73 | 95 |
| Formulation B | none | 200 | 5.0% MON-0818 | 48 | 78 |
| Formulation B | none | 400 | 5.0% MON-0818 | 49 | 88 |
| Formulation B | 1.5% glycerin | 200 | none | 19 | 81 |
| Formulation B | 1.5% glycerin | 400 | none | 55 | 100 |
| Formulation B | 5.0% glycerin | 200 | none | 53 | 88 |
| Formulation B | 5.0% glycerin | 400 | none | 55 | 95 |
| Formulation B | none | 200 | 1.5% glycerin | 24 | 96 |
| Formulation B | none | 400 | 1.5% glycerin | 76 | 99 |
| Formulation B | none | 200 | 5.0% glycerin | 31 | 95 |
| Formulation B | none | 400 | 5.0% glycerin | 50 | 91 |
| Formulation B | 1.5% Tween 20 | 200 | none | 20 | 66 |
| Formulation B | 1.5% Tween 20 | 400 | none | 38 | 68 |
| Formulation B | 5.0% Tween 20 | 200 | none | 29 | 55 |
| Formulation B | 5.0% Tween 20 | 400 | none | 43 | 79 |
| Formulation B | none | 200 | 1.5% Tween 20 | 21 | 71 |
| Formulation B | none | 400 | 1.5% Tween 20 | 66 | 98 |
| Formulation B | none | 200 | 5.0% Tween 20 | 39 | 80 |
| Formulation B | none | 400 | 5.0% Tween 20 | 65 | 94 |
| Formulation B | 1.5% 15-S-9 | 200 | none | 31 | 70 |
| Formulation B | 1.5% 15-S-9 | 400 | none | 51 | 100 |
| Formulation B | 5.0% 15-S-9 | 200 | none | 21 | 33 |
| Formulation B | 5.0% 15-S-9 | 400 | none | 39 | 39 |
| Formulation B | none | 200 | 1.5% 15-S-9 | 38 | 64 |
| Formulation B | none | 400 | 1.5% 15-S-9 | 59 | 86 |
| Formulation B | none | 200 | 5.0% 15-S-9 | 34 | 60 |
| Formulation B | none | 400 | 5.0% 15-S-9 | 66 | 96 |

In this Example antagonism of glyphosate activity in tank mix was seen on Japanese millet with the following solutions: 0.5% Silwet L-77, 1.5% and 5.0% Neodol 91-8, 1.5% and 5.0% Tween 20, and 1.5% and 5.0% Tergitol 15-S-9. Sequential application reduced antagonism on Japanese millet caused by Silwet L-77, Neodol 91-8 (5.0% only), Tween 20 and Tergitol 15-S-9 (5.0% only) but not that caused by 1.5% Neodol 91-8 and 1.5% Tergitol 15-S-9.

Example 37

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, in tank mix with MON-0818 surfactant or with MON- 0818 and a candidate accession agent, were applied 15 days after planting velvetleaf and 18 days after planting Japanese millet. MON-0818 was used at a concentration of 0.09% in the initial application spray solution in all treatments. Formulation B was applied without candidate accession agent at a range of rates from 200 to 1000 g a.e./ha. When a candidate accession agent was included in the treatment, either in tank mix or as a subsequent application, Formulation B was tested only at 200 and 400 g a.e./ha, with 0.09% MON-0818. This Example includes as a candidate accession agent an aqueous solution containing 0.5% Silwet L-77. Other candidate accession agents tested in this Example include aqueous solutions, at concentrations of 1.5% and 5.0%, of the following to surfactants or other substances:

A 1:1 weight/weight blend of Ethomeen C/15 of Akzo Chemicals Inc. with Tergitol 15-S-9 as described above; Ethomeen C/15 is described in Akzo's brochure titled "Ethoxylated and propoxylated surfactants" published 1991 as ethoxylated cocoamine having 5 moles EO; abbreviated in tables herein as "Em C/15".

Agrimul PG 2069 as described above.

Surfynol 465 as described above.

Miranol C2M of Rhone-Poulenc: described in McCutcheon's (loc. cit.) as a dicarboxylic coconut derivative, disodium salt; abbreviated in tables herein as "Miranol".

Ethoquad C/12 of Akzo Chemicals Inc.: described in Akzo's brochure titled "Ethoxylated and propoxylated surfactants" published 1991 as 75% ethoxylated cocoalkylmethyl quaternary ammonium chloride having 2 moles EO; abbreviated in tables herein as "Eq C/12".

Aerosol OT of Cytec Industries, a unit of American Cyanamid: described in McCutcheon's (loc. cit.) as dioctyl ester of sodium sulfosuccinic acid; abbreviated in tables herein as "AOT".

The time interval between initial and subsequent applications was 3 hours.

Twenty days after the initial application, all plants in the test were examined by a single practiced technician to evaluate percent inhibition. Treatments and corresponding percent inhibitions are given in Table 37.

TABLE 37

| herbicide | Initial application 93 l/ha, 0.09% MON-0818 accession agent | Glyphosate rate g a.e./ ha | Subsequent application 93 l/ha accession agent at 3 hrs | % Inhibition ABUTH | ECHCF |
| --- | --- | --- | --- | --- | --- |
| Formulation B | none | 200 | none | 41 | 29 |
| Formulation B | none | 400 | none | 97 | 98 |
| Formulation B | none | 600 | none | 99 | 95 |
| Formulation B | none | 800 | none | 100 | 96 |
| Formulation B | none | 1000 | none | 100 | 100 |
| Formulation B | 0.5% L-77 | 200 | none | 87 | 33 |
| Formulation B | 0.5% L-77 | 400 | none | 95 | 33 |
| Formulation B | none | 200 | 0.5% L-77 | 93 | 91 |
| Formulation B | none | 400 | 0.5% L-77 | 100 | 98 |
| Formulation B | 1.5% Em C/15 + 15-S-9, 1:1 | 200 | none | 14 | 92 |
| Formulation B | 1.5% EmC/15 + 15-S-9, 1:1 | 400 | none | 99 | 86 |
| Formulation B | 5.0% Em C115 + 15-S-9, 1:1 | 200 | none | 55 | 64 |
| Formulation B | 5.0% Em C/15 + 15-S-9, 1:1 | 400 | none | 55 | 72 |
| Formulation B | none | 200 | 1.5% Em C/15 + 15-S-9, 1:1 | 81 | 80 |
| Formulation B | none | 400 | 1.5% Em C/15 + 15-S-9, 1:1 | 100 | 94 |
| Formulation B | none | 200 | 5.0% Em C/15 + 15-S-9, 1:1 | 36 | 53 |
| Formulation B | none | 400 | 5.0% Em C/15 + 15-S-9, 1:1 | 75 | 85 |
| Formulation B | 1.5% PG 2069 | 200 | none | 94 | 94 |
| Formulation B | 1.5% PG 2069 | 400 | none | 100 | 100 |
| Formulation B | 5.0% PG 2069 | 200 | none | 83 | 93 |
| Formulation B | 5.0% PG 2069 | 400 | none | 100 | 100 |
| Formulation B | none | 200 | 1.5% PG 2069 | 66 | 99 |
| Formulation B | none | 400 | 1.5% PG 2069 | 98 | 99 |
| Formulation B | none | 200 | 5.0% PG 2069 | 80 | 96 |
| Formulation B | none | 400 | 5.0% PG 2069 | 100 | 93 |
| Formulation B | 1.5% Surf 465 | 200 | none | 94 | 89 |
| Formulation B | 1.5% Surf 465 | 400 | none | 99 | 98 |
| Formulation B | 5.0% Surf 465 | 200 | none | 79 | 92 |
| Formulation B | 5.0% Surf 465 | 400 | none | 92 | 98 |
| Formulation B | none | 200 | 1.5% Surf 465 | 76 | 79 |
| Formulation B | none | 400 | 1.5% Surf 465 | 99 | 96 |
| Formulation B | none | 200 | 5.0% Surf 465 | 68 | 82 |
| Formulation B | none | 400 | 5.0% Surf 465 | 88 | 95 |
| Formulation B | 1.5% Miranol | 200 | none | 70 | 87 |

TABLE 37-continued

| herbicide | Initial application 93 l/ha, 0.09% MON-0818 accession agent | Glyphosate rate g a.e./ha | Subsequent application 93 l/ha accession agent at 3 hrs | % Inhibition ABUTH | ECHCF |
|---|---|---|---|---|---|
| Formulation B | 1.5% Miranol | 400 | none | 96 | 90 |
| Formulation B | 5.0% Miranol | 200 | none | 90 | 93 |
| Formulation B | 5.0% Miranol | 400 | none | 99 | 95 |
| Formulation B | none | 200 | 1.5% Miranol | 84 | 92 |
| Formulation B | none | 400 | 1.5% Miranol | 99 | 98 |
| Formulation B | none | 200 | 5.0% Miranol | 88 | 88 |
| Formulation B | none | 400 | 5.0% Miranol | 95 | 83 |
| Formulation B | 1.5% Eq C/12 | 200 | none | 66 | 62 |
| Formulation B | 1.5% Eq C/12 | 400 | none | 92 | 78 |
| Formulation B | 5.0% Eq C/12 | 200 | none | 48 | 48 |
| Formulation B | 5.0% Eq C/12 | 400 | none | 81 | 84 |
| Formulation B | none | 200 | 1.5% Eq C/12 | 8 | 21 |
| Formulation B | none | 400 | 1.5% Eq C/12 | 92 | 84 |
| Formulation B | none | 200 | 5.0% Eq C/12 | 31 | 68 |
| Formulation B | none | 400 | 5.0% Eq C/12 | 71 | 92 |
| Formulation B | 1.5% AOT | 200 | none | 75 | 75 |
| Formulation B | 1.5% AOT | 400 | none | 85 | 72 |
| Formulation B | 5.0% AOT | 200 | none | 24 | 24 |
| Formulation B | 5.0% AOT | 400 | none | 53 | 8 |
| Formulation B | none | 200 | 1.5% AOT | 30 | 40 |
| Formulation B | none | 400 | 1.5% AOT | 73 | 89 |
| Formulation B | none | 200 | 5.0% AOT | 53 | 79 |
| Formulation B | none | 400 | 5.0% AOT | 69 | 87 |

In this Example antagonism of glyphosate activity in tank mix was seen on Japanese millet with the following solutions: 0.5% Silwet L-77 and 5.0% Aerosol OT. Sequential application reduced antagonism on Japanese millet in both cases.

Example 38

The procedures of Example 30 were repeated exactly except that initial applications were made 14 days after planting velvetleaf and 17 days after planting Japanese millet, percent inhibition was determined twenty days after initial application, candidate accession agents were applied in tank mix and subsequent applications at concentrations of 0.25% and 0.5%, and the candidate accession agents in addition to Silwet L-77 were the following organosilicone surfactants of OSi Specialties, abbreviated in tables herein by omission of the "Silwet" trademark:

Silwet 408, available from OSi but composition not disclosed.

Silwet 800, available from OSi but composition not disclosed.

Silwet L-7001, described in OSi Specialties brochure titled "Silwet surfactants" published 1994 as a 75% product having the general formula

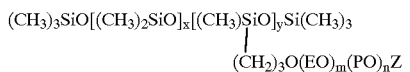

where EO refers to ethylene oxide units and PO to propylene oxide units; in Silwet L-7001 the ratio of m to n is 40/60, Z is methyl and the average molecular weight is 20,000.

Silwet L-7500, described in the OSi Specialties brochure cited above as being a 100% product having the same general formula as Silwet L-7001 but with all PO units (no EO), Z being butyl and the average molecular weight being 3000.

Silwet L-7604, described in the OSi Specialties brochure cited above as being a 100% product having the same general formula as Silwet L-7001 but with all EO units (no PO), Z being hydrogen and the average molecular weight being 4000.

Silwet L-7605, described in the OSi Specialties brochure cited above as being a 100% product having the same general formula as Silwet L-7001 but with all EO units (no PO), Z being methyl and the average molecular weight being 6000.

Treatments and corresponding percent inhibitions are given in Table 38a (Formulation B applied without MON-0818) and 38b (Formulation B applied with 0.09% MON-0818).

TABLE 38a

| herbicide | Initial application 93 l/ha, no MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 30 | 20 |
| Formulation B | none | 300 | none | 73 | 81 |
| Formulation B | none | 400 | none | 78 | 80 |
| Formulation B | none | 500 | none | 83 | 83 |
| Formulation B | 0.25% L-77 | 100 | none | 66 | 5 |
| Formulation B | 0.5% L-77 | 100 | none | 75 | 5 |
| Formulation B | none | 100 | 0.25% L-77 | 70 | 30 |
| Formulation B | none | 100 | 0.5% L-77 | 75 | 10 |
| Formulation B | 0.25% 408 | 100 | none | 70 | 10 |
| Formulation B | 0.5% 408 | 100 | none | 76 | 10 |
| Formulation B | none | 100 | 0.25% 408 | 70 | 20 |
| Formulation B | none | 100 | 0.5% 408 | 74 | 20 |
| Formulation B | 0.25% 800 | 100 | none | 70 | 10 |
| Formulation B | 0.5% 800 | 100 | none | 78 | 10 |
| Formulation B | none | 100 | 0.25% 800 | 69 | 30 |
| Formulation B | none | 100 | 0.5% 800 | 74 | 25 |
| Formulation B | 0.25% L-7001 | 100 | none | 60 | 10 |
| Formulation B | 0.5% L-7001 | 100 | none | 50 | 15 |
| Formulation B | none | 100 | 0.25% L-7001 | 50 | 38 |
| Formulation B | none | 100 | 0.5% L-7001 | 28 | 30 |
| Formulation B | 0.25% L-7500 | 100 | none | 48 | 20 |
| Formulation B | 0.5% L-7500 | 100 | none | 40 | 30 |
| Formulation B | none | 100 | 0.25%L-7500 | 48 | 30 |
| Formulation B | none | 100 | 0.5% L-7500 | 25 | 20 |
| Formulation B | 0.25% L-7604 | 100 | none | 68 | 35 |
| Formulation B | 0.5% L-7604 | 100 | none | 75 | 73 |
| Formulation B | none | 100 | 0.25% L-7604 | 55 | 23 |
| Formulation B | none | 100 | 0.5% L-7604 | 53 | 20 |
| Formulation B | 0.25% L-7605 | 100 | none | 68 | 51 |
| Formulation B | 0.5% L-7605 | 100 | none | 75 | 50 |
| Formulation B | none | 100 | 0.25% L-7605 | 70 | 45 |
| Formulation B | none | 100 | 0.5% L-7605 | 60 | 33 |

TABLE 38b

| herbicide | Initial application 93 l/ha, 0.09% MON-0818 accession agent | Glyphosate rate g a.e./ ha | Subsequent application 93 l/ha accession agent at 4 hrs | % Inhibition ABUTH | ECHCF |
|---|---|---|---|---|---|
| Formulation B | none | 100 | none | 60 | 90 |
| Formulation B | none | 300 | none | 79 | 97 |
| Formulation B | none | 400 | none | 94 | 98 |
| Formulation B | none | 500 | none | 94 | 98 |
| Formulation B | 0.25% L-77 | 100 | none | 68 | 5 |
| Formulation B | 0.5% L-77 | 100 | none | 75 | 5 |
| Formulation B | none | 100 | 0.25% L-77 | 60 | 58 |
| Formulation B | none | 100 | 0.5% L-77 | 75 | 48 |
| Formulation B | 0.25% 408 | 100 | none | 63 | 18 |
| Formulation B | 0.5% 408 | 100 | none | 75 | 20 |
| Formulation B | none | 100 | 0.25% 408 | 68 | 43 |
| Formulation B | none | 100 | 0.5% 408 | 75 | 45 |
| Formulation B | 0.25% 800 | 100 | none | 70 | 10 |
| Formulation B | 0.5% 800 | 100 | none | 78 | 10 |
| Formulation B | none | 100 | 0.25% 800 | 74 | 65 |
| Formulation B | none | 100 | 0.5% 800 | 78 | 43 |
| Formulation B | 0.25% L-7001 | 100 | none | 70 | 30 |
| Formulation B | 0.5% L-7001 | 100 | none | 73 | 35 |
| Formulation B | none | 100 | 0.25% L-7001 | 63 | 43 |
| Formulation B | none | 100 | 0.5% L-7001 | 55 | 79 |

TABLE 38b-continued

| Initial application 93 l/ha, 0.09% MON-0818 | | Glyphosate rate | Subsequent application 93 l/ha accession | | % Inhibition | |
|---|---|---|---|---|---|---|
| herbicide | accession agent | g a.e./ ha | agent | at 4 hrs | ABUTH | ECHCF |
| Formulation B | 0.25% L-7500 | 100 | none | | 66 | 60 |
| Formulation B | 0.5% L-7500 | 100 | none | | 75 | 70 |
| Formulation B | none | 100 | 0.25% L-7500 | | 65 | 68 |
| Formulation B | none | 100 | 0.5% L-7500 | | 53 | 65 |
| Formulation B | 0.25% L-7604 | 100 | none | | 70 | 50 |
| Formulation B | 0.5% L-7604 | 100 | none | | 75 | 60 |
| Formulation B | none | 100 | 0.25% L-7604 | | 65 | 63 |
| Formulation B | none | 100 | 0.5% L-7604 | | 70 | 65 |
| Formulation B | 0.25% L-7605 | 100 | none | | 70 | 55 |
| Formulation B | 0.5% L-7605 | 100 | none | | 80 | 74 |
| Formulation B | none | 100 | 0.25% L-7605 | | 69 | 55 |
| Formulation B | none | 100 | 0.5% L-7605 | | 70 | 60 |

In this Example antagonism of glyphosate activity in tank mix was seen on Japanese millet, in the presence of MON-0818, with all solutions tested. Sequential application reduced antagonism on Japanese millet caused by Silwet L-77, Silwet 408, Silwet 800, Silwet L-7001, Silwet L-7500 (0.25% only) and Silwet L-7604, but not that caused by Silwet L-7500 (0.5%) and Silwet L-7605.

Example 39

The procedures of Example 30 were repeated exactly except that initial applications were made 13 days after planting velvetleaf and 16 days after planting Japanese millet, percent inhibition was determined twenty days after initial application, candidate accession agents were applied in tank mix and subsequent applications at concentrations of 0.25% and 0.5%, and the candidate accession agents in addition to Silwet L-77 were:

Silwet L-720, described in OSi Specialties brochure titled "Silwet surfactants" published 1994 as a 50% product having the general formula

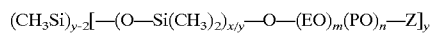

$(CH_3Si)_{y-2}[-(O-Si(CH_3)_2)_{x/y}-O-(EO)_m(PO)_n-Z]_y$ where EO refers to ethylene oxide units and PO to propylene oxide units; in Silwet L-720 the ratio of m to n is 50/50, Z is butyl and the average molecular weight is 12,000.

Ethomeen T/30 of Akzo Chemicals Inc.: not specifically described in Akzo's brochure titled "Ethoxylated and propoxylated surfactants" published 1991 but believed to be ethoxylated tallowamine having an average of 20 moles EO; abbreviated in tables herein as "Em T/30".

Treatments and corresponding percent inhibitions are given in Table 39a (Formulation B applied without MON-0818) and 39b (Formulation B applied with 0.09% MON-0818).

TABLE 39a

| Initial application 93 l/ha, no MON-0818 | | Glyphosate rate | Subsequent application 93 l/ha accession | | % Inhibition | |
|---|---|---|---|---|---|---|
| herbicide | accession agent | g a.e./ ha | agent | at 4 hrs | ABUTH | ECHCF |
| Formulation B | none | 100 | none | | 50 | 20 |
| Formulation B | none | 300 | none | | 93 | 55 |
| Formulation B | none | 400 | none | | 97 | 60 |
| Formulation B | none | 500 | none | | 100 | 92 |
| Formulation B | 0.25% L-77 | 100 | none | | 74 | 10 |
| Formulation B | 0.5% L-77 | 100 | none | | 90 | 10 |
| Formulation B | none | 100 | 0.25% L-77 | | 76 | 30 |
| Formulation B | none | 100 | 0.5% L-77 | | 83 | 20 |
| Formulation B | 0.25% L-720 | 100 | none | | 53 | 58 |
| Formulation B | 0.5% L-720 | 100 | none | | 55 | 60 |
| Formulation B | none | 100 | 0.25% L-720 | | 50 | 40 |
| Formulation B | none | 100 | 0.5% L-720 | | 45 | 20 |
| Formulation B | 0.25% Em T/30 | 100 | none | | 83 | 79 |
| Formulation B | 0.5% Em T/30 | 100 | none | | 80 | 85 |
| Formulation B | none | 100 | 0.25% Em T/30 | | 65 | 40 |
| Formulation B | none | 100 | 0.5% Em T/30 | | 60 | 30 |

TABLE 39b

| Initial application 93 l/ha, 0.09% MON-0818 | | Glyphosate rate | Subsequent application 93 l/ha accession | | % Inhibition | |
|---|---|---|---|---|---|---|
| herbicide | accession agent | g a.e./ ha | agent | at 4 hrs | ABUTH | ECHCF |
| Formulation B | none | 100 | none | | 79 | 78 |
| Formulation B | none | 300 | none | | 98 | 98 |
| Formulation B | none | 400 | none | | 100 | 100 |
| Formulation B | none | 500 | none | | 99 | 100 |
| Formulation B | 0.25% L-77 | 100 | none | | 78 | 15 |
| Formulation B | 0.5% L-77 | 100 | none | | 85 | 20 |
| Formulation B | none | 100 | 0.25% L-77 | | 78 | 69 |
| Formulation B | none | 100 | 0.5% L-77 | | 83 | 75 |
| Formulation B | 0.25% L-720 | 100 | none | | 74 | 73 |
| Formulation B | 0.5% L-720 | 100 | none | | 73 | 70 |
| Formulation B | none | 100 | 0.25% L-720 | | 76 | 78 |
| Formulation B | none | 100 | 0.5% L-720 | | 70 | 71 |
| Formulation B | 0.25% Em T/30 | 100 | none | | 80 | 83 |
| Formulation B | 0.5% Em T/30 | 100 | none | | 80 | 69 |
| Formulation B | none | 100 | 0.25% Em T/30 | | 75 | 69 |
| Formulation B | none | 100 | 0.5% Em T/30 | | 75 | 70 |

In this Example antagonism of glyphosate activity in tank mix was seen on Japanese millet, in the presence of MON-0818, with the following solutions: 0.25% and 0.5% Silwet L-77, 0.25% and 0.5% Silwet L-720, and 0.5% Ethomeen T/30. Sequential application reduced antagonism on Japanese millet caused by Silwet L-77 and Silwet L-720 (0.25% only), but not that caused by 0.5% Silwet L-720 and Ethomeen T/30.

Example 40

The procedures of Example 30 were repeated exactly except that initial applications were made 20 days after planting velvetleaf and 17 days after planting Japanese millet, percent inhibition was determined twenty days after initial application, candidate accession agents were applied in tank mix and subsequent applications at concentrations of 0.25% and 0.5%, and the candidate accession agents in addition to Silwet L-77 were:

Ganex P-904 of ISP: described in ISP Product Literature as alkylated polyvinylpyrollidone; abbreviated in tables herein as "P-904".

Fluorad FC-120 of 3M Company: described in McCutcheon's (loc. cit.) as 25% ammonium perfluoroalkyl sulfonate.

Fluorad FC-129 of 3M Company: described in McCutcheon's (loc. cit.) as 50% potassium fluorinated alkyl carboxylates.

Fluorad FC-170-C of 3M Company: described in McCutcheon's (loc. cit.) as 95% fluorinated alkyl polyoxyethylene ethanols; abbreviated in tables herein as FC-170.

Fluorad FC-171 of 3M Company: described in McCutcheon's (loc. cit.) as 100% fluorinated alkyl alkoxylate.

Fluorad FC-430 of 3M Company: described in McCutcheon's (loc. cit.) as 100% fluorinated alkyl esters.

Treatments and corresponding percent inhibitions are given in Table 40a (Formulation B applied without MON-0818) and 40b (Formulation B applied with 0.09% MON-0818).

TABLE 40a

| Initial application 93 l/ha, no MON-0818 | | Glyphosate rate | Subsequent application 93 l/ha accession | | % Inhibition | |
|---|---|---|---|---|---|---|
| herbicide | accession agent | g a.e./ ha | agent | at 4 hrs | ABUTH | ECHCF |
| Formulation B | none | 100 | none | | 50 | 33 |
| Formulation B | none | 300 | none | | 88 | 75 |
| Formulation B | none | 400 | none | | 95 | 83 |
| Formulation B | none | 500 | none | | 97 | 94 |
| Formulation B | 0.25% L-77 | 100 | none | | 76 | 20 |
| Formulation B | 0.5% L-77 | 100 | none | | 76 | 13 |
| Formulation B | none | 100 | 0.25% L-77 | | 71 | 45 |
| Formulation B | none | 100 | 0.5% L-77 | | 73 | 30 |
| Formulation B | 0.25% P-904 | 100 | none | | 65 | 73 |
| Formulation B | 0.5% P-904 | 100 | none | | 30 | 58 |
| Formulation B | none | 100 | 0.25% P-904 | | 48 | 64 |
| Formulation B | none | 100 | 0.5% P-904 | | 20 | 30 |
| Formulation B | 0.25% FC-120 | 100 | none | | 76 | 25 |
| Formulation B | 0.5% FC-120 | 100 | none | | 70 | 28 |

TABLE 40a-continued

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
| --- | --- | --- | --- | --- | --- |
| Formulation B | none | 100 | 0.25% FC-120 | 63 | 40 |
| Formulation B | none | 100 | 0.5% FC-120 | 75 | 35 |
| Formulation B | 0.25% FC-129 | 100 | none | 50 | 10 |
| Formulation B | 0.5% FC-129 | 100 | none | 63 | 10 |
| Formulation B | none | 100 | 0.25% FC-129 | 60 | 43 |
| Formulation B | none | 100 | 0.5% FC-129 | 58 | 35 |
| Formulation B | 0.25% FC-170 | 100 | none | 70 | 33 |
| Formulation B | 0.5% FC-170 | 100 | none | 69 | 40 |
| Formulation B | none | 100 | 0.25% FC-170 | 68 | 48 |
| Formulation B | none | 100 | 0.5% FC-170 | 75 | 38 |
| Formulation B | 0.25% FC-171 | 100 | none | 55 | 30 |
| Formulation B | 0.5% FC-171 | 100 | none | 25 | 30 |
| Formulation B | none | 100 | 0.25% FC-171 | 48 | 55 |
| Formulation B | none | 100 | 0.5% FC-171 | 30 | 35 |
| Formulation B | 0.25% FC-430 | 100 | none | 45 | 40 |
| Formulation B | 0.5% FC-430 | 100 | none | 53 | 60 |
| Formulation B | none | 100 | 0.25% FC-430 | 50 | 48 |
| Formulation B | none | 100 | 0.5% FC-430 | 33 | 40 |

TABLE 40b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
| --- | --- | --- | --- | --- | --- |
| Formulation B | none | 100 | none | 74 | 97 |
| Formulation B | none | 300 | none | 96 | 99 |
| Formulation B | none | 400 | none | 97 | 100 |
| Formulation B | none | 500 | none | 99 | 100 |
| Formulation B | 0.25% L-77 | 100 | none | 58 | 30 |
| Formulation B | 0.5% L-77 | 100 | none | 78 | 13 |
| Formulation B | none | 100 | 0.25% L-77 | 70 | 75 |
| Formulation B | none | 100 | 0.5% L-77 | 75 | 80 |
| Formulation B | 0.25% P-904 | 100 | none | 73 | 96 |
| Formulation B | 0.5% P-904 | 100 | none | 69 | 89 |
| Formulation B | none | 100 | 0.25% P-904 | 70 | 83 |
| Formulation B | none | 100 | 0.5% P-904 | 30 | 83 |
| Formulation B | 0.25% FC-120 | 100 | none | 74 | 20 |
| Formulation B | 0.5% FC-120 | 100 | none | 66 | 30 |
| Formulation B | none | 100 | 0.25% FC-120 | 80 | 75 |
| Formulation B | none | 100 | 0.5% FC-120 | 60 | 83 |
| Formulation B | 0.25% FC-129 | 100 | none | 73 | 40 |
| Formulation B | 0.5% FC-129 | 100 | none | 73 | 23 |
| Formulation B | none | 100 | 0.25% FC-129 | 68 | 65 |
| Formulation B | none | 100 | 0.5% FC-129 | 65 | 75 |
| Formulation B | 0.25% FC-170 | 100 | none | 75 | 73 |
| Formulation B | 0.5% FC-170 | 100 | none | 73 | 73 |
| Formulation B | none | 100 | 0.25% FC-170 | 75 | 80 |
| Formulation B | none | 100 | 0.5% FC-170 | 78 | 93 |
| Formulation B | 0.25% FC-171 | 100 | none | 79 | 65 |
| Formulation B | 0.5% FC-171 | 100 | none | 55 | 70 |
| Formulation B | none | 100 | 0.25% FC-171 | 70 | 85 |
| Formulation B | none | 100 | 0.5% FC-171 | 45 | 79 |
| Formulation B | 0.25% FC-430 | 100 | none | 75 | 60 |
| Formulation B | 0.5% FC-430 | 100 | none | 69 | 68 |
| Formulation B | none | 100 | 0.25% FC-430 | 65 | 80 |
| Formulation B | none | 100 | 0.5% FC-430 | 58 | 71 |

In this Example antagonism of glyphosate activity in tank mix was seen on Japanese millet, in the presence of MON-0818, with the following solutions: 0.25% and 0.5% Silwet L-77, 0.25% and 0.5% Fluorad FC-120, and 0.25% and 0.5% Fluorad FC-129. Sequential application reduced antagonism on Japanese millet in all cases.

Example 41

The procedures of Example 30 were repeated exactly except that initial applications were made 17 days after planting velvetleaf and 19 days after planting to Japanese millet, percent inhibition was determined eighteen days after initial application, and the candidate accession agents in addition to Silwet L-77 were:

Fluorad FC-129 as described above.

Fluorad FC-135 as described above.

Kinetic: a commercial agricultural spray adjuvant of Helena Chemical Company, containing an organosilicone surfactant.

Treatments and corresponding percent inhibitions are given in Table 41a (Formulation B applied without MON-0818) and 41b (Formulation B applied with 0.09% MON-0818).

TABLE 41a

| Initial application 93 l/ha, no MON-0818 herbicide | accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 3 | 43 |
| Formulation B | none | 300 | none | 40 | 80 |
| Formulation B | none | 400 | none | 65 | 93 |
| Formulation B | none | 500 | none | 83 | 94 |
| Formulation B | 0.5% L-77 | 100 | none | 75 | 25 |
| Formulation B | 3.0% L-77 | 100 | none | 70 | 33 |
| Formulation B | none | 100 | 0.5% L-77 | 75 | 50 |
| Formulation B | none | 100 | 3.0% L-77 | 35 | 38 |
| Formulation B | 0.5% FC-129 | 100 | none | 40 | 33 |
| Formulation B | 3.0% FC-129 | 100 | none | 50 | 50 |
| Formulation B | none | 100 | 0.5% FC-129 | 84 | 65 |
| Formulation B | none | 100 | 3.0% FC-129 | 50 | 43 |
| Formulation B | 0.5% FC-135 | 100 | none | 66 | 83 |
| Formulation B | 3.0% FC-135 | 100 | none | 61 | 64 |
| Formulation B | none | 100 | 0.5% FC-135 | 58 | 55 |
| Formulation B | none | 100 | 3.0% FC-135 | 53 | 40 |
| Formulation B | 0.5% Kinetic | 100 | none | 68 | 35 |
| Formulation B | 3.0% Kinetic | 100 | none | 78 | 38 |
| Formulation B | none | 100 | 0.5% Kinetic | 58 | 48 |
| Formulation B | none | 100 | 3.0% Kinetic | 68 | 38 |
| Formulation B | FC-129+L-77 (1:49) at 0.5% | 100 | none | 83 | 35 |
| Formulation B | FC-129+L-77 (1:49) at 3.0% | 100 | none | 73 | 350 |
| Formulation B | none | 100 | FC-129+L-77 (1:49) at 0.5% | 78 | 49 |
| Formulation B | none | 100 | FC-129+L-77 (1:49) at 3.0% | 58 | 35 |
| Formulation B | FC-129+L-77 (1:19) at 0.5% | 100 | none | 84 | 30 |
| Formulation B | FC-129+L-77 (1:19) at 3.0% | 100 | none | 78 | 40 |
| Formulation B | none | 100 | FC-129+L-77 (1:19) at 0.5% | 75 | 55 |
| Formulation B | none | 100 | FC-129+L-77 (1:19) at 3.0% | 60 | 33 |
| Formulation B | FC-129+L-77 (1:9) at 0.5% | 100 | none | 84 | 38 |
| Formulation B | FC-129+L-77 (1:9) at 3.0% | 100 | none | 75 | 35 |
| Formulation B | none | 100 | FC-129+L-77 (1:9) at 0.5% | 79 | 45 |
| Formulation B | none | 100 | FC-129+L-77 (1:9) at 3.0% | 63 | 33 |

TABLE 41b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 30 | 98 |
| Formulation B | none | 300 | none | 64 | 100 |
| Formulation B | none | 400 | none | 79 | 100 |
| Formulation B | none | 500 | none | 87 | 99 |
| Formulation B | 0.5% L-77 | 100 | none | 85 | 38 |
| Formulation B | 3.0% L-77 | 100 | none | 68 | 35 |
| Formulation B | none | 100 | 0.5% L-77 | 75 | 48 |
| Formulation B | none | 100 | 3.0% L-77 | 70 | 68 |
| Formulation B | 0.5% FC-129 | 100 | none | 25 | 30 |
| Formulation B | 3.0% FC-129 | 100 | none | 70 | 43 |
| Formulation B | none | 100 | 0.5% FC-129 | 83 | 55 |
| Formulation B | none | 100 | 3.0% FC-129 | 55 | 78 |
| Formulation B | 0.5% FC-135 | 100 | none | 70 | 78 |
| Formulation B | 3.0% FC-135 | 100 | none | 73 | 73 |
| Formulation B | none | 100 | 0.5% FC-135 | 63 | 80 |
| Formulation B | none | 100 | 3.0% FC-135 | 63 | 73 |
| Formulation B | 0.5% Kinetic | 100 | none | 35 | 43 |
| Formulation B | 3.0% Kinetic | 100 | none | 75 | 38 |
| Formulation B | none | 100 | 0.5% Kinetic | 55 | 84 |
| Formulation B | none | 100 | 3.0% Kinetic | 55 | 73 |
| Formulation B | FC-129+L-77 (1:49) at 0.5% | 100 | none | 75 | 40 |
| Formulation B | FC-129+L-77 (1:49) at 3.0% | 100 | none | 75 | 35 |
| Formulation B | none | 100 | FC-129+L-77 (1:49) at 0.5% | 74 | 89 |
| Formulation B | none | 100 | FC-129+L-77 (1:49) at 3.0% | 55 | 73 |
| Formulation B | FC-129+L-77 (1:19) at 0.5% | 100 | none | 88 | 33 |
| Formulation B | FC-129+L-77 (1:19) at 3.0% | 100 | none | 78 | 43 |
| Formulation B | none | 100 | FC-129+L-77 (1:19) at 0.5% | 74 | 60 |
| Formulation B | none | 100 | FC-129+L-77 (1:19) at 3.0% | 55 | 73 |
| Formulation B | FC-129+L-77 (1:9) at 0.5% | 100 | none | 90 | 33 |
| Formulation B | FC-129+L-77 (1:9) at 3.0% | 100 | none | 75 | 35 |
| Formulation B | none | 100 | FC-129+L-77 (1:9) at 0.5% | 80 | 50 |
| Formulation B | none | 100 | FC-129+L-77 (1:9) at 3.0% | 60 | 55 |

In this Example antagonism of glyphosate activity in tank mix was seen on Japanese millet, in the presence of MON-0818, with all solutions tested. Sequential application reduced antagonism on Japanese millet caused by Silwet L-77, Fluorad FC-129 and Kinetic but not that caused by Fluorad FC-135.

Example 42

A field test was conducted to confirm the practical effectiveness of the method of the present invention. Weed species were seeded in rows on a farm in Arkansas. The following naturally occurring weed species were used in evaluating treatments of this Example: A, henbit (*Lamium amplexicaule*, LAMAM); B, shepherd's purse (*Capsella bursa-pastoris*, CAPBP); C, small-flowered bittercress (*Cardamine parviflora*, CARPA); D, annual bluegrass (*Poa annua*, POAAN); E, little barley (*Hordeum pusillum*, HORPU).

After emergence of the weeds, rectangular plots, each 2 m wide and about 9 m long, were marked out for herbicide treatments. A randomized complete block experimental design with four replicates was used. One set of plots in each block was left untreated as a reference against which effects of the treatments could later be evaluated.

Initial applications were made when LAMAM, CAPBP and POAAN were in the early bloom stage, CARPA was in the mid bloom stage and HORPU was at the 3–5 tiller stage. Applications were made using a backpack plot sprayer pressurized with carbon dioxide and fitted with a boom having four 95015 tapered flat fan nozzles with 100-mesh screens. Spraying was conducted at walking speed (approximately 5 km/h), and was calibrated to deliver a spray volume of 93 1/ha at a spray pressure of 193 kPa.

Plants treated according to methods of prior art, for comparative purposes, received an initial treatment only. Plants treated by a method illustrative of the present invention received an initial application of Formulation C followed sequentially by a subsequent application of an accession agent. Two intervals between initial and subsequent applications, about 0.05 hour and 3 hours, were tested in this Example. Subsequent applications were applied by spraying an accession agent with a backpack sprayer fitted exactly as for the initial application and calibrated to deliver a spray volume of 93 l/ha at a pressure of 193 kPa.

Formulation C was applied without accession agent at a range of rates from 157 to 1254 g a.e./ha. When an accession agent was included in the treatment, either in tank mix with Formulation C or as a subsequent application, only the four lowest rates of Formulation C, 157, 314, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-nine days after the initial application, all plots in the test were examined by a single practiced technician to evaluate percent inhibition. Treatments and corresponding percent inhibitions are given in Table 42. Results shown are an average of the four replicate plots for each treatment.

marked out for herbicide treatments. A randomized complete block experimental design with four replicates was used. One set of plots in each block was left untreated as a reference against which effects of the treatments could later be evaluated.

Initial applications were made 64 days after planting, using a backpack plot sprayer pressurized with carbon dioxide and fitted with a boom having four 11002 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 179 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A,

TABLE 42

| Initial application 93 l/ha | | Glyphosate rate | Subsequent application, 93 l/ha | % Inhibition | | | | |
|---|---|---|---|---|---|---|---|---|
| herbicide | accession agent | g a.e./ha | accession agent 0.5% L-77 | A | B | C | D | E |
| Formulation C | none | 157 | none | 61 | 65 | 76 | 68 | 83 |
| Formulation C | none | 314 | none | 74 | 76 | 84 | 88 | 90 |
| Formulation C | none | 420 | none | 76 | 81 | 94 | 89 | 94 |
| Formulation C | none | 627 | none | 80 | 84 | 94 | 90 | 96 |
| Formulation C | none | 840 | none | 86 | 89 | 96 | 91 | 99 |
| Formulation C | none | 1254 | none | 95 | 94 | 99 | 100 | 100 |
| Formulation C | 0.5% L-77 | 157 | none | 58 | 60 | 65 | 50 | 63 |
| Formulation C | 0.5% L-77 | 314 | none | 69 | 71 | 80 | 60 | 73 |
| Formulation C | 0.5% L-77 | 420 | none | 79 | 81 | 91 | 76 | 85 |
| Formulation C | 0.5% L-77 | 627 | none | 88 | 90 | 98 | 90 | 98 |
| Formulation C | none | 157 | at ~0.05 hr | 70 | 69 | 80 | 68 | 77 |
| Formulation C | none | 314 | at ~0.05 hr | 83 | 85 | 93 | 83 | 93 |
| Formulation C | none | 420 | at ~0.05 hr | 59 | 60 | 68 | 65 | 69 |
| Formulation C | none | 627 | at ~0.05 hr | 64 | 66 | 71 | 71 | 74 |
| Formulation C | none | 157 | at 3 hrs | 65 | 63 | 69 | 63 | 81 |
| Formulation C | none | 314 | at 3 hrs | 80 | 83 | 93 | 85 | 94 |
| Formulation C | none | 420 | at 3 hrs | 80 | 85 | 93 | 88 | 96 |
| Formulation C | none | 627 | at 3 hrs | 93 | 90 | 96 | 93 | 99 |

Tank mix application of an accession agent containing Silwet L-77 with Formulation C in this Example antagonized glyphosate activity at low glyphosate rates, with the antagonism being especially marked on POAAN and HORPU, the two grass species evaluated. This test demonstrates that, under field conditions, such antagonism can be reduced or overcome by sequential application of the accession agent after the glyphosate composition according to the method of the present invention.

Example 43

A field test was conducted to confirm the practical effectiveness of the method of the present invention. Weed species were seeded in rows on a farm in southern Alabama. The following species were used in evaluating treatments of this Example: A, henbit (*Lamium amplexicaule*, LAMAM); F, cutleaf evening primrose (*Primula trientalis*, PRITR); G, canola (*Brassica napus*, BRSNC); H, carolina geranium (*Geranium carolinianum*, GERCA); I, wild mustard (*Sinapis arvensis*, SINAR).

After emergence of the weeds, rectangular plots, each 2 m wide in the dimension parallel to the weed rows, and of such a length (~4.5 m) as to extend across all planted rows, were B, C or J, followed sequentially one hour later by a subsequent application of an accession agent. Subsequent applications were applied by spraying an accession agent with a backpack sprayer fitted exactly as for the initial application and calibrated to deliver a spray volume of 93 l/ha at a pressure of 179 kPa.

Formulations were applied without accession agent at a range of rates from 314 to 627 g a.e./ha. When an accession agent was included in the treatment, either in tank or as a subsequent application, only the two lowest rates of each formulation, 314 and 420 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-four days after the initial application, all plots in the test were examined by a single practiced technician to evaluate percent inhibition. Treatments and corresponding percent inhibitions are given in Table 43. Results shown are an average of the four replicate plots for each treatment.

TABLE 43

| Initial application 93 l/ha | | Glyphosate | Subsequent application, 93 l/ha | % Inhibition | | | | |
|---|---|---|---|---|---|---|---|---|
| herbicide | accession agent | rate g a.e./ha | accession agent 0.5% L-77 | A | F | G | H | I |
| Formulation A | none | 314 | none | 91 | 64 | 79 | 60 | 76 |
| Formulation A | none | 420 | none | 94 | 75 | 83 | 65 | 83 |
| Formulation A | none | 627 | none | 96 | 78 | 90 | 76 | 90 |
| Formulation A | 0.5% L-77 | 314 | none | 86 | 63 | 69 | 69 | 66 |
| Formulation A | 0.5% L-77 | 420 | none | 91 | 70 | 77 | 68 | 68 |
| Formulation A | none | 314 | at 1 hr | 89 | 64 | 74 | 64 | 76 |
| Formulation A | none | 420 | at 1 hr | 99 | 71 | 85 | 66 | 88 |
| Formulation B | none | 314 | none | 79 | 70 | 81 | 68 | 76 |
| Formulation B | none | 420 | none | 89 | 69 | 80 | 68 | 85 |
| Formulation B | none | 627 | none | 94 | 80 | 89 | 76 | 91 |
| Formulation B | 0.5% L-77 | 314 | none | 91 | 60 | 73 | 65 | 71 |
| Formulation B | 0.5% L-77 | 420 | none | 98 | 71 | 79 | 70 | 81 |
| Formulation B | none | 314 | at 1 hr | 86 | 63 | 78 | 68 | 75 |
| Formulation B | none | 420 | at 1 hr | 98 | 78 | 85 | 68 | 87 |
| Formulation C | none | 314 | none | 89 | 73 | 79 | 69 | 87 |
| Formulation C | none | 420 | none | 96 | 68 | 88 | 65 | 90 |
| Formulation C | none | 627 | none | 99 | 80 | 89 | 80 | 96 |
| Formulation C | 0.5% L-77 | 314 | none | 93 | 55 | 65 | 66 | 63 |
| Formulation C | 0.5% L-77 | 420 | none | 97 | 70 | 80 | 73 | 71 |
| Formulation C | none | 314 | at 1 hr | 89 | 68 | 80 | 65 | 80 |
| Formulation C | none | 420 | at 1 hr | 97 | 76 | 90 | 74 | 88 |
| Formulation J | none | 314 | none | 81 | 74 | 82 | 66 | 85 |
| Formulation J | none | 420 | none | 93 | 76 | 89 | 65 | 91 |
| Formulation J | none | 627 | none | 93 | 79 | 90 | 75 | 85 |
| Formulation J | 0.5% L-77 | 314 | none | 95 | 70 | 67 | 70 | 66 |
| Formulation J | 0.5% L-77 | 420 | none | 98 | 73 | 82 | 74 | 82 |
| Formulation J | none | 314 | at 1 hr | 93 | 66 | 81 | 68 | 73 |
| Formulation J | none | 420 | at 1 hr | 95 | 73 | 89 | 70 | 87 |

Tank mix application of an accession agent containing Silwet L-77 with all four glyphosate formulations in this Example antagonized glyphosate activity at low glyphosate rates, with the antagonism being especially marked on BRSNC and SINAR. This test demonstrates that, under field conditions, such antagonism can be reduced or overcome by sequential application of the accession agent after the glyphosate composition according to the method of the present invention.

Example 44

A field test was conducted to confirm the practical effectiveness of the method of the present invention. Weed species were seeded in rows on a farm in west central Illinois. The following species were used in evaluating treatments of this Example: I, wild mustard (*Sinapis arvensis*, SINAR); J, wild buckwheat (*Polygonum convolvulus*, POLCO); K, winter wheat (*Triticum aestivum*, TRZAW); L, wild oat (*Avena fatua*, AVEFA); M, annual ryegrass (*Lolium multiflorum*, LOLMU), N. giant foxtail (*Setaria faberi*, SETFA); O, redroot pigweed (*Amaranthus retroflexus*, AMARE).

After emergence of the weeds, rectangular plots, each 2 m wide in the dimension parallel to the weed rows, and of such a length (~6.5 m) as to extend across all planted rows, were marked out for herbicide treatments. A randomized complete block experimental design with three replicates was used. One set of plots in each block was left untreated as a reference against which effects of the treatments could later be evaluated.

Initial applications were made 53 days after planting, using a backpack plot sprayer pressurized with carbon dioxide and fitted with a boom having four 80015 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially one hour later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 157 to 627 g a.e./ha. When an accession agent was included in the treatment, either in tank or as a subsequent application, only the two lowest rates of each formulation, 157 and 314 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-one days after the initial application, all plots in the test were examined by a single practiced technician to evaluate percent inhibition. Treatments and corresponding percent inhibitions are given in Table 44. Results shown are an average of the three replicate plots for each treatment.

TABLE 44

| Initial application 93 l/ha | | Glyphosate rate | Subsequent application, 93 l/ha | % Inhibition | | | | | | |
|---|---|---|---|---|---|---|---|---|---|---|
| herbicide | accession agent | g a.e./ha | accession agent 0.5% L-77 | I | J | K | L | M | N | O |
| Formul'n A | none | 157 | none | 23 | 12 | 28 | 50 | 45 | 57 | 20 |
| Formul'n A | none | 314 | none | 35 | 18 | 68 | 85 | 70 | 83 | 50 |
| Formul'n A | none | 420 | none | 55 | 35 | 87 | 97 | 82 | 90 | 68 |
| Formul'n A | none | 627 | none | 87 | 65 | 98 | 99 | 91 | 93 | 82 |
| Formul'n A | 0.5% L-77 | 157 | none | 53 | 62 | 52 | 67 | 60 | 72 | 40 |
| Formul'n A | 0.5% L-77 | 314 | none | 85 | 87 | 89 | 98 | 83 | 94 | 73 |
| Formul'n A | none | 157 | at 1 hr | 53 | 37 | 57 | 77 | 57 | 75 | 43 |
| Formul'n A | none | 314 | at 1 hr | 70 | 47 | 91 | 97 | 88 | 90 | 73 |
| Formul'n B | none | 157 | none | 30 | 17 | 25 | 45 | 40 | 63 | 28 |
| Formul'n B | none | 314 | none | 37 | 20 | 47 | 67 | 65 | 73 | 40 |
| Formul'n B | none | 420 | none | 53 | 30 | 40 | 67 | 70 | 75 | 53 |
| Formul'n B | none | 627 | none | 77 | 55 | 78 | 80 | 82 | 91 | 75 |
| Formul'n B | 0.5% L-77 | 157 | none | 72 | 77 | 62 | 82 | 72 | 77 | 47 |
| Formul'n B | 0.5% L-77 | 314 | none | 75 | 82 | 94 | 93 | 78 | 87 | 63 |
| Formul'n B | none | 157 | at 1 hr | 32 | 23 | 18 | 40 | 33 | 47 | 25 |
| Formul'n B | none | 314 | at 1 hr | 62 | 42 | 47 | 77 | 67 | 77 | 47 |
| Formul'n C | none | 157 | none | 35 | 12 | 55 | 75 | 65 | 78 | 43 |
| Formul'n C | none | 314 | none | 63 | 32 | 84 | 96 | 82 | 85 | 68 |
| Formul'n C | none | 420 | none | 62 | 30 | 92 | 100 | 83 | 82 | 53 |
| Formul'n C | none | 627 | none | 87 | 75 | 98 | 100 | 91 | 93 | 80 |
| Formul'n C | 0.5% L-77 | 157 | none | 45 | 53 | 42 | 65 | 62 | 72 | 40 |
| Formul'n C | 0.5% L-77 | 314 | none | 75 | 65 | 52 | 85 | 78 | 85 | 68 |
| Formul'n C | none | 157 | at 1 hr | 40 | 32 | 43 | 80 | 57 | 75 | 33 |
| Formul'n C | none | 314 | at 1 hr | 63 | 47 | 95 | 99 | 83 | 90 | 70 |
| Formul'n J | none | 157 | none | 30 | 17 | 73 | 89 | 73 | 83 | 60 |
| Formul'n J | none | 314 | none | 37 | 23 | 85 | 96 | 87 | 88 | 52 |
| Formul'n J | none | 420 | none | 68 | 55 | 98 | 100 | 94 | 92 | 68 |
| Formul'n J | none | 627 | none | 75 | 65 | 100 | 98 | 95 | 92 | 70 |
| Formul'n J | 0.5% L-77 | 157 | none | 63 | 43 | 57 | 78 | 60 | 77 | 30 |
| Formul'n J | 0.5% L-77 | 314 | none | 73 | 85 | 82 | 92 | 80 | 92 | 60 |
| Formul'n J | none | 157 | at 1 hr | 37 | 22 | 63 | 77 | 68 | 75 | 35 |
| Formul'n J | none | 314 | at 1 hr | 68 | 50 | 92 | 98 | 88 | 92 | 72 |

Tank mix application of an accession agent containing Silwet L-77 with Formulation C in this Example antagonized glyphosate activity on TRZAW and AVEFA, but this antagonism was substantially reduced when the accession agent was applied sequentially according to the method of the present invention. Tank mix antagonism was also evident with Formulation J on AVEFA, LOLMU and AMARE; again this antagonism was substantially reduced by sequential application according to the method of the present invention.

Example 45

A field test was conducted to confirm the practical effectiveness of the method of the present invention. Weed species were seeded in rows on a farm in Arkansas. The following species were used in evaluating treatments of this Example: I, wild mustard (*Sinapis arvensis*, SINAR); M, annual ryegrass (*Lolium multiflorum*, LOLMU), P, downy brome (*Bromus tectorum*, BROTE); Q, cutleaf geranium (*Geranium dissectum*, GERDI); R, curly dock (*Rumex crispus*, RUMCR).

After emergence of the weeds, rectangular plots, each 2 m wide in the dimension parallel to the weed rows, and of such a length (~4.5 m) as to extend across all planted rows, were marked out for herbicide treatments. A randomized complete block experimental design with four replicates was used. One set of plots in each block was left untreated as a reference against which effects of the treatments could later be evaluated.

Initial applications were made 62 days after planting, using a backpack plot sprayer pressurized with carbon dioxide and fitted with a boom having four 95015 tapered flat fan nozzles with 100-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially five hours later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 314 to 840 g a.e./ha. When an accession agent was included in the treatment, either in tank or as a subsequent application, only two rates of each formulation, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty days after the initial application, all plots in the test were examined by a single practiced technician to evaluate percent inhibition. Treatments and corresponding percent inhibitions are given in Table 45. Results shown are an average of the four replicate plots for each treatment.

TABLE 45

| Initial application 93 l/ha | | Glyphosate | Subsequent application, 93 l/ha | % Inhibition | | | | |
|---|---|---|---|---|---|---|---|---|
| herbicide | accession agent | rate g a.e./ha | accession agent 0.5% L-77 | I | M | P | Q | R |
| Formulation A | none | 314 | none | 83 | 55 | 73 | 65 | 68 |
| Formulation A | none | 420 | none | 98 | 75 | 88 | 90 | 84 |
| Formulation A | none | 627 | none | 96 | 80 | 88 | 95 | 91 |
| Formulation A | none | 840 | none | 100 | 85 | 94 | 96 | 95 |
| Formulation A | 0.5% L-77 | 420 | none | 93 | 63 | 73 | 91 | 88 |
| Formulation A | 0.5% L-77 | 627 | none | 95 | 80 | 93 | 93 | 88 |
| Formulation A | none | 420 | at 5 hrs | 63 | 48 | 58 | 58 | 50 |
| Formulation A | none | 627 | at 5 hrs | 93 | 81 | 95 | 95 | 83 |
| Formulation B | none | 314 | none | 83 | 45 | 63 | 58 | 55 |
| Formulation B | none | 420 | none | 88 | 58 | 78 | 80 | 79 |
| Formulation B | none | 627 | none | 93 | 63 | 83 | 88 | 88 |
| Formulation B | none | 840 | none | 93 | 78 | 88 | 95 | 90 |
| Formulation B | 0.5% L-77 | 420 | none | 83 | 50 | 65 | 80 | 75 |
| Formulation B | 0.5% L-77 | 627 | none | 98 | 71 | 86 | 96 | 88 |
| Formulation B | none | 420 | at 5 hrs | 88 | 55 | 76 | 81 | 75 |
| Formulation B | none | 627 | at 5 hrs | 98 | 70 | 83 | 96 | 94 |
| Formulation C | none | 314 | none | 80 | 58 | 83 | 55 | 58 |
| Formulation C | none | 420 | none | 95 | 78 | 93 | 89 | 88 |
| Formulation C | none | 627 | none | 100 | 80 | 90 | 100 | 95 |
| Formulation C | none | 840 | none | 100 | 93 | 95 | 100 | 95 |
| Formulation C | 0.5% L-77 | 420 | none | 85 | 60 | 65 | 70 | 70 |
| Formulation C | 0.5% L-77 | 627 | none | 90 | 78 | 86 | 94 | 78 |
| Formulation C | none | 420 | at 5 hrs | 88 | 68 | 88 | 85 | 83 |
| Formulation C | none | 627 | at 5 hrs | 95 | 79 | 93 | 93 | 85 |
| Formulation J | none | 314 | none | 83 | 65 | 86 | 68 | 73 |
| Formulation J | none | 420 | none | 98 | 85 | 96 | 90 | 88 |
| Formulation J | none | 627 | none | 98 | 85 | 95 | 96 | 90 |
| Formulation J | none | 840 | none | 100 | 94 | 98 | 100 | 96 |
| Formulation J | 0.5% L-77 | 420 | none | 83 | 63 | 73 | 84 | 66 |
| Formulation J | 0.5% L-77 | 627 | none | 95 | 73 | 89 | 90 | 91 |
| Formulation J | none | 420 | at 5 hrs | 90 | 73 | 88 | 88 | 80 |
| Formulation J | none | 627 | at 5 hrs | 100 | 85 | 98 | 96 | 93 |

Antagonism was observed on particular species with several tank mix accession agent treatments in this Example. It was especially marked with Formulation J. Application of the accession agent sequentially according to the present invention substantially reduced this antagonism wherever it occurred.

Example 46

A field test was conducted to confirm the practical effectiveness of the method of the present invention. Weed species were seeded in rows on a farm in southern Alabama. The following species were used in evaluating treatments of this Example: S, broadleaf signalgrass (*Brachiaria platyphylla*, BRAPP); T, barnyardgrass (*Echinochloa crusgalli*, ECHCG); U, johnsongrass (*Sorghum halepense*, SORHA); V, prickly sida (*Sida spinosa*, SIDSP); W, pigweed (Amaranthus sp., AMASS); X, velvetleaf (*Abutilon theophrasti*, ABUTH); Y, hemp sesbania (*Sesbania exaltata*, SEBEX); Z, sicklepod (*Cassia obtusifolia*, CASOB); AA, pitted morningglory (*Ipomoea lacunosa*, IPOLA).

After emergence of the weeds, rectangular plots, each 2 m wide in the dimension parallel to the weed rows, and of such a length (~4.5 m) as to extend across all planted rows, were marked out for herbicide treatments. A randomized complete block experimental design with four replicates was used. One set of plots in each block was left untreated as a reference against which effects of the treatments could later be evaluated.

Initial applications were made 14 days after planting, using a backpack plot sprayer pressurized with carbon dioxide and fitted with a boom having four 11002 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially four hours later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 420 to 1265 g a.e./ha. When an accession agent was included in the treatment, either in tank or as a subsequent application, only two rates of each formulation, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-six days after the initial application, all plots in the test were examined by a single practiced technician to evaluate percent inhibition. Treatments and corresponding percent inhibitions are given in Table 46a and 46b. Results shown are an average of the four replicate plots for each treatment.

TABLE 46a

| Initial application 93 l/ha herbicide | accession agent | Glyphosate rate g a.e./ha | Subsequent application, 93 l/ha accession agent 0.5% L-77 | % Inhibition S | T | U | V | W |
|---|---|---|---|---|---|---|---|---|
| Formulation A | none | 420 | none | 91 | 91 | 96 | 91 | 97 |
| Formulation A | none | 627 | none | 95 | 90 | 98 | 97 | 98 |
| Formulation A | none | 1265 | none | 93 | 93 | 96 | 100 | 98 |
| Formulation A | 0.5% L-77 | 420 | none | 90 | 88 | 98 | 99 | 99 |
| Formulation A | 0.5% L-77 | 627 | none | 95 | 91 | 99 | 97 | 98 |
| Formulation A | none | 420 | at 4 hrs | 91 | 92 | 95 | 100 | 96 |
| Formulation A | none | 627 | at 4 hrs | 92 | 94 | 98 | 99 | 97 |
| Formulation B | none | 420 | none | 89 | 82 | 91 | 96 | 94 |
| Formulation B | none | 627 | none | 92 | 88 | 95 | 99 | 98 |
| Formulation B | none | 1265 | none | 96 | 97 | 99 | 100 | 100 |
| Formulation B | 0.5% L-77 | 420 | none | 89 | 88 | 91 | 99 | 95 |
| Formulation B | 0.5% L-77 | 627 | none | 90 | 88 | 95 | 99 | 94 |
| Formulation B | none | 420 | at 4 hrs | 91 | 83 | 90 | 95 | 93 |
| Formulation B | none | 627 | at 4 hrs | 94 | 87 | 89 | 95 | 96 |
| Formulation C | none | 420 | none | 90 | 91 | 96 | 92 | 95 |
| Formulation C | none | 627 | none | 94 | 96 | 98 | 97 | 97 |
| Formulation C | none | 1265 | none | 99 | 99 | 100 | 100 | 99 |
| Formulation C | 0.5% L-77 | 420 | none | 89 | 85 | 96 | 94 | 92 |
| Formulation C | 0.5% L-77 | 627 | none | 92 | 92 | 96 | 96 | 95 |
| Formulation C | none | 420 | at 4 hrs | 92 | 93 | 97 | 97 | 98 |
| Formulation C | none | 627 | at 4 hrs | 92 | 90 | 97 | 95 | 95 |
| Formulation J | none | 420 | none | 90 | 92 | 95 | 94 | 94 |
| Formulation J | none | 627 | none | 93 | 95 | 95 | 99 | 99 |
| Formulation J | none | 1265 | none | 95 | 96 | 98 | 100 | 99 |
| Formulation J | 0.5% L-77 | 420 | none | 88 | 84 | 93 | 97 | 94 |
| Formulation J | 0.5% L-77 | 627 | none | 88 | 89 | 94 | 99 | 95 |
| Formulation J | none | 420 | at 4 hrs | 94 | 92 | 95 | 92 | 95 |
| Formulation J | none | 627 | at 4 hrs | 96 | 98 | 99 | 100 | 99 |

TABLE 46b

| Initial application 93 l/ha herbicide | accession agent | Glyphosate rate g a.e./ha | Subsequent application, 93 l/ha accession agent 0.5% L-77 | % Inhibition X | Y | Z | AA |
|---|---|---|---|---|---|---|---|
| Formulation A | none | 420 | none | 79 | 90 | 91 | 65 |
| Formulation A | none | 627 | none | 88 | 97 | 94 | 79 |
| Formulation A | none | 1265 | none | 96 | 100 | 99 | 89 |
| Formulation A | 0.5% L-77 | 420 | none | 97 | 94 | 90 | 68 |
| Formulation A | 0.5% L-77 | 627 | none | 94 | 96 | 93 | 82 |
| Formulation A | none | 420 | at 4 hrs | 90 | 90 | 93 | 60 |
| Formulation A | none | 627 | at 4 hrs | 94 | 96 | 96 | 78 |
| Formulation B | none | 420 | none | 83 | 56 | 78 | 71 |
| Formulation B | none | 627 | none | 86 | 71 | 88 | 71 |
| Formulation B | none | 1265 | none | 97 | 89 | 93 | 90 |
| Formulation B | 0.5% L-77 | 420 | none | 93 | 83 | 85 | 69 |
| Formulation B | 0.5% L-77 | 627 | none | 95 | 93 | 92 | 77 |
| Formulation B | none | 420 | at 4 hrs | 89 | 54 | 74 | 65 |
| Formulation B | none | 627 | at 4 hrs | 94 | 67 | 77 | 70 |
| Formulation C | none | 420 | none | 82 | 90 | 92 | 71 |
| Formulation C | none | 627 | none | 91 | 96 | 97 | 73 |
| Formulation C | none | 1265 | none | 95 | 99 | 100 | 94 |
| Formulation C | 0.5% L-77 | 420 | none | 91 | 93 | 90 | 58 |
| Formulation C | 0.5% L-77 | 627 | none | 85 | 90 | 93 | 63 |
| Formulation C | none | 420 | at 4 hrs | 92 | 92 | 92 | 61 |
| Formulation C | none | 627 | at 4 hrs | 94 | 94 | 95 | 64 |
| Formulation J | none | 420 | none | 84 | 93 | 93 | 66 |
| Formulation J | none | 627 | none | 92 | 98 | 99 | 82 |
| Formulation J | none | 1265 | none | 98 | 100 | 97 | 85 |
| Formulation J | 0.5% L-77 | 420 | none | 93 | 89 | 90 | 59 |
| Formulation J | 0.5% L-77 | 627 | none | 95 | 98 | 98 | 63 |
| Formulation J | none | 420 | at 4 hrs | 91 | 93 | 93 | 63 |
| Formulation J | none | 627 | at 4 hrs | 96 | 94 | 95 | 68 |

Formulations C and J were mildly antagonized in this test on ECHCG and IPOLA by tank mix application of an accession agent containing Silwet L-77. Sequential application according to the present invention reduced antagonism, at least on ECHCG.

Example 47

Morningglory (Ipomea sp., IPOSS) plants were grown in pots, maintained in a greenhouse and treated with initial and subsequent applications by procedures exactly as described for Example 1, except where otherwise noted below.

The herbicide in this Example was Basta, a product of AgrEvo containing as active ingredient the ammonium salt of DL-homoalanin-4-yl(methyl)phosphinate (glufosinate). The particular formulation of Basta used in this Example was an aqueous concentrate containing 200 grams of active ingredient per liter (g a.i./l), and is believed to further contain a surfactant.

Initial applications of Basta, alone or in tank mix with a candidate accession agent, were applied 20 days after planting. Basta was applied without candidate accession agent and in tank mix with a candidate accession agent at a range of rates from 300 to 1200 g a.i./ha. When a candidate accession agent was included in the treatment as a subsequent application, Basta was tested at a range of rates from 300 to 800 g a.i./ha. This Example includes as candidate accession agent an aqueous solution containing 0.5% Silwet L-77.

All subsequent applications in this Example were made by spraying the candidate accession agent with a track sprayer fitted as in Example 1 but calibrated to deliver a spray volume of 280 l/ha at a pressure of 166 kPa. The time interval between initial and subsequent applications was 1 hour.

Seventeen days after the initial application, all plants in the test were examined by a single practiced technician to evaluate percent inhibition. Treatments and corresponding percent inhibitions are given in Table 47.

TABLE 47

| Initial application 93 l/ha | | Herbicide | Subsequent application | % |
|---|---|---|---|---|
| herbicide | accession agent | rate g a.i./ha | 280 l/ha accession agent | Inhibition IPOSS |
| Basta | none | 300 | none | 31 |
| Basta | none | 400 | none | 42 |
| Basta | none | 500 | none | 59 |
| Basta | none | 600 | none | 73 |
| Basta | none | 800 | none | 73 |
| Basta | none | 1000 | none | 90 |
| Basta | none | 1200 | none | 96 |
| Basta | 0.5% L-77 | 300 | none | 37 |
| Basta | 0.5% L-77 | 400 | none | 48 |
| Basta | 0.5% L-77 | 500 | none | 56 |
| Basta | 0.5% L-77 | 600 | none | 59 |
| Basta | 0.5% L-77 | 800 | none | 57 |
| Basta | 0.5% L-77 | 1000 | none | 85 |
| Basta | 0.5% L-77 | 1200 | none | 94 |
| Basta | none | 300 | 0.5% L-77 at 1 hr | 35 |
| Basta | none | 400 | 0.5% L-77 at 1 hr | 35 |

TABLE 47-continued

| Initial application 93 l/ha | | Herbicide | Subsequent application | % |
|---|---|---|---|---|
| herbicide | accession agent | rate g a.i./ha | 280 l/ha accession agent | Inhibition IPOSS |
| Basta | none | 500 | 0.5% L-77 at 1 hr | 41 |
| Basta | none | 600 | 0.5% L-77 at 1 hr | 40 |
| Basta | none | 800 | 0.5% L-77 at 1 hr | 90 |

This test was inconclusive. However, at the Basta rate (800 g a.i./ha) showing strongest tank mix antagonism caused by Silwet L-77, this antagonism was removed by application of the Silwet L-77 as a sequential treatment according to the present invention.

Example 48

Velvetleaf (*Abutilon theophrasti*, ABUTH) and barnyardgrass (*Echinochloa crus-galli*, ECHCG) plants were grown in pots, maintained in a greenhouse and treated with initial and subsequent applications by procedures substantially as described for Example 1, except where otherwise noted below.

Herbicides in this Example included the following formulated products: Weedone LV-4, a low-volatile ester formulation of Rhone-Poulenc containing 480 g a.e./l of 2,4-dichlorophenoxyacetic acid (2,4-D); Goal, an emulsifiable concentrate formulation of Rohm & Haas containing as active ingredient 2-chloro-1-(3-ethoxy-4-nitrophenoxy)-4-(trifluoromethyl)benzene (oxyfluorfen); Amber, a water dispersible granular formulation of Ciba-Geigy containing as active ingredient 2-(2-chloroethoxy)-N-(((4-methoxy-6-methyl- 1,3,5-triazin-2-yl)amino)carbonyl) benzenesulfonamide (triasulfuron); Pursuit, an aqueous concentrate formulation of American Cyanamid containing as active ingredient 2-(4,5-dihydro-4-methyl-4-(1-methylethyl)-5-oxo-1H-imidazol-2-yl)-5-ethyl-3-pyridinecarboxylic acid (imazethapyr); Fusilade 2000, an emulsifiable concentrate formulation of Zeneca containing as active ingredient butyl R-2-(4-((5-(trifluoromethyl)-2-pyridinyl)oxy)phenoxy)propanoate (fluazifop-P-butyl); Gramoxone, an aqueous concentrate formulation of Zeneca containing as active ingredient 1,1'-dimethyl-4,4'-bipyridinium dichloride (paraquat); Ignite, an aqueous concentrate formulation of AgroEvo containing as active ingredient the ammonium salt of DL-homoalanin-4-yl(methyl) phosphinate (glufosinate). The unformulated (technical) active ingredients of all the above herbicides except for Ignite were also included. In the case of 2,4-D, the acid was used. A commercial glyphosate formulation (Formulation A) and, as technical material, the isopropylamine (IPA) salt of glyphosate, were also applied in this Example. Water was used as the spray carrier for all formulated products, and for technical IPA glyphosate and paraquat. Basic water was used as the spray carrier for technical triasulfuron. Acetone was used as the spray carrier for technical 2,4-D acid. Methanol was used as the spray carrier for technical oxyfluorfen, imazethapyr and fluazifop-P-butyl.

TABLE 48

| Initial application 187 l/ha | | Herbicide rate | Subsequent application 187 l/ha | % Inhibition | | | |
|---|---|---|---|---|---|---|---|
| | | | | 12 DAT | | 23 DAT | |
| herbicide | accession agent | g a.i. or a.e./ha | accession agent | ABUTH | ECHCG | ABUTH | ECHCG |
| Formulation A | none | 100 | none | 0 | 0 | 0 | 0 |
| Formulation A | none | 300 | none | 82 | 75 | 67 | 53 |
| Formulation A | none | 500 | none | 100 | 78 | 100 | 60 |
| Formulation A | none | 800 | none | 100 | 96 | 98 | 87 |
| Formulation A | 0.5% L-77 | 100 | none | 90 | 0 | 90 | 0 |
| Formulation A | 0.5% L-77 | 300 | none | 97 | 0 | 97 | 3 |
| Formulation A | 0.5% L-77 | 500 | none | 100 | 10 | 100 | 3 |
| Formulation A | 0.5% L-77 | 800 | none | 100 | 53 | 95 | 40 |
| Formulation A | none | 100 | 0.5% L-77 at 0.5 hr | 96 | 0 | 87 | 0 |
| Formulation A | none | 300 | 0.5% L-77 at 0.5 hr | 100 | 43 | 100 | 27 |
| Formulation A | none | 500 | 0.5% L-77 at 0.5 hr | 100 | 87 | 100 | 75 |
| Formulation A | none | 800 | 0.5% L-77 at 0.5 hr | 100 | 99 | 100 | 94 |
| glyphosate IPA | none | 100 | none | 7 | 7 | 3 | 3 |
| glyphosate IPA | none | 300 | none | 32 | 28 | 47 | 13 |
| glyphosate IPA | none | 500 | none | 33 | 57 | 37 | 30 |
| glyphosate IPA | none | 800 | none | 87 | 78 | 88 | 63 |
| glyphosate IPA | 0.5% L-77 | 100 | none | 92 | 0 | 90 | 0 |
| glyphosate IPA | 0.5% L-77 | 300 | none | 100 | 0 | 100 | 0 |
| glyphosate IPA | 0.5% L-77 | 500 | none | 100 | 0 | 100 | 0 |
| glyphosate IPA | 0.5% L-77 | 800 | none | 100 | 10 | 100 | 10 |
| glyphosate IPA | none | 100 | 0.5% L-77 at 0.5 hr | 100 | 17 | 100 | 10 |
| glyphosate IPA | none | 300 | 0.5% L-77 at 0.5 hr | 100 | 13 | 100 | 3 |
| glyphosate IPA | none | 500 | 0.5% L-77 at 0.5 hr | 100 | 60 | 100 | 40 |
| glyphosate IPA | none | 800 | 0.5% L-77 at 0.5 hr | 100 | 47 | 98 | 33 |
| Weedone | none | 70 | none | 10 | 0 | 30 | 0 |
| Weedone | none | 140 | none | 25 | 0 | 40 | 0 |
| Weedone | none | 280 | none | 57 | 10 | 60 | 7 |
| Weedone | none | 560 | none | 60 | 3 | 72 | 3 |
| Weedone | 0.5% L-77 | 70 | none | 13 | 0 | 37 | 0 |
| Weedone | 0.5% L-77 | 140 | none | 27 | 0 | 43 | 0 |
| Weedone | 0.5% L-77 | 280 | none | 35 | 0 | 67 | 3 |
| Weedone | 0.5% L-77 | 560 | none | 62 | 0 | 89 | 7 |
| Weedone | none | 70 | 0.5% L-77 at 0.5 hr | 10 | 0 | 32 | 0 |
| Weedone | none | 140 | 0.5% L-77 at 0.5 hr | 20 | 7 | 40 | 3 |
| Weedone | none | 280 | 0.5% L-77 at 0.5 hr | 35 | 7 | 60 | 0 |
| Weedone | none | 560 | 0.5% L-77 at 0.5 hr | 58 | 7 | 77 | 0 |
| 2,4-D acid | none | 70 | none | 10 | 10 | 13 | 17 |
| 2,4-D acid | none | 140 | none | 17 | 0 | 17 | 10 |
| 2,4-D acid | none | 280 | none | 30 | 0 | 43 | 10 |
| 2,4-D acid | none | 560 | none | 60 | 17 | 70 | 20 |
| 2,4-D acid | 0.5% L-77 | 70 | none | 27 | 0 | 30 | 10 |
| 2,4-D acid | 0.5% L-77 | 140 | none | 33 | 13 | 57 | 7 |
| 2,4-D acid | 0.5% L-77 | 280 | none | 60 | 7 | 82 | 17 |
| 2,4-D acid | 0.5% L-77 | 560 | none | 63 | 13 | 83 | 10 |
| 2,4-D acid | none | 70 | 0.5% L-77 at 0.5 hr | 13 | 7 | 17 | 7 |
| 2,4-D acid | none | 140 | 0.5% L-77 at 0.5 hr | 47 | 12 | 43 | 17 |
| 2,4-D acid | none | 280 | 0.5% L-77 at 0.5 hr | 62 | 10 | 80 | 10 |
| 2,4-D acid | none | 560 | 0.5% L-77 at 0.5 hr | 67 | 13 | 82 | 17 |
| Goal | none | 70 | none | 30 | 33 | 28 | 0 |
| Goal | none | 140 | none | 37 | 43 | 27 | 20 |
| Goal | none | 280 | none | 73 | 73 | 53 | 43 |
| Goal | none | 560 | none | 58 | 87 | 30 | 80 |
| Goal | 0.5% L-77 | 70 | none | 67 | 47 | 60 | 27 |
| Goal | 0.5% L-77 | 140 | none | 65 | 55 | 63 | 43 |
| Goal | 0.5% L-77 | 280 | none | 87 | 73 | 78 | 60 |
| Goal | 0.5% L-77 | 560 | none | 98 | 95 | 93 | 83 |
| Goal | none | 70 | 0.5% L-77 at 0.5 hr | 28 | 30 | 40 | 0 |
| Goal | none | 140 | 0.5% L-77 at 0.5 hr | 30 | 53 | 40 | 33 |
| Goal | none | 280 | 0.5% L-77 at 0.5 hr | 67 | 68 | 57 | 53 |
| Goal | none | 560 | 0.5% L-77 at 0.5 hr | 75 | 77 | 80 | 60 |
| oxyfluorfen | none | 70 | none | 90 | 53 | 83 | 47 |
| oxyfluorfen | none | 140 | none | 97 | 90 | 90 | 77 |
| oxyfluorfen | none | 280 | none | 100 | 99 | 100 | 99 |
| oxyfluorfen | none | 560 | none | 100 | 99 | 100 | 99 |
| oxyfluorfen | 0.5% L-77 | 70 | none | 67 | 43 | 63 | 23 |
| oxyfluorfen | 0.5% L-77 | 140 | none | 77 | 67 | 75 | 50 |
| oxyfluorfen | 0.5% L-77 | 280 | none | 92 | 88 | 85 | 63 |
| oxyfluorfen | 0.5% L-77 | 560 | none | 88 | 89 | 85 | 70 |
| oxyfluorfen | none | 70 | 0.5% L-77 at 0.5 hr | 80 | 73 | 75 | 47 |
| oxyfluorfen | none | 140 | 0.5% L-77 at 0.5 hr | 93 | 88 | 82 | 63 |
| oxyfluorfen | none | 280 | 0.5% L-77 at 0.5 hr | 99 | 95 | 98 | 87 |
| oxyfluorfen | none | 560 | 0.5% L-77 at 0.5 hr | 98 | 96 | 97 | 90 |

TABLE 48-continued

| | Initial application 187 l/ha | Herbicide rate | Subsequent | % Inhibition | | | |
|---|---|---|---|---|---|---|---|
| | | | | 12 DAT | | 23 DAT | |
| herbicide | accession agent | g a.i. or a.e./ha | application 187 l/ha accession agent | ABUTH | ECHCG | ABUTH | ECHCG |
| Amber | none | 18 | none | 70 | 0 | 70 | 3 |
| Amber | none | 35 | none | 70 | 0 | 75 | 3 |
| Amber | none | 70 | none | 70 | 0 | 75 | 0 |
| Amber | none | 140 | none | 72 | 0 | 75 | 0 |
| Amber | 0.5% L-77 | 18 | none | 88 | 0 | 95 | 0 |
| Amber | 0.5% L-77 | 35 | none | 90 | 0 | 95 | 0 |
| Amber | 0.5% L-77 | 70 | none | 97 | 62 | 99 | 57 |
| Amber | 0.5% L-77 | 140 | none | 96 | 53 | 99 | 43 |
| Amber | none | 18 | 0.5% L-77 at 0.5 hr | 88 | 3 | 90 | 3 |
| Amber | none | 35 | 0.5% L-77 at 0.5 hr | 87 | 0 | 95 | 0 |
| Amber | none | 70 | 0.5% L-77 at 0.5 hr | 96 | 13 | 97 | 27 |
| Amber | none | 140 | 0.5% L-77 at 0.5 hr | 92 | 7 | 96 | 23 |
| triasulfuron | none | 18 | none | 70 | 0 | 75 | 10 |
| triasulfuron | none | 35 | none | 73 | 7 | 80 | 0 |
| triasulfuron | none | 70 | none | 75 | 15 | 83 | 0 |
| triasulfuron | none | 140 | none | 77 | 57 | 80 | 30 |
| triasulfuron | 0.5% L-77 | 18 | none | 72 | 17 | 85 | 3 |
| triasulfuron | 0.5% L-77 | 35 | none | 73 | 23 | 85 | 20 |
| triasulfuron | 0.5% L-77 | 70 | none | 80 | 53 | 93 | 37 |
| triasulfuron | 0.5% L-77 | 140 | none | 78 | 73 | 93 | 60 |
| triasulfuron | none | 18 | 0.5% L-77 at 0.5 hr | 78 | 0 | 80 | 0 |
| triasulfuron | none | 35 | 0.5% L-77 at 0.5 hr | 83 | 17 | 90 | 13 |
| triasulfuron | none | 70 | 0.5% L-77 at 0.5 hr | 82 | 13 | 92 | 10 |
| triasulfuron | none | 140 | 0.5% L-77 at 0.5 hr | 88 | 50 | 92 | 17 |
| Pursuit | none | 9 | none | 30 | 0 | 30 | 0 |
| Pursuit | none | 18 | none | 27 | 0 | 30 | 0 |
| Pursuit | none | 35 | none | 40 | 0 | 30 | 0 |
| Pursuit | none | 70 | none | 72 | 0 | 67 | 7 |
| Pursuit | 0.5% L-77 | 9 | none | 73 | 43 | 72 | 20 |
| Pursuit | 0.5% L-77 | 18 | none | 75 | 75 | 75 | 50 |
| Pursuit | 0.5% L-77 | 35 | none | 75 | 78 | 80 | 72 |
| Pursuit | 0.5% L-77 | 70 | none | 75 | 83 | 85 | 88 |
| Pursuit | none | 9 | 0.5% L-77 at 0.5 hr | 63 | 0 | 73 | 0 |
| Pursuit | none | 18 | 0.5% L-77 at 0.5 hr | 62 | 3 | 77 | 7 |
| Pursuit | none | 35 | 0.5% L-77 at 0.5 hr | 80 | 60 | 77 | 33 |
| Pursuit | none | 70 | 0.5% L-77 at 0.5 hr | 80 | 60 | 93 | 40 |
| imazethapyr | none | 9 | none | 10 | 0 | 10 | 0 |
| imazethapyr | none | 18 | none | 23 | 12 | 20 | 0 |
| imazethapyr | none | 35 | none | 30 | 17 | 37 | 7 |
| imazethapyr | none | 70 | none | 37 | 13 | 50 | 13 |
| imazethapyr | 0.5% L-77 | 9 | none | 60 | 63 | 42 | 30 |
| imazethapyr | 0.5% L-77 | 18 | none | 65 | 82 | 53 | 85 |
| imazethapyr | 0.5% L-77 | 35 | none | 70 | 77 | 70 | 77 |
| imazethapyr | 0.5% L-77 | 70 | none | 72 | 90 | 72 | 95 |
| imazethapyr | none | 9 | 0.5% L-77 at 0.5 hr | 73 | 30 | 68 | 30 |
| imazethapyr | none | 18 | 0.5% L-77 at 0.5 hr | 68 | 40 | 72 | 40 |
| imazethapyr | none | 35 | 0.5% L-77 at 0.5 hr | 68 | 27 | 70 | 37 |
| imazethapyr | none | 70 | 0.5% L-77 at 0.5 hr | 73 | 85 | 73 | 92 |
| Fusilade 2000 | none | 9 | none | 3 | 3 | 0 | 0 |
| Fusilade 2000 | none | 18 | none | 0 | 15 | 0 | 23 |
| Fusilade 2000 | none | 35 | none | 0 | 33 | 0 | 23 |
| Fusilade 2000 | none | 70 | none | 0 | 43 | 0 | 37 |
| Fusilade 2000 | 0.5% L-77 | 9 | none | 7 | 3 | 0 | 10 |
| Fusilade 2000 | 0.5% L-77 | 18 | none | 0 | 57 | 0 | 33 |
| Fusilade 2000 | 0.5% L-77 | 35 | none | 3 | 77 | 0 | 73 |
| Fusilade 2000 | 0.5% L-77 | 70 | none | 0 | 78 | 0 | 78 |
| Fusilade 2000 | none | 9 | 0.5% L-77 at 0.5 hr | 30 | 3 | 20 | 0 |
| Fusilade 2000 | none | 18 | 0.5% L-77 at 0.5 hr | 3 | 17 | 0 | 7 |
| Fusilade 2000 | none | 35 | 0.5% L-77 at 0.5 hr | 0 | 15 | 0 | 17 |
| Fusilade 2000 | none | 70 | 0.5% L-77 at 0.5 hr | 0 | 70 | 0 | 70 |
| fluazifop-p | none | 9 | none | 0 | 20 | 0 | 27 |
| fluazifop-p | none | 18 | none | 0 | 63 | 0 | 63 |
| fluazifop-p | none | 35 | none | 0 | 70 | 0 | 87 |
| fluazifop-p | none | 70 | none | 0 | 85 | 0 | 97 |
| fluazifop-p | 0.5% L-77 | 9 | none | 8 | 23 | 7 | 33 |
| fluazifop-p | 0.5% L-77 | 18 | none | 0 | 60 | 0 | 78 |
| fluazifop-p | 0.5% L-77 | 35 | none | 0 | 85 | 0 | 92 |
| fluazifop-p | 0.5% L-77 | 70 | none | 0 | 97 | 0 | 98 |
| fluazifop-p | none | 9 | 0.5% L-77 at 0.5 hr | 3 | 30 | 7 | 43 |
| fluazifop-p | none | 18 | 0.5% L-77 at 0.5 hr | 0 | 53 | 0 | 63 |
| fluazifop-p | none | 35 | 0.5% L-77 at 0.5 hr | 0 | 70 | 0 | 83 |
| fluazifop-p | none | 70 | 0.5% L-77 at 0.5 hr | 0 | 93 | 0 | 97 |

TABLE 48-continued

| Initial application 187 l/ha | | Herbicide rate | Subsequent | % Inhibition | | | |
|---|---|---|---|---|---|---|---|
| | | | | 12 DAT | | 23 DAT | |
| herbicide | accession agent | g a.i. or a.e./ha | application 187 l/ha accession agent | ABUTH | ECHCG | ABUTH | ECHCG |
| Gramoxone | none | 100 | none | 13 | 3 | 0 | 10 |
| Gramoxone | none | 300 | none | 60 | 13 | 60 | 3 |
| Gramoxone | none | 500 | none | 67 | 33 | 70 | 13 |
| Gramoxone | none | 800 | none | 83 | 53 | 77 | 37 |
| Gramoxone | 0.5% L-77 | 100 | none | 23 | 3 | 10 | 3 |
| Gramoxone | 0.5% L-77 | 300 | none | 63 | 13 | 77 | 13 |
| Gramoxone | 0.5% L-77 | 500 | none | 77 | 50 | 85 | 23 |
| Gramoxone | 0.5% L-77 | 800 | none | 100 | 35 | 100 | 27 |
| Gramoxone | none | 100 | 0.5% L-77 at 0.5 hr | 23 | 0 | 10 | 0 |
| Gramoxone | none | 300 | 0.5% L-77 at 0.5 hr | 90 | 13 | 93 | 10 |
| Gramoxone | none | 500 | 0.5% L-77 at 0.5 hr | 100 | 50 | 100 | 47 |
| Gramoxone | none | 800 | 0.5% L-77 at 0.5 hr | 100 | 70 | 100 | 63 |
| paraquat | none | 100 | none | 13 | 10 | 7 | 10 |
| paraquat | none | 300 | none | 50 | 13 | 53 | 13 |
| paraquat | none | 500 | none | 40 | 30 | 53 | 20 |
| paraquat | none | 800 | none | 67 | 50 | 77 | 53 |
| paraquat | 0.5% L-77 | 100 | none | 10 | 0 | 10 | 0 |
| paraquat | 0.5% L-77 | 300 | none | 30 | 15 | 63 | 10 |
| paraquat | 0.5% L-77 | 500 | none | 47 | 23 | 65 | 7 |
| paraquat | 0.5% L-77 | 800 | none | 93 | 30 | 97 | 10 |
| paraquat | none | 100 | 0.5% L-77 at 0.5 hr | 13 | 13 | 13 | 0 |
| paraquat | none | 300 | 0.5% L-77 at 0.5 hr | 33 | 27 | 40 | 0 |
| paraquat | none | 500 | 0.5% L-77 at 0.5 hr | 87 | 30 | 83 | 23 |
| paraquat | none | 800 | 0.5% L-77 at 0.5 hr | 90 | 40 | 80 | 20 |
| Ignite | none | 100 | none | 0 | 3 | 0 | 0 |
| Ignite | none | 300 | none | 20 | 37 | 0 | 27 |
| Ignite | none | 500 | none | 67 | 55 | 50 | 40 |
| Ignite | none | 800 | none | 94 | 83 | 78 | 77 |
| Ignite | 0.5% L-77 | 100 | none | 23 | 3 | 13 | 7 |
| Ignite | 0.5% L-77 | 300 | none | 33 | 0 | 17 | 0 |
| Ignite | 0.5% L-77 | 500 | none | 87 | 7 | 80 | 0 |
| Ignite | 0.5% L-77 | 800 | none | 77 | 23 | 67 | 23 |
| Ignite | none | 100 | 0.5% L-77 at 0.5 hr | 27 | 0 | 27 | 0 |
| Ignite | none | 300 | 0.5% L-77 at 0.5 hr | 92 | 7 | 92 | 3 |
| Ignite | none | 500 | 0.5% L-77 at 0.5 hr | 93 | 57 | 93 | 53 |
| Ignite | none | 800 | 0.5% L-77 at 0.5 hr | 95 | 60 | 92 | 48 |

Tank mix antagonism was evident from Silwet L-77 on the following herbicides in this Example: glyphosate (both as Formulation A and as technical IPA salt), oxyfluorfen (as technical material), paraquat (as technical material) and glufosinate (as Ignite). Sequential application according to the present invention reduced the antagonism in all the above cases.

Example 49

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 1, except where otherwise noted below.

Glufosinate as its ammonium salt in unformulated (technical) form was used as the herbicidally active agent for this Example. Initial applications of glufosinate, alone or in tank mix with a candidate accession agent, were applied on the same day, 14 days after planting velvetleaf, 14 days after planting Japanese millet, and 21 days after planting prickly sida. All treatments were applied by spraying with a track sprayer fitted with a single 8002E nozzle calibrated to deliver a spray volume of 187 l/ha at a pressure of 173 kPa. Glufosinate was applied in water with and without candidate accession agent at a range of rates from 200 to 900 g a.e./ha. This Example includes as candidate accession agents aqueous solutions containing Silwet L-77 at concentrations ranging from 0.25% to 1.5% by volume. When Silwet L-77 was applied subsequently, the time interval between initial and subsequent applications ranged from 1 to 24 hours.

Fifteen days after the initial application, all plants in the test were examined by a single practiced technician to evaluate percent inhibition. Treatments and corresponding percent inhibitions are given in Table 49.

TABLE 49

| herbicide | Initial application 187 l/ha accession agent | Herbicide rate g a.i./ha | Subsequent application 187 l/ha accession agent | % Inhibition ABUTH | ECHCF | SIDSP |
|---|---|---|---|---|---|---|
| Glufosinate | none | 200 | none | 23 | 5 | 12 |
| Glufosinate | none | 400 | none | 89 | 15 | 38 |
| Glufosinate | none | 600 | none | 91 | 15 | 65 |
| Glufosinate | none | 900 | none | 98 | 30 | 62 |
| Glufosinate | 0.25% L-77 | 200 | none | 87 | 0 | 53 |
| Glufosinate | 0.25% L-77 | 400 | none | 98 | 7 | 72 |
| Glufosinate | 0.25% L-77 | 600 | none | 96 | 13 | 95 |
| Glufosinate | 0.25% L-77 | 900 | none | 96 | 13 | 97 |
| Glufosinate | 0.5% L-77 | 200 | none | 90 | 10 | 66 |
| Glufosinate | 0.5% L-77 | 400 | none | 97 | 12 | 85 |
| Glufosinate | 0.5% L-77 | 600 | none | 96 | 7 | 81 |
| Glufosinate | 0.5% L-77 | 900 | none | 99 | 42 | 88 |
| Glufosinate | 1.5% L-77 | 200 | none | 82 | 8 | 62 |
| Glufosinate | 1.5% L-77 | 400 | none | 98 | 10 | 63 |
| Glufosinate | 1.5% L-77 | 600 | none | 98 | 42 | 82 |
| Glufosinate | 1.5% L-77 | 900 | none | 97 | 70 | 85 |
| Glufosinate | none | 200 | 0.25% L-77 at 1 hr | 87 | 30 | 58 |
| Glufosinate | none | 400 | 0.25% L-77 at 1 hr | 96 | 33 | 75 |
| Glufosinate | none | 600 | 0.25% L-77 at 1 hr | 90 | 32 | 87 |
| Glufosinate | none | 900 | 0.25% L-77 at 1 hr | 98 | 42 | 96 |
| Glufosinate | none | 200 | 0.25% L-77 at 4 hr | 67 | 15 | 60 |
| Glufosinate | none | 400 | 0.25% L-77 at 4 hr | 85 | 20 | 83 |
| Glufosinate | none | 600 | 0.25% L-77 at 4 hr | 96 | 15 | 83 |
| Glufosinate | none | 900 | 0.25% L-77 at 4 hr | 89 | 25 | 94 |
| Glufosinate | none | 200 | 0.25% L-77 at 24 hr | 67 | 5 | 62 |
| Glufosinate | none | 400 | 0.25% L-77 at 24 hr | 97 | 35 | 72 |
| Glufosinate | none | 600 | 0.25% L-77 at 24 hr | 99 | 25 | 87 |
| Glufosinate | none | 900 | 0.25% L-77 at 24 hr | 94 | 60 | 91 |
| Glufosinate | none | 200 | 0.5% L-77 at 1 hr | 90 | 23 | 60 |
| Glufosinate | none | 400 | 0.5% L-77 at 1 hr | 94 | 23 | 78 |
| Glufosinate | none | 600 | 0.5% L-77 at 1 hr | 97 | 35 | 88 |
| Glufosinate | none | 900 | 0.5% L-77 at 1 hr | 97 | 52 | 92 |
| Glufosinate | none | 200 | 0.5% L-77 at 4 hr | 78 | 5 | 65 |
| Glufosinate | none | 400 | 0.5% L-77 at 4 hr | 96 | 15 | 80 |
| Glufosinate | none | 600 | 0.5% L-77 at 4 hr | 96 | 7 | 95 |
| Glufosinate | none | 900 | 0.5% L-77 at 4 hr | 98 | 40 | 87 |
| Glufosinate | none | 200 | 0.5% L-77 at 24 hr | 72 | 20 | 70 |
| Glufosinate | none | 400 | 0.5% L-77 at 24 hr | 96 | 45 | 63 |
| Glufosinate | none | 600 | 0.5% L-77 at 24 hr | 99 | 3 | 75 |
| Glufosinate | none | 900 | 0.5% L-77 at 24 hr | 97 | 70 | 80 |
| Glufosinate | none | 200 | 1.5% L-77 at 1 hr | 92 | 8 | 60 |
| Glufosinate | none | 400 | 1.5% L-77at 1 hr | 92 | 15 | 63 |
| Glufosinate | none | 600 | 1.5% L-77 at 1 hr | 94 | 37 | 62 |
| Glufosinate | none | 900 | 1.5% L-77 at 1 hr | 98 | 47 | 73 |
| Glufosinate | none | 200 | 1.5% L-77 at 4 hr | 95 | 3 | 77 |
| Glufosinate | none | 400 | 1.5% L-77 at 4 hr | 99 | 25 | 80 |
| Glufosinate | none | 600 | 1.5% L-77 at 4 hr | 99 | 62 | 88 |
| Glufosinate | none | 900 | 1.5% L-77 at 4 hr | 99 | 80 | 94 |
| Glufosinate | none | 200 | 1.5% L-77 at 24 hr | 88 | 18 | 67 |
| Glufosinate | none | 400 | 1.5% L-77 at 24 hr | 93 | 32 | 68 |
| Glufosinate | none | 600 | 1.5% L-77 at 24 hr | 98 | 65 | 87 |
| Glufosinate | none | 900 | 1.5% L-77 at 24 hr | 99 | 40 | 83 |

In this Example, the herbicidal activity of glufosinate ammonium applied as unformulated product was not antagonized on any of the three species by Silwet L-77 applied in tank mix, therefore no reduction in antagonism by sequential application was observable. By contrast, Ignite, the commercial formulation of glufosinate ammonium used in Example 48, did show antagonism on barnyardgrass (ECHCG) by Silwet L-77 in tank mix, this antagonism being much reduced when the Silwet L-77 was instead applied as a subsequent application 0.5 hours after herbicide application.

Example 50

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Paraquat as its dichloride salt in unformulated (technical) form was used as the herbicidally active agent for this Example. Initial applications of paraquat, alone or in tank mix with a candidate accession agent, were applied on the same day, 15 days after planting velvetleaf, 14 days after planting Japanese millet, and 20 days after planting prickly sida. Paraquat was applied in water with and without candidate accession agent at a range of rates from 50 to 400 g a.i./ha. Candidate accession agent treatments were exactly as in Example 49.

Twelve days after the initial application, all plants in the test were examined by a single practiced technician to evaluate percent inhibition. Treatments and corresponding percent inhibitions are given in Table 50.

TABLE 50

| herbicide | Initial application 187 l/ha accession agent | Herbicide rate g a.i./ha | Subsequent application 187 l/ha accession agent | % Inhibition ABUTH | ECHCF | SIDSP |
|---|---|---|---|---|---|---|
| Paraquat | none | 50 | none | 48 | 15 | 8 |
| Paraquat | none | 100 | none | 67 | 30 | 50 |
| Paraquat | none | 200 | none | 86 | 88 | 42 |
| Paraquat | none | 400 | none | 98 | 98 | 89 |
| Paraquat | 0.25% L-77 | 50 | none | 78 | 35 | 68 |
| Paraquat | 0.25% L-77 | 100 | none | 97 | 40 | 94 |
| Paraquat | 0.25% L-77 | 200 | none | 100 | 42 | 88 |
| Paraquat | 0.25% L-77 | 400 | none | 100 | 92 | 99 |
| Paraquat | 0.5% L-77 | 50 | none | 78 | 20 | 65 |
| Paraquat | 0.5% L-77 | 100 | none | 100 | 65 | 85 |
| Paraquat | 0.5% L-77 | 200 | none | 100 | 55 | 91 |
| Paraquat | 0.5% L-77 | 400 | none | 99 | 80 | 94 |
| Paraquat | 1.5% L-77 | 50 | none | 78 | 20 | 57 |
| Paraquat | 1.5% L-77 | 100 | none | 73 | 43 | 70 |
| Paraquat | 1.5% L-77 | 200 | none | 98 | 63 | 72 |
| Paraquat | 1.5% L-77 | 400 | none | 98 | 93 | 92 |
| Paraquat | none | 50 | 0.25% L-77 at 1 hr | 50 | 8 | 32 |
| Paraquat | none | 100 | 0.25% L-77 at 1 hr | 86 | 35 | 52 |
| Paraquat | none | 200 | 0.25% L-77 at 1 hr | 93 | 70 | 85 |
| Paraquat | none | 400 | 0.25% L-77 at 1 hr | 100 | 96 | 93 |
| Paraquat | none | 50 | 0.25% L-77 at 4 hr | 60 | 25 | 52 |
| Paraquat | none | 100 | 0.25% L-77 at 4 hr | 68 | 65 | 65 |
| Paraquat | none | 200 | 0.25% L-77 at 4 hr | 78 | 67 | 63 |
| Paraquat | none | 400 | 0.25% L-77 at 4 hr | 93 | 98 | 92 |
| Paraquat | none | 50 | 0.25% L-77 at 24 hr | 32 | 25 | 35 |
| Paraquat | none | 100 | 0.25% L-77 at 24 hr | 75 | 40 | 62 |
| Paraquat | none | 200 | 0.25% L-77 at 24 hr | 86 | 91 | 55 |
| Paraquat | none | 400 | 0.25% L-77 at 24 hr | 99 | 98 | 70 |
| Paraquat | none | 50 | 0.5% L-77 at 1 hr | 67 | 35 | 47 |
| Paraquat | none | 100 | 0.5% L-77 at 1 hr | 85 | 45 | 67 |
| Paraquat | none | 200 | 0.5% L-77 at 1 hr | 99 | 73 | 82 |
| Paraquat | none | 400 | 0.5% L-77 at 1 hr | 100 | 80 | 93 |
| Paraquat | none | 50 | 0.5% L-77 at 4 hr | 42 | 20 | 52 |
| Paraquat | none | 100 | 0.5% L-77 at 4 hr | 80 | 40 | 57 |
| Paraquat | none | 200 | 0.5% L-77 at 4 hr | 97 | 68 | 80 |
| Paraquat | none | 400 | 0.5% L-77 at 4 hr | 98 | 94 | 82 |
| Paraquat | none | 50 | 0.5% L-77 at 24 hr | 42 | 33 | 47 |
| Paraquat | none | 100 | 0.5% L-77 at 24 hr | 68 | 78 | 58 |
| Paraquat | none | 200 | 0.5% L-77 at 24 hr | 88 | 83 | 65 |
| Paraquat | none | 400 | 0.5% L-77 at 24 hr | 97 | 99 | 85 |
| Paraquat | none | 50 | 1.5% L-77 at 1 hr | 65 | 33 | 62 |
| Paraquat | none | 100 | 1.5% L-77 at 1 hr | 85 | 37 | 73 |
| Paraquat | none | 200 | 1.5% L-77 at 1 hr | 99 | 63 | 91 |
| Paraquat | none | 400 | 1.5% L-77 at 1 hr | 99 | 97 | 96 |
| Paraquat | none | 50 | 1.5% L-77 at 4 hr | 53 | 20 | 55 |
| Paraquat | none | 100 | 1.5% L-77 at 4 hr | 83 | 57 | 65 |
| Paraquat | none | 200 | 1.5% L-77 at 4 hr | 98 | 85 | 83 |
| Paraquat | none | 400 | 1.5% L-77 at 4 hr | 100 | 98 | 93 |
| Paraquat | none | 50 | 1.5% L-77 at 24 hr | 53 | 35 | 55 |
| Paraquat | none | 100 | 1.5% L-77 at 24 hr | 60 | 62 | 63 |
| Paraquat | none | 200 | 1.5% L-77 at 24 hr | 87 | 83 | 68 |
| Paraquat | none | 400 | 1.5% L-77 at 24 hr | 100 | 96 | 75 |

Some antagonism by Silwet L-77 at all three concentrations in tank mix was evident on ECHCF, particularly at the 200 g a.i./ha paraquat rate. This antagonism was generally reduced or eliminated when the Silwet L-77 was applied as a subsequent application at any time from 1 to 24 hours after paraquat application.

Example 51

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Acifluorfen as acid in unformulated (technical) form was used as the herbicidally active agent for this Example. Initial applications of acifluorfen, alone or in tank mix with a candidate accession agent, were applied on the same day, 15 days after planting velvetleaf, 14 days after planting Japanese millet, and 20 days after planting prickly sida. Acifluorfen was applied in a diluent comprising 50% water and 50% dimethylsulfoxide (DMSO) with and without candidate accession agent at a range of rates from 50 to 400 g a.i./ha. Candidate accession agent treatments were exactly as in Example 49.

Thirteen days after the initial application, all plants in the test were examined by a is single practiced technician to evaluate percent inhibition.

In this Example, the herbicidal activity of acifluorfen was generally not antagonized on any of the three species by Silwet L-77 applied in tank mix, therefore no reduction in antagonism by sequential application was observable.

Example 52

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Bentazon in unformulated (technical) form was used as the herbicidally active agent for this Example. Initial applications of bentazon, alone or in tank mix with a candidate accession agent, were applied on the same day, 15 days after planting velvetleaf, 14 days after planting Japanese millet, and 20 days after planting prickly sida. Bentazon was applied in a diluent comprising 50% water and 50% DMSO with and without candidate accession agent at a range of rates from 50 to 600 g a.i./ha. Candidate accession agent treatments were exactly as in Example 49.

Twelve days after the initial application, all plants in the test were examined by a single practiced technician to evaluate percent inhibition.

In this Example, the herbicidal activity of bentazon was generally not antagonized on any of the three species by Silwet L-77 applied in tank mix, therefore no reduction in antagonism by sequential application was observable.

Example 53

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Isoproturon in unformulated (technical) form was used as the herbicidally active agent for this Example. Initial applications of isoproturon, alone or in tank mix with a candidate accession agent, were applied on the same day, 15 days after planting velvetleaf, 14 days after planting Japanese millet, and 20 days after planting prickly sida. Isoproturon was applied in a diluent comprising 50% water and 50% DMSO with and without candidate accession agent at a range of rates from 50 to 600 g a.i./ha. Candidate accession agent treatments were exactly as in Example 49.

Eleven days after the initial application, all plants in the test were examined by a single practiced technician to evaluate percent inhibition.

In this Example, the herbicidal activity of isoproturon was generally not antagonized on any of the three species by Silwet L-77 applied in tank mix, therefore no reduction in antagonism by sequential application was observable.

Example 54

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Oxyfluorfen in unformulated (technical) form was used as the herbicidally active agent for this Example. Initial applications of oxyfluorfen, alone or in tank mix with a candidate accession agent, were applied on the same day, 15 days after planting velvetleaf, 14 days after planting Japanese millet, and 20 days after planting prickly sida. Oxyfluorfen was applied in a diluent comprising 50% water and 50% ethanol with and without candidate accession agent at a range of rates from 25 to 300 g a.i./ha. Candidate accession agent treatments were exactly as in Example 49.

Ten days after the initial application, all plants in the test were examined by a single practiced technician to evaluate percent inhibition. Treatments and corresponding percent inhibitions are given in Table 54.

TABLE 54

| | Initial application 187 l/ha | Herbicide | Subsequent | | | |
| | | rate | application 187 l/ha | % Inhibition | | |
| herbicide | accession agent | g a.i./ha | accession agent | ABUTH | ECHCF | SIDSP |
|---|---|---|---|---|---|---|
| Oxyfluorfen | none | 25 | none | 78 | 37 | 40 |
| Oxyfluorfen | none | 50 | none | 91 | 70 | 53 |
| Oxyfluorfen | none | 100 | none | 88 | 88 | 63 |
| Oxyfluorfen | none | 300 | none | 98 | 99 | 68 |
| Oxyfluorfen | 0.25% L-77 | 25 | none | 82 | 40 | 35 |
| Oxyfluorfen | 0.25% L-77 | 50 | none | 80 | 67 | 43 |
| Oxyfluorfen | 0.25% L-77 | 100 | none | 92 | 97 | 63 |
| Oxyfluorfen | 0.25% L-77 | 300 | none | 91 | 100 | 63 |
| Oxyfluorfen | 0.5% L-77 | 25 | none | 85 | 45 | 40 |
| Oxyfluorfen | 0.5% L-77 | 50 | none | 83 | 45 | 48 |
| Oxyfluorfen | 0.5% L-77 | 100 | none | 91 | 98 | 63 |
| Oxyfluorfen | 0.5% L-77 | 300 | none | 96 | 98 | 65 |
| Oxyfluorfen | 1.5% L-77 | 25 | none | 85 | 73 | 35 |

TABLE 54-continued

| | Initial application 187 l/ha | Herbicide | Subsequent | % Inhibition | | |
|---|---|---|---|---|---|---|
| herbicide | accession agent | rate g a.i./ha | application 187 l/ha accession agent | ABUTH | ECHCF | SIDSP |
| Oxyfluorfen | 1.5% L-77 | 50 | none | 85 | 73 | 37 |
| Oxyfluorfen | 1.5% L-77 | 100 | none | 90 | 90 | 58 |
| Oxyfluorfen | 1.5% L-77 | 300 | none | 93 | 100 | 65 |
| Oxyfluorfen | none | 25 | 0.25% L-77 at 1 hr | 87 | 52 | 57 |
| Oxyfluorfen | none | 50 | 0.25% L-77 at 1 hr | 96 | 65 | 63 |
| Oxyfluorfen | none | 100 | 0.25% L-77 at 1 hr | 97 | 89 | 62 |
| Oxyfluorfen | none | 300 | 0.25% L-77 at 1 hr | 91 | 63 | 62 |
| Oxyfluorfen | none | 25 | 0.25% L-77 at 4 hr | 83 | 32 | 50 |
| Oxyfluorfen | none | 50 | 0.25% L-77 at 4 hr | 85 | 72 | 53 |
| Oxyfluorfen | none | 100 | 0.25% L-77 at 4 hr | 94 | 92 | 65 |
| Oxyfluorfen | none | 300 | 0.25% L-77 at 4 hr | 95 | 94 | 63 |
| Oxyfluorfen | none | 25 | 0.25% L-77 at 24 hr | 87 | 63 | 52 |
| Oxyfluorfen | none | 50 | 0.25% L-77 at 24 hr | 90 | 60 | 55 |
| Oxyfluorfen | none | 100 | 0.25% L-77 at 24 hr | 93 | 68 | 65 |
| Oxyfluorfen | none | 300 | 0.25% L-77 at 24 hr | 98 | 97 | 67 |
| Oxyfluorfen | none | 25 | 0.5% L-77 at 1 hr | 80 | 55 | 53 |
| Oxyfluorfen | none | 50 | 0.5% L-77 at 1 hr | 93 | 76 | 58 |
| Oxyfluorfen | none | 100 | 0.5% L-77 at 1 hr | 95 | 83 | 67 |
| Oxyfluorfen | none | 300 | 0.5% L-77 at 1 hr | 92 | 73 | 65 |
| Oxyfluorfen | none | 25 | 0.5% L-77 at 4 hr | 78 | 62 | 50 |
| Oxyfluorfen | none | 50 | 0.5% L-77 at 4 hr | 88 | 78 | 60 |
| Oxyfluorfen | none | 100 | 0.5% L-77 at 4 hr | 90 | 88 | 60 |
| Oxyfluorfen | none | 300 | 0.5% L-77 at 4 hr | 96 | 90 | 65 |
| Oxyfluorfen | none | 25 | 0.5% L-77 at 24 hr | 87 | 65 | 60 |
| Oxyfluorfen | none | 50 | 0.5% L-77 at 24 hr | 93 | 65 | 60 |
| Oxyfluorfen | none | 100 | 0.5% L-77 at 24 hr | 95 | 72 | 63 |
| Oxyfluorfen | none | 300 | 0.5% L-77 at 24 hr | 98 | 97 | 65 |
| Oxyfluorfen | none | 25 | 1.5% L-77 at 1 hr | 83 | 68 | 50 |
| Oxyfluorfen | none | 50 | 1.5% L-77 at 1 hr | 89 | 52 | 48 |
| Oxyfluorfen | none | 100 | 1.5% L-77 at 1 hr | 96 | 82 | 57 |
| Oxyfluorfen | none | 300 | 1.5% L-77 at 1 hr | 90 | 78 | 58 |
| Oxyfluorfen | none | 25 | 1.5% L-77 at 4 hr | 82 | 65 | 57 |
| Oxyfluorfen | none | 50 | 1.5% L-77 at 4 hr | 92 | 68 | 58 |
| Oxyfluorfen | none | 100 | 1.5% L-77 at 4 hr | 96 | 90 | 65 |
| Oxyfluorfen | none | 300 | 1.5% L-77 at 4 hr | 97 | 96 | 65 |
| Oxyfluorfen | none | 25 | 1.5% L-77 at 24 hr | 91 | 65 | 55 |
| Oxyfluorfen | none | 50 | 1.5% L-77 at 24 hr | 96 | 65 | 60 |
| Oxyfluorfen | none | 100 | 1.5% L-77 at 24 hr | 97 | 83 | 63 |
| Oxyfluorfen | none | 300 | 1.5% L-77 at 24 hr | 98 | 87 | 65 |

Silwet L-77 in tank mix slightly antagonized oxyfluorfen activity on SIDSP in this Example. With few exceptions no such antagonism was seen when the Silwet L-77 was applied as a subsequent treatment 1 to 24 hours after oxyfluorfen application.

Example 55

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Aminotriazole in unformulated (technical) form was used as the herbicidally active agent for this Example. Initial applications of aminotriazole, alone or in tank mix with a candidate accession agent, were applied on the same day, 15 days after planting velvetleaf, 14 days after planting Japanese millet, and 20 days after planting prickly sida. Aminotriazole was applied in water with and without candidate accession agent at a range of rates from 100 to 800 g a.i./ha. Candidate accession agent treatments were exactly as in Example 49.

Nineteen days after the initial application, all plants in the test were examined by a single practiced technician to evaluate percent inhibition. Treatments and corresponding percent inhibitions are given in Table 55.

TABLE 55

| herbicide | Initial application 187 l/ha accession agent | Herbicide rate g a.i./ha | Subsequent application 187 l/ha accession agent | % Inhibition ABUTH | ECHCF | SIDSP |
|---|---|---|---|---|---|---|
| Aminotriazole | none | 100 | none | 67 | 0 | 25 |
| Aminotriazole | none | 200 | none | 75 | 7 | 62 |
| Aminotriazole | none | 400 | none | 93 | 5 | 75 |
| Aminotriazole | none | 800 | none | 94 | 10 | 77 |
| Aminotriazole | 0.25% L-77 | 100 | none | 73 | 0 | 15 |
| Aminotriazole | 0.25% L-77 | 200 | none | 88 | 5 | 43 |
| Aminotriazole | 0.25% L-77 | 400 | none | 93 | 3 | 70 |
| Aminotriazole | 0.25% L-77 | 800 | none | 92 | 35 | 78 |
| Aminotriazole | 0.5% L-77 | 100 | none | 92 | 0 | 27 |
| Aminotriazole | 0.5% L-77 | 200 | none | 82 | 1 | 28 |
| Aminotriazole | 0.5% L-77 | 400 | none | 95 | 3 | 73 |
| Aminotriazole | 0.5% L-77 | 800 | none | 97 | 28 | 75 |
| Aminotriazole | 1.5% L-77 | 100 | none | 88 | 10 | 30 |
| Aminotriazole | 1.5% L-77 | 200 | none | 83 | 13 | 40 |
| Aminotriazole | 1.5% L-77 | 400 | none | 92 | 15 | 67 |
| Aminotriazole | 1.5% L-77 | 800 | none | 90 | 30 | 70 |
| Aminotriazole | none | 100 | 0.25% L-77 at 1 hr | 73 | 3 | 35 |
| Aminotriazole | none | 200 | 0.25% L-77 at 1 hr | 92 | 7 | 70 |
| Aminotriazole | none | 400 | 0.25% L-77 at 1 hr | 95 | 0 | 77 |
| Aminotriazole | none | 800 | 0.25% L-77 at 1 hr | 98 | 22 | 85 |
| Aminotriazole | none | 100 | 0.25% L-77 at 4 hr | 68 | 0 | 22 |
| Aminotriazole | none | 200 | 0.25% L-77 at 4 hr | 91 | 2 | 65 |
| Aminotriazole | none | 400 | 0.25% L-77 at 4 hr | 95 | 3 | 77 |
| Aminotriazole | none | 800 | 0.25% L-77 at 4 hr | 97 | 10 | 85 |
| Aminotriazole | none | 100 | 0.25% L-77 at 24 hr | 88 | 0 | 35 |
| Aminotriazole | none | 200 | 0.25% L-77 at 24 hr | 96 | 12 | 65 |
| Aminotriazole | none | 400 | 0.25% L-77 at 24 hr | 95 | 3 | 75 |
| Aminotriazole | none | 800 | 0.25% L-77 at 24 hr | 97 | 8 | 80 |
| Aminotriazole | none | 100 | 0.5% L-77 at 1 hr | 82 | 0 | 67 |
| Aminotriazole | none | 200 | 0.5% L-77 at 1 hr | 96 | 3 | 67 |
| Aminotriazole | none | 400 | 0.5% L-77 at 1 hr | 96 | 13 | 82 |
| Aminotriazole | none | 800 | 0.5% L-77 at 1 hr | 95 | 20 | 77 |
| Aminotriazole | none | 100 | 0.5% L-77 at 4 hr | 80 | 0 | 25 |
| Aminotriazole | none | 200 | 0.5% L-77 at 4 hr | 97 | 0 | 70 |
| Aminotriazole | none | 400 | 0.5% L-77 at 4 hr | 93 | 0 | 80 |
| Aminotriazole | none | 800 | 0.5% L-77 at 4 hr | 93 | 3 | 82 |
| Aminotriazole | none | 100 | 0.5% L-77 at 24 hr | 94 | 2 | 40 |
| Aminotriazole | none | 200 | 0.5% L-77 at 24 hr | 96 | 2 | 65 |
| Aminotriazole | none | 400 | 0.5% L-77 at 24 hr | 98 | 8 | 83 |
| Aminotriazole | none | 800 | 0.5% L-77 at 24 hr | 97 | 17 | 87 |
| Aminotriazole | none | 100 | 1.5% L-77 at 1 hr | 91 | 8 | 62 |
| Aminotriazole | none | 200 | 1.5% L-77 at 1 hr | 84 | 2 | 67 |
| Aminotriazole | none | 400 | 1.5% L-77 at 1 hr | 89 | 8 | 77 |
| Aminotriazole | none | 800 | 1.5% L-77 at 1 hr | 98 | 22 | 78 |
| Aminotriazole | none | 100 | 1.5% L-77 at 4 hr | 72 | 0 | 72 |
| Aminotriazole | none | 200 | 1.5% L-77 at 4 hr | 84 | 0 | 75 |
| Aminotriazole | none | 400 | 1.5% L-77 at 4 hr | 98 | 0 | 83 |
| Aminotriazole | none | 800 | 1.5% L-77 at 4 hr | 97 | 5 | 83 |
| Aminotriazole | none | 100 | 1.5% L-77 at 24 hr | 87 | 0 | 45 |
| Aminotriazole | none | 200 | 1.5% L-77 at 24 hr | 90 | 7 | 68 |
| Aminotriazole | none | 400 | 1.5% L-77 at 24 hr | 98 | 12 | 80 |
| Aminotriazole | none | 800 | 1.5% L-77 at 24 hr | 98 | 17 | 88 |

Silwet L-77 in tank mix slightly antagonized aminotriazole activity on SIDSP in this Example. No such antagonism was seen when the Silwet L-77 was applied as a subsequent treatment 1 to 24 hours after aminotriazole application.

Example 56

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Asulam as its methyl ester in unformulated (technical) form was used as the herbicidally active agent for this Example. Initial applications of asulam, alone or in tank mix with a candidate accession agent, were applied on the same day, 15 days after planting velvetleaf, 14 days after planting Japanese millet, and 20 days after planting prickly sida. Asulam was applied in a diluent comprising 50% water and 50% acetone with and without candidate accession agent at a range of rates from 200 to 1400 g a.i./ha. Candidate accession agent treatments were exactly as in Example 49.

Eighteen days after the initial application, all plants in the test were examined by a single practiced technician to evaluate percent inhibition.

In this Example, the herbicidal activity of asulam was generally not antagonized on any of the three species by Silwet L-77 applied in tank mix, therefore no reduction in antagonism by sequential application was observable.

Example 57

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

2,4-Dichlorophenoxyacetic acid (2,4-D) as its dimethylamine salt in unformulated (technical) form was used as the herbicidally active agent for this Example. Initial applications of 2,4-D, alone or in tank mix with a candidate accession agent, were applied on the same day, 15 days after planting velvetleaf, 14 days after planting Japanese millet, and 20 days after planting prickly sida. 2,4-D was applied in water with and without candidate accession agent at a range of rates from 25 to 400 g a.i./ha. Candidate accession agent treatments were exactly as in Example 49.

Eighteen days after the initial application, all plants in the test were examined by a single practiced technician to evaluate percent inhibition. Treatments and corresponding percent inhibitions are given in Table 57.

TABLE 57

| | Initial application 187 l/ha | Herbicide rate | Subsequent application 187 l/ha | % Inhibition | | |
|---|---|---|---|---|---|---|
| herbicide | accession agent | g a.i./ha | accession agent | ABUTH | ECHCF | SIDSP |
| 2,4-D | none | 25 | none | 8 | 10 | 35 |
| 2,4-D | none | 50 | none | 22 | 15 | 37 |
| 2,4-D | none | 100 | none | 85 | 18 | 63 |
| 2,4-D | none | 400 | none | 96 | 38 | 80 |
| 2,4-D | 0.25% L-77 | 25 | none | 12 | 13 | 47 |
| 2,4-D | 0.25% L-77 | 50 | none | 38 | 22 | 65 |
| 2,4-D | 0.25% L-77 | 100 | none | 94 | 33 | 70 |
| 2,4-D | 0.25% L-77 | 400 | none | 98 | 58 | 78 |
| 2,4-D | 0.5% L-77 | 25 | none | 15 | 10 | 47 |
| 2,4-D | 0.5% L-77 | 50 | none | 48 | 23 | 52 |
| 2,4-D | 0.5% L-77 | 100 | none | 94 | 57 | 60 |
| 2,4-D | 0.5% L-77 | 400 | none | 98 | 58 | 78 |
| 2,4-D | 1.5% L-77 | 25 | none | 15 | 10 | 40 |
| 2,4-D | 1.5% L-77 | 50 | none | 42 | 23 | 53 |
| 2,4-D | 1.5% L-77 | 100 | none | 52 | 25 | 75 |
| 2,4-D | 1.5% L-77 | 400 | none | 86 | 47 | 73 |
| 2,4-D | none | 25 | 0.25% L-77 at 1 hr | 15 | 15 | 60 |
| 2,4-D | none | 50 | 0.25% L-77 at 1 hr | 32 | 22 | 65 |
| 2,4-D | none | 100 | 0.25% L-77 at 1 hr | 81 | 20 | 70 |
| 2,4-D | none | 400 | 0.25% L-77 at 1 hr | 99 | 47 | 88 |
| 2,4-D | none | 25 | 0.25% L-77 at 4 hr | 98 | 45 | 77 |
| 2,4-D | none | 50 | 0.25% L-77 at 4 hr | 20 | 5 | 47 |
| 2,4-D | none | 100 | 0.25% L-77 at 4 hr | 40 | 7 | 63 |
| 2,4-D | none | 400 | 0.25% L-77 at 4.hr | 96 | 25 | 75 |
| 2,4-D | none | 25 | 0.25% L-77 at 24 hr | 25 | 5 | 60 |
| 2,4-D | none | 50 | 0.25% L-77 at 24 hr | 55 | 35 | 65 |
| 2,4-D | none | 100 | 0.25% L-77 at 24 hr | 94 | 35 | 65 |
| 2,4-D | none | 400 | 0.25% L-77 at 24 hr | 98 | 40 | 73 |
| 2,4-D | none | 25 | 0.5% L-77 at 1 hr | 32 | 15 | 58 |
| 2,4-D | none | 50 | 0.5% L-77 at 1 hr | 76 | 20 | 62 |
| 2,4-D | none | 100 | 0.5% L-77 at 1 hr | 93 | 20 | 73 |
| 2,4-D | none | 400 | 0.5% L-77 at 1 hr | 98 | 45 | 75 |
| 2,4-D | none | 25 | 0.5% L-77 at 4 hr | 15 | 0 | 55 |
| 2,4-D | none | 50 | 0.5% L-77 at 4 hr | 33 | 10 | 60 |
| 2,4-D | none | 100 | 0.5% L-77 at 4 hr | 78 | 20 | 62 |
| 2,4-D | none | 400 | 0.5% L-77 at 4 hr | 90 | 33 | 65 |
| 2,4-D | none | 25 | 0.5% L-77 at 24 hr | 42 | 7 | 58 |
| 2,4-D | none | 50 | 0.5% L-77 at 24 hr | 77 | 12 | 60 |
| 2,4-D | none | 100 | 0.5% L-77 at 24 hr | 88 | 35 | 62 |
| 2,4-D | none | 400 | 0.5% L-77 at 24 hr | 98 | 52 | 65 |
| 2,4-D | none | 25 | 1.5% L-77 at 1 hr | 30 | 10 | 58 |
| 2,4-D | none | 50 | 1.5% L-77 at 1 hr | 67 | 15 | 68 |
| 2,4-D | none | 100 | 1.5% L-77 at 1 hr | 83 | 17 | 75 |
| 2,4-D | none | 400 | 1.5% L-77 at 1 hr | 94 | 45 | 90 |
| 2,4-D | none | 25 | 1.5% L-77 at 4 hr | 28 | 5 | 42 |
| 2,4-D | none | 50 | 1.5% L-77 at 4 hr | 43 | 7 | 60 |
| 2,4-D | none | 100 | 1.5% L-77 at 4 hr | 94 | 23 | 60 |
| 2,4-D | none | 400 | 1.5% L-77 at 4 hr | 98 | 37 | 65 |
| 2,4-D | none | 25 | 1.5% L-77 at 24 hr | 25 | 25 | 35 |
| 2,4-D | none | 50 | 1.5% L-77 at 24 hr | 67 | 20 | 60 |
| 2,4-D | none | 100 | 1.5% L-77 at 24 hr | 91 | 23 | 60 |
| 2,4-D | none | 400 | 1.5% L-77 at 24 hr | 98 | 48 | 65 |

Slight antagonism on ABUTH was evident when 1.5% Silwet L-77 was added in tank mix to 2,4-D, at the higher rates tested. This antagonism was completely eliminated when instead the Silwet L-77 was applied as a subsequent application 1 to 24 hours after 2,4-D application.

Example 58

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Propanil was used as the herbicidally active agent for this Example. Initial applications of propanil, alone or in tank mix with a candidate accession agent, were applied on the same day, 15 days after planting velvetleaf, 14 days after planting Japanese millet, and 20 days after planting prickly sida. Propanil was applied in a diluent comprising 50% water and 50% acetone with and without candidate accession agent at a range of rates from 200 to 1500 g a.i./ha. Candidate accession agent treatments were exactly as in Example 49.

Twelve days after the initial application, all plants in the test were examined by a single practiced technician to evaluate percent inhibition. Treatments and corresponding percent inhibitions are given in Table 58.

TABLE 58

| | Initial application 187 l/ha | Herbicide rate | Subsequent application 187 l/ha | % Inhibition | | |
|---|---|---|---|---|---|---|
| herbicide | accession agent | g a.i./ha | accession agent | ABUTH | ECHCF | SIDSP |
| Propanil | none | 200 | none | 0 | 0 | 0 |
| Propanil | none | 500 | none | 62 | 32 | 7 |
| Propanil | none | 1000 | none | 70 | 37 | 32 |
| Propanil | none | 1500 | none | 88 | 55 | 27 |
| Propanil | 0.25% L-77 | 200 | none | 15 | 0 | 0 |
| Propanil | 0.25% L-77 | 500 | none | 30 | 10 | 27 |
| Propanil | 0.25% L-77 | 1000 | none | 80 | 17 | 25 |
| Propanil | 0.25% L-77 | 1500 | none | 90 | 30 | 25 |
| Propanil | 0.5% L-77 | 200 | none | 20 | 10 | 8 |
| Propanil | 0.5% L-77 | 500 | none | 52 | 20 | 28 |
| Propanil | 0.5% L-77 | 1000 | none | 65 | 55 | 28 |
| Propanil | 0.5% L-77 | 1500 | none | 75 | 62 | 30 |
| Propanil | 1.5% L-77 | 200 | none | 27 | 5 | 15 |
| Propanil | 1.5% L-77 | 500 | none | 37 | 38 | 27 |
| Propanil | 1.5% L-77 | 1000 | none | 68 | 57 | 37 |
| Propanil | 1.5% L-77 | 1500 | none | 86 | 57 | 32 |
| Propanil | none | 200 | 0.25% L-77 at 1 hr | 27 | 7 | 17 |
| Propanil | none | 500 | 0.25% L-77 at 1 hr | 47 | 12 | 28 |
| Propanil | none | 1000 | 0.25% L-77 at 1 hr | 52 | 8 | 30 |
| Propanil | none | 1500 | 0.25% L-77 at 1 hr | 77 | 65 | 52 |
| Propanil | none | 200 | 0.25% L-77 at 4 hr | 33 | 20 | 15 |
| Propanil | none | 500 | 0.25% L-77 at 4 hr | 50 | 20 | 23 |
| Propanil | none | 1000 | 0.25% L-77 at 4 hr | 75 | 27 | 37 |
| Propanil | none | 1500 | 0.25% L-77 at 4 hr | 78 | 63 | 37 |
| Propanil | none | 200 | 0.25% L-77 at 24 hr | 33 | 3 | 15 |
| Propanil | none | 500 | 0.25% L-77 at 24 hr | 58 | 25 | 33 |
| Propanil | none | 1000 | 0.25% L-77 at 24 hr | 45 | 53 | 33 |
| Propanil | none | 1500 | 0.25% L-77 at 24 hr | 80 | 40 | 33 |
| Propanil | none | 200 | 0.5% L-77 at 1 hr | 35 | 10 | 32 |
| Propanil | none | 500 | 0.5% L-77 at 1 hr | 42 | 10 | 33 |
| Propanil | none | 1000 | 0.5% L-77 at 1 hr | 40 | 57 | 38 |
| Propanil | none | 1500 | 0.5% L-77 at 1 hr | 68 | 35 | 60 |
| Propanil | none | 200 | 0.5% L-77 at 4 hr | 33 | 17 | 25 |
| Propanil | none | 500 | 0.5% L-77 at 4 hr | 57 | 20 | 35 |
| Propanil | none | 1000 | 0.5% L-77 at 4 hr | 67 | 35 | 43 |
| Propanil | none | 1500 | 0.5% L-77 at 4 hr | 70 | 43 | 42 |
| Propanil | none | 200 | 0.5% L-77 at 24 hr | 42 | 20 | 20 |
| Propanil | none | 500 | 0.5% L-77 at 24 hr | 72 | 30 | 35 |
| Propanil | none | 1000 | 0.5% L-77 at 24 hr | 73 | 53 | 42 |
| Propanil | none | 1500 | 0.5% L-77 at 24 hr | 80 | 55 | 40 |
| Propanil | none | 200 | 1.5% L-77 at 1 hr | 28 | 0 | 30 |
| Propanil | none | 500 | 1.5% L-77 at 1 hr | 45 | 13 | 38 |
| Propanil | none | 1000 | 1.5% L-77 at 1 hr | 65 | 25 | 45 |
| Propanil | none | 1500 | 1.5% L-77 at 1 hr | 72 | 33 | 50 |
| Propanil | none | 200 | 1.5% L-77 at 4 hr | 62 | 33 | 43 |
| Propanil | none | 500 | 1.5% L-77 at 4 hr | 68 | 32 | 53 |
| Propanil | none | 1000 | 1.5% L-77 at 4 hr | 77 | 45 | 52 |
| Propanil | none | 1500 | 1.5% L-77 at 4 hr | 88 | 55 | 52 |
| Propanil | none | 200 | 1.5% L-77 at 24 hr | 55 | 33 | 37 |
| Propanil | none | 500 | 1.5% L-77 at 24 hr | 63 | 30 | 38 |
| Propanil | none | 1000 | 1.5% L-77 at 24 hr | 77 | 57 | 42 |
| Propanil | none | 1500 | 1.5% L-77 at 24 hr | 85 | 65 | 48 |

In this Example, the herbicidal activity of propanil, particularly on ABUTH, was slightly antagonized by certain Silwet L-77 tank mix treatments, though no clear pattern of antagonism was evident. Several, but not all, of the sequential applications showed reduced antagonism.

Example 59

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Dicamba acid in unformulated (technical) form was used as the herbicidally active agent for this Example. Initial applications of dicamba, alone or in tank mix with a candidate accession agent, were applied on the same day, 14 days after planting velvetleaf, 14 days after planting Japanese millet, and 21 days after planting prickly sida. Dicamba was applied in a diluent comprising 50% water and 50% acetone with and without candidate accession agent at a range of rates from 50 to 300 g a.i./ha. Candidate accession agent treatments were exactly as in Example 49.

Fifteen days after the initial application, all plants in the test were examined by a single practiced technician to evaluate percent inhibition. Treatments and corresponding percent inhibitions are given in Table 59.

TABLE 59

| Herbicide | Initial application 187 l/ha accession agent | rate g a.i./ha | Herbicide Subsequent application 187 l/ha accession agent | % Inhibition ABUTH | ECHCF | SIDSP |
| --- | --- | --- | --- | --- | --- | --- |
| Dicamba | none | 50 | none | 30 | 0 | 20 |
| Dicamba | none | 100 | none | 32 | 0 | 35 |
| Dicamba | none | 200 | none | 50 | 3 | 50 |
| Dicamba | none | 300 | none | 88 | 10 | 70 |
| Dicamba | 0.25% L-77 | 50 | none | 38 | 0 | 20 |
| Dicamba | 0.25% L-77 | 100 | none | 40 | 0 | 30 |
| Dicamba | 0.25% L-77 | 200 | none | 43 | 0 | 40 |
| Dicamba | 0.25% L-77 | 300 | none | 90 | 0 | 75 |
| Dicamba | 0.5% L-77 | 50 | none | 33 | 0 | 20 |
| Dicamba | 0.5% L-77 | 100 | none | 43 | 0 | 33 |
| Dicamba | 0.5% L-77 | 200 | none | 60 | 0 | 50 |
| Dicamba | 0.5% L-77 | 300 | none | 93 | 13 | 83 |
| Dicamba | 1.5% L-77 | 50 | none | 33 | 0 | 15 |
| Dicamba | 1.5% L-77 | 100 | none | 45 | 0 | 35 |
| Dicamba | 1.5% L-77 | 200 | none | 85 | 0 | 43 |
| Dicamba | 1.5% L-77 | 300 | none | 93 | 17 | 85 |
| Dicamba | none | 50 | 0.25% L-77 at 1 hr | 43 | 0 | 48 |
| Dicamba | none | 100 | 0.25% L-77 at 1 hr | 85 | 3 | 62 |
| Dicamba | none | 200 | 0.25% L-77 at 1 hr | 88 | 12 | 75 |
| Dicamba | none | 300 | 0.25% L-77 at 1 hr | 93 | 20 | 85 |
| Dicamba | none | 50 | 0.25% L-77 at 4 hr | 37 | 0 | 52 |
| Dicamba | none | 100 | 0.25% L-77 at 4 hr | 57 | 5 | 55 |
| Dicamba | none | 200 | 0.25% L-77 at 4 hr | 77 | 0 | 65 |
| Dicamba | none | 300 | 0.25% L-77 at 4 hr | 89 | 10 | 83 |
| Dicamba | none | 50 | 0.25% L-77 at 24 hr | 47 | 10 | 50 |
| Dicamba | none | 100 | 0.25% L-77 at 24 hr | 48 | 17 | 60 |
| Dicamba | none | 200 | 0.25% L-77 at 24 hr | 80 | 15 | 67 |
| Dicamba | none | 300 | 0.25% L-77 at 24 hr | 83 | 20 | 73 |
| Dicamba | none | 50 | 0.5% L-77 at 1 hr | 45 | 5 | 47 |
| Dicamba | none | 100 | 0.5% L-77 at 1 hr | 70 | 10 | 58 |
| Dicamba | none | 200 | 0.5% L-77 at 1 hr | 93 | 17 | 75 |
| Dicamba | none | 300 | 0.5% L-77 at 1 hr | 95 | 23 | 75 |
| Dicamba | none | 50 | 0.5% L-77 at 4 hr | 35 | 0 | 48 |
| Dicamba | none | 100 | 0.5% L-77 at 4 hr | 53 | 0 | 60 |
| Dicamba | none | 200 | 0.5% L-77 at 4 hr | 90 | 10 | 67 |
| Dicamba | none | 300 | 0.5% L-77 at 4 hr | 92 | 17 | 77 |
| Dicamba | none | 50 | 0.5% L-77 at 24 hr | 38 | 10 | 47 |
| Dicamba | none | 100 | 0.5% L-77 at 24 hr | 63 | 13 | 63 |
| Dicamba | none | 200 | 0.5% L-77 at 24 hr | 83 | 12 | 67 |
| Dicamba | none | 300 | 0.5% L-77 at 24 hr | 87 | 17 | 70 |
| Dicamba | none | 50 | 1.5% L-77 at 1 hr | 82 | 12 | 48 |
| Dicamba | none | 100 | 1.5% L-77 at 1 hr | 87 | 5 | 63 |
| Dicamba | none | 200 | 1.5% L-77 at 1 hr | 93 | 12 | 73 |
| Dicamba | none | 300 | 1.5% L-77 at 1 hr | 95 | 18 | 80 |
| Dicamba | none | 50 | 1.5% L-77 at 4 hr | 55 | 15 | 42 |
| Dicamba | none | 100 | 1.5% L-77 at 4 hr | 72 | 15 | 63 |
| Dicamba | none | 200 | 1.5% L-77 at 4 hr | 90 | 17 | 70 |
| Dicamba | none | 300 | 1.5% L-77 at 4 hr | 95 | 25 | 80 |
| Dicamba | none | 50 | 1.5% L-77 at 24 hr | 65 | 13 | 47 |
| Dicamba | none | 100 | 1.5% L-77 at 24 hr | 78 | 15 | 65 |
| Dicamba | none | 200 | 1.5% L-77 at 24 hr | 91 | 10 | 75 |
| Dicamba | none | 300 | 1.5% L-77 at 24 hr | 94 | 20 | 73 |

In this Example, the herbicidal activity of dicamba was generally not antagonized on any of the three species by Silwet L-77 applied in tank mix, therefore no reduction in antagonism by sequential application was observable. However, very unexpectedly the activity of sequential treatments of dicamba followed by Silwet L-77 was significantly greater than that of the corresponding tank mix treatments, or of dicamba applied alone.

Example 60

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Imazethapyr in unformulated (technical) form was used as the herbicidally active agent for this Example. Initial applications of imazethapyr, alone or in tank mix with a candidate accession agent, were applied on the same day, 21 days after planting velvetleaf, 21 days after planting Japanese millet, and 28 days after planting prickly sida. Imazethapyr was applied in a diluent comprising 50% water and 50% acetone with and without candidate accession agent at a range of rates from 10 to 100 g a.i./ha. Candidate accession agent treatments were exactly as in Example 49.

Thirteen days after the initial application, all plants in the test were examined by a single practiced technician to evaluate percent inhibition.

In this Example, the herbicidal activity of imazethapyr was generally not antagonized on any of the three species by Silwet L-77 applied in tank mix, therefore no reduction in antagonism by sequential application was observable.

Example 61

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

Metsulfuron-methyl (abbreviated in tables herein as metsulfuron) was used as the herbicidally active agent for this Example. Initial applications of metsulfuron-methyl, alone or in tank mix with a candidate accession agent, were applied on the same day, 15 days after planting velvetleaf, 14 days after planting Japanese millet, and 21 days after planting prickly sida. Metsulfuron-methyl in unformulated (technical) form was applied in a diluent comprising 50% water and 50% acetone with and without candidate accession agent at a range of rates from 5 to 50 g a.i./ha. Candidate accession agent treatments were exactly as in Example 49. Also included in this Example are treatments with the glyphosate formulation defined herein as Formulation C, applied alone, and with Silwet L-77 at a concentration of 0.25% by volume applied in tank mix or as a subsequent application 4 hours after herbicide application. Formulation C was applied diluted in water.

Fourteen days after the initial application, all plants in the test were examined by a single practiced technician to evaluate percent inhibition.

In this Example, the herbicidal activity of metsulfuron-methyl was generally not antagonized on any of the three species by Silwet L-77 applied in tank mix, therefore no reduction in antagonism by sequential application was observable.

Example 62

Velvetleaf (*Abutilon theophrasti*, ABUTH), Japanese millet, a form of barnyardgrass (*Echinochloa crus-galli*, ECHCF), and broadleaf signalgrass (*Brachiaria platyphylla*, BRAPP) plants were grown in pots, maintained in a greenhouse and treated with initial and subsequent applications by procedures exactly as described for Example 49, except where otherwise noted below.

Sethoxydim was used as the herbicidally active agent for this Example. Initial applications of sethoxydim, alone or in tank mix with a candidate accession agent, were applied on the same day, 15 days after planting velvetleaf, 14 days after planting Japanese millet, and 15 days after planting broadleaf signalgrass. Sethoxydim was applied in a diluent comprising 60% water and 40% ethanol with and without candidate accession agent at a range of rates from 10 to 100 g a.i./ha. Candidate accession agent treatments were exactly as in Example 49. Treatments with Formulation C were included as in Example 61.

Thirteen days after the initial application, all plants in the test were examined by a single practiced technician to evaluate percent inhibition.

In this Example, the herbicidal activity of sethoxydim was generally not antagonized on any of the three species by Silwet L-77 applied in tank mix, therefore no reduction in antagonism by sequential application was observable.

Example 63

Velvetleaf (*Abutilon theophrasti*, ABUTH), Japanese millet, a form of barnyardgrass (*Echinochloa crus-galli*, ECHCF), and, broadleaf signalgrass(*Brachiaria platyphylla*, BRAPP) plants were grown in pots, maintained in a greenhouse and treated with initial and subsequent applications by procedures exactly as described for Example 49, except where otherwise noted below.

Quizalofop-ethyl (abbreviated in tables herein as quizalofop) was used as the herbicidally active agent for this Example. Initial applications of quizalofop-ethyl, alone or in tank mix with a candidate accession agent, were applied on the same day, 15 days after planting velvetleaf, 14 days after planting Japanese millet, and 15 days after planting broadleaf signalgrass. Quizalofop-ethyl was applied in unformulated (technical) form in a diluent comprising 50% water and 50% acetone with and without candidate accession agent at a range of rates from 3 to 40 g a.i./ha. Candidate accession agent treatments were exactly as in Example 49. Treatments with Formulation C were included as in Example 61.

Fourteen days after the initial application, all plants in the test were examined by a single practiced technician to evaluate percent inhibition.

In this Example, the herbicidal activity of quizalofop-ethyl was generally not antagonized on any of the three species by Silwet L-77 applied in tank mix, therefore no reduction in antagonism by sequential application was observable.

Example 64

A backpack sprayer pressurized with propane is modified to have two tanks, one containing a herbicidal spray solution made by diluting Formulation F in water, and the other containing accession agent. Each tank is connected via a flexible tube to a separate lance fitted with a boom on which six flat-fan nozzles are arranged at regular spacing. The two lances and booms are taped together so that each nozzle on one boom is paired with a nozzle on the other boom. When in use, the boom fed from the accession agent tank has nozzles pointing vertically downward and is set behind the boom fed from the tank containing the herbicidal spray solution, which has nozzles pointing forward at an angle of about 45 degrees from the vertical.

In operation, the accession agent spray pattern falls about 0.25 m behind the herbicidal spray pattern. Walking speed during spraying is about 1.15 m/s. It is therefore calculated that the time interval between applications of herbicide and accession agent is 0.22 second.

Example 65

Figure 2:
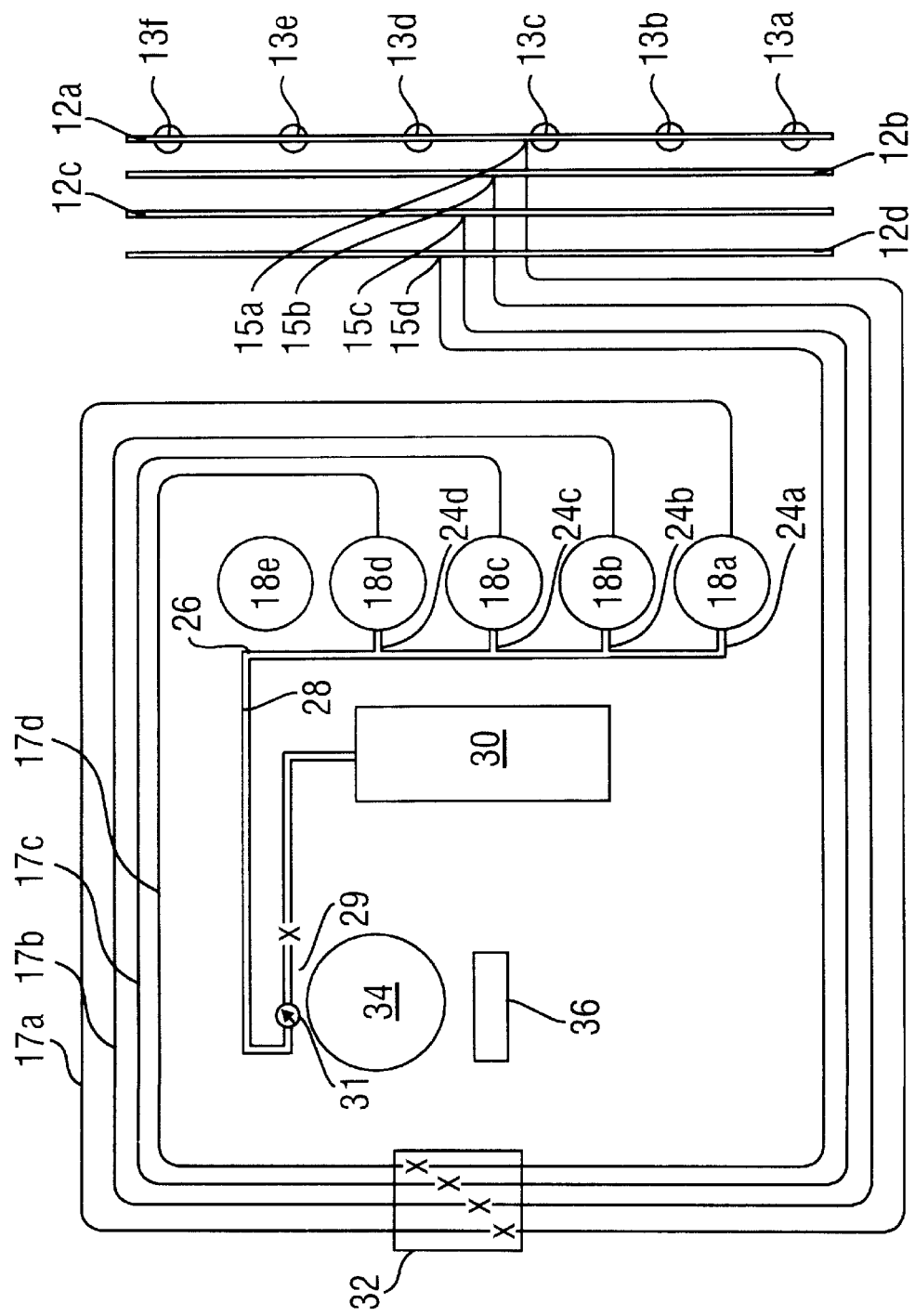
FIG. 2 is a schematic view of spraying apparatus and control apparatus therefor that can be used in the method of the present invention.

A tractor-driven sprayer apparatus 10 is constructed as shown in FIGS. 1 and 2, having four parallel booms 12a, 12b, 12c, and 12d, each 2.54 m in length that each sprays a 3.05 m path. The booms 12 are mounted on a rigid frame 14 attached to the rear of a tractor 16 such that the booms are spaced 51 mm from center to center in a single horizontal plane and are oriented at 90 degrees to the longitudinal axis of the tractor. The frame 14 can be raised or lowered to adjust the height of the booms above ground or above a crop or weed canopy. Each boom 12 is constructed of a tube with two of six replaceable nozzles 13a and 13f at either end of the 2.54 m length of the spray boom and four additional nozzles 13b, 13c, 13d, and 13e spaced evenly between the ends. (The nozzles 13 are only shown in FIGS. 1 and 2 for one of the four booms 12.) The six nozzles 13a–13e are all fed from the interior of the spray boom tube 12. There is a connector 15 near the mid point of each spray boom tube, which supplies the spray solution from a pressurizable container, as shown in FIG. 2. Four such pressurizable containers 18a, 18b, 18c, and 18d are mounted on a platform 20 at the rear of the tractor for use as spray solution reservoirs. Four flexible tubes 17a–17d which attach at one end to the respective connector 15a–15d near the mid point of the spray boom tube 12a–12d each has its other end attached to a connector on the pressurized container 18a–18d which holds the spray solution. The connector on the pressurized container 18 is part of the draw that is immersed in the spray solution. A fifth pressurizable container 18e is carried on the platform 20 for use when cleaning out the tubes and nozzles. Connectors and flexible tubing can be moved to this fifth container 18e holding clean water to rinse the tubes and nozzles. Each of the four spray solution reservoirs 18a–18d is connected to a flexible airline 24 and the four airlines 24a, 24b, 24c, and 24d are in turn connected through a manifold 26 to a single line 28 running from an air compressor 30 driven by the tractor. This single line 28 from the compressor is furnished with a pressure control valve 29 and pressure gauge 31, within convenient reach of an operator driving the tractor. A panel 32 of spray boom solenoid switches can be mounted on the tractor 16 near the operator's seat 34. A bank of control switches 36 to control the solenoid switches in panel 32 and thus to control fluid flow from the spray reservoirs 18a–18d to the spray booms 12a–12d can also be mounted on the tractor near the operator's seat 34. Alternatively, the solenoid switches and control switches can be combined in a single panel.

To operate this spray apparatus, the operator adjusts the pressure control valve 29 to supply the desired amount of air pressure from compressor 30 to the containers 18a–18d, which hold the spray solutions. The operator selects which two or more of the spray solutions in containers 18a–18d he wants to apply, by means of the bank of control switches 36, which activate the desired solenoid switches in panel 32. Based on the activation of the desired solenoid switches, a pathway through the corresponding flexible tubes 17a–17d is established, allowing the desired spray solutions to flow from the selected containers 18 to the corresponding booms 12, from which they are then sprayed onto foliage or soil through nozzles 13.

By selecting a first boom and its corresponding container for an exogenous chemical spray solution and a second boom, posterior to the first boom, for an accession agent spray solution, the apparatus described above can be used for sequential application of exogenous chemical substance and accession agent according to the method of the invention. The spatial separation of the two booms can be varied from 50 mm to 150 mm depending on the booms selected. The interval between initial application of exogenous chemical substance and subsequent application of accession agent depends upon this spatial separation and on forward speed of the apparatus while spraying. For example, at a forward speed of 10 m/sec, the interval can be varied from 0.005 sec to 0.015 sec, and at a forward speed of 3 m/sec, the interval can be varied from 0.017 sec to 0.05 sec. The interval can also be modified by varying the angle at which the nozzles are set on each boom.

Example 66

Aqueous solutions or dispersions of the following materials were tested as candidate accession agents, using the in vitro test described previously in this application. The following table summarizes the results of the tests of those materials. The materials tested in aqueous solution or dispersion as candidate accession agents are grouped by class (anionic surfactants, cationic surfactants, amphoteric surfactants, nonionic surfactants, and non-surfactant materials). The four columns (1–4) on the right side of the table indicate (1) whether each material displayed antagonism when applied at 0.5% concentration to Japanese millet as a tank mix with glyphosate as Formulation B, unless otherwise indicated in the presence of 0.09% MON 0818, in a greenhouse test, (2) whether in the same greenhouse test antagonism was reduced when the material was applied at the same concentration sequentially 4 hours after an application of the same glyphosate formulation, (3) whether the substance produced a positive result in the in vitro test at 0.5% concentration, and (4) whether the in vitro test correctly predicted whether the candidate material at 0.5% concentration would reduce antagonism when applied sequentially to Japanese millet. The greenhouse tests in virtually all instances used the procedure of Example 30 and a glyphosate rate of 100 g a.e./ha.

Chemical descriptions of the materials tested are derived from standard reference sources (McCutcheon's Emulsifiers & Detergents, 1996; Gower Handbook of Industrial Surfactants, 1993) or from manufacturers' published trade literature. Where only a generic chemical description has been found, this is given in italics in the following table.

TABLE 66A

| Agent | Chemical description | Class | TM antag? (1) | Antag reduced? (2) | In vitro infiltrant? (3) | In vitro test predicts antag reduced? (4) |
|---|---|---|---|---|---|---|
| Aerosol 22 | dicarboxyethyl stearyl sulfosuccinamate, Na4 salt | anionic | yes | no | no | yes |
| Aerosol A-102 | decanol ethoxylate sulfosuccinate, Na2 salt | anionic | yes | yes | no | no |
| Aerosol A-103 | nonylphenol 10EO sulfosuccinate, Na2 salt | anionic | yes | yes | no | no |
| Aerosol A-268 | isodecyl sulfosuccinate, Na2 salt | anionic | no | no | yes | no |
| Aerosol OS | diisopropyl naphthalene sulfonate, Na salt | anionic | yes | yes | no | no |
| Aerosol OT | dioctyl sulfosuccinate, Na salt | anionic | yes | yes | yes | yes |
| Alpha-Step MC-48 | methyl 2-sulfococoate, Na salt | anionic | yes | yes | no | no |
| Alpha-Step ML-40 | methyl-2-sulfolaurate, Na salt | anionic | yes | yes | | |
| Bio-Soft D-62 | alkyl benzene sulfonate | anionic | yes | yes | | |
| Bio-Soft MG-50 | alkyl benzene sulfonate | anionic | yes | yes | no | no |
| Bio-Soft N-300 | triethanolamine dodecylbenzene sulfonate | anionic | yes | yes | | |
| Bio-Terge AS-40 | C14–16 olefin sulfonate, Na salt | anionic | yes | yes | | |
| Bio-Terge PAS-85 | octane sulfonate, Na salt | anionic | yes | yes | | |
| Cedepal TD-407 | tridecyl EO sulfate, Na salt | anionic | yes | yes | | |
| Cedephos FA-600 | decyl 4EO phosphate | anionic | yes | yes | | |
| Daxad 15 | naphthalene sulfonate formaldehyde condensate | anionic | yes | yes | no | no |
| Daxad 17 | naphthalene sulfonate formaldehyde condensate | anionic | yes | yes | | |
| Dowfax 3B2 | decyl diphenyloxide disulfonate, Na salt | anionic | yes | yes | | |
| Emcol CNP-110 | nonylphenol 9EO carboxylate | anionic | yes | yes | no | no |
| Emery 5366 | naphthalene sulfonate, NH4 salt | anionic | yes | yes | no | no |
| Emphos CS-121 | nonylphenol 4EO phosphate | anionic | yes | yes | no | no |
| Emphos CS-136 | nonylphenol 6EO phosphate | anionic | yes | yes | no | no |
| Emphos CS-141 | nonylphenol 10EO phosphate | anionic | yes | yes | no | no |
| Emphos PS-121 | isotridecyl 4EO phosphate | anionic | yes | yes | | |
| Emphos PS-131 | isotridecyl 6EO phosphate | anionic | yes | yes | yes | yes |
| Emphos PS-21A | C10–12 alkyl 6EO phosphate | anionic | yes | yes | yes | yes |
| Emphos PS-400 | alcohol EO phosphate | anionic | yes | yes | yes | yes |
| Fluorad FC-120 | perfluoroalkyl sulfonate, NH4 salt | anionic | yes | yes | yes | yes |
| Fluorad FC-129 | fluoroalkyl carboxylate, K salt | anionic | yes | yes | | |
| Fluorad FC-98 | perfluoroalkyl sulfonate, K salt | anionic | yes | yes | no | no |
| Fluorad FC-99 | perfluoroalkyl sulfonate, amine salt | anionic | yes | yes | | |
| heptanoate, Na salt | | anionic | yes | yes | no | no |
| hexanesulfonate, Na salt | | anionic | yes | yes | no | no |
| hexanoate, Na salt | | anionic | yes | yes | no | no |
| lecithin from soya | | anionic | no | no | | |
| Miranol C2M | coco dicarboxylate, Na2 salt | anionic | no | no | no | yes |
| Ninate 401-HF | dodecyl benzene sultonate, Ca salt | anionic | yes | yes | yes | yes |
| perfluorobutanesulfonate | | anionic | yes | yes | no | no |
| perfluoroheptanoate | | anionic | yes | no | | |
| perfluorooctanesulfonate | | anionic | yes | yes | | |
| perfluoropentanoate | | anionic | yes | yes | | |
| Polyfon H | lignosulfonate | anionic | yes | yes | no | no |
| PolyStep B-25 | decyl sulfate, Na salt | anionic | yes | yes | no | no |
| PolyStep B-29 | octyl sulfate, Na salt | anionic | yes | yes | no | no |
| Reax 100M | lignosulfonate | anionic | yes | yes | no | no |
| Reax 85A | lignosulfonate | anionic | yes | yes | no | no |
| Reax 88B | lignosulfonate | anionic | yes | yes | no | no |
| Soprophor 3D33 | tristyrylphenol EO phosphate | anionic | no | no | no | yes |
| Soprophor 4D384 | tristyrylphenol EO sulfate | anionic | yes | yes | no | no |
| Steol CS-4 | fatty acid EO sulfate | anionic | yes | yes | | |
| Steol CS-370 | lauryl EO sulfate, Na salt | anionic | yes | yes | no | no |
| Steol KS-460 | lauryl EO sulfate, Na salt | anionic | yes | yes | | |
| Stepanol AEG | lauryl sulfate, NH4 salt | anionic | no | no | no | yes |
| Stepanol AEM | lauryl sulfate, NH4 salt | anionic | yes | yes | no | no |
| Stepanol ME Dry | lauryl sulfate, Na salt | anionic | yes | yes | no | no |
| Stepanol WAC | lauryl sulfate, Na salt | anionic | yes | yes | no | no |
| Stepfac 8170 | nonylphenol EO phosphate | anionic | yes | yes | no | no |
| Stepfac 8171 | nonylphenol EO phosphate | anionic | yes | yes | no | no |
| Stepfac 8172 | nonylphenol EO phosphate | anionic | yes | yes | no | no |
| Stepfac 8173 | nonylphenol EO phosphate | anionic | yes | yes | no | no |
| Tryfac 5552 | alcohol EO phosphate | anionic | yes | yes | yes | yes |
| Tryfac 5556 | alkylphenol EO phosphate | anionic | yes | yes | no | no |
| Aerosol C-61 | alkyl guanidine-amine ethoxylate | cationic | no | no | | |
| Ethoduomeen T/13 | tallow aminopropylamine 3EO | cationic | no | no | no | yes |
| Ethoduomeen T/25 | tallow aminopropylamine 15EO | cationic | no | no | no | yes |
| Ethomeen C/12 | cocoamine 2EO | cationic | yes | yes | yes | yes |
| Ethomeen T/25 | tallowamine 15EO | cationic | no | no | no | yes |
| Ethomeen T/30 | tallowamine 20EO | cationic | yes | no | | |
| Ethoquad 18/25 | stearyl methyl ammonium chloride 15EO | cationic | no | no | no | yes |
| Ethoquad C/12 | coco methyl ammonium chloride 2EO | cationic | no | no | no | yes |
| Fluorad FC-135 | fluoroalkyl methyl ammonium iodide | cationic | yes | no | no | yes |

TABLE 66A-continued

| Agent | Chemical description | Class | TM antag? (1) | Antag reduced? (2) | In vitro infiltrant? (3) | In vitro test predicts antag reduced? (4) |
|---|---|---|---|---|---|---|
| Fluorad FC-750 | fluoroalkyl methyl ammonium iodide | cationic | yes | yes | | |
| Fluorad FC-754 | fluoroalkyl methyl ammonium chloride | cationic | no | no | | |
| MON-0818 | product containing tallowamine 15EO | cationic | no | no | no | yes |
| Silamine C-100 | | cationic | no | no | no | yes |
| Surfonic AGM-550 | alkyl etheramine EO | cationic | yes | yes | | |
| Ammonyx CDO | cocoamidopropylamine oxide | amphoteric | no | no | no | yes |
| Ammonyx CO | palmitylamine oxide | amphoteric | no | no | no | yes |
| Ammonyx LO | laurylamine oxide | amphoteric | no | no | no | yes |
| Ammonyx MO | myristylamine oxide | amphoteric | no | no | no | yes |
| Ammonyx SO | stearylamine oxide | amphoteric | no | no | no | yes |
| Amphosol CA | cocoamidopropyl betaine | amphoteric | no | no | | |
| Fluorad FC-751 | fluorinated amphoteric | amphoteric | no | no | | |
| Varion CDG | lauryl betaine | amphoteric | no | no | no | yes |
| Velvetex AB-45 | coco betaine | amphoteric | no | no | no | yes |
| Velvetex BA-35 | cocoamidopropyl betaine | amphoteric | no | no | no | yes |
| Agrimul PG 2062 | alkyl polyglucoside | nonionic | yes | no | | |
| Agrimul PG 2065 | alkyl polyglucoside | nonionic | yes | no | | |
| Agrimul PG 2069 | C9–11 alkyl 1.5 polyglucoside | nonionic | no | no | no | yes |
| Agrimul PG 2072 | alkyl polyglucoside | nonionic | yes | no | | |
| Agrimul PG 2076 | C8–10 alkyl 1.5 polyglucoside | nonionic | yes | no | no | yes |
| Alcodet 218 | isolauryl 10EO thioether | nonionic | no | no | no | yes |
| Alcodet 260 | isolauryl 6EO thioether | nonionic | yes | yes | yes | yes |
| Alcodet SK | isolauryl 8EO thioether | nonionic | yes | yes | yes | yes |
| Amidox C-5 | cocoamide 6EO | nonionic | no | no | | |
| Amidox L-5 | lauramide 7EO | nonionic | yes | no | no | yes |
| Crodesta SL-40 | sucrose cocoate | nonionic | yes | yes | | |
| Ethylan CPG-945 | alcohol EO/PO | nonionic | yes | yes | yes | yes |
| Fluorad FC-170C | fluoroalcohol EO | nonionic | yes | yes | yes | yes |
| Fluorad FC-171 | fluoroalcohol EO/PO | nonionic | yes | yes | | |
| Fluorad FC-430 | fluoroalkyl ester | nonionic | yes | yes | yes | yes |
| Fluorad FC431 | fluoroalkyl ester | nonionic | no | no | | |
| Kinetic | adjuvant containing trisiloxane EO methyl ether | nonionic | yes | yes | | |
| Makon 12 | nonylphenol 12EO | nonionic | yes | no | no | yes |
| Makon 30 | nonylphenol 30EO | nonionic | yes | no | no | yes |
| Makon 4 | nonylphenol 4EO | nonionic | yes | yes | yes | yes |
| Masil 1066C | organosilicone EO | nonionic | yes | yes | | |
| Masil 1066D | organosilicone EO | nonionic | yes | no | | |
| Masil 2132 | organosilicone EO | nonionic | yes | yes | | |
| Myrj 45 | stearate 8EO | nonionic | no | no | no | yes |
| Myrj 52 | stearate 40EO | nonionic | no | no | no | yes |
| Myrj 59 | stearate 100EO | nonionic | no | no | no | yes |
| Neodol 1-5 | undecanol 5EO | nonionic | yes | yes | yes | yes |
| Neodol 25-3 | C12–15 alcohol 3EO | nonionic | yes | no | yes | no |
| Neodol 25-9 | C12–15 alcohol 9EO | nonionic | no | no | no | yes |
| Neodol 91-8 | C9–11 alcohol 8EO | nonionic | no | no | no | yes |
| Ninex MT-610 | tall oil fatty acid 10EO | nonionic | no | no | no | yes |
| Ninol 40-CO | cocoamide DEA | nonionic | no | no | no | yes |
| Ninol 49-CE | cocoamide DEA | nonionic | yes | no | no | yes |
| Nipol 2782 | nonylphenol 32EO/19PO mixed | nonionic | no | no | no | yes |
| Nipol 4472 | nonylphenol 41EO/41PO mixed | nonionic | yes | no | no | yes |
| Nipol 5595 | nonylphenol 66EO/41PO mixed | nonionic | no | no | no | yes |
| nonanol 2EO | | nonionic | yes | yes | yes | yes |
| nonanol 4EO | | nonionic | yes | yes | yes | yes |
| Pluronic 10-R-5 | PO/EO/PO block copolymer | nonionic | no | no | no | yes |
| Pluronic 31-R-1 | PO/EO/PO block copolymer | nonionic | yes | no | no | yes |
| Pluronic F-127 | EO/PO/EO block copolymer | nonionic | no | no | no | yes |
| Pluronic F-68 | EO/PO/EO block copolymer | nonionic | no | no | no | yes |
| Pluronic L-35 | EO/PO/EO block copolymer | nonionic | yes | no | no | yes |
| Pluronic P-103 | EO/PO/EO block copolymer | nonionic | no | no | no | yes |
| Pluronic P-105 | EO/PO/EO block copolymer | nonionic | no | no | no | yes |
| Silwet 408 | polysiloxane EO | nonionic | yes | yes | yes | yes |
| Silwet 800 | polysiloxane EO | nonionic | yes | yes | yes | yes |
| Silwet L-7001 | organosilicone EO | nonionic | yes | yes | no | no |
| Silwet L-720 | organosilicone EO | nonionic | yes | yes | | |
| Silwet L-7200 | organosilicone EO | nonionic | no | no | no | yes |
| Silwet L-7210 | organosilicone EO | nonionic | yes | no | no | yes |
| Silwet L-7500 | organosilicone EO | nonionic | yes | no | | |
| Silwet L-7600 | organosilicone EO | nonionic | yes | no | no | yes |
| Silwet L-7602 | organosilicone EO | nonionic | yes | no | no | yes |
| Silwet L-7604 | organosilicone EO | nonionic | yes | yes | yes | yes |
| Silwet L-7605 | organosilicone EO | nonionic | yes | no | no | yes |
| Silwet L-7607 | polysiloxane EO | nonionic | yes | yes | | |
| Silwet L-7614 | organosilicone EO | nonionic | yes | no | no | yes |

TABLE 66A-continued

| Agent | Chemical description | Class | TM antag? (1) | Antag reduced? (2) | In vitro infiltrant? (3) | In vitro test predicts antag reduced? (4) |
|---|---|---|---|---|---|---|
| Silwet L-7622 | organosilicone EO | nonionic | yes | yes | | |
| Silwet L-77 | trisiloxane 7EO methyl ether | nonionic | yes | yes | yes | yes |
| Simulsol SL-10 | alkyl polyglucoside | nonionic | no | no | no | yes |
| Simulsol SL-11 | undecyl glucoside | nonionic | no | no | yes | no |
| Simulsol SL-4 | alkyl polyglucoside | nonionic | no | no | no | yes |
| Simuisol SL-62 | alkyl polyglucoside | nonionic | no | no | | |
| Soprophor 796/P | tristyrylphenol EO/PO | nonionic | no | no | no | yes |
| Soprophor CY/8 | tristyrylphenol 20EO | nonionic | no | no | no | yes |
| Surfynol 465 | tetramethyl decyne diol 10EO | nonionic | no | no | no | yes |
| Sylgard 309 | organosilicone EO | nonionic | yes | yes | yes | yes |
| Tegopren 5840 | organosilicone EO | nonionic | yes | yes | yes | yes |
| Tegopren 5847 | organosilicone EO | nonionic | yes | yes | | |
| Tegopren 5878 | organosilicone EO | nonionic | yes | yes | yes | yes |
| Tergitol 15-S-7 | C11–15 secondary alcohol 7EO | nonionic | yes | yes | yes | yes |
| Tergitol 15-S-9 | C11–15 secondary alcohol 9EO | nonionic | no | no | no | yes |
| Tergitol TMN-10 | trimethylnonanol 10EO | nonionic | yes | no | no | yes |
| Tergitol TMN-6 | trimethylnonanol 6EO | nonionic | yes | yes | yes | yes |
| Toximul 8240 | castor oil fatty acid 36EO | nonionic | yes | no | no | yes |
| Toximul 8302 | alcohol EO/PO | nonionic | no | no | yes | no |
| Toximul 8303 | alcohol EO/PO | nonionic | no | no | yes | no |
| Toximul 8304 | alcohol EO/PO | nonionic | yes | yes | yes | yes |
| Toximul 8320 | alcohol EO/PO | nonionic | no | no | | |
| Toximul 8322 | PO/EO/PO block copolymer | nonionic | no | no | no | yes |
| Triton XL-80N | adjuvant containing alcohol EO | nonionic | yes | yes | | |
| Tween 20 | sorbitan monolaurate 20EO | nonionic | yes | no | no | yes |
| Tween 40 | sorbitan monopalmitate 20EO | nonionic | no | no | no | yes |
| Tween 61 | sorbitan monostearate 4EO | nonionic | no | no | | |
| Tween 80 | sorbitan monooleate 20EO | nonionic | no | no | no | yes |
| Tween 85 | sorbitan trioleate 20EO | nonionic | yes | yes | no | no |
| Witconol 14 | polyglyceryl 4-oleate | nonionic | yes | yes | no | no |
| Witconol 18L | polyglyceryl 4-isostearate | nonionic | yes | yes | yes | yes |
| Ganex P-904 | | | yes | no | | |
| GE 1161-11-178 | | | yes | yes | | |
| GE 1161-11-877 | | | yes | no | | |
| GE 407-2174 | | | no | no | | |
| Masil 280 | | | yes | yes | | |
| Masil 280-LB | | | yes | yes | | |
| Masil SF-19 | | | yes | yes | | |
| Tego Wet 260 | | | yes | yes | | |
| Toximul 856A | | | no | no | yes | no |
| 18-crown-6 | crown ether | non-surf | no | no | no | yes |
| amylamine | | non-surf | yes | no | no | yes |
| aniline | | non-surf | no | no | no | yes |
| Crop Oil Concentrate | petroleum oil based product with emulsifier | non-surf | yes | yes | no | no |
| dimethyl sulfoxide | | non-surf | yes | no | no | yes |
| ethanolamine | | non-surf | yes | no | no | yes |
| glycerin | | non-surf | no | no | no | yes |
| bexylamine | | non-surf | yes | yes | | |
| Indicate 5 | buffering agent with surfactant | non-surf | no | no | no | yes |
| Kelzan S | xanthan gum | non-surf | yes | yes | | |
| lactate, Na | | non-surf | no | no | no | yes |
| methanol | | non-surf | no | no | no | yes |
| mineral oil, light | | non-surf | yes | no | | |
| N-methyl pyrrolidone | | non-surf | no | no | | |
| pentanol | | non-surf | no | no | no | yes |
| polyethylene glycol 600 | | non-surf | yes | no | no | yes |
| propylene glycol | | non-surf | yes | no | no | yes |
| SAG-47 | organosilicone antifoam | non-surf | no | no | | |
| tetraethylene glycol | | non-surf | yes | no | | |
| WD-40 | penetrating oil product | non-surf | yes | yes | | |
| xanthan gum (Sigma) | | non-surf | yes | yes | | |

From this table it can be seen that the in vitro test is an excellent predictor of which candidate materials will in fact act as accession agents in aqueous solution or dispersion, for all classes except anionic surfactants. It can also be seen that the very fact that a candidate material is an anionic surfactant is an excellent predictor that an aqueous solution or dispersion of that material will in fact act as an accession agent.

The results shown in Table 66A are further summarized in Tables 66B, 66C, and 66D. Data for candidate materials which we have been unable to classify based on published information are excluded from the following summary tables.

TABLE 66B

Candidate materials giving tank mix antagonism with glyphosate

| | |
|---|---|
| Anionic surfactants | 92% (62 examples) |
| Cationic surfactants | 36% (14 examples) |
| Amphoteric surfactants | 0% (10 examples) |
| Nonionic surfactants | 62% (89 examples) |
| Non-surfactant agents | 57% (21 examples) |
| All except anionics | 54% (134 examples) |

TABLE 66C

Candidate materials reducing antagonism when applied sequentially

| | |
|---|---|
| Anionic surfactants | 89% (62 examples) |
| Cationic surfactants | 21% (14 examples) |
| Amphoteric surfactants | 0% (10 examples) |
| Nonionic surfactants | 37% (89 examples) |
| Non-surfactant agents | 24% (21 examples) |
| All except anionics | 31% (134 examples) |

TABLE 66D

Candidate materials for which in vitro test correctly predicts (1) tank mix antagonism and (2) reduced antagonism by sequential application

| | |
|---|---|
| Anionic surfactants | 32% (44 examples) |
| Cationic surfactants | 100% (9 examples) |
| Amphoteric surfactants | 100% (8 examples) |
| Nonionic surfactants | 90% (69 examples) |
| Non-surfactant agents | 92% (13 examples) |
| All except anionics | 92% (99 examples) |

Example 67

Aqueous glyphosate solutions prepared by tank mixing Formulation B with 0.09% MON-0818 surfactant were sprayed on the following species in greenhouse tests, alone and in a tank mix with Silwet L-77:

*Brassica juncea* (BRSJU, indian mustard)
*Erodium cicutarium* (EROCI, redstem filaree)
*Helianthus annuus* (HELAN, common sunflower)
*Kochia scoparia* (KCHSC, kochia)
*Xanthium strumarium* (XANST, common cocklebur)

Antagonism was evident on the plants treated with the tank mix.

When these same species were treated by sequential application according to the present invention (glyphosate followed by Silwet L-77), in every species the antagonism was partially or totally overcome.

Example 68

Aqueous glyphosate solutions prepared by tank mixing Formulation B with 0.09% MON-0818 surfactant were sprayed on the following species in greenhouse tests, alone and in a tank mix with Silwet L-77:

*Amaranthus retroflexus* (AMARE, redroot pigweed)
*Malva sylvestris* (MALSI, cheeseweed)
*Portulaca oleracea* (POROL, common purslane)

No antagonism was evident on any of these species in these tests, and therefore no determination could be made as to whether sequential application was effective to reduce antagonism.

Example 69

Velvetleaf (*Abutilon theophrasti*, ABUTH), Japanese millet, a form of barnyardgrass (*Echinochloa crus-galli*, ECHCF), and prickly sida (*Sida spinosa*, SIDSP) plants were grown in pots, maintained in a greenhouse and treated with initial and subsequent applications by procedures exactly as described for Example 49, except where otherwise noted below.

The herbicide used in this Example was Liberty, a product of AgrEvo containing as active ingredient the ammonium salt of glufosinate. Initial applications of herbicide, alone or in tank mix with a candidate accession agent, were applied on the same day, 16 days after planting velvetleaf, 14 days after planting Japanese millet, and 24 days after planting prickly sida. All treatments were applied by spraying with a track sprayer fitted with a single 8002E nozzle calibrated to deliver a spray volume of 187 l/ha at a pressure of 173 kPa. Liberty was applied in water with and without candidate accession agent at a range of rates from 50 to 900 g a.e./ha. This Example includes as the candidate accession agent aqueous solutions containing Silwet L-77 at concentrations ranging from 0.25% to 1.5% by volume. When Silwet L-77 was applied subsequently, the time interval between initial and subsequent applications ranged from 1 to 24 hours.

Fourteen days after the initial application, all plants in the test were examined by a single practiced technician to evaluate percent inhibition. Treatments and corresponding percent inhibitions are given in Table 69.

TABLE 69

| Initial application | | herbicide | subsequent application | % inhibition | | |
|---|---|---|---|---|---|---|
| herbicide | accession agent | rate g a.e./ha | accession agent | ABUTH | ECHCF | SIDSP |
| Liberty | none | 50 | none | 0 | 0 | 0 |
| Liberty | none | 100 | none | 37 | 50 | 42 |
| Liberty | none | 400 | none | 91 | 98 | 72 |
| Liberty | none | 900 | none | 99 | 97 | 94 |
| Liberty | 0.25% L-77 | 50 | none | 75 | 5 | 53 |
| Liberty | 0.25% L-77 | 100 | none | 78 | 5 | 60 |
| Liberty | 0.25% L-77 | 400 | none | 95 | 88 | 88 |
| Liberty | 0.25% L-77 | 900 | none | 99 | 98 | 96 |
| Liberty | 0.5% L-77 | 50 | none | 72 | 2 | 35 |
| Liberty | 0.5% L-77 | 100 | none | 88 | 5 | 60 |
| Liberty | 0.5% L-77 | 400 | none | 96 | 63 | 90 |
| Liberty | 0.5% L-77 | 900 | none | 98 | 93 | 93 |
| Liberty | 1.5% L-77 | 50 | none | 80 | 5 | 35 |

TABLE 69-continued

| Initial application | | herbicide | subsequent application | % inhibition | | |
|---|---|---|---|---|---|---|
| herbicide | accession agent | rate g a.e./ha | accession agent | ABUTH | ECHCF | SIDSP |
| Liberty | 1.5% L-77 | 100 | none | 82 | 5 | 43 |
| Liberty | 1.5% L-77 | 400 | none | 97 | 43 | 60 |
| Liberty | 1.5% L-77 | 900 | none | 98 | 68 | 83 |
| Liberty | none | 50 | 0.25% L-77 at 1 hr | 43 | 12 | 53 |
| Liberty | none | 100 | 0.25% L-77 at 1 hr | 89 | 45 | 60 |
| Liberty | none | 400 | 0.25% L-77 at 1 hr | 88 | 78 | 78 |
| Liberty | none | 900 | 0.25% L-77 at 1 hr | 95 | 97 | 91 |
| Liberty | none | 50 | 0.25% L-77 at 4 hr | 87 | 15 | 48 |
| Liberty | none | 100 | 0.25% L-77 at 4 hr | 83 | 35 | 60 |
| Liberty | none | 400 | 0.25% L-77 at 4 hr | 88 | 60 | 72 |
| Liberty | none | 900 | 0.25% L-77 at 4 hr | 98 | 98 | 95 |
| Liberty | none | 50 | 0.25% L-77 at 24 hr | 57 | 0 | 35 |
| Liberty | none | 100 | 0.25% L-77 at 24 hr | 72 | 25 | 47 |
| Liberty | none | 400 | 0.25% L-77 at 24 hr | 97 | 97 | 91 |
| Liberty | none | 900 | 0.25% L-77 at 24 hr | 94 | 91 | 93 |
| Liberty | none | 50 | 0.5% L-77 at 1 hr | 77 | 10 | 25 |
| Liberty | none | 100 | 0.5% L-77 at 1 hr | 83 | 20 | 42 |
| Liberty | none | 400 | 0.5% L-77 at 1 hr | 95 | 93 | 87 |
| Liberty | none | 900 | 0.5% L-77 at 1 hr | 95 | 98 | 93 |
| Liberty | none | 50 | 0.5% L-77 at 4 hr | 78 | 28 | 40 |
| Liberty | none | 100 | 0.5% L-77 at 4 hr | 85 | 38 | 62 |
| Liberty | none | 400 | 0.5% L-77 at 4 hr | 97 | 97 | 88 |
| Liberty | none | 900 | 0.5% L-77 at 4 hr | 99 | 97 | 88 |
| Liberty | none | 50 | 0.5% L-77 at 24 hr | 40 | 3 | 38 |
| Liberty | none | 100 | 0.5% L-77 at 24 hr | 75 | 42 | 58 |
| Liberty | none | 400 | 0.5% L-77 at 24 hr | 93 | 96 | 85 |
| Liberty | none | 900 | 0.5% L-77 at 24 hr | 99 | 100 | 94 |
| Liberty | none | 50 | 1.5% L-77 at 1 hr | 63 | 10 | 35 |
| Liberty | none | 100 | 1.5% L-77 at 1 hr | 82 | 10 | 32 |
| Liberty | none | 400 | 1.5% L-77 at 1 hr | 93 | 72 | 82 |
| Liberty | none | 900 | 1.5% L-77 at 1 hr | 95 | 96 | 88 |
| Liberty | none | 50 | 1.5% L-77 at 4 hr | 77 | 27 | 60 |
| Liberty | none | 100 | 1.5% L-77 at 4 hr | 77 | 22 | 58 |
| Liberty | none | 400 | 1.5% L-77 at 4 hr | 94 | 87 | 87 |
| Liberty | none | 900 | 1.5% L-77 at 4 hr | 94 | 94 | 89 |
| Liberty | none | 50 | 1.5% L-77 at 24 hr | 60 | 15 | 38 |
| Liberty | none | 100 | 1.5% L-77 at 24 hr | 78 | 58 | 52 |
| Liberty | none | 400 | 1.5% L-77 at 24 hr | 90 | 96 | 80 |
| Liberty | none | 900 | 1.5% L-77 at 24 hr | 99 | 99 | 92 |
| none | none | 0 | none | 0 | 0 | 0 |
| none (water) | none | 0 | none | 0 | 0 | 0 |
| none | 0.25% L-77 | 0 | none | 0 | 0 | 0 |
| none | 0.5% L-77 | 0 | none | 0 | 0 | 0 |
| none | 1.5% L-77 | 0 | none | 42 | 0 | 5 |

Silwet L-77 antagonized the performance of Liberty on Japanese millet when added in tank mix, high Silwet L-77 concentrations being more antagonistic than low. In all cases antagonism was reduced when the Silwet L-77 was instead applied as a sequential treatment according to the present invention.

Example 70

Velvetleaf (*Abutilon theophrasti*, ABUTH), Japanese millet, a form of barnyardgrass (*Echinochloa crus-galli*, ECHCF), and broadleaf signalgrass (*Brachiaria platyphylla*, BRAPP) plants were grown in pots, maintained in a greenhouse and treated with initial and subsequent applications by procedures exactly as described for Example 49, except where otherwise noted below.

The herbicide used in this Example was alachlor in unformulated (technical) form. Initial applications of herbicide, alone or in tank mix with a candidate accession agent, were applied on the same day, 16 days after planting velvetleaf, 8 days after planting Japanese millet, and 17 days after planting broadleaf signalgrass. All treatments were applied by spraying with a track sprayer fitted with a single 8002E nozzle calibrated to deliver a spray volume of 187 l/ha at a pressure of 173 kPa. Alachlor was applied in water with and without candidate accession agent at a range of rates from 500 to 4,000 g/ha. This Example includes as the candidate accession agent aqueous solutions containing Silwet L-77 at concentrations ranging from 0.25% to 1.5% by volume. When Silwet L-77 was applied subsequently, the time interval between initial and subsequent applications ranged from 1 to 24 hours.

Fourteen days after the initial application, all plants in the test were examined by a single practiced technician to evaluate percent inhibition. Treatments and corresponding percent inhibitions are given in Table 70.

TABLE 70

| Initial application | | herbicide | subsequent application | % inhibition | | |
|---|---|---|---|---|---|---|
| herbicide | accession agent | rate (g/ha) | accession agent | ABUTH | ECHCF | BRAPP |
| alachlor | none | 500 | none | 0 | 0 | 0 |
| alachlor | none | 1000 | none | 0 | 2 | 10 |
| alachlor | none | 2000 | none | 17 | 58 | 17 |
| alachlor | none | 4000 | none | 30 | 55 | 30 |
| alachlor | 0.25% L-77 | 500 | none | 0 | 0 | 0 |
| alachlor | 0.25% L-77 | 1000 | none | 0 | 0 | 0 |
| alachlor | 0.25% L-77 | 2000 | none | 0 | 43 | 0 |
| alachlor | 0.25% L-77 | 4000 | none | 25 | 50 | 12 |
| alachlor | 0.5% L-77 | 500 | none | 0 | 0 | 0 |
| alachlor | 0.5% L-77 | 1000 | none | 0 | 30 | 0 |
| alachlor | 0.5% L-77 | 2000 | none | 5 | 38 | 7 |
| alachlor | 0.5% L-77 | 4000 | none | 32 | 48 | 38 |
| alachlor | 1.5% L-77 | 500 | none | 23 | 3 | 0 |
| alachlor | 1.5% L-77 | 1000 | none | 40 | 7 | 22 |
| alachlor | 1.5% L-77 | 2000 | none | 33 | 47 | 25 |
| alachlor | 1.5% L-77 | 4000 | none | 50 | 58 | 48 |
| alachlor | none | 500 | 0.25% L-77 at 1 hr | 3 | 0 | 10 |
| alachlor | none | 1000 | 0.25% L-77 at 1 hr | 15 | 30 | 17 |
| alachlor | none | 2000 | 0.25% L-77 at 1 hr | 22 | 37 | 32 |
| alachlor | none | 4000 | 0.25% L-77 at 1 hr | 23 | 45 | 60 |
| alachlor | none | 500 | 0.25% L-77 at 4 hr | 0 | 0 | 0 |
| alachlor | none | 1000 | 0.25% L-77 at 4 hr | 10 | 7 | 10 |
| alachlor | none | 2000 | 0.25% L-77 at 4 hr | 7 | 30 | 33 |
| alachlor | none | 4000 | 0.25% L-77 at 4 hr | 23 | 50 | 25 |
| alachlor | none | 500 | 0.25% L-77 at 24 hr | 0 | 0 | 2 |
| alachlor | none | 1000 | 0.25% L-77 at 24 hr | 15 | 17 | 2 |
| alachlor | none | 2000 | 0.25% L-77 at 24 hr | 20 | 35 | 12 |
| alachlor | none | 4000 | 0.25% L-77 at 24 hr | 27 | 52 | 25 |
| alachlor | none | 500 | 0.5% L-77 at 1 hr | 15 | 0 | 0 |
| alachlor | none | 1000 | 0.5% L-77 at 1 hr | 5 | 0 | 10 |
| alachlor | none | 2000 | 0.5% L-77 at 1 hr | 28 | 35 | 18 |
| alachlor | none | 4000 | 0.5% L-77 at 1 hr | 32 | 50 | 62 |
| alachlor | none | 500 | 0.5% L-77 at 4 hr | 20 | 0 | 0 |
| alachlor | none | 1000 | 0.5% L-77 at 4 hr | 22 | 0 | 7 |
| alachlor | none | 2000 | 0.5% L-77 at 4 hr | 30 | 32 | 15 |
| alachlor | none | 4000 | 0.5% L-77 at 4 hr | 37 | 45 | 35 |
| alachlor | none | 500 | 0.5% L-77 at 24 hr | 33 | 5 | 5 |
| alachlor | none | 1000 | 0.5% L-77 at 24 hr | 32 | 7 | 3 |
| alachlor | none | 2000 | 0.5% L-77 at 24 hr | 37 | 30 | 3 |
| alachlor | none | 4000 | 0.5% L-77 at 24 hr | 50 | 67 | 43 |
| alachlor | none | 500 | 1.5% L-77 at 1 hr | 53 | 13 | 8 |
| alachlor | none | 1000 | 1.5% L-77 at 1 hr | 45 | 15 | 22 |
| alachlor | none | 2000 | 1.5% L-77 at 1 hr | 58 | 30 | 25 |
| alachlor | none | 4000 | 1.5% L-77 at 1 hr | 52 | 37 | 47 |
| alachlor | none | 500 | 1.5% L-77 at 4 hr | 63 | 0 | 0 |
| alachlor | none | 1000 | 1.5% L-77 at 4 hr | 53 | 0 | 7 |
| alachlor | none | 2000 | 1.5% L-77 at 4 hr | 63 | 45 | 20 |
| alachlor | none | 4000 | 1.5% L-77 at 4 hr | 63 | 35 | 53 |
| alachlor | none | 500 | 1.5% L-77 at 24 hr | 52 | 25 | 2 |
| alachlor | none | 1000 | 1.5% L-77 at 24 hr | 63 | 27 | 22 |
| alachlor | none | 2000 | 1.5% L-77 at 24 hr | 58 | 37 | 22 |
| alachlor | none | 4000 | 1.5% L-77 at 24 hr | 67 | 60 | 67 |
| none | none | 0 | none | 0 | 0 | 0 |
| none (water/acetone 50/50) | none | 0 | none | 0 | 0 | 0 |
| none | 0.25% L-77 | 0 | none | 5 | 0 | 0 |
| none | 0.5% L-77 | 0 | none | 0 | 0 | 0 |
| none | 1.5% L-77 | 0 | none | 23 | 0 | 3 |

Alachlor is normally used as a pre-emergent herbicide but this test was for post-emergent foliar-applied herbicidal activity. Sequential application of accession agent following alachlor according to the present invention generally enhanced herbicidal efficacy over that obtained with alachlor alone or in tank mix with the accession agent.

Example 71

Velvetleaf (*Abutilon theophrasti*, ABUTH), Japanese millet, a form of barnyardgrass (*Echinochloa crus-galli*, ECHCF), and broadleaf signalgrass (*Brachiaria platyphylla*, BRAPP) plants were grown in pots, maintained in a greenhouse and treated with initial and subsequent applications by procedures exactly as described for Example 49, except where otherwise noted below.

The herbicide used in this Example was pendimethalin in unformulated (technical) form. Initial applications of herbicide, alone or in tank mix with a candidate accession agent, were applied on the same day, 16 days after planting velvetleaf, 8 days after planting Japanese millet, and 17 days after planting broadleaf signalgrass. All treatments were applied by spraying with a track sprayer fitted with a single 8002E nozzle calibrated to deliver a spray volume of 187 l/ha at a pressure of 173 kPa. Pendimethalin was applied in water with and without candidate accession agent at a range evaluate percent inhibition. Treatments and corresponding percent inhibitions are given in Table 71.

TABLE 71

| Initial application | | herbicide | subsequent application | % inhibition | | |
|---|---|---|---|---|---|---|
| herbicide | accession agent | rate g/ha | accession agent | ABUTH | ECHCF | BRAPP |
| pendimethalin | none | 100 | none | 62 | 0 | 10 |
| pendimethalin | none | 500 | none | 77 | 53 | 35 |
| pendimethalin | none | 1000 | none | 77 | 68 | 57 |
| pendimethalin | none | 4000 | none | 87 | 73 | 67 |
| pendimethalin | 0.25% L-77 | 100 | none | 42 | 5 | 0 |
| pendimethalin | 0.25% L-77 | 500 | none | 72 | 50 | 5 |
| pendimethalin | 0.25% L-77 | 1000 | none | 80 | 67 | 35 |
| pendimethalin | 0.25% L-77 | 4000 | none | 87 | 73 | 57 |
| pendimethalin | 0.5% L-77 | 100 | none | 68 | 30 | 0 |
| pendimethalin | 0.5% L-77 | 500 | none | 73 | 58 | 25 |
| pendimethalin | 0.5% L-77 | 1000 | none | 80 | 67 | 35 |
| pendimethalin | 0.5% L-77 | 4000 | none | 85 | 75 | 52 |
| pendimethalin | 1.5% L-77 | 100 | none | 70 | 35 | 10 |
| pendimethalin | 1.5% L-77 | 500 | none | 75 | 48 | 30 |
| pendimethalin | 1.5% L-77 | 1000 | none | 77 | 68 | 65 |
| pendimethalin | 1.5% L-77 | 4000 | none | 85 | 72 | 67 |
| pendimethalin | none | 100 | 0.25% L-77 at 1 hr | 65 | 10 | 25 |
| pendimethalin | none | 500 | 0.25% L-77 at 1 hr | 75 | 55 | 42 |
| pendimethalin | none | 1000 | 0.25% L-77 at 1 hr | 78 | 62 | 47 |
| pendimethalin | none | 4000 | 0.25% L-77 at 1 hr | 85 | 75 | 67 |
| pendimethalin | none | 100 | 0.25% L-77 at 4 hr | 58 | 7 | 23 |
| pendimethalin | none | 500 | 0.25% L-77 at 4 hr | 77 | 55 | 15 |
| pendimethalin | none | 1000 | 0.25% L-77 at 4 hr | 80 | 50 | 30 |
| pendimethalin | none | 4000 | 0.25% L-77 at 4 hr | 85 | 72 | 52 |
| pendimethalin | none | 100 | 0.25% L-77 at 24 hr | 65 | 10 | 8 |
| pendimethalin | none | 500 | 0.25% L-77 at 24 hr | 78 | 57 | 18 |
| pendimethalin | none | 1000 | 0.25% L-77 at 24 hr | 83 | 60 | 17 |
| pendimethalin | none | 4000 | 0.25% L-77 at 24 hr | 85 | 75 | 57 |
| pendimethalin | none | 100 | 0.5% L-77 at 1 hr | 70 | 7 | 30 |
| pendimethalin | none | 500 | 0.5% L-77 at 1 hr | 77 | 52 | 25 |
| pendimethalin | none | 1000 | 0.5% L-77 at 1 hr | 82 | 55 | 35 |
| pendimethalin | none | 4000 | 0.5% L-77 at 1 hr | 85 | 72 | 45 |
| pendimethalin | none | 100 | 0.5% L-77 at 4 hr | 65 | 18 | 13 |
| pendimethalin | none | 500 | 0.5% L-77 at 4 hr | 73 | 58 | 20 |
| pendimethalin | none | 1000 | 0.5% L-77 at 4 hr | 75 | 62 | 22 |
| pendimethalin | none | 4000 | 0.5% L-77 at 4 hr | 83 | 72 | 60 |
| pendimethalin | none | 100 | 0.5% L-77 at 24 hr | 68 | 10 | 25 |
| pendimethalin | none | 500 | 0.5% L-77 at 24 hr | 75 | 60 | 17 |
| pendimethalin | none | 1000 | 0.5% L-77 at 24 hr | 80 | 65 | 27 |
| pendimethalin | none | 4000 | 0.5% L-77 at 24 hr | 85 | 73 | 47 |
| pendimethalin | none | 100 | 1.5% L-77 at 1 hr | 70 | 15 | 45 |
| pendimethalin | none | 500 | 1.5% L-77 at 1 hr | 78 | 57 | 42 |
| pendimethalin | none | 1000 | 1.5% L-77 at 1 hr | 80 | 63 | 55 |
| pendimethalin | none | 4000 | 1.5% L-77 at 1 hr | 85 | 73 | 63 |
| pendimethalin | none | 100 | 1.5% L-77 at 4 hr | 68 | 20 | 18 |
| pendimethalin | none | 500 | 1.5% L-77 at 4 hr | 75 | 58 | 25 |
| pendimethalin | none | 1000 | 1.5% L-77 at 4 hr | 73 | 57 | 30 |
| pendimethalin | none | 4000 | 1.5% L-77 at 4 hr | 85 | 75 | 68 |
| pendimethalin | none | 100 | 1.5% L-77 at 24 hr | 68 | 25 | 32 |
| pendimethalin | none | 500 | 1.5% L-77 at 24 hr | 72 | 60 | 27 |
| pendimethalin | none | 1000 | 1.5% L-77 at 24 hr | 77 | 63 | 43 |
| pendimethalin | none | 4000 | 1.5% L-77 at 24 hr | 85 | 75 | 50 |
| none | none | 0 | none | 0 | 0 | 0 |
| none (water/acetone 50/50) | none | 0 | none | 0 | 0 | 0 |
| none | 0.25% L-77 | 0 | none | 0 | 0 | 0 |
| none | 0.5% L-77 | 0 | none | 0 | 0 | 0 |
| none | 1.5% L-77 | 0 | none | 37 | 0 | 5 | of rates from 100 to 4,000 g/ha. This Example includes as the candidate accession agent aqueous solutions containing Silwet L-77 at concentrations ranging from 0.25% to 1.5% by volume. When Silwet L-77 was applied subsequently, the time interval between initial and subsequent applications ranged from 1 to 24 hours.

Thirteen days after the initial application, all plants in the test were examined by a single practiced technician to Some antagonism of pendimethalin herbicidal activity on broadleaf signalgrass was noted with addition of Silwet L-77 in tank mix at 0.25% and 0.5%. This antagonism was reduced when the Silwet L-77 was instead applied as a sequential treatment after the pendimethalin according to the present invention.

Example 72

The following herbicides were applied to velvetleaf (*Abutilon theophrasti*, ABUTH), Japanese millet, a form of barnyardgrass (*Echinochloa crus-galli*, ECHCF) and prickly sida (*Sida spinosa*, SIDSP) in greenhouse tests, alone and in tank mix with Silwet L-77: 2,4-D dimethylamine, chlorimuron-ethyl, atrazine, and asulam sodium, all as unformulated (technical) material. No antagonism was evident in these tests when Silwet L-77 was applied in tank mix.

Example 73

A test was conducted to apply the method of the present invention to gibberellic acid, a plant growth regulator (PGR) having the effect of stimulating shoot elongation in sensitive plants. Seeds of dwarf Phaseolus bean (Phaseolus vulgaris, PHSVN) cv. Blue Lake were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. After emergence, seedlings were thinned to 2 or 3 healthy plants per pot.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and 18° C. during the night. Plants were sub-irrigated throughout the test to ensure adequate soil moisture levels.

Pots were assigned to different treatments in a randomized experimental design with 6 replications. Randomization was constricted in the following respects: (1) as considerable variation in plant height was evident at the time of treatment, pots were assigned to treatments in such a way as to distribute the height range evenly among treatments; (2) for each treatment 4 pots were selected having 3 plants each and 2 pots were selected having 2 plants each, making a total of 16 plants per treatment. One such set of 16 plants was left untreated as a reference against which effects of the treatments could later be evaluated.

Initial treatments with gibberellic acid in unformulated (technical) form, alone or in tank mix with a candidate accession agent, were applied 13 days after planting. Initial treatments were applied by spraying with a track sprayer fitted with a single 8002E nozzle calibrated to deliver a spray volume of 187 l/ha at a pressure of 173 kPa. Plants treated according to methods of prior art, for comparative purposes, received an initial treatment only. Plants treated by a method illustrative of the present invention received an initial application of gibberellic acid followed sequentially by a subsequent application of a candidate accession agent. Various intervals between initial and subsequent applications were tested in this Example. All subsequent applications in this Example were applied by spraying a candidate accession agent with a track sprayer fitted exactly as for the initial application and calibrated to deliver a spray volume of 187 l/ha at a pressure of 173 kPa.

Gibberellic acid was applied without and with each candidate accession agent at a range of rates from 0.0004 to 0.05 g/ha. Candidate accession agents in this Example were aqueous solutions of Silwet L-77 at concentrations of 0.25%, 0.5% and 1.5% by volume. Solutions of Silwet L-77 were prepared immediately before application because of hydrolytic instability. Time intervals between initial and subsequent applications were 1 hour and 4 hours.

Twelve days after application, the height of each individual plant was measured to the nearest centimeter, from the soil surface to the shoot apex. Plants in which the main stem was broken or the shoot apex physically damaged were discarded. An average height of all plants in each treatment was calculated.

Gibberellic acid treatments and results are given in Table 73. The height values are averages for the 16 plants in each treatment.

TABLE 73

| Initial application | | PGR | subsequent application | Height |
|---|---|---|---|---|
| PGR | accession agent | rate g/ha | accession agent | (cm) PHSVN |
| gibberellic acid | none | 0.0004 | none | 41 |
| gibberellic acid | none | 0.002 | none | 47 |
| gibberellic acid | none | 0.01 | none | 44 |
| gibberellic acid | none | 0.05 | none | 44 |
| gibberellic acid | 0.25% L-77 | 0.0004 | none | 47 |
| gibberellic acid | 0.25% L-77 | 0.002 | none | 51 |
| gibberellic acid | 0.25% L-77 | 0.01 | none | 55 |
| gibberellic acid | 0.25% L-77 | 0.05 | none | 64 |
| gibberellic acid | 0.5% L-77 | 0.0004 | none | 56 |
| gibberellic acid | 0.5% L-77 | 0.002 | none | 52 |
| gibberellic acid | 0.5% L-77 | 0.01 | none | 53 |
| gibberellic acid | 0.5% L-77 | 0.05 | none | 67 |
| gibberellic acid | 1.5% L-77 | 0.0004 | none | 47 |
| gibberellic acid | 1.5% L-77 | 0.002 | none | 42 |
| gibberellic acid | 1.5% L-77 | 0.01 | none | 50 |
| gibberellic acid | 1.5% L-77 | 0.05 | none | 55 |
| gibberellic acid | none | 0.0004 | 0.25% L-77 at 1 hr | 36 |
| gibberellic acid | none | 0.002 | 0.25% L-77 at 1 hr | 39 |
| gibberellic acid | none | 0.01 | 0.25% L-77 at 1 hr | 41 |
| gibberellic acid | none | 0.05 | 0.25% L-77 at 1 hr | 44 |
| gibberellic acid | none | 0.0004 | 0.25% L-77 at 4 hr | 51 |
| gibberellic acid | none | 0.002 | 0.25% L-77 at 4 hr | 65 |
| gibberellic acid | none | 0.01 | 0.25% L-77 at 4 hr | 67 |
| gibberellic acid | none | 0.05 | 0.25% L-77 at 4 hr | 67 |
| gibberellic acid | none | 0.0004 | 0.5% L-77 at 1 hr | 46 |
| gibberellic acid | none | 0.002 | 0.5% L-77 at 1 hr | 37 |
| gibberellic acid | none | 0.01 | 0.5% L-77 at 1 hr | 49 |
| gibberellic acid | none | 0.05 | 0.5% L-77 at 1 hr | 54 |
| gibberellic acid | none | 0.0004 | 0.5% L-77 at 4 hr | 63 |
| gibberellic acid | none | 0.002 | 0.5% L-77 at 4 hr | 55 |
| gibberellic acid | none | 0.01 | 0.5% L-77 at 4 hr | 60 |
| gibberellic acid | none | 0.05 | 0.5% L-77 at 4 hr | 60 |
| gibberellic acid | none | 0.0004 | 0.5% L-77 at 1 hr | 41 |
| gibberellic acid | none | 0.002 | 0.5% L-77 at 1 hr | 45 |
| gibberellic acid | none | 0.01 | 1.5% L-77 at 1 hr | 40 |
| gibberellic acid | none | 0.05 | 1.5% L-77 at 1 hr | 40 |
| gibberellic acid | none | 0.0004 | 0.5% L-77 at 4 hr | 48 |
| gibberellic acid | none | 0.002 | 1.5% L-77 at 4 hr | 47 |
| gibberellic acid | none | 0.01 | 1.5% L-77 at 4 hr | 44 |
| gibberellic acid | none | 0.05 | 1.5% L-77 at 4 hr | 42 |
| none | none | 0 | none | 44 |
| none (water) | none | 0 | none | 46 |
| none | 0.25% L-77 | 0 | none | 45 |
| none | 0.5% L-77 | 0 | none | 46 |
| none | 1.5% L-77 | 0 | none | 41 |

Gibberellic acid shoot elongation activity was enhanced rather than antagonized by Silwet L-77 in tank mix. However, even more positive results were obtained by sequential application of 0.25% or 0.5% Silwet L-77 according to the present invention, at an interval of 4 hours after application of the gibberellic acid.

Example 74

A test was conducted to apply the method of the present invention to ethephon ((2-chloroethyl)phosphonic acid), a plant growth regulator having the effect of inhibiting shoot elongation in sensitive plants.

Dwarf Phaseolus bean (*Phaseolus vulgaris*, PHSVN) cv. Roman II Italian plants were grown in pots, maintained in a greenhouse and treated with initial and subsequent applications by procedures exactly as described for Example 73, except where otherwise noted below.

Ethephon in unformulated (technical) form was used as the plant growth regulator for this Example. Initial applications of ethephon, alone or in tank mix with a candidate accession agent, were applied 19 days after planting. Ethephon was applied in water with and without candidate accession agent at a range of rates from 125 to 1000 g/ha. Candidate accession agent treatments were exactly as in Example 73.

Sixteen days after application, plants were measured as in Example 73.

TABLE 74

| Initial application | | PGR | subsequent application | Height |
|---|---|---|---|---|
| PGR | accession agent | rate g/ha | accession agent | (cm) PHSVN |
| ethephon | none | 125 | none | 37 |
| ethephon | none | 250 | none | 31 |
| ethephon | none | 500 | none | 23 |
| ethephon | none | 1000 | none | 20 |
| ethephon | 0.25% L-77 | 125 | none | 47 |
| ethephon | 0.25% L-77 | 250 | none | 37 |
| ethephon | 0.25% L-77 | 500 | none | 27 |
| ethephon | 0.25% L-77 | 1000 | none | 23 |
| ethephon | 0.5% L-77 | 125 | none | 44 |
| ethephon | 0.5% L-77 | 250 | none | 35 |
| ethephon | 0.5% L-77 | 500 | none | 29 |
| ethephon | 0.5% L-77 | 1000 | none | 24 |
| ethephon | 1.5% L-77 | 125 | none | 38 |
| ethephon | 1.5% L-77 | 250 | none | 37 |
| ethephon | 1.5% L-77 | 500 | none | 29 |
| ethephon | 1.5% L-77 | 1000 | none | 24 |
| ethephon | none | 125 | 0.25% L-77 at 1 hr | 38 |
| ethephon | none | 250 | 0.25% L-77 at 1 hr | 32 |
| ethephon | none | 500 | 0.25% L-77 at 1 hr | 24 |
| ethephon | none | 1000 | 0.25% L-77 at 1 hr | 21 |
| ethephon | none | 125 | 0.25% L-77 at 4 hr | 42 |
| ethephon | none | 250 | 0.25% L-77 at 4 hr | 31 |
| ethephon | none | 500 | 0.25% L-77 at 4 hr | 23 |
| ethephon | none | 1000 | 0.25% L-77 at 4 hr | 19 |
| ethephon | none | 125 | 0.5% L-77 at 1 hr | 40 |
| ethephon | none | 250 | 0.5% L-77 at 1 hr | 29 |
| ethephon | none | 500 | 0.5% L-77 at 1 hr | 24 |
| ethephon | none | 1000 | 0.5% L-77 at 1 hr | 21 |
| ethephon | none | 125 | 0.5% L-77 at 4 hr | 43 |
| ethephon | none | 250 | 0.5% L-77 at 4 hr | 39 |
| ethephon | none | 500 | 0.5% L-77 at 4 hr | 27 |
| ethephon | none | 1000 | 0.5% L-77 at 4 hr | 20 |
| ethephon | none | 125 | 1.5% L-77 at 1 hr | 35 |
| ethephon | none | 250 | 1.5% L-77 at 1 hr | 34 |
| ethephon | none | 500 | 1.5% L-77 at 1 hr | 24 |
| ethephon | none | 1000 | 1.5% L-77 at 1 hr | 20 |
| ethephon | none | 125 | 1.5% L-77 at 4 hr | 40 |
| ethephon | none | 250 | 1.5% L-77 at 4 hr | 29 |
| ethephon | none | 500 | 1.5% L-77 at 4 hr | 23 |
| ethephon | none | 1000 | 1.5% L-77 at 4 hr | 20 |
| none | none | 0 | none | 97 |
| none (water) | none | 0 | none | 92 |
| none | 0.25% L-77 | 0 | none | 90 |
| none | 0.5% L-77 | 0 | none | 94 |
| none | 1.5% L-77 | 0 | none | 89 |

Ethephon was very effective in this test in reducing the height of the bean plants. Adding Silwet L-77 in tank mix tended to reduce effectiveness, indicating antagonism. This antagonism was reduced or eliminated by applying the Silwet L-77 as a sequential treatment after the ethephon according to the present invention.

Example 75

A test was conducted to apply the method of the present invention to Peters 27-15-12 Foliar Feed, a compound fertilizer marketed for foliar application.

Seeds of hybrid corn (*Zea mays*, ZEAMD) cv. Pioneer PN 3394 were planted in 85 mm square pots in river sand (Meramec WB-20 below the seeds; Meramec WB-35 for the 18 mm cover layer) which was previously steam sterilized but contained no added fertilizer. The pots were placed in a greenhouse with sub-irrigation. After emergence, seedlings were thinned to 3 healthy plants per pot. The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and 18° C. during the night. Plants were sub-irrigated throughout the test to ensure adequate soil moisture levels.

Pots were assigned to different treatments in a fully randomized experimental design with 6 replications. One set of 6 pots was left untreated as a reference against which effects of the treatments could later be evaluated.

All foliar fertilizer treatments were made with addition of nonionic surfactant as recommended on the Peters label; the surfactant used was Tween 20 at 0.5% by volume. Initial treatments with foliar fertilizer, with Tween 20 only or in tank mix with a candidate accession agent in addition to Tween 20, were applied 18 days after planting. Initial treatments were applied by spraying with a track sprayer fitted with a single 8002E nozzle calibrated to deliver a spray volume of 374 l/ha at a pressure of 173 kPa. Plants treated according to methods of prior art, for comparative purposes, received an initial treatment only. Plants treated by a method illustrative of the present invention received an initial application of foliar fertilizer plus Tween 20 followed sequentially by a subsequent application of a candidate accession agent. Various intervals between initial and subsequent applications were tested in this Example. All subsequent applications in this Example were applied by spraying a candidate accession agent with a track sprayer fitted exactly as for the initial application and calibrated to deliver a spray volume of 374 l/ha at a pressure of 173 kPa.

Foliar fertilizer was applied without and with each candidate accession agent at a range of rates from 5.6 to 44.8 kg N/ha. Candidate accession agents in this Example were aqueous solutions of Silwet L-77 at concentrations of 0.25%, 0.5% and 1.5% by volume. Solutions of Silwet L-77 were prepared immediately before application because of hydrolytic instability. Time intervals between initial and subsequent applications were 4 hours and 24 hours. Thirteen days after application, a chlorophyll meter (SPAD-502) reading was taken on the lamina, avoiding the mid-vein, near the mid-point of the fifth leaf of each plant (3 readings per pot; total 18 per treatment). It was observed that leaves having a tear or other injury distal to the mid-point had elevated chlorophyll readings at the mid-point on the injured side; in such cases the reading recorded was from the side of the leaf opposite the injured side. An average chlorophyll reading for each treatment was calculated.

Thirty-one days after application, the height of each individual plant was measured to the nearest centimeter, from the soil surface to the shoot apex. An average height of all plants in each treatment was calculated. Plants were then clipped at soil level and the total fresh weight per treatment determined.

Table 75A summarizes the results obtained with the chlorophyll meter. An "A" indicates that antagonism (reduced chlorophyll reading) was evident when Silwet L-77 was applied as part of a tank mix, by comparison with the treatment receiving the same rate of fertilizer but no Silwet L-77, and "S" indicates that the antagonism was reduced or eliminated when Silwet L-77 was instead applied as a separate, sequential treatment. An "X" indicates that the chlorophyll reading for a particular treatment was lower than that for the next lower fertilizer rate. (It is believed that in the 24 hour and possibly the 4 hour sequential treatments, the 11.2 kg N/ha results reflect an application error.)

TABLE 75A

| Initial application | | Nitrogen | subsequent | Chloro- |
|---|---|---|---|---|
| fertilizer | accession agent | rate kg/ha | application accession agent | phyll reading |
| Foliar Feed | none | 5.6 | none | |
| Foliar Feed | none | 11.2 | none | |
| Foliar Feed | none | 22.4 | none | |
| Foliar Feed | none | 44.8 | none | |
| Foliar Feed | 0.25% L-77 | 5.6 | none | A |
| Foliar Feed | 0.25% L-77 | 11.2 | none | A |
| Foliar Feed | 0.25% L-77 | 22.4 | none | A |
| Foliar Feed | 0.25% L-77 | 44.8 | none | XA |
| Foliar Feed | 0.5% L-77 | 5.6 | none | A |
| Foliar Feed | 0.5% L-77 | 11.2 | none | A |
| Foliar Feed | 0.5% L-77 | 22.4 | none | XA |
| Foliar Feed | 0.5% L-77 | 44.8 | none | A |
| Foliar Feed | 1.5% L-77 | 5.6 | none | A |
| Foliar Feed | 1.5% L-77 | 11.2 | none | A |
| Foliar Feed | 1.5% L-77 | 22.4 | none | A |
| Foliar Feed | 1.5% L-77 | 44.8 | none | A |
| Foliar Feed | none | 5.6 | 0.25% L-77 at 4 hr | S |
| Foliar Feed | none | 11.2 | 0.25% L-77 at 4 hr | S |

TABLE 75A-continued

| Initial application | | Nitrogen | subsequent | Chloro- |
|---|---|---|---|---|
| fertilizer | accession agent | rate kg/ha | application accession agent | phyll reading |
| Foliar Feed | none | 22.4 | 0.25% L-77 at 4 hr | S |
| Foliar Feed | none | 44.8 | 0.25% L-77 at 4 hr | S |
| Foliar Feed | none | 5.6 | 0.25% L-77 at 24 hr | S |
| Foliar Feed | none | 11.2 | 0.25% L-77 at 24 hr | X |
| Foliar Feed | none | 22.4 | 0.25% L-77 at 24 hr | S |
| Foliar Feed | none | 44.8 | 0.25% L-77 at 24 hr | S |
| Foliar Feed | none | 5.6 | 0.5% L-77 at 4 hr | S |
| Foliar Feed | none | 11.2 | 0.5% L-77 at 4 hr | X |
| Foliar Feed | none | 22.4 | 0.5% L-77 at 4 hr | S |
| Foliar Feed | none | 44.8 | 0.5% L-77 at 4 hr | S |
| Foliar Feed | none | 5.6 | 0.5% L-77 at 24 hr | S |
| Foliar Feed | none | 11.2 | 0.5% L-77 at 24 hr | X |
| Foliar Feed | none | 22.4 | 0.5% L-77 at 24 hr | S |
| Foliar Feed | none | 44.8 | 0.5% L-77 at 24 hr | S |
| Foliar Feed | none | 5.6 | 1.5% L-77 at 4 hr | S |
| Foliar Feed | none | 11.2 | 1.5% L-77 at 4 hr | XS |
| Foliar Feed | none | 22.4 | 1.5% L-77 at 4 hr | S |
| Foliar Feed | none | 44.8 | 1.5% L-77 at 4 hr | S |
| Foliar Feed | none | 5.6 | 1.5% L-77 at 24 hr | S |
| Foliar Feed | none | 11.2 | 1.5% L-77 at 24 hr | X |
| Foliar Feed | none | 22.4 | 1.5% L-77 at 24 hr | S |
| Foliar Feed | none | 44.8 | 1.5% L-77 at 24 hr | S |

Table 75B gives height and weight data.

TABLE 75B

| Initial application | | Nitrogen | subsequent application | Height | Weight |
|---|---|---|---|---|---|
| Fertilizer | accession agent | rate kg/ha | accession agent | (cm) ZEAMD | (g) ZEAMD |
| Foliar Feed | none | 5.6 | none | 47 | 11.4 |
| Foliar Feed | none | 11.2 | none | 51 | 12.2 |
| Foliar Feed | none | 22.4 | none | 56 | 14.0 |
| Foliar Feed | none | 44.8 | none | 62 | 18.6 |
| Foliar Feed | 0.25% L-77 | 5.6 | none | 44 | 10.9 |
| Foliar Feed | 0.25% L-77 | 11.2 | none | 48 | 13.6 |
| Foliar Feed | 0.25% L-77 | 22.4 | none | 53 | 15.6 |
| Foliar Feed | 0.25% L-77 | 44.8 | none | 56 | 16.2 |
| Foliar Feed | 0.5% L-77 | 5.6 | none | 43 | 10.6 |
| Foliar Feed | 0.5% L-77 | 11.2 | none | 51 | 14.8 |
| Foliar Feed | 0.5% L-77 | 22.4 | none | 49 | 13.8 |
| Foliar Feed | 0.5% L-77 | 44.8 | none | 53 | 15.0 |
| Foliar Feed | 1.5% L-77 | 5.6 | none | 47 | 12.3 |
| Foliar Feed | 1.5% L-77 | 11.2 | none | 48 | 12.6 |
| Foliar Feed | 1.5% L-77 | 22.4 | none | 51 | 11.8 |
| Foliar Feed | 1.5% L-77 | 44.8 | none | 55 | 15.0 |
| Foliar Feed | none | 5.6 | 0.25% L-77 at 4 hr | 50 | 13.8 |
| Foliar Feed | none | 11.2 | 0.25% L-77 at 4 hr | 51 | 12.8 |
| Foliar Feed | none | 22.4 | 0.25% L-77 at 4 hr | 52 | 15.9 |
| Foliar Feed | none | 44.8 | 0.25% L-77 at 4 hr | 60 | 22.7 |
| Foliar Feed | none | 5.6 | 0.25% L-77 at 24 hr | 49 | 12.6 |
| Foliar Feed | none | 11.2 | 0.25% L-77 at 24 hr | 44 | 10.5 |
| Foliar Feed | none | 22.4 | 0.25% L-77 at 24 hr | 58 | 18.2 |
| Foliar Feed | none | 44.8 | 0.25% L-77 at 24 hr | 62 | 20.7 |
| Foliar Feed | none | 5.6 | 0.5% L-77 at 4 hr | 48 | 13.7 |
| Foliar Feed | none | 11.2 | 0.5% L-77 at 4 hr | 49 | 13.6 |
| Foliar Feed | none | 22.4 | 0.5% L-77 at 4 hr | 57 | 17.7 |
| Foliar Feed | none | 44.8 | 0.5% L-77 at 4 hr | 54 | 15.9 |
| Foliar Feed | none | 5.6 | 0.5% L-77 at 24 hr | 46 | 11.8 |
| Foliar Feed | none | 11.2 | 0.5% L-77 at 24 hr | 42 | 9.6 |
| Foliar Feed | none | 22.4 | 0.5% L-77 at 24 hr | 54 | 15.8 |
| Foliar Feed | none | 44.8 | 0.5% L-77 at 24 hr | 60 | 20.6 |
| Foliar Feed | none | 5.6 | 1.5% L-77 at 4 hr | 47 | 13.4 |

TABLE 75B-continued

| Initial application | | Nitrogen | subsequent application | Height | Weight |
|---|---|---|---|---|---|
| Fertilizer | accession agent | rate kg/ha | accession agent | (cm) ZEAMD | (g) ZEAMD |
| Foliar Feed | none | 11.2 | 1.5% L-77 at 4 hr | 50 | 13.6 |
| Foliar Feed | none | 22.4 | 1.5% L-77 at 4 hr | 57 | 17.0 |
| Foliar Feed | none | 44.8 | 1.5% L-77 at 4 hr | 59 | 18.7 |
| Foliar Feed | none | 5.6 | 1.5% L-77 at 24 hr | 43 | 10.0 |
| Foliar Feed | none | 11.2 | 1.5% L-77 at 24 hr | 40 | 8.9 |
| Foliar Feed | none | 22.4 | 1.5% L-77 at 24 hr | 50 | 14.4 |
| Foliar Feed | none | 44.8 | 1.5% L-77 at 24 hr | 55 | 16.9 |
| none | none | 0 | none | 40 | 10.1 |
| none (water) | none | 0 | none | 38 | 8.5 |
| none | 0.25% L-77 | 0 | none | 39 | 8.3 |
| none | 0.5% L-77 | 0 | none | 39 | 8.4 |
| none | 1.5% L-77 | 0 | none | 37 | 7.5 |
| none | 0.5% Tween 20 | 0 | none | 37 | 8.2 |

Fertilizer effects on growth of corn plants in this test were reduced by addition of Silwet L-77 in tank mix, indicating antagonism. When the Silwet L-77 was instead applied as a sequential treatment after the foliar fertilizer according to the present invention, this antagonism was reduced or eliminated.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A method of applying an exogenous chemical to a plant, comprising sequentially the steps of (a) contacting foliage of the plant with a biologically effective amount of an exogenous chemical composition, and (b) thereafter contacting at least a part of the same foliage of the plant with an accession agent, whereby antagonism to biological effectiveness that would be exhibited were the plant contacted with a tank mix or a simple coformulation of the exogenous chemical and the accession agent is substantially reduced.

2. The method of claim 1 wherein the accession agent is an aqueous solution of a surfactant.

3. The method of claim 1 wherein the accession agent is an aqueous solution of an organosilicone wetting agent.

4. The method of claim 1 wherein the accession agent is an aqueous solution of an organosilicone wetting agent of the following average formula:

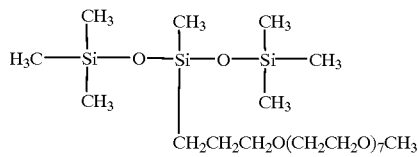

5. The method of claim 1 wherein the accession agent is an aqueous solution of a fluoro-organic wetting agent.

6. The method of claim 1 wherein the exogenous chemical is a herbicide and is applied to the plant in a herbicidally effective amount.

7. The method of claim 6, wherein the herbicide is selected from the group consisting of acetanilides, bipyridyls, cyclohexenones, dinitroanilines, diphenylethers, hydroxybenzonitriles, imidazolinones, phenoxies, phenoxypropionates, substituted ureas, sulfonylureas, thiocarbamates, and triazines.

8. The method of claim 6, wherein the herbicide is selected from the group consisting of acetochlor, alachlor, metolachlor, aminotriazole, asulam, bentazon, bialaphos, paraquat, bromacil, clethodim, sethoxydim, dicamba, diflufenican, pendimethalin, acifluorfen, fomesafen, oxyfluorfen, fosamine, flupoxam, glufosinate, glyphosate, bromoxynil, imazaquin, imazethapyr, isoxaben, norflurazon, 2,4-D, diclofop, fluazifop, quizalofop, picloram, propanil, fluometuron, isoproturon, chlorimuron, chlorsulfuron, halosulfuron, metsulfuron, primisulfuron, sulfometuron, sulfosulfuron, triallate, atrazine, metribuzin, and triclopyr.

9. The method of claim 1, wherein the exogenous chemical is a foliar-applied exogenous chemical.

10. The method of claim 9 wherein the foliar applied exogenous chemical is applied as a composition further comprising a surfactant.

11. The method of claim 9, wherein the foliar-applied exogenous chemical is water soluble.

12. The method of claim 11, wherein the water soluble foliar-applied exogenous chemical is a salt comprising at least one biologically active ion.

13. The method of claim 12, wherein the salt or a biologically active moiety thereof is systemic in the plant.

14. The method of claim 13, wherein the salt comprises a biologically active ion and a counterion that is less biologically active or biologically inert, and wherein the exogenous chemical has a molecular weight, excluding the counterion, of less than about 300.

15. The method of claim 14, wherein the foliar applied exogenous chemical has one or more functional groups selected from the group consisting of amine, amide, carboxylate, phosphonate and phosphinate groups.

16. The method of claim 15, wherein the foliar-applied exogenous chemical is selected from the group consisting of herbicides, plant growth regulators and nematicides.

17. The method of claim 16, wherein the exogenous chemical is a nematicidal salt of 3,4,4-trifluoro-3-butenoic acid or of N-(3,4,4-trifluoro-1-oxo-3-butenyl)glycine.

18. The method of claim 12, wherein the foliar-applied exogenous chemical is selected from the group consisting of herbicides, plant growth regulators and nematicides.

19. The method of claim 18, wherein the foliar applied exogenous chemical is a herbicidal or plant growth regulating compound having at least one of each of amine, carboxylate and either phosphonate or phosphinate functional groups.

20. The method of claim 19, wherein the herbicidal or plant growth regulating compound is a salt of N-phosphonomethylglycine.

21. The method of claim 20 wherein the salt is selected from the group consisting of ammonium, alkylamine, alkanolamine, alkali metal, alkylsulfonium, and sulfoxonium salts of N-phosphonomethylglycine.

22. The method of claim 21 wherein the salt is an ammonium or an alkylamine salt of N-phosphonomethylglycine.

23. The method of claim 21 wherein the salt is the monoisopropylamine salt of N-phosphonomethylglycine.

24. The method of claim 20 wherein the herbicide is applied as a composition further comprising a surfactant.

25. The method of claim 24 wherein the surfactant in the herbicide composition is a tertiary or quaternary polyoxyalkylene alkylamine.

26. The method of claim 25 wherein the surfactant in the herbicide composition is a polyoxyethylene tallowamine.

27. The method of claim 20 wherein the accession agent is an aqueous solution of a surfactant.

28. The method of claim 27 wherein the accession agent is an aqueous solution of a superwetting surfactant.

29. The method of claim 28 wherein the superwetting surfactant is an organosilicone wetting agent.

30. The method of claim 29 wherein the superwetting surfactant is an organosilicone wetting agent of the following average formula:

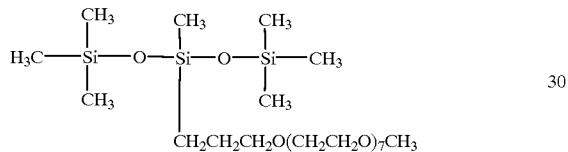

31. The method of claim 29 wherein the concentration of the surfactant in the aqueous solution is at least about 0.25% by volume.

32. The method of claim 29 wherein the concentration of the surfactant in the aqueous solution is at least about 0.5% by volume.

33. The method of claim 28 wherein the superwetting surfactant is a fluoro-organic wetting agent.

34. The method of claim 20 wherein the accession agent is applied during a period of time ranging from immediately after up to about 24 hours after application of the herbicide.

35. The method of claim 34 wherein the period of time is from about one hour to about three hours after application of the herbicide.

36. The method of claim 34 wherein the period of time is from about 0.005 to about 10 seconds after application of the herbicide.

37. The method of claim 20 wherein the application of the salt of N-phosphonomethylglycine and the application of the accession agent are performed in a single pass over the plant.

38. The method of claim 37 wherein the application of the salt of N-phosphonomethylglycine and the application of the accession agent are performed by two separate spray booms connected to a single vehicle.

39. The method of claim 20 wherein the method effectively controls one or more plant species of one or more of the following genera: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

40. The method of claim 20 wherein the method effectively controls one or more of the following plant species:

velvetleaf (*Abutilon theophrasti*)

pigweed (Amaranthus spp.)

buttonweed (Borreria spp.)

oilseed rape, canola, indian mustard, etc. (Brassica spp.)

commelina (Commelina spp.)

filaree (Erodium spp.)

sunflower (Helianthus spp.)

morningglory (Ipomoea spp.)

kochia (*Kochia scoparia*)

mallow (Malva spp.)

wild buckwheat, smartweed, etc. (Polygonum spp.)

purslane (Portulaca spp.)

russian thistle (Salsola spp.)

sida (Sida spp.)

wild mustard (*Sinapis arvensis*)

cocklebur (Xanthium spp.)

wild oat (*Avena fatua*)

carpetgrass (Axonopus spp.)

downy brome (*Bromus tectorum*)

crabgrass (Digitaria spp.)

barnyardgrass (*Echinochloa crus-galli*)

goosegrass (*Eleusine indica*)

annual ryegrass (*Lolium multiflorum*)

rice (*Oryza sativa*)

ottochloa (*Ottochloa nodosa*)

bahiagrass (*Paspalum notatum*)

canarygrass (Phalaris spp.)

foxtail (Setaria spp.)

wheat (*Triticum aestivum*)

corn (*Zea mays*)

mugwort (Artemisia spp.)

milkweed (Asclepias spp.)

canada thistle (*Cirsium arvense*)

field bindweed (*Convolvulus arvensis*)

kudzu (Pueraria spp.)

brachiaria (Brachiaria spp.)

bermudagrass (*Cynodon dactylon*)

yellow nutsedge (*Cyperus esculentus*)

purple nutsedge (*C. rotundus*)

quackgrass (*Elymus repens*)

lalang (*Imperata cylindrica*)

perennial ryegrass (*Lolium perenne*)

guineagrass (*Panicum maximum*)

dallisgrass (*Paspalum dilatatum*)

reed (Phragmites spp.)

johnsongrass (*Sorghum halepense*)

cattail (Typha spp.)

horsetail (Equisetum spp.)

bracken (*Pteridium aquilinum*)

blackberry (Rubus spp.)

gorse (*Ulex europaeus*).

41. The method of claim 20 wherein the method effectively controls one or more of the following plant species:

velvetleaf (*Abutilon theophrasti*)

redroot pigweed (*Amaranthus retroflexus*)

wild oat (*Avena fatua*)
broadleaf signalgrass (*Brachiaria platyphylla*)
canola (*Brassica napus*)
downy brome (*Bromus tectorum*)
sicklepod (*Cassia obtusifolia*)
common lambsquarter (*Chenopodium album*)
barnyardgrass (*Echinochloa crus-galli*)
redstem filaree (*Erodium cicutarium*)
cutleaf geranium (*Geranium dissectum*)
soybean (*Glycine max*)
little barley (*Hordeum pusillum*)
pitted morningglory (*Ipomoea lacunosa*)
annual ryegrass (*Lolium multiflorum*)
annual bluegrass (*Poa annua*)
wild buckwheat (*Polygonum convolvulus*)
cutleaf evening primrose (*Primula trientalis*)
curly dock (*Rumex crispus*)
hemp sesbania (*Sesbania exaltata*)
prickly sida (*Sida spinosa*)
wild mustard (*Sinapis arvensis*)
johnsongrass (*Sorghum halepense*)
wheat (*Triticum aestivum*).

42. The method of claim 19, wherein the herbicidal or plant growth regulating compound is ammonium DL-homoalanin-4-yl(methyl)phosphinate.

43. The method of claim 1, wherein the application of exogenous chemical and the application of the accession agent are performed in a single pass over the plant.

44. The method of claim 43, wherein the application of exogenous chemical and the application of the accession agent are performed by at least two separate spray booms connected to a single vehicle.

45. The method of claim 1 wherein the foliage is contacted with the accession agent during a period of time ranging from immediately after up to about 24 hours after contacting the foliage with the exogenous chemical.

46. The method of claim 45 wherein the period of time is from about one hour up to about three hours after contacting the plant with the exogenous chemical.

47. The method of claim 45 wherein the period of time is from about 0.005 to about 10 seconds after contacting the plant with the exogenous chemical.

48. The method of claim 1 wherein the exogenous chemical is a foliar fertilizer.

49. The method of claim 48 wherein the foliar fertilizer is applied as a composition further comprising a surfactant.

50. A method of applying an exogenous chemical to a plant, comprising sequentially the steps of (a) contacting foliage of a plant with a biologically effective amount of an exogenous chemical composition, and (b) thereafter contacting at least a part of the same foliage with an aqueous solution or dispersion of an anionic surfactant.

51. The method of claim 50, whereby antagonism to biological effectiveness that would be exhibited were the plant contacted with a tank mix or simple coformulation of the exogenous chemical and the anionic surfactant is substantially reduced.

52. The method of claim 50, wherein the exogenous chemical is a herbicide and is applied to the plant in a herbicidally effective amount.

53. The method of claim 52, wherein the herbicide is N-phosphonomethylglycine or a herbicidal derivative thereof.

54. The method of claim 53, wherein the herbicide is a water soluble salt of N-phosphonomethylglycine.

55. The method of claim 50, wherein the anionic surfactant is selected from the group consisting of alkyl and alkylaryl carboxylates, alkyl and alkylaryl polyoxyalkylene carboxylates, alkyl and alkylaryl sulfates and sulfonates, alkyl and alkylaryl polyoxyalkylene sulfates and sulfonates, naphthalene sulfonates and formaldehyde condensates thereof, lignosulfonates, sulfosuccinates and semisulfosuccinates, and alkyl and alkylaryl polyoxyalkylene phosphates.

56. A method of applying an exogenous chemical to a plant, comprising sequentially the steps of (a) contacting foliage of the plant with a biologically effective amount of an exogenous chemical composition, and (b) thereafter contacting at least a part of the same foliage of the plant with an accession agent, wherein the exogenous chemical and the accession agent are contacted with one or more plants selected from the group consisting of:

velvetleaf (*Abutilon theophrasti*)
pigweed (Amaranthus spp.)
buttonweed (Borreria spp.)
oilseed rape, canola, indian mustard, etc. (Brassica spp.)
commelina (Commelina spp.)
filaree (Erodium spp.)
sunflower (Helianthus spp.)
morningglory (Ipomoea spp.)
kochia (*Kochia scoparia*)
mallow (Malva spp.)
wild buckwheat, smartweed, etc. (Polygonum spp.)
purslane (Portulaca spp.)
russian thistle (Salsola spp.)
sida (Sida spp.)
wild mustard (*Sinapis arvensis*)
cocklebur (Xanthium spp.)
wild oat (*Avena fatua*)
carpetgrass (Axonopus spp.)
downy brome (*Bromus tectorum*)
crabgrass (Digitaria spp.)
barnyardgrass (*Echinochloa crus-galli*)
goosegrass (*Eleusine indica*)
annual ryegrass (*Lolium multiflorum*)
rice (*Oryza sativa*)
ottochloa (*Ottochloa nodosa*)
bahiagrass (*Paspalum notatum*)
canarygrass (Phalaris spp.)
foxtail (Setaria spp.)
corn (*Zea mays*)
mugwort (Artemisia spp.)
milkweed (Asclepias spp.)
canada thistle (*Cirsium arvense*)
field bindweed (*Convolvulus arvensis*)
kudzu (Pueraria spp.)
brachiaria (Brachiaria spp.)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)

perennial ryegrass (*Lolium perenne*)
guineagrass (*Panicum maximum*)
dallisgrass (*Paspalum dilatatum*)
reed (Phragmites spp.)
johnsongrass (*Sorghum halepense*)
cattail (Typha spp.)
horsetail (Equisetum spp.)
bracken (*Pteridium aquilinum*)
blackberry (Rubus spp.)
gorse (*Ulex europaeus*)
sicklepod (*Cassia obtusifolia*)
common lambsquarter (*Chenopodium album*)
cutleaf geranium (*Geranium dissectum*)
soybean (*Glycine max*)
little barley (*Hordeum pusillum*)
annual bluegrass (*Poa annua*)
cutleaf evening primrose (*Primula trientalis*)
curly dock (*Rumex crispus*)
hemp sesbania (*Sesbania exaltata*).

57. The method of claim 56, wherein the exogenous chemical is a herbicide and is applied to foliage of the plant in a herbicidally effective amount.

58. The method of claim 57, wherein the herbicide is a water soluble salt of N-phosphonomethylglycine.

59. The method of claim 57, wherein the herbicide and the accession agent are contacted with one or more plants selected from the group consisting of:

velvetleaf (*Abutilon theophrasti*)
redroot pigweed (*Amaranthus retroflexus*)
wild oat (*Avena fatua*)
broadleaf signalgrass (*Brachiaria platyphylla*)
canola (*Brassica napus*)
downy brome (*Bromus tectorum*)
sicklepod (*Cassia obtusifolia*)
common lambsquarter (*Chenopodium album*)
barnyardgrass (*Echinochloa crus-galli*)
redstem filaree (*Erodium cicutarium*)
cutleaf geranium (*Geranium dissectum*)
soybean (*Glycine max*)
little barley (*Hordeum pusillum*)
pitted morningglory (*Ipomoea lacunosa*)
annual ryegrass (*Lolium multiflorum*)
annual bluegrass (*Poa annua*)
wild buckwheat (*Polygonum convolvulus*)
cutleaf evening primrose (*Primula trientalis*)
curly dock (*Rumex crispus*)
hemp sesbania (*Sesbania exaltata*)
prickly sida (*Sida spinosa*)
wild mustard (*Sinapis arvensis*)
johnsongrass (*Sorghum halepense*).

60. A method of applying a herbicide to a plant, comprising sequentially the steps of (a) contacting foliage of the plant with a herbicidally effective amount of a herbicide composition, and (b) thereafter contacting at least a part of the same foliage of the plant with an accession agent, whereby ultimate herbicidal inhibition of the plant is substantially improved over that exhibited by contacting the plant with a tank mix or simple coformulation of the herbicide composition and the accession agent.

61. A herbicidal method comprising sequentially the steps of (a) contacting foliage of a plant with a herbicide comprising N-phosphonomethylglycine or a herbicidal derivative thereof and (b) thereafter contacting at least a part of the same foliage with an accession agent, whereby antagonism to herbicidal effectiveness that would be exhibited were the plant contacted with a tank mix or simple coformulation of the herbicide and the accession agent is substantially reduced.

62. A method for enhancing the herbicidal effectiveness of a herbicide for a plurality of plant species in a field comprising the steps of (a) applying to the foliage of the plurality of plant species a herbicide comprising N-phosphonomethylglycine or a herbicidal derivative thereof and (b) thereafter applying to the same foliage an accession agent, whereby the herbicidal effectiveness of the herbicide for at least one of the plurality of plant species is substantially enhanced.

63. A method for reducing the antagonism of an accession agent to the herbicidal effectiveness of a herbicide comprising N-phosphonomethylglycine or a herbicidal derivative thereof comprising the steps of (a) applying the herbicide to foliage of a plant species for which the accession agent is antagonistic to the herbicidal effectiveness of the herbicide when tank mixed therewith or admixed therewith in a simple coformulation and (b) thereafter applying to at least a part of the same foliage the accession agent, whereby the herbicidal effectiveness of the herbicide for the plant species is substantially preserved or enhanced.

64. The method of claim 61 wherein the herbicide is a water soluble salt of N-phosphonomethylglycine.

65. The method of claim 62 wherein the herbicide is a water soluble salt of N-phosphonomethylglycine.

66. The method of claim 63 wherein the herbicide is a water soluble salt of N-phosphonomethylglycine.

67. A herbicidal method comprising sequentially the steps of (a) contacting foliage of a plant with a herbicide comprising a water soluble salt of N-phosphonomethylglycine and (b) thereafter contacting at least a part of the same foliage with an aqueous solution containing at least about 0.5% by weight or volume of a superwetting surfactant selected from the group consisting of organosilicone wetting agents and fluoro-organic wetting agents, whereby antagonism to herbicidal effectiveness that would be exhibited were the plant contacted with a tank mix or simple coformulation of the herbicide and the superwetting surfactant is substantially reduced.

68. The method of claim 67 wherein the herbicide is applied as a composition further comprising a surfactant.

69. The method as in claim 68 wherein the surfactant in the herbicide composition is a tertiary or quaternary polyoxyalkylene alkylamine.

70. The method of claim 69 wherein the surfactant in the herbicide composition is a polyoxyethylene tallowamine.

71. The method of claim 67 wherein the foliage is contacted with the aqueous solution of superwetting surfactant during a period of time ranging from immediately after up to about 24 hours after contacting the plant with the herbicide.

72. The method of claim 71 wherein the period of time is from about one hour to about three hours after application of the herbicide.

73. The method of claim 50 wherein the period of time is from about 0.005 to about 10 seconds after application of the herbicide.

74. A method for enhancing the herbicidal effectiveness of a glyphosate herbicide for a plurality of plant species in a field comprising the steps of (a) applying to foliage of the plurality of plant species in the field a herbicide comprising a water soluble salt of N-phosphonomethylglycine and (b) thereafter applying to the same foliage an aqueous solution containing at least about 0.5% by weight or volume of a superwetting surfactant selected from the group consisting of organosilicone wetting agents and fluoro-organic wetting agents, whereby the herbicidal effectiveness of the herbicide is substantially enhanced for at least one of the plurality of plant species.

75. The method of claim 74 wherein the aqueous solution of superwetting surfactant is applied during a period of time ranging from immediately after up to about 24 hours after application of the herbicide.

76. The method of claim 75 wherein the period of time is from about one hour to about three hours after application of the herbicide.

77. The method of claim 75 wherein the period of time is from about 0.005 to about 10 seconds after application of the herbicide.

78. A method for enhancing the yield of a field crop comprising the steps of:
    (a) planting a crop in a field,
    (b) substantially freeing the field of one or more weed species that would diminish the yield of the crop by
        (i) applying to foliage of the weed species a herbicide comprising N-phosphonomethylglycine or a herbicidal derivative thereof and
        (ii) thereafter applying to at least a part of the same foliage an accession agent, whereby antagonism to herbicidal effectiveness that would be exhibited by application of a tank mix or simple coformulation of the herbicide and the accession agent is substantially reduced,
    (c) allowing the crop to mature, and
    (d) harvesting the crop.

79. The method of claim 78 wherein the herbicide comprises a water soluble salt of N-phosphonomethylglycine and the accession agent comprises an aqueous solution of a superwetting surfactant selected from the group consisting of organosilicone wetting agents and fluoro-organic wetting agents.

80. The method of claim 79 wherein the herbicide is applied as a composition further comprising a surfactant.

81. The method of claim 80 wherein the surfactant in the herbicide composition is a tertiary or quaternary polyoxyalkylene alkylamine.

82. The method of claim 81 wherein the surfactant in the herbicide composition is a polyoxyethylene tallowamine.

83. A method of enhancing the yield of a field crop comprising the steps of:
    (a) selecting a field for planting a crop,
    (b) substantially freeing the field of one or more weed species that would diminish the yield of the crop by:
        (i) applying to foliage of the weed species a herbicide comprising N-phosphonomethylglycine or a herbicidal derivative thereof and
        (ii) thereafter applying to at least a part of the same foliage an accession agent, whereby antagonism to herbicidal effectiveness that would be exhibited by application of a tank mix or coformulation of the herbicide and the accession agent is substantially reduced,
    (c) planting the crop in the field,
    (d) allowing the crop to mature, and
    (e) harvesting the crop.

84. The method of claim 83 wherein the herbicide comprises a water soluble salt of N-phosphonomethylglycine and the accession agent comprises an aqueous solution of a superwetting surfactant selected from the group consisting of organosilicone wetting agents and fluoro-organic wetting agents.

85. The method of claim 84 wherein the herbicide is applied as a composition further comprising a surfactant.

86. The method of claim 85 wherein the surfactant in the herbicide composition is a tertiary or quaternary polyoxyalkylene alkylamine.

87. The method of claim 86 wherein the surfactant in the herbicide composition is a polyoxyethylene tallowamine.

88. A herbicidal method comprising sequentially the steps of (a) contacting foliage of a plant with a herbicide comprising dicamba or a herbicidal derivative thereof and (b) thereafter contacting at least a part of the same foliage with an accession agent.

89. The method of claim 88, wherein the plant is Abutilon theophrasti.

90. The method of claim 89, wherein the plant is Echinochloa crus-*galli*.

91. The method of claim 88, wherein the plant is Sida spinosa.

92. A method of applying an exogenous chemical to a plant, comprising sequentially the steps of (a) contacting foliage of the plant with a biologically effective amount of an exogenous chemical composition, and (b) thereafter contacting at least a part of the same foliage of the plant with an aqueous solution or dispersion of a sulfonylamino compound having the formula

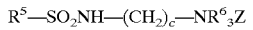

wherein $R^5$ is alkyl or fluoroalkyl having from about 6 to about 20 carbon atoms, c is 1–4, $R^6$ groups are independently $C_{1-4}$ alkyl and Z is an agriculturally acceptable counterion.

* * * * *